US008168858B2

(12) United States Patent
McGonigle et al.

(10) Patent No.: US 8,168,858 B2
(45) Date of Patent: May 1, 2012

(54) DELTA-9 FATTY ACID ELONGASE GENES AND THEIR USE IN MAKING POLYUNSATURATED FATTY ACIDS

(75) Inventors: Brian McGonigle, Wilmington, DE (US); Anthony J. Kinney, Wilmington, DE (US); Howard Glenn Damude, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 236 days.

(21) Appl. No.: 12/487,768

(22) Filed: Jun. 19, 2009

(65) Prior Publication Data
US 2009/0320161 A1     Dec. 24, 2009

Related U.S. Application Data

(60) Provisional application No. 61/132,582, filed on Jun. 20, 2008.

(51) Int. Cl.
*A01H 1/00* (2006.01)
*A01H 5/00* (2006.01)
*A01H 5/10* (2006.01)
*C12N 15/82* (2006.01)

(52) U.S. Cl. ........ 800/278; 800/281; 800/298; 800/306; 800/312; 800/314; 800/320.1; 800/322; 435/410; 435/419; 435/320.1; 536/23.74

(58) Field of Classification Search .................. None
See application file for complete search history.

(56) References Cited

U.S. PATENT DOCUMENTS

| | | | |
|---|---|---|---|
| 5,972,664 A | 10/1999 | Knutzon et al. | |
| 6,075,183 A | 6/2000 | Knutzon et al. | |
| 6,677,145 B2 * | 1/2004 | Mukerji et al. | 435/193 |
| 7,645,604 B2 * | 1/2010 | Damude et al. | 435/193 |
| 2005/0132441 A1 | 6/2005 | Damude et al. | |
| 2006/0094092 A1 | 5/2006 | Damude et al. | |
| 2006/0110806 A1 | 5/2006 | Damude et al. | |
| 2006/0115881 A1 | 6/2006 | Damude et al. | |
| 2007/0117190 A1 | 5/2007 | Damude et al. | |
| 2007/0118929 A1 | 5/2007 | Damude et al. | |
| 2007/0237876 A1 | 10/2007 | Kinney et al. | |
| 2007/0271632 A1 | 11/2007 | Damude et al. | |
| 2007/0292924 A1 | 12/2007 | Damude et al. | |

FOREIGN PATENT DOCUMENTS

| | | |
|---|---|---|
| WO | 02/077213 A2 | 10/2002 |
| WO | WO 2004/011671 A1 | 2/2004 |
| WO | 2004/071467 A2 | 8/2004 |
| WO | 2004/101753 A2 | 11/2004 |
| WO | 2004/101757 A2 | 11/2004 |
| WO | 2006/052870 A2 | 5/2006 |
| WO | 2006/052871 A2 | 5/2006 |
| WO | 2006/055322 A2 | 5/2006 |
| WO | WO 2008/130248 A1 | 10/2008 |
| WO | WO 2008/104559 A1 | 11/2008 |
| WO | WO 2009/129582 A1 | 10/2009 |

OTHER PUBLICATIONS

Jennifer M. Parker-Barnes et al., identification and characterization of an enzyme involved in the elongation of n-6 and n-3 polyunsaturated fatty acids, PNAS, Jul. 18, 2000, pp. 8284-8289, vol. 97, No. 15.
National Center for Biotechnology Information, General Identification No. 7861836, Accession No. AAF70417, Jul. 20, 2000.
National Center for Biotechnology Information, General Identification No. 17226123, Accession No. AAL37626, Mar. 9, 2006.
National Center for Biotechnology Information, General Identification No. 4150956, Accession No. AB022097, Mar. 19, 2009.
National Center for Biotechnology Information, General Identification No. 16151828, Accession No. AB072976, Oct. 16, 2001.
National Center for Biotechnology Information, General Identification No. 3127024, Accession No. AF007879, May 11, 1998.
National Center for Biotechnology Information, General Identification No. 3859487, Accession No. AF067654, Nov. 11, 1998.
National Center for Biotechnology Information, General Identification No. 6842049, Accession No. AF199596, Jun. 21, 2000.
National Center for Biotechnology Information, General Identification No. 7861835, Accession No. AF206662, Jul. 20, 2000.
National Center for Biotechnology Information, General Identification No. 7861969, Accession No. AF226273, May 17, 2000.
National Center for Biotechnology Information, General Identification No. 11386008, Accession No. AF320509, Aug. 13, 2001.
National Center for Biotechnology Information, General Identification No. 16033739, Accession No. AF419297, Mar. 24, 2005.
National Center for Biotechnology Information, General Identification No. 20069122, Accession No. AF489588, Apr. 8, 2002.
National Center for Biotechnology Information, General Identification No. 23894017, Accession No. AJ610244, Apr. 15, 2005.
U.S. Appl. No. 12/102,979, filed Apr. 15, 2008.
U.S. Appl. No. 12/111,228, filed Apr. 23, 2008.
U.S. Appl. No. 12/061,738, filed Apr. 3, 2008.
Cahoon et al., "Enginerring oilseeds for sustainable production of industrial and nutritional feedstocks . . . ", Curr. Op. Plant Biol., vol. 10, pp. 236-244 (2007).
Cahoon et al., "Conjugated fatty acids accumulate to high levels in phosopholipids of metabolically engineered soybean . . . ", Phytochemistry, vol. 67, pp. 1166-1176 (2006).
Dyer, et al., "Engineering plant oils as high-value industrial feedstocks for biorefining . . . ", Physiologia Plantarum, vol. 132, pp. 11-22 (2008).
Lardizabal, et al., "Expression of *Umbelopsis ramanniana* DGAT2A in seed increases oil in soybean", Plant Physiol., vol. 148, pp. 89-96 (2008).
International Search Report and Written Opinion in PCT/US2010/060654, mailed May 25, 2011.

* cited by examiner

*Primary Examiner* — Eileen B O Hara

(57) ABSTRACT

Isolated nucleic acid fragments and recombinant constructs comprising such fragments encoding novel delta-9 elongases along with a method of making long-chain polyunsaturated fatty acids (PUFAs) using these delta-9 elongases in plants.

28 Claims, 15 Drawing Sheets

|     |   |   |   |   |   |   |
|-----|---|---|---|---|---|---|
| 256 | K | K | K |   | E | L | Q |
| 261 | K | Q | I |   |   |   |   |
| 256 | K | K | K |   |   |   | Q |
| 259 | . | . | . |   |   | D |   |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |
| 316 | K | K | K |   |   |   | Q |

SEQ ID NO 80.pro
SEQ ID NO 81.pro
SEQ ID NO 82.pro
SEQ ID NO 83.pro
SEQ ID NO 6.pro
SEQ ID NO 8.pro
SEQ ID NO 10.pro
SEQ ID NO 12.pro
SEQ ID NO 14.pro
SEQ ID NO 16.pro
SEQ ID NO 18.pro
SEQ ID NO 20.pro
SEQ ID NO 22.pro
SEQ ID NO 24.pro
SEQ ID NO 26.pro
SEQ ID NO 28.pro
SEQ ID NO 30.pro
SEQ ID NO 2.pro

FIG. 9

Percent Identity

| | 1 | 2 | 3 | 4 | 5 | 6 | 7 | 8 | 9 | 10 | 11 | 12 | 13 | 14 | 15 | 16 | 17 | 18 | |
|---|---|---|---|---|---|---|---|---|---|---|---|---|---|---|---|---|---|---|---|
| 1 | ■ | 32.9 | 77.1 | 62.0 | 17.4 | 17.4 | 17.4 | 17.8 | 17.4 | 17.4 | 17.4 | 17.8 | 17.8 | 17.4 | 17.4 | 18.6 | 17.1 | 17.8 | 1 |
| 2 | 109.0 | ■ | 31.8 | 33.2 | 18.6 | 18.3 | 18.6 | 19.0 | 18.6 | 18.6 | 19.0 | 18.6 | 18.6 | 18.6 | 18.6 | 18.3 | 18.3 | 18.6 | 2 |
| 3 | 27.3 | 115.3 | ■ | 64.7 | 17.8 | 17.4 | 17.4 | 17.8 | 17.4 | 17.8 | 17.4 | 18.2 | 18.2 | 17.4 | 17.8 | 17.4 | 17.1 | 17.8 | 3 |
| 4 | 50.4 | 108.1 | 45.3 | ■ | 18.9 | 18.5 | 18.5 | 18.5 | 18.5 | 18.5 | 18.5 | 18.5 | 18.9 | 18.1 | 18.5 | 18.1 | 18.1 | 18.5 | 4 |
| 5 | 195.0 | 189.7 | 213.0 | 218.0 | ■ | 98.1 | 97.2 | 97.8 | 97.5 | 98.7 | 98.1 | 98.4 | 98.7 | 97.5 | 98.7 | 97.8 | 97.2 | 97.8 | 5 |
| 6 | 199.0 | 189.7 | 213.0 | 218.0 | 1.9 | ■ | 99.1 | 98.4 | 98.7 | 96.9 | 98.7 | 96.5 | 96.9 | 95.6 | 96.9 | 96.5 | 96.5 | 99.1 | 6 |
| 7 | 195.0 | 189.7 | 209.0 | 214.0 | 2.9 | 0.9 | ■ | 98.1 | 98.4 | 95.9 | 99.1 | 96.2 | 95.9 | 95.3 | 96.5 | 95.6 | 95.6 | 98.1 | 7 |
| 8 | 195.7 | 193.1 | 209.0 | 214.0 | 2.2 | 1.6 | 1.9 | ■ | 98.4 | 97.2 | 98.7 | 98.1 | 97.8 | 95.9 | 97.2 | 96.2 | 96.2 | 98.7 | 8 |
| 9 | 195.7 | 189.7 | 209.0 | 214.0 | 2.6 | 1.3 | 1.6 | 1.6 | ■ | 96.9 | 98.7 | 97.2 | 96.9 | 96.2 | 96.9 | 96.5 | 96.5 | 97.8 | 9 |
| 10 | 195.0 | 189.7 | 213.0 | 222.0 | 1.3 | 3.2 | 4.2 | 2.9 | 3.2 | ■ | 96.9 | 99.1 | 99.4 | 97.5 | 99.4 | 98.4 | 97.8 | 96.5 | 10 |
| 11 | 195.7 | 189.7 | 209.0 | 214.0 | 1.9 | 1.3 | 0.9 | 0.9 | 1.3 | 3.2 | ■ | 97.2 | 96.9 | 96.2 | 96.9 | 95.9 | 95.9 | 98.4 | 11 |
| 12 | 195.0 | 189.7 | 218.0 | 218.0 | 1.6 | 3.5 | 3.9 | 1.9 | 2.9 | 0.9 | 2.9 | ■ | 99.1 | 97.8 | 99.1 | 98.1 | 97.5 | 96.9 | 12 |
| 13 | 195.0 | 193.1 | 213.0 | 218.0 | 1.3 | 3.2 | 4.2 | 2.2 | 3.2 | 0.9 | 3.2 | 0.9 | ■ | 96.9 | 98.7 | 97.8 | 97.2 | 97.2 | 13 |
| 14 | 195.0 | 193.1 | 213.0 | 222.0 | 2.6 | 4.5 | 4.9 | 4.2 | 3.9 | 2.6 | 3.9 | 2.2 | 3.2 | ■ | 97.5 | 96.5 | 96.5 | 95.3 | 14 |
| 15 | 195.0 | 189.7 | 213.0 | 222.0 | 1.3 | 3.2 | 3.5 | 2.9 | 3.2 | 0.6 | 3.2 | 0.9 | 1.3 | 2.6 | ■ | 98.4 | 97.8 | 96.5 | 15 |
| 16 | 195.0 | 189.7 | 213.0 | 222.0 | 2.2 | 3.5 | 4.5 | 3.9 | 3.5 | 1.6 | 4.2 | 1.9 | 2.2 | 3.5 | 1.6 | ■ | 98.7 | 95.6 | 16 |
| 17 | 195.0 | 193.1 | 213.0 | 222.0 | 2.9 | 3.5 | 4.5 | 3.9 | 3.5 | 2.2 | 4.2 | 2.6 | 2.9 | 3.5 | 2.2 | 1.3 | ■ | 95.6 | 17 |
| 18 | 199.0 | 189.7 | 213.0 | 218.0 | 2.2 | 0.9 | 1.9 | 1.3 | 2.2 | 3.5 | 1.6 | 3.2 | 2.9 | 4.9 | 3.5 | 4.5 | 4.5 | ■ | 18 |
| | 1 | 2 | 3 | 4 | 5 | 6 | 7 | 8 | 9 | 10 | 11 | 12 | 13 | 14 | 15 | 16 | 17 | 18 | |

| # | SEQ ID |
|---|---|
| 1 | SEQ ID NO 80.pro |
| 2 | SEQ ID NO 81.pro |
| 3 | SEQ ID NO 82.pro |
| 4 | SEQ ID NO 83.pro |
| 5 | SEQ ID NO 6.pro |
| 6 | SEQ ID NO 8.pro |
| 7 | SEQ ID NO 10.pro |
| 8 | SEQ ID NO 12.pro |
| 9 | SEQ ID NO 14.pro |
| 10 | SEQ ID NO 16.pro |
| 11 | SEQ ID NO 18.pro |
| 12 | SEQ ID NO 20.pro |
| 13 | SEQ ID NO 22.pro |
| 14 | SEQ ID NO 24.pro |
| 15 | SEQ ID NO 26.pro |
| 16 | SEQ ID NO 28.pro |
| 17 | SEQ ID NO 30.pro |
| 18 | SEQ ID NO 2.pro |

SEQUENCE LISTING

<160> NUMBER OF SEQ ID NOS: 83

<210> SEQ ID NO 1
<211> LENGTH: 957
<212> TYPE: DNA
<213> ORGANISM: Artificial Sequence
<220> FEATURE:
<223> OTHER INFORMATION: codon optimized Mortierella alpina delta-6 elongase, optimized for expression in Yarrowia

<400> SEQUENCE: 1

```
atggagtcga ttgcgccatt cctcccatca agatgccgc aagatctgtt tatggacctt      60
gccaccgcta tcggtgtccg ggccgcgccc tatgtcgatc ctctcgaggc cgcgctggtg     120
gcccaggccg agaagtacat ccccacgatt gtccatcaca cgcgtgggtt cctggtcgcg     180
gtggagtcgc ctttggcccg tgagctgccg ttgatgaacc cgttccacgt gctgttgatc     240
gtgctcgctt atttggtcac ggtctttgtg ggcatgcaga tcatgaagaa ctttgagcgg     300
ttcgaggtca agacgttttc gctcctgcac aacttttgtc tggtctcgat cagcgcctac     360
atgtgcggtg ggatcctgta cgaggcttat caggccaact atggactgtt tgagaacgct     420
gctgatcata ccttcaaggg tcttcctatg gccaagatga tctggctctt ctacttctcc     480
aagatcatgg agtttgtcga caccatgatc atggtcctca agaagaacaa ccgccagatc     540
tccttcttgc acgtttacca ccacagctcc atcttcacca tctggtggtt ggtcaccttt     600
gttgcaccca acggtgaagc ctacttctct gctgcgttga actcgttcat ccatgtgatc     660
atgtacggct actacttctt gtcggccttg ggcttcaagc aggtgtcgtt catcaagttc     720
tacatcacgc gctcgcagat gacacagttc tgcatgatgt cggtccagtc ttcctgggac     780
atgtacgcca tgaaggtcct tggccgcccc ggatacccct tcttcatcac ggctctgctt     840
tggttctaca tgtggaccat gctcggtctc ttctacaact tttacagaaa gaacgccaag     900
ttggccaagc aggccaaggc cgacgctgcc aaggagaagg caaggaagtt gcagtaa       957
```

<210> SEQ ID NO 2
<211> LENGTH: 318
<212> TYPE: PRT
<213> ORGANISM: Mortierella alpina
<220> FEATURE:
<221> NAME/KEY: MISC_FEATURE
<222> LOCATION: (1)..(319)
<223> OTHER INFORMATION: M. alpina delta-6 elongase codon optimized for expression in Yarrowia

<400> SEQUENCE: 2

```
Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30
```

Asp Pro Leu Glu Ala Ala Leu Val Ala Gln Ala Glu Lys Tyr Ile Pro
         35                  40                  45

Thr Ile Val His His Thr Arg Gly Phe Leu Val Ala Val Glu Ser Pro
     50                  55                  60

Leu Ala Arg Glu Leu Pro Leu Met Asn Pro Phe His Val Leu Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 3
<211> LENGTH: 957
<212> TYPE: DNA
<213> ORGANISM: Mortierella alpina
<220> FEATURE:
<221> NAME/KEY: misc_feature
<222> LOCATION: (1)..(957)
<223> OTHER INFORMATION: M. alpina delta-6 elongase

<400> SEQUENCE: 3
atggagtcga ttgcgccatt cctcccatca aagatgccgc aagatctgtt tatggacctt      60
gccaccgcta tcggtgtccg ggccgcgccc tatgtcgatc ctctcgaggc cgcgctggtg     120
gcccaggccg agaagtacat ccccacgatt gtccatcaca cgcgtgggtt cctggtcgcg     180
gtggagtcgc ctttggcccg tgagctgccg ttgatgaacc cgttccacgt gctgttgatc     240
gtgctcgctt atttggtcac ggtctttgtg ggcatgcaga tcatgaagaa ctttgagcgg     300
ttcgaggtca agacgttttc gctcctgcac aacttttgtc tggtctcgat cagcgcctac     360
atgtgcggtg ggatcctgta cgaggcttat caggccaact atggactgtt tgagaacgct     420

```
gctgatcata ccttcaaggg tcttcctatg gccaagatga tctggctctt ctacttctcc      480
aagatcatgg agtttgtcga caccatgatc atggtcctca agaagaacaa ccgccagatc      540
tccttcttgc acgtttacca ccacagctcc atcttcacca tctggtggtt ggtcaccttt      600
gttgcaccca acggtgaagc ctacttctct gctgcgttga actcgttcat ccatgtgatc      660
atgtacggct actacttctt gtcggccttg ggcttcaagc aggtgtcgtt catcaagttc      720
tacatcacgc gctcgcagat gacacagttc tgcatgatgt cggtccagtc ttcctgggac      780
atgtacgcca tgaaggtcct tggccgcccc ggatacccct tcttcatcac ggctctgctt      840
tggttctaca tgtggaccat gctcggtctc ttctacaact tttacagaaa gaacgccaag      900
ttggccaagc aggccaaggc cgacgctgcc aaggagaagg caaggaagtt gcagtaa        957
```

<210> SEQ ID NO 4
<211> LENGTH: 318
<212> TYPE: PRT
<213> ORGANISM: Mortierella alpina
<220> FEATURE:
<221> NAME/KEY: MISC_FEATURE
<222> LOCATION: (1)..(318)
<223> OTHER INFORMATION: M. alpina delta-6 elongase

<400> SEQUENCE: 4

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
```

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
        290                 295                 300

Ala Lys Ala Asp Ala Ala Lys Glu Lys Ala Arg Lys Leu Gln
305                 310                 315

<210> SEQ ID NO 5
<211> LENGTH: 957
<212> TYPE: DNA
<213> ORGANISM: Artificial sequence
<220> FEATURE:
<223> OTHER INFORMATION: clone 004-3.1b-f2 from KS376

<400> SEQUENCE: 5

```
atggagtcca ttgctccctt cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggattctc ccctggctcg agagctgcct ctgatgaacc ccttccacgt gctcctgatt    240
gtgctcgcct acctggtcac cgtgtttgtg ggtatgcaga tcatgaagaa ctttgaacga    300
ttcgaggtca gacgttctc gctcctgtac aacttctgtc tggtctcgct gagcgcctac    360
atgtgcggtg gcatcctgta cgaggctttc aggccaact atggactgtt tgagaacgct    420
gccgatcaca ccttcaaggg tctccctatg gctaagatga tctggctctt ctacttctcc    480
aagctgatgg agtttgtcga caccatgatc atggtcctca aaaagaacaa ccgacagatt    540
tcctttctgc acgtgtacca ccactcttcc atcttcacca tctggtggct ggtcaccttc    600
gttgctccca acggtgaagc ctacttctct gctgccctga actcgttcat ccatgttatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggataccct tcttcctgac cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaa      957
```

<210> SEQ ID NO 6
<211> LENGTH: 318
<212> TYPE: PRT
<213> ORGANISM: Artificial sequence
<220> FEATURE:
<223> OTHER INFORMATION: clone 004-3.1b-f2

<400> SEQUENCE: 6

Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

```
Asn Phe Glu Arg Phe Glu Val Lys Thr Phe Ser Leu Leu Tyr Asn Phe
                100                 105                 110
Cys Leu Val Ser Leu Ser Ala Tyr Met Cys Gly Gly Ile Leu Tyr Glu
            115                 120                 125
Ala Phe Gln Ala Asn Tyr Gly Leu Phe Glu Asn Ala Ala Asp His Thr
        130                 135                 140
Phe Lys Gly Leu Pro Met Ala Lys Met Ile Trp Leu Phe Tyr Phe Ser
145                 150                 155                 160
Lys Leu Met Glu Phe Val Asp Thr Met Ile Met Val Leu Lys Lys Asn
                165                 170                 175
Asn Arg Gln Ile Ser Phe Leu His Val Tyr His Ser Ser Ile Phe
            180                 185                 190
Thr Ile Trp Trp Leu Val Thr Phe Val Ala Pro Asn Gly Glu Ala Tyr
        195                 200                 205
Phe Ser Ala Ala Leu Asn Ser Phe Ile His Val Ile Met Tyr Gly Tyr
    210                 215                 220
Tyr Phe Leu Ser Ala Leu Gly Phe Lys Gln Val Ser Phe Ile Lys Phe
225                 230                 235                 240
Tyr Ile Thr Arg Ser Gln Met Thr Gln Phe Cys Met Met Ser Val Gln
                245                 250                 255
Ser Ser Trp Asp Met Tyr Ala Met Lys Val Leu Gly Arg Pro Gly Tyr
            260                 265                 270
Pro Phe Phe Leu Thr Ala Leu Leu Trp Phe Tyr Met Trp Thr Met Leu
        275                 280                 285
Gly Leu Phe Tyr Asn Phe Tyr Arg Lys Asn Ala Lys Leu Ala Lys Gln
    290                 295                 300
Ala Lys Ala Asp Ala Ala Lys Glu Lys Ala Arg Lys Leu Gln
305                 310                 315

<210> SEQ ID NO 7
<211> LENGTH: 957
<212> TYPE: DNA
<213> ORGANISM: Artificial sequence
<220> FEATURE:
<223> OTHER INFORMATION: clone 006-2.1b-e11 from KS372

<400> SEQUENCE: 7
atggagtcca ttgccccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacgg     300
ttcgaggtca agacgttctc gctcctgcac aacttctgtc tggtctcgat tagcgcctac     360
atgtgcggtg gcatcctgta cgaggctttc caggccaact atggactgtt tgagaacgct     420
gccgatcaca ccttcaaggg tctccctatg gctaagatga tctggctctt ctacttctcc     480
aagatcatgg agtttgtcga caccatgatc atggtcctca agaagaacaa ccgacagatt     540
tcctttctgc acgtgtacca ccactcttcc atcttcacca tctggtggct ggtcaccttc     600
gttgctccca cggtgaagc ctacttctct gctgccctga actcgttcat ccatgttatc     660
atgtacggct actactttct gtctgccctg gcttcaagc aggtgtcgct gatcaagttc     720
tacatcactc gatcccagat gacccagttc tgcatgatgt ctgtccagtc ttcctgggac     780
atgtacgcca tgaaggtcct tggccgacct ggatacccct tcttcatcac cgctctgctc     840
```

-continued

```
tggttctaca tgtggaccat gctcggtctc ttctacaact tttaccgaaa gaacgccaag    900
ctcgccaagc aggccaaggc tgacgctgcc aaggagaagg ccagaaagct ccagtaa      957
```

<210> SEQ ID NO 8
<211> LENGTH: 318
<212> TYPE: PRT
<213> ORGANISM: Artificial sequence
<220> FEATURE:
<223> OTHER INFORMATION: clone 006-2.1b-e11

<400> SEQUENCE: 8

```
Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Leu Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 9
<211> LENGTH: 957
<212> TYPE: DNA
<213> ORGANISM: Artificial sequence
<220> FEATURE:
<223> OTHER INFORMATION: clone 009-2.1b-h9 from KS369

<400> SEQUENCE: 9

```
atggagtcca ttgctcccttcctgccctccaagatgcctcaggacctgttcatggacctc     60
gccagcgcta tcggtgtccg agctgctccc tacgtcgatc cctggaggc tgccctggtt    120
gcccaggccg agaagtacat tcccaccatt gtccatcaca ctcgaggctt cctggttgcc   180
gtggagtctc ccctggctcg agagctgcct ctgatgaacc ccttccacgt gctcctgatc   240
gtgctcgcct acctggtcac cgtgtttgtg ggtatgcaga tcatgaagaa ctttgaacga   300
ttcgaggtca agacgtattc gctcctgcac aacttctgtc tggtctcgat tagcgcctac   360
atgtgcggtg gcatcctgta cgaggctttc caggccaact atggactgtt tgagaacgct   420
gccgatcaca ccttcaaggg tctccctatg gctaagatga tctggctctt ctacttctcc   480
aagatcatgg agtttgtcga cacccttatc atggtcctca agaagaacaa ccgacagatt   540
tcctttctgc acgtgtacca ccactcttcc atcttcacca tctggtggct ggtcaccttc   600
gttgctccca acggtgaagc ctacttctct gctgccctga actcgttcat ccatgttatc   660
atgtacggct actactttct gtctgccctg ggcttcaagc aggtgtcgct gatcaagttc   720
tacatcactc gatcccagat gacccagttc tgcatgatgt ctgtccagtc ttcctgggac   780
atgtacgcca tgaaggtcct tggccgacct ggataccct tcttcatcgc cgctctgctc   840
tggttctaca tgtggaccat gctcggtctc ttctacaact tttaccgaaa gaacgccaag   900
ctcgccaagc aggccaaggc tgacgctgcc aaggagaagg ccagaaagct ccagtaa     957
```

<210> SEQ ID NO 10
<211> LENGTH: 318
<212> TYPE: PRT
<213> ORGANISM: Artificial sequence
<220> FEATURE:
<223> OTHER INFORMATION: clone 009-2.1b-h9

<400> SEQUENCE: 10

```
Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Tyr Ser Leu Leu His Asn Phe
            100                 105                 110

Cys Leu Val Ser Ile Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Leu Ile Met Val Leu Lys Lys Asn
                165                 170                 175
```

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Leu Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Ala Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 11
<211> LENGTH: 957
<212> TYPE: DNA
<213> ORGANISM: Artificial sequence
<220> FEATURE:
<223> OTHER INFORMATION: clone 010-2.1b-c3 from KS370

<400> SEQUENCE: 11
atggagtcca ttgttccctt cctgccctcc aagatgcctc aggacctgtt catgaccctc      60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggagtctc ccctggctcg agagctgcct ctgatgaacc ccttccacgt gctcctgatc    240
gtgctcgcct acctggtcac cgtgtttgtg ggtatgcaga tcatgaagaa ctttgaacga    300
ttcgaggtca gacgtattc gctcctgcac aacttctgtc tggtctcgct gagcgcctac    360
atgtgcggtg gcattctgta cgaggcttat caggccaact atggactgtt tgagaacgct    420
gccgatcaca ccttcaaggg tctccctatg gctaagatga tctggctctt ctacttctcc    480
aagatcatgg agtttgtcga caccatgatc atggtcctca gaagaacaa ccgacagatt    540 tcctttctgc acgtgtacca ccactcttcc atcttcacca tctggtggct ggtcaccttc    600
gttgctccca acggtgaagc ctacttctct gctgccctga actcgttcat ccatgttatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggataccct tcttcatcac cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaa      957

<210> SEQ ID NO 12
<211> LENGTH: 318
<212> TYPE: PRT
<213> ORGANISM: Artificial sequence
<220> FEATURE:
<223> OTHER INFORMATION: clone 010-2.1b-c3

<400> SEQUENCE: 12

Met Glu Ser Ile Val Pro Phe Leu Pro Ser Lys Met Pro Gln Asp Leu

```
  1               5                  10                 15
Phe Met Asp Leu Ala Ser Ala Ile Gly Val Arg Ala Pro Tyr Val
                20                 25                 30
Asp Pro Leu Glu Ala Ala Leu Val Ala Gln Ala Glu Lys Tyr Ile Pro
                35                 40                 45
Thr Ile Val His His Thr Arg Gly Phe Leu Val Ala Val Glu Ser Pro
 50                 55                 60
Leu Ala Arg Glu Leu Pro Leu Met Asn Pro Phe His Val Leu Leu Ile
 65                 70                 75                 80
Val Leu Ala Tyr Leu Val Thr Val Phe Val Gly Met Gln Ile Met Lys
                85                 90                 95
Asn Phe Glu Arg Phe Glu Val Lys Thr Tyr Ser Leu Leu His Asn Phe
                100                105                110
Cys Leu Val Ser Leu Ser Ala Tyr Met Cys Gly Gly Ile Leu Tyr Glu
                115                120                125
Ala Tyr Gln Ala Asn Tyr Gly Leu Phe Glu Asn Ala Ala Asp His Thr
                130                135                140
Phe Lys Gly Leu Pro Met Ala Lys Met Ile Trp Leu Phe Tyr Phe Ser
145                 150                155                160
Lys Ile Met Glu Phe Val Asp Thr Met Ile Met Val Leu Lys Lys Asn
                165                170                175
Asn Arg Gln Ile Ser Phe Leu His Val Tyr His His Ser Ser Ile Phe
                180                185                190
Thr Ile Trp Trp Leu Val Thr Phe Val Ala Pro Asn Gly Glu Ala Tyr
                195                200                205
Phe Ser Ala Ala Leu Asn Ser Phe Ile His Val Ile Met Tyr Gly Tyr
                210                215                220
Tyr Phe Leu Ser Ala Leu Gly Phe Lys Gln Val Ser Phe Ile Lys Phe
225                 230                235                240
Tyr Ile Thr Arg Ser Gln Met Thr Gln Phe Cys Met Met Ser Val Gln
                245                250                255
Ser Ser Trp Asp Met Tyr Ala Met Lys Val Leu Gly Arg Pro Gly Tyr
                260                265                270
Pro Phe Phe Ile Thr Ala Leu Leu Trp Phe Tyr Met Trp Thr Met Leu
                275                280                285
Gly Leu Phe Tyr Asn Phe Tyr Arg Lys Asn Ala Lys Leu Ala Lys Gln
                290                295                300
Ala Lys Ala Asp Ala Ala Lys Glu Lys Ala Arg Lys Leu Gln
305                 310                315

<210> SEQ ID NO 13
<211> LENGTH: 957
<212> TYPE: DNA
<213> ORGANISM: Artificial sequence
<220> FEATURE:
<223> OTHER INFORMATION: clone 012-2.1b-c3 from KS371

<400> SEQUENCE: 13
atggagtcca ttgctcccctt cctgctctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctgttgcc     180 gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agacgtattc gctcctgcac aacttctgtc tggtctcgct gagcgcctac     360
```

```
atgtgcggtg gcattctgta cgaggctttt caggccaact atggactgtt tgagaacgct      420
gccgatcaca ccttcaaggg tctccctatg ctaagatga tctggctctt ctacttctcc       480
aagatcatgg agtttgtcga caccatgatc atggtcctca agaagaacaa ccgacagatt      540
tcctttctgc acgtgtacca ccactcttcc atcttcacca tctggtggct ggtcaccttc      600
gttgctccca acggtgaagc ctacttctct gctgccctga actcgttcat ccatgttatc      660
atgtacggct actactttct gtctgccctg ggcttcaagc aggtgtcgct gatcaagttc      720
tacatcactc gatcccagat gacccagttc tgcatgttgt ctgtccagtc ttcctgggac      780
atgtacgcca tgaaggtcct tggccgacct ggatacccct tcttcatcac cgctctgctc      840
tggttctaca tgtggaccat gctcggtctc ttctacaact tttaccgaaa gaacgccaag      900
ctcgccaagc aggccaaggc tgacgctgcc aaggagaagg ccagaaagct ccagtaa        957
```

<210> SEQ ID NO 14
<211> LENGTH: 318
<212> TYPE: PRT
<213> ORGANISM: Artificial sequence
<220> FEATURE:
<223> OTHER INFORMATION: clone 012-2.1b-c3

<400> SEQUENCE: 14

```
Met Glu Ser Ile Ala Pro Phe Leu Leu Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Tyr Ser Leu Leu His Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Leu Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
```

Pro Phe Phe Ile Thr Ala Leu Leu Trp Phe Tyr Met Trp Thr Met Leu
                275                 280                 285

Gly Leu Phe Tyr Asn Phe Tyr Arg Lys Asn Ala Lys Leu Ala Lys Gln
            290                 295                 300

Ala Lys Ala Asp Ala Ala Lys Glu Lys Ala Arg Lys Leu Gln
305                 310                 315

<210> SEQ ID NO 15
<211> LENGTH: 957
<212> TYPE: DNA
<213> ORGANISM: Artificial sequence
<220> FEATURE:
<223> OTHER INFORMATION: clone 014-3.1b-F1 from KS375

<400> SEQUENCE: 15
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca gacgttctc gctcctgtac aacttctgtc tggtctcgct gagcgcctac     360
atgtgcggtg gcattctgta cgaggctttt caggccaact atggactgtt tcagaacgct     420
gccgatcaca ccttcaaggg tctccctatg gctaagatga tctggctctt ctacttctcc     480
aagctgatgg agtttgtcga caccatgatc atggtcctca aaagaacaa ccgacagatt     540 tcctttctgc acgtgtacca ccactcttcc atcttcacca tctggtggct ggtcaccttc     600
gttgctccca acggtgaagc ctacttctct gctgccctga actcgttcat ccatgttatc     660
atgtacggct actactttct gtctgccctg ggcttcaagc aggtgtcgtt catcaagttc     720
tacatcactc gatcccagat gacccagttc tgcatgttgt ctgtccagtc ttcctgggac     780
atgtacgcca tgaaggtcct tggccgacct ggataccct tcttcctgac cgctctgctc     840
tggttctaca tgtggaccat gctcggtctc ttctacaact tttaccgacg aaacgccaag     900
ctcgccaagc aggccaaggc tgacgctgcc aaggagaagg ccagaaagct ccagtaa       957

<210> SEQ ID NO 16
<211> LENGTH: 318
<212> TYPE: PRT
<213> ORGANISM: Artificial sequence
<220> FEATURE:
<223> OTHER INFORMATION: clone 014-3.1b-F1

<400> SEQUENCE: 16

Met Glu Ser Ile Val Pro Phe Leu Pro Ser Lys Met Pro Gln Asp Leu
1               5                  10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Gln Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Met Val Leu Lys Lys Asn
                165                 170                 175

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Arg Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 17
<211> LENGTH: 957
<212> TYPE: DNA
<213> ORGANISM: Artificial sequence
<220> FEATURE:
<223> OTHER INFORMATION: clone 027-2.1b from KS374

<400> SEQUENCE: 17
atggagtcca ttgctcccct cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agacgtattc gctcctgcac aacttctgtc tggtctcgct gagcgcctac     360
atgtgcggtg gcatcctgta cgaggctttc caggccaact atggactgtt tgagaacgct     420
gccgatcaca ccttcaaggg tctccctatg gctaagatga tctggctctt ctacttctcc     480
aagatcatgg agtttgtcga caccatgatc atggtcctca agaagaacaa ccgacagatt     540
tcctttctgc acgtgtacca ccactcttcc atcttcacca tctggtggct ggtcaccttc     600
gttgctccca cggtgaagc ctacttctct gctgccctga actcgttcat ccatgttatc     660
atgtacggct actactttct gtctgccctg ggcttcaagc aggtgtcgtt catcaagttc     720
tacatcactc gatcccagat gacccagttc tgcatgatgc tgtccagtc ttcctgggac     780 atgtacgcca tgaaggtcct tggccgacct ggatacccct tcttcatcgc cgctctgctc     840
tggttctaca tgtggaccat gctcggtctc ttctacaact tttaccgaaa gaacgccaag    900
ctcgccaagc aggccaaggc tgacgctgcc aaggagaagg ccagaaagct ccagtaa       957

<210> SEQ ID NO 18
<211> LENGTH: 318
<212> TYPE: PRT
<213> ORGANISM: Artificial sequence
<220> FEATURE:
<223> OTHER INFORMATION: clone 027-2.1b

<400> SEQUENCE: 18

Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
                20                  25                  30

Asp Pro Leu Glu Ala Ala Leu Val Ala Gln Ala Glu Lys Tyr Ile Pro
            35                  40                  45

Thr Ile Val His His Thr Arg Gly Phe Leu Val Ala Val Glu Ser Pro
        50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Tyr Ser Leu Leu His Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Ala Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 19
<211> LENGTH: 957
<212> TYPE: DNA
<213> ORGANISM: Artificial sequence
<220> FEATURE:
<223> OTHER INFORMATION: clone 046-3.1b-C2 from KS384

<400> SEQUENCE: 19

```
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agacgtattc gctcctgtac aacttctgtc tggtctcgct gagcgcctac     360
atgtgcggtg gcattctgta cgaggcttat caggccaact atggactgtt tgagaacgct     420
gccgatcaca ccttcaaggg tctccctatg gctaagatga tctggctctt ctacttctcc     480
aagctgatgg agtttgtcga caccatgatc atggtcctca aaagaacaa ccgacagatt     540
tcctttctgc acgtgtacca ccactcttcc atcttcacca tctggtggct ggtcaccttc     600
gttgctccca acggtgaagc ctacttctct gctgccctga actcgttcat ccatgttatc     660
atgtacggct actactttct gtctgccctg ggcttcaagc aggtgtcgtt catcaagttc     720
tacatcactc gatcccagat gacccagttc tgcatgttgt ctgtccagtc ttcctgggac     780
atgtacgcca tgaaggtcct tggccgacct ggatacccct tcttcctgac cgctctgctc     840
tggttctaca tgtggaccat gctcggtctc ttctacaact tttaccgacg aaacgccaag     900
ctcgccaagc aggccaaggc tgacgctgcc aaggagaagg ccagaaagct ccagtaa       957
```

<210> SEQ ID NO 20
<211> LENGTH: 318
<212> TYPE: PRT
<213> ORGANISM: Artificial sequence
<220> FEATURE:
<223> OTHER INFORMATION: clone 046-3.1b-C2

<400> SEQUENCE: 20

```
Met Glu Ser Ile Val Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Tyr Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Met Val Leu Lys Lys Asn
                165                 170                 175
```

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Arg Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 21
<211> LENGTH: 957
<212> TYPE: DNA
<213> ORGANISM: Artificial sequence
<220> FEATURE:
<223> OTHER INFORMATION: clone 051-3.1b-B5 from KS382

<400> SEQUENCE: 21
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agacgttctc gctcctgtac aacttctgtc tggtctcgct gagcgcctac     360
atgtgcggtg gcattctgta cgaggcttat caggccaact atggactgtt tcagaacgct     420
gccgatcaca ccttcaaggg tctccctatg gctaagatga tctggctctt ctacttctcc     480
aagctgatgg agtttgtcga caccatgatc atggtcctca aaaagaacaa ccgacagatt     540
tcctttctgc acgtgtacca ccactcttcc atcttcacca tctggtggct ggtcaccttc     600
gttgctccca acggtgaagc ctacttctct gctgccctga actcgttcat ccatgttatc     660
atgtacggct actactttct gtctgccctg ggcttcaagc aggtgtcgtt catcaagttc     720
tacatcactc gatcccagat gacccagttc tgcatgttgt ctgtccagtc ttcctgggac     780
atgtacgcca tgaaggtcct tggccgacct ggatacccct tcttcctgac cgctctgctc     840
tggttctaca tgtggaccat gctcggtctc ttctacaact tttaccgaaa gaacgccaag     900
ctcgccaagc aggccaaggc tgacgctgcc aaggagaagg ccagaaagct ccagtaa       957

<210> SEQ ID NO 22
<211> LENGTH: 318
<212> TYPE: PRT
<213> ORGANISM: Artificial sequence
<220> FEATURE:
<223> OTHER INFORMATION: clone 051-3.1b-B5

<400> SEQUENCE: 22

Met Glu Ser Ile Val Pro Phe Leu Pro Ser Lys Met Pro Gln Asp Leu

```
                1               5                   10                  15
Phe Met Asp Leu Ala Ser Ala Ile Gly Val Arg Ala Pro Tyr Val
                    20                  25                  30

Asp Pro Leu Glu Ala Ala Leu Val Ala Gln Ala Glu Lys Tyr Ile Pro
                35                  40                  45

Thr Ile Val His His Thr Arg Gly Phe Leu Val Ala Val Asp Ser Pro
        50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu Tyr Asn Phe
                    100                 105                 110

Cys Leu Val Ser Leu Ser Ala Tyr Met Cys Gly Gly Ile Leu Tyr Glu
                115                 120                 125

Ala Tyr Gln Ala Asn Tyr Gly Leu Phe Gln Asn Ala Ala Asp His Thr
                130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Met Val Leu Lys Lys Asn
                    165                 170                 175

Asn Arg Gln Ile Ser Phe Leu His Val Tyr His His Ser Ser Ile Phe
                180                 185                 190

Thr Ile Trp Trp Leu Val Thr Phe Val Ala Pro Asn Gly Glu Ala Tyr
                195                 200                 205

Phe Ser Ala Ala Leu Asn Ser Phe Ile His Val Ile Met Tyr Gly Tyr
                210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Leu Ser Val Gln
                    245                 250                 255

Ser Ser Trp Asp Met Tyr Ala Met Lys Val Leu Gly Arg Pro Gly Tyr
                260                 265                 270

Pro Phe Phe Leu Thr Ala Leu Leu Trp Phe Tyr Met Trp Thr Met Leu
                275                 280                 285

Gly Leu Phe Tyr Asn Phe Tyr Arg Lys Asn Ala Lys Leu Ala Lys Gln
                290                 295                 300

Ala Lys Ala Asp Ala Ala Lys Glu Lys Ala Arg Lys Leu Gln
305                 310                 315
```

<210> SEQ ID NO 23
<211> LENGTH: 957
<212> TYPE: DNA
<213> ORGANISM: Artificial sequence
<220> FEATURE:
<223> OTHER INFORMATION: clone 052-3.1b-C9 from KS385

<400> SEQUENCE: 23

```
atggagtcca ttgctcccct cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggattctc ccctggctcg agagctgcct ctgatgaacc ccttccacgt gctcctgatt    240
gtgctcgcct acctggtcac cgtgtttgtg ggtatgcaga tcatgaagaa ctttgaacga    300
ttcgaggtca agacgtattc gctcctgtac aacttctgtc tggtctcgct gagcgcctac    360
```

```
atgtgcggtg gcattctgta cgaggctttt caggccaact atggactgtt tgagaacgct    420
gccgatcaca ccttcaaggg tctccctatg ctaagatga tctggctctt ctacttctcc     480
aagctgatgg agtttgtcga caccatgatc ctggtcctca aaagaacaa ccgacagatt    540 tcctttctgc acgtgtacca ccactcttcc ctgttcacca tctggtggct ggtcaccttc    600
gttgctccca acgtgaagc ctacttctct gctgccatga actcgttcat ccatgttatc    660
atgtacggct actactttct gtctgccctg ggcttcaagc aggtgtcgtt catcaagttc    720
tacctgactc gatcccagat gacccagttc tgcatgttgt ctgtccagtc ttcctgggac    780
atgtacgcca tgaaggtcct ggccgacct ggatacccct tcttcctgac cgctctgctc    840
tggttctaca tgtggaccct tctcggtctc ttctacaact tttaccgacg aaacgccaag    900
ctcgccaagc aggccaaggc tgacgctgcc aaggagaagg ccagaaagct ccagtaa      957
```

<210> SEQ ID NO 24
<211> LENGTH: 318
<212> TYPE: PRT
<213> ORGANISM: Artificial sequence
<220> FEATURE:
<223> OTHER INFORMATION: clone 052-3.1b-C9

<400> SEQUENCE: 24

```
Met Glu Ser Ile Ala Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Tyr Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Leu Val Leu Lys Lys Asn
                165                 170                 175

Asn Arg Gln Ile Ser Phe Leu His Val Tyr His His Ser Ser Leu Phe
            180                 185                 190

Thr Ile Trp Trp Leu Val Thr Phe Val Ala Pro Asn Gly Glu Ala Tyr
        195                 200                 205

Phe Ser Ala Ala Met Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Leu Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
```

```
              260                 265                 270
Pro Phe Phe Leu Thr Ala Leu Leu Trp Phe Tyr Met Trp Thr Leu Leu
            275                 280                 285

Gly Leu Phe Tyr Asn Phe Tyr Arg Arg Asn Ala Lys Leu Ala Lys Gln
            290                 295                 300

Ala Lys Ala Asp Ala Ala Lys Glu Lys Ala Arg Lys Leu Gln
305                 310                 315

<210> SEQ ID NO 25
<211> LENGTH: 957
<212> TYPE: DNA
<213> ORGANISM: Artificial sequence
<220> FEATURE:
<223> OTHER INFORMATION: clone 062-3.1b-C5 from KS380

<400> SEQUENCE: 25
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcctgatt     240
gtgctcgcct acctggtcac cgtgtttgtg ggtatgcaga tcatgaagaa ctttgaacga     300
ttcgaggtca gacgttctc gctcctgtac aacttctgtc tggtctcgct gagcgcctac     360
atgtgcggtg gcattctgta cgaggctttt caggccaact atggactgtt tgagaacgct     420
gccgatcaca ccttcaaggg tctccctatg gctaagatga tctggctctt ctacttctcc     480
aagctgatgg agtttgtcga cacccttatc atggtcctca gaagaacaa ccgacagatt     540 tcctttctgc acgtgtacca ccactcttcc atcttcacca tctggtggct ggtcaccttc     600
gttgctccca cggtgaggc ctacttctct gctgccctga actcgttcat ccatgttatc     660
atgtacggct actactttct gtctgccctg ggcttcaagc aggtgtcgtt catcaagttc     720
tacatcactc gatcccagat gacccagttc tgcatgttgt ctgtccagtc ttcctgggac     780
atgtacgcca tgaaggtcct tggccgacct ggatacccct tcttcctgac cgctctgctc     840
tggttctaca tgtggaccat gctcggtctc ttctacaact tttaccgacg aaacgccaag     900
ctcgccaagc aggccaaggc tgacgctgcc aaggagaagg ccagaaagct ccagtaa      957

<210> SEQ ID NO 26
<211> LENGTH: 318
<212> TYPE: PRT
<213> ORGANISM: Artificial sequence
<220> FEATURE:
<223> OTHER INFORMATION: clone 062-3.1b-C5

<400> SEQUENCE: 26

Met Glu Ser Ile Val Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95
```

Asn Phe Glu Arg Phe Glu Val Lys Thr Phe Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Leu Ile Met Val Leu Lys Lys Asn
                165                 170                 175

Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Arg Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 27
<211> LENGTH: 957
<212> TYPE: DNA
<213> ORGANISM: Artificial sequence
<220> FEATURE:
<223> OTHER INFORMATION: clone 077-3.1b-B1 from KS386

<400> SEQUENCE: 27

```
atggagtcca ttgttcccct cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcatgctt     240
gtgctcgcct acctggtcac cgtgtttgtg ggtatgcaga tcatgaagaa ctttgaacga     300
ttcgaggtca agacgttctc gctcctgtac aacttctgtc tggtctcgct gagcgcctac     360
atgtgcggtg gcattctgta cgaggctttt caggccaact atggactgtt tgagaacgct     420
gccgatcaca ccttcaaggg tctccctatg gctaagatga tctggctctt ctacttctcc     480
aagctgatgg agtttgtcga caccatgatc atggtcctca aaagaacaa ccgacagatt     540 tcctttctgc acgtgtacca ccactcttcc atcttcacca tctggtggct ggtcaccttc     600
gttgctccca acggtgaagc ctacttctct gctgccctga actcgttcat ccatgttatc     660
atgtacggct actactttct gtctgccctg ggcttcaagc aggtgtcgct gatcaagttc     720
tacatcactc gatcccagat gacccagttc tgcatgttgt ctgtccagtc ttcctgggac     780
atgtacgcca tgaaggtcct tggccgacct ggatacccct tcttcctgac cgctctgctc     840
```

```
tggttctaca tgtggaccat gctcggtctc ttctacaact tttaccgacg aaacgccaag    900
ctcgccaagc aggccaaggc tgacgctgcc aaggagaagg ccagaaagct ccagtaa       957
```

<210> SEQ ID NO 28
<211> LENGTH: 318
<212> TYPE: PRT
<213> ORGANISM: Artificial sequence
<220> FEATURE:
<223> OTHER INFORMATION: clone 077-3.1b-B1

<400> SEQUENCE: 28

```
Met Glu Ser Ile Val Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Met Leu
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Met Val Leu Arg Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Leu Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Arg Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 29
<211> LENGTH: 957
<212> TYPE: DNA
<213> ORGANISM: Artificial sequence
<220> FEATURE:
<223> OTHER INFORMATION: clone 078-3.1b-B4 from KS383

<400> SEQUENCE: 29

```
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcatgctt     240
gtgctcgcct acctggtcac cgtgtttgtg ggtatgcaga tcatgaagaa ctttgaacga     300
ttcgaggtca agacgttctc gctcctgtac aacttctgtc tggtctcgct gagcgcctac     360
atgtgcggtg gcattctgta cgaggctttt caggccaact atggactgtt tgagaacgct     420
gccgatcaca ccttcaaggg tctccctatg gctaagatga tctggctctt ctacttctcc     480
aagctgatgg agtttgtcga caccatgatc atggtcctca aaagaacaa ccgacagatt     540
tcctttctgc acgtgtacca ccactcttcc atcttcacca tctggtggct ggtcaccttc     600
gttgctccca acggtgaagc ctggttctct gctgccctga actcgttcat ccatgttatc     660
atgtacggct actactttct gtctgccctg ggcttcaagc aggtgtcgct gatcaagttc     720
tacctgactc gatcccagat gacccagttc tgcatgttgt ctgtccagtc ttcctgggac     780
atgtacgcca tgaaggtcct tggccgacct ggatacccct tcttcctgac cgctctgctc     840
tggttctaca tgtggaccat gctcggtctc ttctacaact tttaccgacg aaacgccaag     900
ctcgccaagc aggccaaggc tgacgctgcc aaggagaagg ccagaaagct ccagtaa       957
```

<210> SEQ ID NO 30
<211> LENGTH: 318
<212> TYPE: PRT
<213> ORGANISM: Artificial sequence
<220> FEATURE:
<223> OTHER INFORMATION: clone 078-3.1b-B4

<400> SEQUENCE: 30

```
Met Glu Ser Ile Val Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Met Leu
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Phe Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Leu Met Glu Phe Val Asp Thr Met Ile Met Val Leu Lys Lys Asn
                165                 170                 175
```

```
Asn Arg Gln Ile Ser Phe Leu His Val Tyr His Ser Ser Ile Phe
            180                 185                 190

Thr Ile Trp Trp Leu Val Thr Phe Val Ala Pro Asn Gly Glu Ala Trp
        195                 200                 205

Phe Ser Ala Ala Leu Asn Ser Phe Ile His Val Ile Met Tyr Gly Tyr
210                 215                 220

Tyr Phe Leu Ser Ala Leu Gly Phe Lys Gln Val Ser Leu Ile Lys Phe
225                 230                 235                 240

Tyr Leu Thr Arg Ser Gln Met Thr Gln Phe Cys Met Leu Ser Val Gln
            245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Arg Asn Ala Lys Leu Ala Lys Gln
        290                 295                 300

Ala Lys Ala Asp Ala Ala Lys Glu Lys Ala Arg Lys Leu Gln
305                 310                 315

<210> SEQ ID NO 31
<211> LENGTH: 7783
<212> TYPE: DNA
<213> ORGANISM: Artificial sequence
<220> FEATURE:
<223> OTHER INFORMATION: pY115

<400> SEQUENCE: 31
catggctctg gccaacgacg ctggcgagcg aatctgggct gccgtcaccg atcccgaaat      60
cctcattggc accttctcct acctgctcct gaagcctctc ctgcgaaact ctggtctcgt     120
ggacgagaag aaaggagcct accgaacctc catgatctgg tacaacgtcc tcctggctct     180
cttctctgcc ctgtccttct acgtgactgc caccgctctc ggctgggact acggtactgg     240
agcctggctg cgaagacaga ccggtgatac tccccagcct ctctttcagt gtccctctcc     300
tgtctgggac tccaagctgt tcacctggac tgccaaggcc ttctactatt ctaagtacgt     360
ggagtacctc gacaccgctt ggctggtcct caagggcaag cgagtgtcct ttctgcaggc     420
cttccatcac tttggagctc cctgggacgt ctacctcggc attgactgc acaacgaggg      480
tgtgtggatc ttcatgttct ttaactcgtt cattcacacc atcatgtaca cctactatgg     540
actgactgcc gctggctaca gttcaaggc caagcctctg atcactgcca tgcagatttg      600
ccagttcgtc ggtggctttc tcctggtctg ggactacatc aacgttccct gcttcaactc     660
tgacaagggc aagctgttct cctgggcttt caactacgcc tacgtcggat ctgtctttct     720
cctgttctgt cacttctttt accaggacaa cctggccacc aagaaatccg ctaaggctgg     780
taagcagctt tagcggccgc aagtgtggat ggggaagtga gtgcccggtt ctgtgtgcac     840
aattggcaat ccaagatgga tggattcaac acagggatat agcgagctac gtggtggtgc     900
gaggatatag caacggatat ttatgtttga cacttgagaa tgtacgatac aagcactgtc     960
caagtacaat actaaacata ctgtacatac tcatactcgt acccgggcaa cggtttcact    1020
tgagtgcagt ggctagtgct cttactcgta cagtgtgcaa tactgcgtat catagtcttt    1080
gatgtatatc gtattcattc atgttagttg cgtacgagcc ggaagcataa agtgtaaagc    1140
ctggggtgcc taatgagtga gctaactcac attaattgcg ttgcgctcac tgcccgcttt    1200
ccagtcggga aacctgtcgt gccagctgca ttaatgaatc ggccaacgcg cggggagagg    1260
cggtttgcgt attgggcgct cttccgcttc ctcgctcact gactcgctgc gctcggtcgt    1320
```

```
tcggctgcgg cgagcggtat cagctcactc aaaggcggta atacggttat ccacagaatc   1380 agggataac  gcaggaaaga acatgtgagc aaaaggccag caaaaggcca ggaaccgtaa    1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag tcgttcgct  ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gttttttttgt ttgcaagcag cagattacgc gcagaaaaaa  2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta agtatatat  gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg agggcttac  catctggccc   2340 cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaatagggggt  3180 tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctcccttag ggttccgatt tagtgcttta cggcacctcg accccaaaaa    3420
acttgattag ggtgatggtt cacgtagtgg gccatcgccc tgatagacgg ttttcgccc    3480 tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
```

```
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct aaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttccttgttat ataatccttt tgtttattac   4800
atgggctgga tacataaagg tattttgatt taatttttttg cttaaattca atccccctc    4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgttttt tttgttttt ttttttctaa tgattcatta ccgctatgta tacctacttg     5160
tacttgtagt aagccggggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
actcgccagt ggccagagag cccttgcaag acagctcggc cagcatgagc agacctctgg   5940
ccagcttctc gttgggagag gggactagga actccttgta ctgggagttc tcgtagtcag   6000
agacgtcctc cttcttctgt tcagagacag tttcctcggc accagctcgc aggccagcaa   6060
tgattccggt tccgggtaca ccgtgggcgt tggtgatatc ggaccactcg gcgattcggt   6120
```

| | |
|---|---|
| gacaccggta ctggtgcttg acagtgttgc caatatctgc gaactttctg tcctcgaaca | 6180 |
| ggaagaaacc gtgcttaaga gcaagttcct tgaggggag cacagtgccg gcgtaggtga | 6240 |
| agtcgtcaat gatgtcgata tgggttttga tcatgcacac ataaggtccg accttatcgg | 6300 |
| caagctcaat gagctccttg gtggtggtaa catccagaga agcacacagg ttggttttct | 6360 |
| tggctgccac gagcttgagc actcgagcgg caaaggcgga cttgtggacg ttagctcgag | 6420 |
| cttcgtagga gggcattttg gtggtgaaga ggagactgaa ataaatttag tctgcagaac | 6480 |
| tttttatcgg aaccttatct ggggcagtga agtatatgtt atggtaatag ttacgagtta | 6540 |
| gttgaactta tagatagact ggactatacg gctatcggtc caaattagaa agaacgtcaa | 6600 |
| tggctctctg ggcgtcgcct ttgccgacaa aaatgtgatc atgatgaaag ccagcaatga | 6660 |
| cgttgcagct gatattgttg tcggccaacc gcgccgaaaa cgcagctgtc agacccacag | 6720 |
| cctccaacga agaatgtatc gtcaaagtga tccaagcaca ctcatagttg gagtcgtact | 6780 |
| ccaaaggcgg caatgacgag tcagacagat actcgtcgac gtttaaacag tgtacgcaga | 6840 |
| tctactatag aggaacattt aaattgcccc ggagaagacg gccaggccgc ctagatgaca | 6900 |
| aattcaacaa ctcacagctg actttctgcc attgccacta ggggggggcc tttttatatg | 6960 |
| gccaagccaa gctctccacg tcggttgggc tgcacccaac aataaatggg tagggttgca | 7020 |
| ccaacaaagg gatgggatgg ggggtagaag atacagagat aacggggctc aatggcacaa | 7080 |
| ataagaacga atactgccat taagactcgt gatccagcga ctgacaccat tgcatcatct | 7140 |
| aagggcctca aaactacctc ggaactgctg cgctgatctg gacaccacag aggttccgag | 7200 |
| cactttaggt tgcaccaaat gtcccaccag gtgcaggcag aaaacgctgg aacagcgtgt | 7260 |
| acagtttgtc ttaacaaaaa gtgagggcgc tgaggtcgag cagggtggtg tgacttgtta | 7320 |
| tagcctttag agctgcgaaa gcgcgtatgg atttggctca tcaggccaga ttgagggtct | 7380 |
| gtggacacat gtcatgttag tgtacttcaa tcgcccctg gatatagccc cgacaatagg | 7440 |
| ccgtggcctc atttttttgc cttccgcaca tttccattgc tcgatacca caccttgctt | 7500 |
| ctcctgcact tgccaacctt aatactggtt tacattgacc aacatcttac aagcgggggg | 7560 |
| cttgtctagg gtatatataa acagtggctc tcccaatcgg ttgccagtct cttttttcct | 7620 |
| ttctttcccc acagattcga aatctaaact acacatcaca gaattccgag ccgtgagtat | 7680 |
| ccacgacaag atcagtgtcg agacgacgcg ttttgtgtaa tgacacaatc cgaaagtcgc | 7740 |
| tagcaacaca cactctctac acaaactaac ccagctctgg tac | 7783 |

<210> SEQ ID NO 32
<211> LENGTH: 792
<212> TYPE: DNA
<213> ORGANISM: Isochrysis galbana
<220> FEATURE:
<221> NAME/KEY: misc_feature
<222> LOCATION: (1)..(792)
<223> OTHER INFORMATION: IgD9ES

<400> SEQUENCE: 32

| | |
|---|---|
| atggctctgg ccaacgacgc tggcgagcga atctgggctg ccgtcaccga tcccgaaatc | 60 |
| ctcattggca ccttctccta cctgctcctg aagcctctcc tgcgaaactc tggtctcgtg | 120 |
| gacgagaaga aaggagccta ccgaacctcc atgatctggt acaacgtcct cctggctctc | 180 |
| ttctctgccc tgtccttcta cgtgactgcc accgctctcg gctgggacta cggtactgga | 240 |
| gcctggctgc gaagacagac cggtgatact ccccagcctc tctttcagtg tcctctcct | 300 |
| gtctgggact ccaagctgtt cacctggact gccaaggcct tctactattc taagtacgtg | 360 |

```
gagtacctcg acaccgcttg gctggtcctc aagggcaagc gagtgtcctt tctgcaggcc    420
ttccatcact ttggagctcc ctgggacgtc tacctcggca ttcgactgca caacgagggt    480
gtgtggatct tcatgttctt taactcgttc attcacacca tcatgtacac ctactatgga    540
ctgactgccg ctggctacaa gttcaaggcc aagcctctga tcactgccat gcagatttgc    600
cagttcgtcg gtggctttct cctggtctgg gactacatca cgttccctg cttcaactct     660 gacaagggca agctgttctc ctgggctttc aactacgcct acgtcggatc tgtctttctc    720
ctgttctgtc acttctttta ccaggacaac ctggccacca agaaatccgc taaggctggt    780
aagcagcttt ag                                                        792

<210> SEQ ID NO 33
<211> LENGTH: 6619
<212> TYPE: DNA
<213> ORGANISM: Artificial sequence
<220> FEATURE:
<223> OTHER INFORMATION: pKUNF-KEA_HD

<400> SEQUENCE: 33
tttgaatcga atcgatgagc taaaatgaa cccgagtata tctcataaaa ttctcggtga      60
gaggtctgtg actgtcagta caaggtgcct tcattatgcc ctcaacctta ccatacctca    120
ctgaatgtag tgtacctcta aaatgaaat acagtgccaa aagccaaggc actgagctcg     180
tctaacggac ttgatataca accaattaaa acaaatgaaa agaaatacag ttctttgtat    240
catttgtaac aattaccctg tacaaactaa ggtattgaaa tcccacaata ttcccaaagt    300
ccaccccttt ccaaattgtc atgcctacaa ctcatatacc aagcactaac ctaccgttta    360
aacagtgtac gcagatctac tatagaggaa catttaaatt gccccggaga agacggccag    420
gccgcctaga tgacaaattc aacaactcac agctgacttt ctgccattgc cactaggggg    480
gggccttttt atatggccaa gccaagctct ccacgtcggt tgggctgcac ccaacaataa    540
atgggtaggg ttgcaccaac aaagggatgg gatggggggt agaagatacg aggataacgg    600
ggctcaatgg cacaaataag aacgaatact gccattaaga ctcgtgatcc agcgactgac    660
accattgcat catctaaggg cctcaaaact acctcggaac tgctgcgctg atctggacac    720
cacagaggtt ccgagcactt taggttgcac caaatgtccc accaggtgca ggcagaaaac    780
gctggaacag cgtgtacagt ttgtcttaac aaaaagtgag ggcgctgagg tcgagcaggg    840
tggtgtgact tgtttatagcc tttagagctg cgaaagcgcg tatggatttg gctcatcagg    900
ccagattgag ggtctgtgga cacatgtcat gttagtgtac ttcaatcgcc ccctgggatat   960 agccccgaca ataggccgtg gcctcatttt tttgccttcc gcacatttcc attgctcggt   1020
acccacacct tgcttctcct gcacttgcca accttaatac tggtttacat tgaccaacat   1080
cttacaagcg gggggcttgt ctagggtata tataaacagt ggctctccca atcggttgcc   1140
agtctctttt ttccttttctt tccccacaga ttcgaaatct aaactacaca tcacagaatt   1200
ccgagccgtg agtatccacg acaagatcag tgtcgagacg acgcgttttg tgtaatgaca   1260
caatccgaaa gtcgctagca acacacactc tctacacaaa ctaacccagc tctggtacca   1320
tggagtccat tgctcccttc ctgccctcca agatgcctca ggacctgttc atggacctcg   1380
ccagcgctat cggtgtccga gctgctccct acgtcgatcc cctggaggct gcctggttg    1440 cccaggccga gaagtacatt cccaccattg tccatcacac tcgaggcttc ctggttgccg   1500
tggagtctcc cctggctcga gagctgcctc tgatgaaccc cttccacgtg ctcctgatcg   1560
tgctcgccta cctggtcacc gtgtttgtgg gtatgcagat catgaagaac tttgaacgat   1620
```

```
tcgaggtcaa gaccttctcc ctcctgcaca acttctgtct ggtctccatc tccgcctaca  1680
tgtgcggtgg catcctgtac gaggcttatc aggccaacta tggactgttt gagaacgctg  1740
ccgatcacac cttcaagggt ctccctatgg ctaagatgat ctggctcttc tacttctcca  1800
agatcatgga gtttgtcgac accatgatca tggtcctcaa gaagaacaac cgacagattt  1860
cctttctgca cgtgtaccac cactcttcca tcttcaccat ctggtggctg gtcaccttcg  1920
ttgctcccaa cggtgaagcc tacttctctg ctgccctgaa ctccttcatc cacgtcatca  1980
tgtacggcta ctactttctg tctgccctgg gcttcaagca ggtgtcgttc atcaagttct  2040
acatcactcg atcccagatg acccagttct gcatgatgtc tgtccagtct tcctgggaca  2100
tgtacgccat gaaggtcctt ggccgacctg gataccccct cttcatcacc gctctgctct  2160
ggttctacat gtggaccatg ctcggtctct tctacaactt ttaccgaaag aacgccaagc  2220
tcgccaagca ggccaaggct gacgctgcca aggagaaggc cagaaagctc cagtaagcgg  2280
ccgcaagtgt ggatggggaa gtgagtgccc ggttctgtgt gcacaattgg caatccaaga  2340
tggatggatt caacacaggg atatagcgag ctacgtggtg gtgcgaggat atagcaacgg  2400
atatttatgt ttgacacttg agaatgtacg atacaagcac tgtccaagta caatactaaa  2460
catactgtac atactcatac tcgtacccgg gcaacggttt cacttgagtg cagtggctag  2520
tgctcttact cgtacagtgt gcaatactgc gtatcatagt ctttgatgta tatcgtattc  2580
attcatgtta gttgcgtacg aagtcgtcaa tgatgtcgat atgggttttg atcatgcaca  2640
cataaggtcc gaccttatcg gcaagctcaa tgagctcctt ggtggtggta acatccagag  2700
aagcacacag gttggttttc ttggctgcca cgagcttgag cactcgagcg gcaaaggcgg  2760
acttgtggac gttagctcga gcttcgtagg agggcatttt ggtggtgaag aggagactga  2820
aataaattta gtctgcagaa cttttttatcg gaaccttatc tggggcagtg aagtatatgt  2880
tatggtaata gttacgagtt agttgaactt atagatagac tggactatac ggctatcggt  2940
ccaaattaga agaacgtca atggctctct gggcgtcgcc tttgccgaca aaaatgtgat  3000
catgatgaaa gccagcaatg acgttgcagc tgatattgtt gtcggccaac cgcgccgaaa  3060
acgcagctgt cagacccaca gcctccaacg aagaatgtat cgtcaaagtg atccaagcac  3120
actcatagtt ggagtcgtac tccaaaggcg gcaatgacga gtcagacaga tactcgtcga  3180
ccttttcctt gggaaccacc accgtcagcc cttctgactc acgtattgta gccaccgaca  3240
caggcaacag tccgtggata gcagaatatg tcttgtcggt ccatttctca ccaacttttag  3300
gcgtcaagtg aatgttgcag aagaagtatg tgccttcatt gagaatcggt gttgctgatt  3360
tcaataaagt cttgagatca gtttggcgcg ccagctgcat taatgaatcg gccaacgcgc  3420
ggggagaggc ggtttgcgta ttgggcgctc ttccgcttcc tcgctcactg actcgctgcg  3480
ctcggtcgtt cggctgcggc gagcggtatc agctcactca aaggcggtaa tacggttatc  3540
cacagaatca ggggataacg caggaaagaa catgtgagca aaaggccagc aaaaggccag  3600
gaaccgtaaa aaggccgcgt tgctggcgtt tttccatagg ctccgccccc ctgacgagca  3660
tcacaaaaat cgacgctcaa gtcagaggtg gcgaaacccg acaggactat aaagatacca  3720
ggcgtttccc cctggaagct ccctcgtgcg ctctcctgtt ccgaccctgc cgcttaccgg  3780
atacctgtcc gcctttctcc cttcgggaag cgtggcgctt tctcatagct cacgctgtag  3840
gtatctcagt tcggtgtagg tcgttcgctc caagctgggc tgtgtgcacg aaccccccgt  3900
tcagcccgac cgctgcgcct tatccggtaa ctatcgtctt gagtccaacc cggtaagaca  3960
cgacttatcg ccactggcag cagccactgg taacaggatt agcagagcga ggtatgtagg  4020
```

```
cggtgctaca gagttcttga agtggtggcc taactacggc tacactagaa gaacagtatt   4080
tggtatctgc gctctgctga agccagttac cttcggaaaa agagttggta gctcttgatc   4140
cggcaaacaa accaccgctg gtagcggtgg ttttttgttt tgcaagcagc agattacgcg   4200
cagaaaaaaa ggatctcaag aagatccttt gatcttttct acggggtctg acgctcagtg   4260
gaacgaaaac tcacgttaag ggattttggt catgagatta tcaaaaagga tcttcaccta   4320
gatccttta aattaaaaat gaagttttaa atcaatctaa agtatatatg agtaaacttg   4380
gtctgacagt taccaatgct taatcagtga ggcacctatc tcagcgatct gtctatttcg   4440
ttcatccata gttgcctgac tccccgtcgt gtagataact acgatacggg agggcttacc   4500
atctggcccc agtgctgcaa tgataccgcg agacccacgc tcaccggctc cagatttatc   4560
agcaataaac cagccagccg gaagggccga gcgcagaagt ggtcctgcaa ctttatccgc   4620
ctccatccag tctattaatt gttgccggga agctagagta agtagttcgc cagttaatag   4680
tttgcgcaac gttgttgcca ttgctacagg catcgtggtg tcacgctcgt cgtttggtat   4740
ggcttcattc agctccggtt cccaacgatc aaggcgagtt acatgatccc ccatgttgtg   4800
caaaaaagcg gttagctcct tcggtcctcc gatcgttgtc agaagtaagt tggccgcagt   4860
gttatcactc atggttatgg cagcactgca taattctctt actgtcatgc catccgtaag   4920
atgcttttct gtgactggtg agtactcaac caagtcattc tgagaatagt gtatgcggcg   4980
accgagttgc tcttgcccgg cgtcaatacg ggataatacc gcgccacata gcagaacttt   5040
aaaagtgctc atcattggaa aacgttcttc ggggcgaaaa ctctcaagga tcttaccgct   5100
gttgagatcc agttcgatgt aacccactcg tgcacccaac tgatcttcag catcttttac   5160
tttcaccagc gtttctgggt gagcaaaaac aggaaggcaa aatgccgcaa aaaagggaat   5220
aagggcgaca cggaaatgtt gaatactcat actcttcctt tttcaatatt attgaagcat   5280
ttatcagggt tattgtctca tgagcggata catatttgaa tgtatttaga aaaataaaca   5340
aataggggtt ccgcgcacat ttccccgaaa agtgccacct gatgcggtgt gaaataccgc   5400
acagatgcgt aaggagaaaa taccgcatca ggaaattgta agcgttaata ttttgttaaa   5460
attcgcgtta aatttttgtt aaatcagctc attttttaac caataggccg aaatcggcaa   5520
aatcccttat aaatcaaaag aatagaccga gatagggttg agtgttgttc cagtttggaa   5580
caagagtcca ctattaaaga acgtggactc caacgtcaaa gggcgaaaaa ccgtctatca   5640
gggcgatggc ccactacgtg aaccatcacc ctaatcaagt tttttggggt cgaggtgccg   5700
taaagcacta aatcggaacc ctaaagggag cccccgattt agagcttgac ggggaaagcc   5760
ggcgaacgtg gcgagaaagg aagggaagaa agcgaaagga gcgggcgcta gggcgctggc   5820
aagtgtagcg gtcacgctgc gcgtaaccac cacacccgcc gcgcttaatg cgccgctaca   5880
gggcgcgtcc attcgccatt caggctgcgc aactgttggg aagggcgatc ggtgcgggcc   5940
tcttcgctat tacgccagct ggcgaaaggg ggatgtgctg caaggcgatt aagttgggta   6000
acgccagggt tttcccagtc acgacgttgt aaaacgacgg ccagtgaatt gtaatacgac   6060
tcactatagg gcgaattggg cccgacgtcg catgcagtgg tggtattgtg actggggatg   6120
tagttgagaa taagtcatac acaagtcagc tttcttcgag cctcatataa gtataagtag   6180
ttcaacgtat tagcactgta cccagcatct ccgtatcgag aaacacaaca acatgcccca   6240
ttggacagat catgcggata cacaggttgt gcagtatcat acatactcga tcagacaggt   6300
cgtctgacca tcatacaagc tgaacaagcg ctccatactt gcacgctctc tatatacaca   6360
gttaaattac atatccatag tctaacctct aacagttaat cttctggtaa gcctcccagc   6420
```

```
cagccttctg gtatcgcttg gcctcctcaa taggatctcg gttctggccg tacagacctc    6480
ggccgacaat tatgatatcc gttccggtag acatgacatc ctcaacagtt cggtactgct    6540
gtccgagagc gtctcccttg tcgtcaagac ccaccccggg ggtcagaata agccagtcct    6600
cagagtcgcc cttaattaa                                                 6619

<210> SEQ ID NO 34
<211> LENGTH: 7949
<212> TYPE: DNA
<213> ORGANISM: Artificial sequence
<220> FEATURE:
<223> OTHER INFORMATION: plasmid pY116

<400> SEQUENCE: 34
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac ccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaaggatct tcacctagat cctttttaaat taaaaatgaa    1380 gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt cgcaacgtt gttgccattg    1740 ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
```

```
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt aatagtgga ctcttgttcc aaactggaac aacactcaac cctatctcgg    2760
tctattcttt tgatttataa gggatttttgc cgatttcggc ctattggtta aaaaatgagc    2820
tgatttaaca aaaatttaac gcgaattta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattcatgg gctggataca    4020 taaaggtatt ttgatttaat ttttgctta aattcaatcc ccctcgttc agtgtcaact    4080 gtaatggtag gaaattacca tacttttgaa gaagcaaaaa aaatgaaaga aaaaaaaaat    4140
cgtatttcca ggttagacgt tccgcagaat ctagaatgcg gtatgcgta cattgttctt    4200 cgaacgtaaa agttgcgctc cctgagatat tgtacatttt tgcttttaca agtacaagta    4260
```

```
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct tcttcgagc    4560 ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgt tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
```

| | |
|---|---|
| ttttgccttc cgcacatttc cattgctcga tacccacacc ttgcttctcc tgcacttgcc | 6720 |
| aaccttaata ctggtttaca ttgaccaaca tcttacaagc ggggggcttg tctagggtat | 6780 |
| atataaacag tggctctccc aatcggttgc cagtctcttt tttcctttct ttccccacag | 6840 |
| attcgaaatc taaactacac atcacagaat tccgagccgt gagtatccac gacaagatca | 6900 |
| gtgtcgagac gacgcgtttt gtgtaatgac acaatccgaa agtcgctagc aacacacact | 6960 |
| ctctacacaa actaacccag ctctggtacc atggagtcca ttgctcccctt cctgccctcc | 7020 |
| aagatgcctc aggacctgtt catggacctc gccagcgcta tcggtgtccg agctgctccc | 7080 |
| tacgtcgatc ccctggaggc tgccctggtt gcccaggccg agaagtacat tcccaccatt | 7140 |
| gtccatcaca ctcgaggctt cctggttgcc gtggagtctc ccctggctcg agagctgcct | 7200 |
| ctgatgaacc ccttccacgt gctcctgatc gtgctcgcct acctggtcac cgtgtttgtg | 7260 |
| ggtatgcaga tcatgaagaa ctttgaacga ttcgaggtca agaccttctc cctcctgcac | 7320 |
| aacttctgtc tggtctccat ctccgcctac atgtgcggtg catcctgta cgaggcttat | 7380 |
| caggccaact atggactgtt tgagaacgct gccgatcaca ccttcaaggg tctccctatg | 7440 |
| gctaagatga tctggctctt ctacttctcc aagatcatgg agtttgtcga caccatgatc | 7500 |
| atggtcctca agaagaacaa ccgacagatt tcctttctgc acgtgtacca ccactcttcc | 7560 |
| atcttccacca tctggtggct ggtcaccttc gttgctccca cggtgaagc ctacttctct | 7620 |
| gctgccctga actccttcat ccacgtcatc atgtacggct actactttct gtctgccctg | 7680 |
| ggcttcaagc aggtgtcgtt catcaagttc tacatcactc gatcccagat gacccagttc | 7740 |
| tgcatgatgt ctgtccagtc ttcctgggac atgtacgcca tgaaggtcct tggccgacct | 7800 |
| ggatacccct tcttcatcac cgctctgctc tggttctaca tgtggaccat gctcggtctc | 7860 |
| ttctacaact tttaccgaaa gaacgccaag ctcgccaagc aggccaaggc tgacgctgcc | 7920 |
| aaggagaagg ccagaaagct ccagtaagc | 7949 |

```
<210> SEQ ID NO 35
<211> LENGTH: 8704
<212> TYPE: DNA
<213> ORGANISM: Artificial sequence
<220> FEATURE:
<223> OTHER INFORMATION: plasmid pBY1

<400> SEQUENCE: 35
```

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgagccggaa gcataaagtg taaagcctgg ggtgcctaat | 360 |
| gagtgagcta actcacatta attgcgttgc gctcactgcc cgctttccag tcgggaaacc | 420 |
| tgtcgtgcca gctgcattaa tgaatcggcc aacgcgcggg gagaggcggt ttgcgtattg | 480 |
| ggcgctcttc cgcttcctcg ctcactgact cgctgcgctc ggtcgttcgg ctgcggcgag | 540 |
| cggtatcagc tcactcaaag gcggtaatac ggttatccac agaatcaggg gataacgcag | 600 |
| gaaagaacat gtgagcaaaa ggccagcaaa aggccaggaa ccgtaaaaag gccgcgttgc | 660 |
| tggcgttttt ccataggctc cgcccccctg acgagcatca caaaaatcga cgctcaagtc | 720 |
| agaggtggcg aaacccgaca ggactataaa gataccaggc gtttccccct ggaagctccc | 780 |

-continued

```
tcgtgcgctc tcctgttccg accctgccgc ttaccggata cctgtccgcc tttctccctt      840
cgggaagcgt ggcgctttct catagctcac gctgtaggta tctcagttcg gtgtaggtcg      900
ttcgctccaa gctgggctgt gtgcacgaac cccccgttca gcccgaccgc tgcgccttat      960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg ggtctgacg ctcagtggaa cgaaaactca cgttaaggga     1320
ttttggtcat gagattatca aaaggatct tcacctagat ccttttaaat taaaaatgaa     1380
gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt gcgcaacgtt gttgccattg     1740
ctacaggcat cgtggtgtca cgctcgtcgt ttggtatggc ttcattcagc tccggttccc     1800
aacgatcaag gcgagttaca tgatcccccca tgttgtgcaa aaaagcggtt agctccttcg     1860
gtcctccgat cgttgtcaga agtaagttgg ccgcagtgtt atcactcatg gttatggcag     1920
cactgcataa ttctcttact gtcatgccat ccgtaagatg cttttctgtg actggtgagt     1980
actcaaccaa gtcattctga aatagtgta tgcggcgacc gagttgctct gcccggcgt     2040 caatacggga taataccgcg ccacatagca gaactttaaa agtgctcatc attggaaaac     2100
gttcttcggg gcgaaaactc tcaaggatct taccgctgtt gagatccagt tcgatgtaac     2160
ccactcgtgc acccaactga tcttcagcat cttttacttt caccagcgtt tctgggtgag     2220
caaaaacagg aaggcaaaat gccgcaaaaa agggaataag ggcgacacgg aaatgttgaa     2280
tactcatact cttcctttt caatattatt gaagcattta tcagggttat tgtctcatga     2340
gcggatacat atttgaatgt atttagaaaa ataaacaaat aggggttccg cgcacatttc     2400
cccgaaaagt gccacctgac gcgccctgta gcggcgcatt aagcgcggcg ggtgtggtgg     2460
ttacgcgcag cgtgaccgct acacttgcca gcgccctagc gcccgctcct ttcgctttct     2520
tcccttcctt tctcgccacg ttcgccggct tccccgtca agctctaaat cgggggctcc     2580
ctttagggtt ccgatttagt gctttacggc acctcgaccc caaaaaactt gattagggtg     2640
atggttcacg tagtgggcca tcgccctgat agacggtttt tcgccctttg acgttggagt     2700
ccacgttctt taatagtgga ctcttgttcc aaactggaac aacactcaac cctatctcgg     2760
tctattcttt tgatttataa gggattttgc cgatttcggc ctattggtta aaaaatgagc     2820
tgatttaaca aaaatttaac gcgaatttta acaaatatt aacgcttaca atttccattc     2880
gccattcagg ctgcgcaact gttgggaagg gcgatcggtg cgggcctctt cgctattacg     2940
ccagctggcg aaagggggat gtgctgcaag gcgattaagt tgggtaacgc cagggttttc     3000
ccagtcacga cgttgtaaaa cgacggccag tgaattgtaa tacgactcac tatagggcga     3060
attgggtacc gggccccccc tcgaggtcga tggtgtcgat aagcttgata tcgaattcat     3120
gtcacacaaa ccgatcttcg cctcaaggaa acctaattct acatccgaga gactgccgag     3180
```

```
atccagtccta cactgattaa ttttcgggcc aataatttaa aaaaatcgtg ttatataata  3240
ttatatgtat tatatatata catcatgatg atactgacag tcatgtccca ttgctaaata  3300
gacagactcc atctgccgcc tccaactgat gttctcaata tttaaggggt catctcgcat  3360
tgtttaataa taaacagact ccatctaccg cctccaaatg atgttctcaa aatatattgt  3420
atgaacttat ttttattact tagtattatt agacaactta cttgctttat gaaaaacact  3480
tcctatttag gaaacaattt ataatggcag ttcgttcatt taacaattta tgtagaataa  3540
atgttataaa tgcgtatggg aaatcttaaa tatggatagc ataaatgata tctgcattgc  3600
ctaattcgaa atcaacagca acgaaaaaaa tcccttgtac aacataaata gtcatcgaga  3660
aatatcaact atcaaagaac agctattcac acgttactat tgagattatt attggacgag  3720
aatcacacac tcaactgtct ttctctcttc tagaaataca ggtacaagta tgtactattc  3780
tcattgttca tacttctagt catttcatcc cacatattcc ttggatttct ctccaatgaa  3840
tgacattcta tcttgcaaat tcaacaatta taataagata taccaaagta gcggtatagt  3900
ggcaatcaaa aagcttctct ggtgtgcttc tcgtatttat ttttattcta atgatccatt  3960
aaaggtatat atttatttct tgttatataa tccttttgtt tattacatgg gctggataca  4020
taaaggtatt ttgatttaat tttttgctta aattcaatcc cccctcgttc agtgtcaact  4080
gtaatggtag gaaattacca tacttttgaa gaagcaaaaa aaatgaaaga aaaaaaaaat  4140
cgtatttcca ggttagacgt tccgcagaat ctagaatgcg gtatgcggta cattgttctt  4200
cgaacgtaaa agttgcgctc cctgagatat tgtacatttt tgcttttaca agtacaagta  4260
catcgtacaa ctatgtacta ctgttgatgc atccacaaca gtttgttttg tttttttttg  4320
tttttttttt ttctaatgat tcattaccgc tatgtatacc tacttgtact tgtagtaagc  4380
cgggttattg gcgttcaatt aatcatagac ttatgaatct gcacggtgtg cgctgcgagt  4440
tacttttagc ttatgcatgc tacttgggtg taatattggg atctgttcgg aaatcaacgg  4500
atgctcaatc gatttcgaca gtaattaatt aagtcataca caagtcagct ttcttcgagc  4560
ctcatataag tataagtagt tcaacgtatt agcactgtac ccagcatctc cgtatcgaga  4620
aacacaacaa catgccccat tggacagatc atgcggatac acaggttgtg cagtatcata  4680
catactcgat cagacaggtc gtctgaccat catacaagct gaacaagcgc tccatacttg  4740
cacgctctct atatacacag ttaaattaca tatccatagt ctaacctcta acagttaatc  4800
ttctggtaag cctcccagcc agccttctgg tatcgcttgg cctcctcaat aggatctcgg  4860
ttctggccgt acagacctcg gccgacaatt atgatatccg ttccggtaga catgacatcc  4920
tcaacagttc ggtactgctg tccgagagcg tctcccttgt cgtcaagacc caccccgggg  4980
gtcagaataa gccagtcctc agagtcgccc ttaggtcggt tctgggcaat gaagccaacc  5040
acaaactcgg ggtcggatcg ggcaagctca atggtctgct tggagtactc gccagtggcc  5100
agagagccct tgcaagacag ctcggccagc atgagcagac ctctggccag cttctcgttg  5160
ggagagggga ctaggaactc cttgtactgg gagttctcgt agtcagagac gtcctccttc  5220
ttctgttcag agacagtttc ctcggcacca gctcgcaggc cagcaatgat tccggttccg  5280
ggtacaccgt gggcgttggt gatatcggac cactcggcga ttcggtgaca ccggtactgg  5340
tgcttgacag tgttgccaat atctgcgaac tttctgtcct cgaacaggaa gaaaccgtgc  5400
ttaagagcaa gttccttgag ggggagcaca gtgccggcgt aggtgaagtc gtcaatgatg  5460
tcgatatggg ttttgatcat gcacacataa ggtccgacct tatcggcaag ctcaatgagc  5520
tccttggtgg tggtaacatc cagagaagca cacaggttgg ttttcttggc tgccacgagc  5580
```

```
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480 caaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atgatcacaa gtttgtacaa aaaagctgaa    7020
cgagaaacgt aaaatgatat aaatatcaat atattaaatt agattttgca taaaaaacag    7080
actacataat actgtaaaac acaacatatc cagtcatatt ggcggccgca ttaggcaccc    7140
caggctttac actttatgct tccggctcgt ataatgtgtg gattttgagt taggatccgt    7200
cgagattttc aggagctaag gaagctaaaa tggagaaaaa aatcactgga tataccaccg    7260
ttgatatatc ccaatggcat cgtaaagaac attttgaggc atttcagtca gttgctcaat    7320
gtacctataa ccagaccgtt cagctggata ttacggcctt tttaaagacc gtaaagaaaa    7380
ataagcacaa gttttatccg gcctttattc acattcttgc ccgcctgatg aatgctcatc    7440
cggaattccg tatggcaatg aaagacggtg agctggtgat atgggatagt gttcaccctt    7500
gttacaccgt tttccatgag caaactgaaa cgttttcatc gctctggagt gaataccacg    7560
acgatttccg gcagtttcta cacatatatt cgcaagatgt ggcgtgttac ggtgaaaacc    7620
tggcctattt ccctaaaggg tttattgaga atatgttttt cgtctcagcc aatccctggg    7680
tgagtttcac cagttttgat ttaaacgtgg ccaatatgga caacttcttc gcccccgttt    7740
tcaccatggg caaatattat acgcaaggcg acaaggtgct gatgccgctg gcgattcagg    7800
ttcatcatgc cgtttgtgat ggcttccatg tcggcagaat gcttaatgaa ttacaacagt    7860
actgcgatga gtggcagggc ggggcgtaaa cgcgtggatc cggcttacta aaagccagat    7920
aacagtatgc gtatttgcgc gctgattttt gcggtataag aatatatact gatatgtata    7980
```

```
cccgaagtat gtcaaaaaga ggtatgctat gaagcagcgt attacagtga cagttgacag    8040
cgacagctat cagttgctca aggcatatat gatgtcaata tctccggtct ggtaagcaca    8100
accatgcaga atgaagcccg tcgtctgcgt gccgaacgct ggaaagcgga aaatcaggaa    8160
gggatggctg aggtcgcccg gtttattgaa atgaacggct cttttgctga cgagaacagg    8220
ggctggtgaa atgcagttta aggtttacac ctataaaaga gagagccgtt atcgtctgtt    8280
tgtggatgta cagagtgata ttattgacac gcccgggcga cggatggtga tcccctggc     8340 cagtgcacgt ctgctgtcag ataaagtctc ccgtgaactt acccggtgg tgcatatcgg     8400 ggatgaaagc tggcgcatga tgaccaccga tatggccagt gtgccggtct ccgttatcgg    8460
ggaagaagtg gctgatctca gccaccgcga aaatgacatc aaaaacgcca ttaacctgat    8520
gttctgggga atataaatgt caggctccct tatacacagc cagtctgcag gtcgaccata    8580
gtgactggat atgttgtgtt ttacagcatt atgtagtctg ttttttatgc aaaatctaat    8640
ttaatatatt gatatttata tcattttacg tttctcgttc agctttcttg tacaaagtgg    8700
tgat                                                                 8704

<210> SEQ ID NO 36
<211> LENGTH: 7949
<212> TYPE: DNA
<213> ORGANISM: Artificial sequence
<220> FEATURE:
<223> OTHER INFORMATION: plasmid 027-2.1b-e9/pY116

<400> SEQUENCE: 36
atggagtcca ttgctcccctt cctgcccctcc aagatgcctc aggacctgtt catggacctc    60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggagtctc ccctggctcg agagctgcct ctgatgaacc ccttccacgt gctcctgatc    240
gtgctcgcct acctggtcac cgtgtttgtg ggtatgcaga tcatgaagaa ctttgaacga    300
ttcgaggtca agacgtattc gctcctgcac aacttctgtc tggtctcgct gagcgcctac    360
atgtgcggtg gcatcctgta cgaggctttc caggccaact atggactgtt tgagaacgct    420
gccgatcaca ccttcaaggg tctccctatg gctaagatga tctggctctt ctacttctcc    480
aagatcatgg agtttgtcga caccatgatc atggtcctca gaagaacaa ccgacagatt    540 tcctttctgc acgtgtacca ccactcttcc atcttcacca tctggtggct ggtcacccttc    600 gttgctccca acggtgaagc ctacttctct gctgccctga actcgttcat ccatgttatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggatacccct tcttcatcgc cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaagcg    960
gccgcaagtg tggatgggga agtgagtgcc cggttctgtg tgcacaattg caatccaag     1020 atggatggat tcaacacagg gatatagcga gctacgtggt ggtgcgagga tatagcaacg    1080
gatatttatg tttgacactt gagaatgtac gatacaagca ctgtccaagt acaatactaa    1140
acatactgta catactcata ctcgtacccg ggcaacggtt tcacttgagt gcagtggcta    1200
gtgctcttac tcgtacagtg tgcaaactg cgtatcatag tctttgatgt atatcgtatt    1260
cattcatgtt agttgcgtac gagccggaag cataaagtgt aaagcctggg gtgcctaatg    1320
```

```
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg tcgttcggc tgcggcgagc    1500 ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620 ggcgttttc cataggctcc gcccccctga cgagcatcac aaaaatcgac gctcaagtca    1680
gaggtggcga acccgacag gactataaag ataccaggcg tttccccctg aagctccct     1740 cgtgcgctct cctgttccga ccctgccgct taccggatac ctgtccgcct ttctcccttc   1800
gggaagcgtg gcgctttctc atagctcacg ctgtaggtat ctcagttcgg tgtaggtcgt   1860
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaaggac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaggat ctcaagaaga    2220 tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacgggaggg cttaccatct ggccccagtg ctgcaatgat   2520
accgcgagac ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatccccat gttgtgcaaa aaagcggtta gctccttcgg    2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
aatacgggat aataccgcgc cacatagcag aactttaaaa gtgctcatca ttggaaaacg   3060
ttcttcgggg cgaaaactct caaggatctt accgctgttg agatccagtt cgatgtaacc   3120
cactcgtgca cccaactgat cttcagcatc ttttactttc accagcgttt ctgggtgagc   3180
aaaaacagga aggcaaaatg ccgcaaaaaa gggaataagg gcgacacgga atgttgaat    3240 actcatactc ttccttttc aatattattg aagcatttat cagggttatt gtctcatgag    3300
cggatacata tttgaatgta tttagaaaaa taaacaaata ggggttccgc gcacatttcc   3360
ccgaaaagtg ccacctgacg cgccctgtag cggcgcatta agcgcggcgg gtgtggtggt   3420
tacgcgcagc gtgaccgcta cacttgccag cgccctagcg cccgctcctt tcgctttctt   3480
cccttccttt ctcgccacgt tcgccggctt tccccgtcaa gctctaaatc ggggctccc    3540 tttagggttc cgatttagtg ctttacggca cctcgacccc aaaaaacttg attagggtga   3600
tggttcacgt agtgggccat cgccctgata cggttttt cgcccttga cgttggagtc     3660 cacgttcttt aatagtggac tcttgttcca aactggaaca acactcaacc ctatctcggt   3720
```

```
ctattcttttt gatttataag ggattttgcc gatttcggcc tattggttaa aaaatgagct    3780
gatttaacaa aaatttaacg cgaattttaa caaaatatta acgcttacaa tttccattcg    3840
ccattcaggc tgcgcaactg ttgggaaggg cgatcggtgc gggcctcttc gctattacgc    3900
cagctggcga aaggggatg tgctgcaagg cgattaagtt gggtaacgcc agggttttcc     3960
cagtcacgac gttgtaaaac gacggccagt gaattgtaat acgactcact ataggcgaa     4020 ttgggtaccg ggccccccct cgaggtcgat ggtgtcgata agcttgatat cgaattcatg    4080
tcacacaaac cgatcttcgc ctcaaggaaa cctaattcta catccgagag actgccgaga    4140
tccagtctac actgattaat tttcgggcca ataatttaaa aaaatcgtgt tatataatat    4200
tatatgtatt atatatatac atcatgatga tactgacagt catgtcccat tgctaaatag    4260
acagactcca tctgccgcct ccaactgatg ttctcaatat ttaaggggtc atctcgcatt    4320
gtttaataat aaacagactc catctaccgc ctccaaatga tgttctcaaa atatattgta    4380
tgaacttatt tttattactt agtattatta gacaacttac ttgctttatg aaaaacactt    4440
cctatttagg aaacaattta taatggcagt tcgttcattt aacaatttat gtagaataaa    4500
tgttataaat gcgtatggga atcttaaat atggatagca taaatgatat ctgcattgcc    4560
taattcgaaa tcaacagcaa cgaaaaaaat cccttgtaca acataaatag tcatcgagaa    4620
atatcaacta tcaagaaca gctattcaca cgttactatt gagattatta ttggacgaga     4680
atcacacact caactgtctt tctctcttct agaaatacag gtacaagtat gtactattct    4740
cattgttcat acttctagtc atttcatccc acatattcct tggatttctc tccaatgaat    4800
gacattctat cttgcaaatt caacaattat aataagatat accaaagtag cggtatagtg    4860
gcaatcaaaa agcttctctg gtgtgcttct cgtatttatt tttattctaa tgatccatta    4920
aaggtatata tttatttctt gttatataat ccttttgttt attacatggg ctggatacat    4980
aaaggtattt tgatttaatt ttttgcttaa attcaatccc ccctcgttca gtgtcaactg    5040
taatggtagg aaattaccat acttttgaag aagcaaaaaa aatgaaagaa aaaaaaaatc    5100
gtatttccag gttagacgtt ccgcagaatc tagaatgcgg tatgcggtac attgttcttc    5160
gaacgtaaaa gttgcgctcc ctgagatatt gtacattttt gcttttacaa gtacaagtac    5220
atcgtacaac tatgtactac tgttgatgca tccacaacag tttgttttgt ttttttttgt    5280 ttttttttt tctaatgatt cattaccgct atgtatacct acttgtactt gtagtaagcc     5340
gggttattgg cgttcaatta atcatagact tatgaatctg cacggtgtgc gctgcgagtt    5400
acttttagct tatgcatgct acttgggtgt aatattggga tctgttcgga aatcaacgga    5460
tgctcaatcg atttcgacag taattaatta agtcatacac aagtcagctt tcttcgagcc    5520
tcatataagt ataagtagtt caacgtatta gcactgtacc cagcatctcc gtatcgagaa    5580
acacaacaac atgccccatt ggacagatca tgcggataca caggttgtgc agtatcatac    5640
atactcgatc agacaggtcg tctgaccatc atacaagctg aacaagcgct ccatacttgc    5700
acgctctcta tatacacagt taaattacat atccatagtc taacctctaa cagttaatct    5760
tctggtaagc ctcccagcca gccttctggt atcgcttggc ctcctcaata ggatctcggt    5820
tctggccgta cagacctcgg ccgacaatta tgatatccgt tccggtagac atgcatcct     5880 caacagttcg gtactgctgt ccgagagcgt ctcccttgtc gtcaagaccc accccggggg    5940
tcagaataag ccagtcctca gagtcgccct taggtcggtt ctgggcaatg aagccaacca    6000
caaactcggg gtcggatcgg gcaagctcaa tggtctgctt ggagtactcg ccagtggcca    6060
gagagccctt gcaagacagc tcggccagca tgagcagacc tctgccagc ttctcgttgg     6120
```

```
gagaggggac taggaactcc ttgtactggg agttctcgta gtcagagacg tcctccttct    6180
tctgttcaga gacagtttcc tcggcaccag ctcgcaggcc agcaatgatt ccggttccgg    6240
gtacaccgtg ggcgttggtg atatcggacc actcggcgat tcggtgacac cggtactggt    6300
gcttgacagt gttgccaata tctgcgaact ttctgtcctc gaacaggaag aaaccgtgct    6360
taagagcaag ttccttgagg gggagcacag tgccggcgta ggtgaagtcg tcaatgatgt    6420
cgatatgggt tttgatcatg cacacataag gtccgacctt atcggcaagc tcaatgagct    6480
ccttggtggt ggtaacatcc agagaagcac acaggttggt tttcttggct gccacgagct    6540
tgagcactcg agcggcaaag gcggacttgt ggacgttagc tcgagcttcg taggagggca    6600
ttttggtggt gaagaggaga ctgaaataaa tttagtctgc agaacttttt atcggaacct    6660
tatctggggc agtgaagtat atgttatggt aatagttacg agttagttga acttatagat    6720
agactggact atacggctat cggtccaaat tagaaagaac gtcaatggct ctctgggcgt    6780
cgcctttgcc gacaaaaatg tgatcatgat gaaagccagc aatgacgttg cagctgatat    6840
tgttgtcggc caaccgcgcc gaaaacgcag ctgtcagacc cacagcctcc aacgaagaat    6900
gtatcgtcaa agtgatccaa gcacactcat agttggagtc gtactccaaa ggcggcaatg    6960
acgagtcaga cagatactcg tcgacgttta acagtgtac gcagatctac tatagaggaa    7020
catttaaatt gccccggaga agacggccag gccgcctaga tgacaaattc aacaactcac    7080
agctgacttt ctgccattgc cactaggggg gggcctttt atatggccaa gccaagctct    7140
ccacgtcggt tgggctgcac ccaacaataa atgggtaggg ttgcaccaac aaagggatgg    7200 gatgggggt agaagatacg aggataacgg ggctcaatgg cacaaataag aacgaatact    7260
gccattaaga ctcgtgatcc agcgactgac accattgcat catctaaggg cctcaaaact    7320
acctcggaac tgctgcgctg atctggacac cacagaggtt ccgagcactt taggttgcac    7380
caaatgtccc accaggtgca ggcagaaaac gctggaacag cgtgtacagt ttgtcttaac    7440
aaaaagtgag ggcgctgagg tcgagcaggg tggtgtgact tgttatagcc tttagagctg    7500
cgaaagcgcg tatggatttg gctcatcagg ccagattgag ggtctgtgga cacatgtcat    7560
gttagtgtac ttcaatcgcc ccctggatat agccccgaca ataggccgtg gcctcatttt    7620
tttgccttcc gcacatttcc attgctcgat acccacacct tgcttctcct gcacttgcca    7680
accttaatac tggtttacat tgaccaacat cttacaagcg gggggcttgt ctagggtata    7740
tataaacagt ggctctccca atcggttgcc agtctctttt ttcctttctt tccccacaga    7800
ttcgaaatct aaactacaca tcacagaatt ccgagccgtg agtatccacg acaagatcag    7860
tgtcgagacg acgcgttttg tgtaatgaca caatccgaaa gtcgctagca acacacactc    7920
tctacacaaa ctaacccagc tctggtacc                                      7949

<210> SEQ ID NO 37
<211> LENGTH: 7949
<212> TYPE: DNA
<213> ORGANISM: Artificial sequence
<220> FEATURE:
<223> OTHER INFORMATION: plasmid 077-3.1b-b1/pY116

<400> SEQUENCE: 37
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
```

```
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc   2580
ctttagggtt ccgatttagt gctttacggc acctcgaccc caaaaaactt gattagggtg   2640
```

```
atggttcacg tagtgggcca tcgccctgat agacggtttt tcgcccttttg acgttggagt    2700
ccacgttctt taatagtgga ctcttgttcc aaactggaac aacactcaac cctatctcgg    2760
tctattctttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tcctttttgtt tattacatgg gctggataca    4020
taaaggtatt ttgatttaat ttttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttttg    4320
ttttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccccgggg    4980
gtcagaataa gccagtcctc agagtcgccc ttaggtcggt tctgggcaat gaagccaacc    5040
```

```
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240 ggatggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc gggggcttg tctagggtat   6780 atataaacag tggctctccc aatcggttgc cagtctcttt tttccttct ttccccacag   6840 attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggagtcca ttgttccctt cctgccctcc   7020
aagatgcctc aggacctgtt catggacctc gccagcgcta tcggtgtccg agctgctccc   7080
tacgtcgatc ccctggaggc tgccctggtt gcccaggccg agaagtacat tcccaccatt   7140
gtccatcaca ctcgaggctt cctggttgcc gtggattctc ccctggctcg agagctgcct   7200
ctgatgaacc ccttccacgt gctcatgctt gtgctcgcct acctggtcac cgtgtttgtg   7260
ggtatgcaga tcatgaagaa ctttgaacga ttcgaggtca agacgttctc gctcctgtac   7320
aacttctgtc tggtctcgct gagcgcctac atgtgcggtg cattctgta cgaggctttt   7380 caggccaact atggactgtt tgagaacgct gccgatcaca ccttcaaggg tctccctatg   7440
```

```
gctaagatga tctggctctt ctacttctcc aagctgatgg agtttgtcga caccatgatc    7500
atggtcctca gaaagaacaa ccgacagatt tcctttctgc acgtgtacca ccactcttcc    7560
atcttcacca tctggtggct ggtcaccttc gttgctccca acggtgaagc ctacttctct    7620
gctgccctga actcgttcat ccatgttatc atgtacggct actactttct gtctgccctg    7680
ggcttcaagc aggtgtcgct gatcaagttc tacatcactc gatcccagat gacccagttc    7740
tgcatgttgt ctgtccagtc ttcctgggac atgtacgcca tgaaggtcct tggccgacct    7800
ggataccccT tcttcctgac cgctctgctc tggttctaca tgtggaccat gctcggtctc    7860
ttctacaact tttaccgacg aaacgccaag ctcgccaagc aggccaaggc tgacgctgcc    7920
aaggagaagg ccagaaagct ccagtaagc                                       7949
```

<210> SEQ ID NO 38
<211> LENGTH: 7949
<212> TYPE: DNA
<213> ORGANISM: Artificial sequence
<220> FEATURE:
<223> OTHER INFORMATION: plasmid 046-3.1b-c2/pY116

<400> SEQUENCE: 38

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg ggtctgacgc tcagtggaa cgaaaactca cgttaaggga    1320
ttttggtcat gagattatca aaaaggatct tcacctagat ccttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
```

```
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaagcggtt agctccttcg    1860 gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga aatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat ctttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgcctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaatgagc    2820 tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggcccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat    3360 tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
```

```
aaaggtatat atttatttct tgttatataa tccttttgtt tattacatgg gctggataca  4020
taaaggtatt ttgatttaat ttttttgctta aattcaatcc ccctcgttc agtgtcaact  4080 gtaatggtag gaaattacca tacttttgaa gaagcaaaaa aaatgaaaga aaaaaaaaat  4140
cgtatttcca ggttagacgt tccgcagaat ctagaatgcg gtatgcggta cattgttctt  4200
cgaacgtaaa agttgcgctc cctgagatat tgtacatttt tgcttttaca agtacaagta  4260
catcgtacaa ctatgtacta ctgttgatgc atccacaaca gtttgttttg tttttttttg  4320
tttttttttt ttctaatgat tcattaccgc tatgtatacc tacttgtact tgtagtaagc  4380
cgggttattg gcgttcaatt aatcatagac ttatgaatct gcacggtgtg cgctgcgagt  4440
tacttttagc ttatgcatgc tacttgggtg taatattggg atctgttcgg aaatcaacgg  4500
atgctcaatc gatttcgaca gtaattaatt aagtcataca caagtcagct ttcttcgagc  4560
ctcatataag tataagtagt tcaacgtatt agcactgtac ccagcatctc cgtatcgaga  4620
aacacaacaa catgccccat tggacagatc atgcggatac acaggttgtg cagtatcata  4680
catactcgat cagacaggtc gtctgaccat catacaagct gaacaagcgc tccatacttg  4740
cacgctctct atatacacag ttaaattaca tatccatagt ctaacctcta acagttaatc  4800
ttctggtaag cctcccagcc agccttctgg tatcgcttgg cctcctcaat aggatctcgg  4860
ttctggccgt acagacctcg gccgacaatt atgatatccg ttccggtaga catgacatcc  4920
tcaacagttc ggtactgctg tccgagagcg tctcccttgt cgtcaagacc caccccgggg  4980
gtcagaataa gccagtcctc agagtcgccc ttaggtcggt tctgggcaat gaagccaacc  5040
acaaactcgg ggtcggatcg ggcaagctca atggtctgct tggagtactc gccagtggcc  5100
agagagccct tgcaagacag ctcggccagc atgagcagac ctctggccag cttctcgttg  5160
ggagagggga ctaggaactc cttgtactgg gagttctcgt agtcagagac gtcctccttc  5220
ttctgttcag agacagtttc ctcggcacca gctcgcaggc cagcaatgat tccggttccg  5280
ggtacaccgt gggcgttggt gatatcggac cactcggcga ttcggtgaca ccggtactgg  5340
tgcttgacag tgttgccaat atctgcgaac tttctgtcct cgaacaggaa gaaaccgtgc  5400
ttaagagcaa gttccttgag ggggagcaca gtgccggcgt aggtgaagtc gtcaatgatg  5460
tcgatatggg ttttgatcat gcacacataa ggtccgacct tatcggcaag ctcaatgagc  5520
tccttggtgg tggtaacatc cagagaagca cacaggttgg ttttcttggc tgccacgagc  5580
ttgagcactc gagcggcaaa ggcggacttg tggacgttag ctcgagcttc gtaggagggc  5640
attttggtgg tgaagaggag actgaaataa atttagtctg cagaactttt tatcggaacc  5700
ttatctgggg cagtgaagta tatgttatgg taatagttac gagttagttg aacttataga  5760
tagactggac tatacggcta tcggtccaaa ttagaaagaa cgtcaatggc tctctgggcg  5820
tcgcctttgc cgacaaaaat gtgatcatga tgaaagccag caatgacgtt gcagctgata  5880
ttgttgtcgg ccaaccgcgc cgaaaacgca gctgtcagac ccacagcctc caacgaagaa  5940
tgtatcgtca aagtgatcca agcacactca tagttggagt cgtactccaa aggcggcaat  6000
gacgagtcag acagatactc gtcgacgttt aaacagtgta cgcagatcta ctatagagga  6060
acatttaaat tgccccggag aagacggcca ggccgcctag atgacaaatt caacaactca  6120
cagctgactt tctgccattg ccactagggg ggggcctttt tatatggcca agccaagctc  6180
tccacgtcgg ttgggctgca cccaacaata aatgggtagg gttgcaccaa caaagggatg  6240
ggatgggggg tagaagatac gaggataacg gggctcaatg gcacaaataa gaacgaatac  6300
tgccattaag actcgtgatc cagcgactga caccattgca tcatctaagg gcctcaaaac  6360
```

```
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc ccctggata tagccccgac aataggccgt ggcctcattt     6660
ttttgccttc cgcacatttc cattgctcga tacccacacc ttgcttctcc tgcacttgcc    6720
aaccttaata ctggtttaca ttgaccaaca tcttacaagc gggggcttg tctagggtat     6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggagtcca ttgttccctt cctgccctcc    7020
aagatgcctc aggacctgtt catggacctc gccagcgcta tcggtgtccg agctgctccc    7080
tacgtcgatc ccctggaggc tgccctggtt gccaggccg agaagtacat tcccaccatt     7140
gtccatcaca ctcgaggctt cctggttgcc gtggattctc ccctggctcg agagctgcct    7200
ctgatgaacc ccttccacgt gctcctgatc gtgctcgcct acctggtcac cgtgtttgtg    7260
ggtatgcaga tcatgaagaa ctttgaacga ttcgaggtca agacgtattc gctcctgtac    7320
aacttctgtc tggtctcgct gagcgcctac atgtgcggtg cattctgta cgaggcttat     7380 caggccaact atggactgtt tgagaacgct gccgatcaca ccttcaaggg tctccctatg    7440
gctaagatga tctggctctt ctacttctcc aagctgatgg agtttgtcga caccatgatc    7500
atggtcctca aaagaacaa ccgacagatt cctttctgc acgtgtacca ccactcttcc     7560
atcttcacca tctggtggct ggtcaccttc gttgctccca acggtgaagc ctacttctct    7620
gctgccctga actcgttcat ccatgttatc atgtacggct actacttcct gtctgccctg    7680
ggcttcaagc aggtgtcgtt catcaagttc tacatcactc gatcccagat gacccagttc    7740
tgcatgttgt ctgtccagtc ttcctgggac atgtacgcca tgaaggtcct tggccgacct    7800
ggatacccct tcttcctgac cgctctgctc tggttctaca tgtggaccat gctcggtctc    7860
ttctacaact tttaccgacg aaacgccaag ctcgccaagc aggccaaggc tgacgctgcc    7920
aaggagaagg ccagaaagct ccagtaagc                                       7949

<210> SEQ ID NO 39
<211> LENGTH: 7949
<212> TYPE: DNA
<213> ORGANISM: Artificial sequence
<220> FEATURE:
<223> OTHER INFORMATION: plasmid 052-3.1b-c9/pY116

<400> SEQUENCE: 39
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
```

```
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca aaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgaacgtt gttgccattg    1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc    2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
```

```
gccattcagg ctgcgcaact gttgggaagg gcgatcggtg cgggcctctt cgctattacg    2940
ccagctggcg aaaggggat gtgctgcaag gcgattaagt tgggtaacgc cagggttttc     3000
ccagtcacga cgttgtaaaa cgacggccag tgaattgtaa tacgactcac tatagggcga    3060
attgggtacc gggcccccc tcgaggtcga tggtgtcgat aagcttgata tcgaattcat     3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat     3360 tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataatgata tctgcattgc     3600 ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttgctta aattcaatcc cccctcgttc agtgtcaact     4080
gtaatggtag gaaattacca tacttttgaa gaagcaaaaa aaatgaaaga aaaaaaaat     4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccgggg    4980 gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
```

```
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggccttttt tatatggcca agccaagctc   6180
tccacgtcgg ttgggctgca cccaacaata aatgggtagg gttgcaccaa caagggatg   6240
ggatgggggg tagaagatac gaggataacg gggctcaatg cacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc ggggggcttg tctagggtat   6780
atataaacag tggctctccc aatcggttgc cagtctcttt tttccttttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggagtcca ttgctcccctt cctgccctcc   7020
aagatgcctc aggacctgtt catggacctc gccagcgcta tcggtgtccg agctgctccc   7080
tacgtcgatc ccctggaggc tgccctggtt gcccaggccg agaagtacat tcccaccatt   7140
gtccatcaca ctcgaggctt cctggttgcc gtggattctc ccctggctcg agagctgcct   7200
ctgatgaacc ccttccacgt gctcctgatt gtgctcgcct acctggtcac cgtgtttgtg   7260
ggtatgcaga tcatgaagaa ctttgaacga ttcgaggtca agacgtattc gctcctgtac   7320
aacttctgtc tggtctcgct gagcgcctac atgtgcggtg gcattctgta cgaggctttt   7380
caggccaact atggactgtt tgagaacgct gccgatcaca ccttcaaggg tctccctatg   7440
gctaagatga tctggctctt ctacttctcc aagctgatgg agtttgtcga caccatgatc   7500
ctggtcctca aaagaacaa ccgacagatt tcctttctgc acgtgtacca ccactcttcc   7560
ctgttcacca tctggtggct ggtcaccttc gttgctccca acggtgaagc ctacttctct   7620
gctgccatga actcgttcat ccatgttatc atgtacggct actactttct gtctgccctg   7680
```

```
ggcttcaagc aggtgtcgtt catcaagttc tacctgactc gatcccagat gacccagttc   7740
tgcatgttgt ctgtccagtc ttcctgggac atgtacgcca tgaaggtcct tggccgacct   7800 ggataccct tcttcctgac cgctctgctc tggttctaca tgtggaccct tctcggtctc   7860
```
(Note: line at 7860 as printed)
```
ttctacaact tttaccgacg aaacgccaag ctcgccaagc aggccaaggc tgacgctgcc   7920
aaggagaagg ccagaaagct ccagtaagc                                      7949
```

<210> SEQ ID NO 40
<211> LENGTH: 7949
<212> TYPE: DNA
<213> ORGANISM: Artificial sequence
<220> FEATURE:
<223> OTHER INFORMATION: plasmid 078-3.1b-b4/pY116

<400> SEQUENCE: 40

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacgtt tcacttgag tgcagtggct     240 agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta ttgcgttgc gctcactgcc cgctttccag tcgggaaacc     420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca aaaaatcga cgctcaagtc    720 agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg ggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
```

```
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cgggggctcc     2580 ctttaggggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt aatagtgga ctcttgttcc aaactggaac aacactcaac cctatctcgg     2760
tctattcttt tgatttataa gggattttgc cgatttcggc ctattggtta aaaaatgagc    2820
tgatttaaca aaaatttaac gcgaattta acaaaatatt aacgcttaca atttccattc    2880
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tataggggcga   3060 attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttttgctta aattcaatcc cccctcgttc agtgtcaact    4080
gtaatggtag gaaattacca tacttttgaa gaagcaaaaa aaatgaaaga aaaaaaaat    4140 cgtatttcca ggttagacgt tccgcagaat ctagaatgcg gtatgcggta cattgttctt    4200
```

```
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct ggagtactc gccagtggcc    5100 agagagccct gcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa gcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240 ggatggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480 caaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
```

```
tgttagtgta cttcaatcgc ccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggagtcca ttgttccctt cctgccctcc    7020
aagatgcctc aggacctgtt catggacctc gccagcgcta tcggtgtccg agctgctccc    7080
tacgtcgatc ccctggaggc tgccctggtt gcccaggccg agaagtacat tcccaccatt    7140
gtccatcaca ctcgaggctt cctggttgcc gtggagtctc ccctggctcg agagctgcct    7200
ctgatgaacc ccttccacgt gctcatgctt gtgctcgcct acctggtcac cgtgtttgtg    7260
ggtatgcaga tcatgaagaa ctttgaacga ttcgaggtca agacgttctc gctcctgtac    7320
aacttctgtc tggtctcgct gagcgcctac atgtgcggtg cattctgta cgaggctttt    7380 caggccaact atggactgtt tgagaacgct gccgatcaca ccttcaaggg tctccctatg    7440
gctaagatga tctggctctt ctacttctcc aagctgatgg agtttgtcga caccatgatc    7500
atggtcctca aaaagaacaa ccgacagatt tcctttctgc acgtgtacca ccactcttcc    7560
atcttcacca tctggtggct ggtcaccttc gttgctccca acggtgaagc ctggttctct    7620
gctgccctga actcgttcat ccatgttatc atgtacggct actactttct gtctgccctg    7680
ggcttcaagc aggtgtcgct gatcaagttc tacctgactc gatcccagat gacccagttc    7740
tgcatgttgt ctgtccagtc ttcctgggac atgtacgcca tgaaggtcct tggccgacct    7800
ggatacccct tcttcctgac cgctctgctc tggttctaca tgtggaccat gctcggtctc    7860
ttctacaact tttaccgacg aaacgccaag ctcgccaagc aggccaaggc tgacgctgcc    7920
aaggagaagg ccagaaagct ccagtaagc                                      7949
```

<210> SEQ ID NO 41
<211> LENGTH: 7949
<212> TYPE: DNA
<213> ORGANISM: Artificial sequence
<220> FEATURE:
<223> OTHER INFORMATION: plasmid 014-3.1b-f1/pY116

<400> SEQUENCE: 41

```
atggagtcca ttgttccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggattctc ccctggctcg agagctgcct ctgatgaacc ccttccacgt gctcctgatc     240
gtgctcgcct acctggtcac cgtgtttgtg ggtatgcaga tcatgaagaa ctttgaacga     300
ttcgaggtca agacgttctc gctcctgtac aacttctgtc tggtctcgct gagcgcctac     360
atgtgcggtg cattctgta cgaggctttt caggccaact atggactgtt tcagaacgct      420
gccgatcaca ccttcaaggg tctccctatg gctaagatga tctggctctt ctacttctcc     480
aagctgatgg agtttgtcga caccatgatc atggtcctca aaaagaacaa ccgacagatt     540
tcctttctgc acgtgtacca ccactcttcc atcttcacca tctggtggct ggtcaccttc     600
gttgctccca acggtgaagc ctacttctct gctgccctga actcgttcat ccatgttatc     660
atgtacggct actactttct gtctgccctg ggcttcaagc aggtgtcgtt catcaagttc     720
```

```
tacatcactc gatcccagat gacccagttc tgcatgttgt ctgtccagtc ttcctgggac    780
atgtacgcca tgaaggtcct tggccgacct ggatacccct tcttcctgac cgctctgctc    840
tggttctaca tgtggaccat gctcggtctc ttctacaact tttaccgacg aaacgccaag    900
ctcgccaagc aggccaaggc tgacgctgcc aaggagaagg ccagaaagct ccagtaagcg    960
gccgcaagtg tggatgggga agtgagtgcc cggttctgtg tgcacaattg gcaatccaag   1020
atggatggat tcaacacagg gatatagcga gctacgtggt ggtgcgagga tatagcaacg   1080
gatatttatg tttgacactt gagaatgtac gatacaagca ctgtccaagt acaatactaa   1140
acatactgta catactcata ctcgtacccg ggcaacggtt tcacttgagt gcagtggcta   1200
gtgctcttac tcgtacagtg tgcaatactg cgtatcatag tctttgatgt atatcgtatt   1260
cattcatgtt agttgcgtac gagccggaag cataaagtgt aaagcctggg gtgcctaatg   1320
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg tcgttcggc tgcggcgagc    1500
ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620
ggcgtttttc cataggctcc gcccccctga cgagcatcac aaaaatcgac gctcaagtca   1680
gaggtggcga aacccgacag gactataaag ataccaggcg tttccccctg gaagctccct   1740
cgtgcgctct cctgttccga ccctgccgct taccggatac ctgtccgcct ttctcccttc   1800
gggaagcgtg gcgctttctc atagctcacg ctgtaggtat ctcagttcgg tgtaggtcgt   1860
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaaggac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaaggat ctcaagaaga   2220
tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacgggaggg cttaccatct ggccccagtg ctgcaatgat   2520
accgcgagac ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatcccccat gttgtgcaaa aaagcggtta gctccttcgg   2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
aatacggat aataccgcgc cacatagcag aactttaaaa gtgctcatca ttggaaaacg    3060
ttcttcgggg cgaaaactct caaggatctt accgctgttg agatccagtt cgatgtaacc   3120
```

```
cactcgtgca cccaactgat cttcagcatc ttttactttc accagcgttt ctgggtgagc    3180
aaaaacagga aggcaaaatg ccgcaaaaaa gggaataagg gcgacacgga aatgttgaat    3240
actcatactc ttccttttc aatattattg aagcatttat cagggttatt gtctcatgag    3300
cggatacata tttgaatgta tttagaaaaa taaacaaata ggggttccgc gcacatttcc    3360
ccgaaaagtg ccacctgacg cgccctgtag cggcgcatta agcgcggcgg gtgtggtggt    3420
tacgcgcagc gtgaccgcta cacttgccag cgccctagcg cccgctcctt tcgctttctt    3480
cccttccttt ctcgccacgt tcgccggctt tccccgtcaa gctctaaatc ggggctccc    3540 tttagggttc cgatttagtg ctttacggca cctcgacccc aaaaaacttg attagggtga    3600
tggttcacgt agtgggccat cgccctgata cacggttttt cgcccttga cgttggagtc    3660 cacgttcttt aatagtggac tcttgttcca aactggaaca cactcaacc ctatctcggt    3720 ctattcttt gatttataag ggattttgcc gatttcggcc tattggttaa aaatgagct    3780 gatttaacaa aaatttaacg cgaattttaa caaaatatta cgcttacaa tttccattcg    3840 ccattcaggc tgcgcaactg ttgggaaggg cgatcggtgc gggcctcttc gctattacgc    3900
cagctggcga aggggggatg tgctgcaagg cgattaagtt gggtaacgcc aggggttttcc    3960 cagtcacgac gttgtaaaac gacggccagt gaattgtaat acgactcact atagggcgaa    4020
ttgggtaccg ggcccccct cgaggtcgat ggtgtcgata agcttgatat cgaattcatg    4080
tcacacaaac cgatcttcgc ctcaaggaaa cctaattcta catccgagag actgccgaga    4140
tccagtctac actgattaat tttcgggcca ataatttaaa aaaatcgtgt tatataatat    4200
tatatgtatt atatatatac atcatgatga tactgacagt catgtcccat tgctaaatag    4260
acagactcca tctgccgcct ccaactgatg ttctcaatat ttaagggtc atctcgcatt    4320 gtttaataat aaacagactc catctaccgc ctccaaatga tgttctcaaa atatattgta    4380
tgaacttatt tttattactt agtattatta gacaacttac ttgctttatg aaaaacactt    4440
cctatttagg aaacaattta taatggcagt tcgttcattt aacaatttat gtagaataaa    4500
tgttataaat gcgtatggga aatcttaaat atggatagca taaatgatat ctgcattgcc    4560
taattcgaaa tcaacagcaa cgaaaaaat cccttgtaca acataaatag tcatcgagaa    4620
atatcaacta tcaaagaaca gctattcaca cgttactatt gagattatta ttggacgaga    4680
atcacacact caactgtctt tctctcttct agaaatacag gtacaagtat gtactattct    4740
cattgttcat acttctagtc atttcatccc acatattcct tggattctc tccaatgaat    4800 gacattctat cttgcaaatt caacaattat aataagatat accaaagtag cggtatagtg    4860
gcaatcaaaa agcttctctg gtgtgcttct cgtatttatt tttattctaa tgatccatta    4920
aaggtatata tttatttctt gttatataat ccttttgttt attacatggg ctggatacat    4980 aaaggtatt tgatttaatt ttttgcttaa attcaatccc ccctcgttca gtgtcaactg    5040
taatggtagg aaattaccat actttgaag aagcaaaaaa aatgaaagaa aaaaaaatc    5100 gtatttccag gttagacgtt ccgcagaatc tagaatgcgg tatgcggtac attgttcttc    5160
gaacgtaaaa gttgcgctcc ctgagatatt gtacattttt gcttttacaa gtacaagtac    5220
atcgtacaac tatgtactac tgttgatgca tccacaacag tttgttttgt tttttttgt    5280 ttttttttt tctaatgatt cattaccgct atgtatacct acttgtactt gtagtaagcc    5340
gggttattgg cgttcaatta atcatagact tatgaatctg cacggtgtgc gctgcgagtt    5400
acttttagct tatgcatgct acttgggtgt aatattggga tctgttcgga aatcaacgga    5460
tgctcaatcg atttcgacag taattaatta agtcatacac aagtcagctt cttcgagcc    5520
```

```
tcatataagt ataagtagtt caacgtatta gcactgtacc cagcatctcc gtatcgagaa   5580
acacaacaac atgccccatt ggacagatca tgcggataca caggttgtgc agtatcatac   5640
atactcgatc agacaggtcg tctgaccatc atacaagctg aacaagcgct ccatacttgc   5700
acgctctcta tatacacagt taaattacat atccatagtc taacctctaa cagttaatct   5760
tctggtaagc ctcccagcca gccttctggt atcgcttggc ctcctcaata ggatctcggt   5820
tctggccgta cagacctcgg ccgacaatta tgatatccgt tccggtagac atgacatcct   5880
caacagttcg gtactgctgt ccgagagcgt ctcccttgtc gtcaagaccc accccggggg   5940
tcagaataag ccagtcctca gagtcgccct taggtcggtt ctgggcaatg aagccaacca   6000
caaactcggg gtcggatcgg gcaagctcaa tggtctgctt ggagtactcg ccagtggcca   6060
gagagccctt gcaagacagc tcggccagca tgagcagacc tctggccagc ttctcgttgg   6120
gagaggggac taggaactcc ttgtactggg agttctcgta gtcagagacg tcctccttct   6180
tctgttcaga gacagtttcc tcggcaccag ctcgcaggcc agcaatgatt ccggttccgg   6240
gtacaccgtg ggcgttggtg atatcggacc actcggcgat tcggtgacac cggtactggt   6300
gcttgacagt gttgccaata tctgcgaact ttctgtcctc gaacaggaag aaaccgtgct   6360
taagagcaag ttccttgagg gggagcacag tgccggcgta ggtgaagtcg tcaatgatgt   6420
cgatatgggt tttgatcatg cacacataag gtccgacctt atcggcaagc tcaatgagct   6480
ccttggtggt ggtaacatcc agagaagcac acaggttggt tttcttggct gccacgagct   6540
tgagcactcg agcggcaaag gcggacttgt ggacgttagc tcgagcttcg taggagggca   6600
ttttggtggt gaagaggaga ctgaaataaa tttagtctgc agaacttttt atcggaacct   6660
tatctggggc agtgaagtat atgttatggt aatagttacg agttagttga acttatagat   6720
agactggact atacggctat cggtccaaat tagaaagaac gtcaatggct ctctgggcgt   6780
cgcctttgcc gacaaaaatg tgatcatgat gaaagccagc aatgacgttg cagctgtatat  6840 tgttgtcggc caaccgcgcc gaaaacgcag ctgtcagacc cacagcctcc aacgaagaat   6900
gtatcgtcaa agtgatccaa gcacactcat agttggagtc gtactccaaa ggcggcaatg   6960
acgagtcaga cagatactcg tcgacgttta acagtgtac gcagatctac tatagaggaa    7020
catttaaatt gccccggaga agacggccag gccgcctaga tgacaaattc aacaactcac   7080
agctgacttt ctgccattgc cactaggggg gggccttttt atatggccaa gccaagctct   7140
ccacgtcggt tgggctgcac ccaacaataa atgggtaggg ttgcaccaac aaagggatgg   7200 gatgggggt agaagatacg aggataacgg ggctcaatgg cacaaataag aacgaatact    7260
gccattaaga ctcgtgatcc agcgactgac accattgcat catctaaggg cctcaaaact   7320
acctcggaac tgctgcgctg atctggacac cacagaggtt ccgagcactt taggttgcac   7380
caaatgtccc accaggtgca ggcagaaaac gctggaacag cgtgtacagt ttgtcttaac   7440
aaaaagtgag ggcgctgagg tcgagcaggg tggtgtgact tgttatagcc tttagagctg   7500
cgaaagcgcg tatggatttg gctcatcagg ccagattgag ggtctgtgga cacatgtcat   7560
gttagtgtac ttcaatcgcc ccctggatat agccccgaca ataggccgtg gcctcatttt   7620
tttgccttcc gcacatttcc attgctcgat acccacacct tgcttctcct gcacttgcca   7680
accttaatac tggtttacat tgaccaacat cttacaagcg gggggcttgt ctagggtata   7740
tataaacagt ggctctccca atcggttgcc agtctctttt ttccttctct tccccacaga   7800
ttcgaaatct aaactacaca tcacagaatt ccgagccgtg agtatccacg acaagatcag   7860
tgtcgagacg acgcgttttg tgtaatgaca caatccgaaa gtcgctagca acacacactc   7920
```

<210> SEQ ID NO 42
<211> LENGTH: 7949
<212> TYPE: DNA
<213> ORGANISM: Artificial sequence
<220> FEATURE:
<223> OTHER INFORMATION: plasmid 051-3.1b-b5/pY116

<400> SEQUENCE: 42

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg ggtctgacg ctcagtggaa cgaaaactca cgttaaggga    1320
ttttggtcat gagattatca aaaaggatct tcacctagat ccttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt cgcaacgtt gttgccattg     1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga aatagtgta tgcggcgacc gagttgctct tgcccggcgt     2040
```

| | | | | |
|---|---|---|---|---|
| caatacggga | taataccgcg | ccacatagca | gaactttaaa | agtgctcatc attggaaaac | 2100 |
| gttcttcggg | gcgaaaactc | tcaaggatct | taccgctgtt | gagatccagt tcgatgtaac | 2160 |
| ccactcgtgc | acccaactga | tcttcagcat | cttttacttt | caccagcgtt tctgggtgag | 2220 |
| caaaaacagg | aaggcaaaat | gccgcaaaaa | agggaataag | ggcgacacgg aaatgttgaa | 2280 |
| tactcatact | cttccttttt | caatattatt | gaagcattta | tcagggttat tgtctcatga | 2340 |
| gcggatacat | atttgaatgt | atttagaaaa | ataaacaaat | aggggttccg cgcacatttc | 2400 |
| cccgaaaagt | gccacctgac | gcgccctgta | gcggcgcatt | aagcgcggcg ggtgtggtgg | 2460 |
| ttacgcgcag | cgtgaccgct | acacttgcca | gcgccctagc | gcccgctcct ttcgctttct | 2520 |
| tcccttcctt | tctcgccacg | ttcgccggct | ttccccgtca | agctctaaat cgggggctcc | 2580 |
| ctttagggtt | ccgatttagt | gctttacggc | acctcgaccc | caaaaaactt gattagggtg | 2640 |
| atggttcacg | tagtgggcca | tcgccctgat | agacggtttt | tcgccctttg acgttggagt | 2700 |
| ccacgttctt | taatagtgga | ctcttgttcc | aaactggaac | aacactcaac cctatctcgg | 2760 |
| tctattcttt | tgatttataa | gggattttgc | cgatttcggc | ctattggtta aaaaatgagc | 2820 |
| tgatttaaca | aaaatttaac | gcgaatttta | acaaaatatt | aacgcttaca atttccattc | 2880 |
| gccattcagg | ctgcgcaact | gttgggaagg | gcgatcggtg | cgggcctctt cgctattacg | 2940 |
| ccagctggcg | aaagggggat | gtgctgcaag | gcgattaagt | tgggtaacgc cagggttttc | 3000 |
| ccagtcacga | cgttgtaaaa | cgacggccag | tgaattgtaa | tacgactcac tatagggcga | 3060 |
| attgggtacc | gggccccccc | tcgaggtcga | tggtgtcgat | aagcttgata tcgaattcat | 3120 |
| gtcacacaaa | ccgatcttcg | cctcaaggaa | acctaattct | acatccgaga gactgccgag | 3180 |
| atccagtcta | cactgattaa | ttttcgggcc | aataatttaa | aaaaatcgtg ttatataata | 3240 |
| ttatatgtat | tatatatata | catcatgatg | atactgacag | tcatgtccca ttgctaaata | 3300 |
| gacagactcc | atctgccgcc | tccaactgat | gttctcaata | tttaaggggt catctcgcat | 3360 |
| tgtttaataa | taaacagact | ccatctaccg | cctccaaatg | atgttctcaa aatatattgt | 3420 |
| atgaacttat | ttttattact | tagtattatt | agacaactta | cttgctttat gaaaaacact | 3480 |
| tcctatttag | gaaacaattt | ataatggcag | ttcgttcatt | taacaattta tgtagaataa | 3540 |
| atgttataaa | tgcgtatggg | aaatcttaaa | tatggatagc | ataaatgata tctgcattgc | 3600 |
| ctaattcgaa | atcaacagca | acgaaaaaaa | tcccttgtac | aacataaata gtcatcgaga | 3660 |
| aatatcaact | atcaaagaac | agctattcac | acgttactat | tgagattatt attggacgag | 3720 |
| aatcacacac | tcaactgtct | ttctctcttc | tagaaataca | ggtacaagta tgtactattc | 3780 |
| tcattgttca | tacttctagt | catttcatcc | cacatattcc | ttggatttct ctccaatgaa | 3840 |
| tgacattcta | tcttgcaaat | tcaacaatta | taataagata | taccaaagta gcggtatagt | 3900 |
| ggcaatcaaa | aagcttctct | ggtgtgcttc | tcgtatttat | ttttattcta atgatccatt | 3960 |
| aaaggtatat | atttatttct | tgttatataa | tccttttgtt | tattacatgg gctggataca | 4020 |
| taaaggtatt | ttgatttaat | tttttgctta | aattcaatcc | ccctcgttc agtgtcaact | 4080 |
| gtaatggtag | gaaattacca | tacttttgaa | gaagcaaaaa | aaatgaaaga aaaaaaaat | 4140 |
| cgtatttcca | ggttagacgt | tccgcagaat | ctagaatgcg | gtatgcggta cattgttctt | 4200 |
| cgaacgtaaa | agttgcgctc | cctgagatat | tgtacatttt | tgcttttaca agtacaagta | 4260 |
| catcgtacaa | ctatgtacta | ctgttgatgc | atccacaaca | gtttgttttg ttttttttg | 4320 |
| ttttttttt | ttctaatgat | tcattaccgc | tatgtatacc | tacttgtact tgtagtaagc | 4380 |
| cgggttattg | gcgttcaatt | aatcatagac | ttatgaatct | gcacggtgtg cgctgcgagt | 4440 |

```
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc cacccgggg   4980 gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggccttt tatatggcca agccaagctc   6180
tccacgtcgg ttgggctgca cccaacaata aatgggtagg gttgcaccaa caagggatg   6240 ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc ccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc gggggcttg tctagggtat   6780 atataaacag tggctctccc aatcggttgc cagtctcttt tttcctttct ttccccacag   6840
```

| | |
|---|---|
| attcgaaatc taaactacac atcacagaat tccgagccgt gagtatccac gacaagatca | 6900 |
| gtgtcgagac gacgcgtttt gtgtaatgac acaatccgaa agtcgctagc aacacacact | 6960 |
| ctctacacaa actaacccag ctctggtacc atggagtcca ttgttccctt cctgccctcc | 7020 |
| aagatgcctc aggacctgtt catggacctc gccagcgcta tcggtgtccg agctgctccc | 7080 |
| tacgtcgatc ccctggaggc tgccctggtt gcccaggccg agaagtacat tcccaccatt | 7140 |
| gtccatcaca ctcgaggctt cctggttgcc gtggattctc ccctggctcg agagctgcct | 7200 |
| ctgatgaacc ccttccacgt gctcctgatc gtgctcgcct acctggtcac cgtgtttgtg | 7260 |
| ggtatgcaga tcatgaagaa ctttgaacga ttcgaggtca agacgttctc gctcctgtac | 7320 |
| aacttctgtc tggtctcgct gagcgcctac atgtgcggtg cattctgta cgaggcttat | 7380 |
| caggccaact atggactgtt tcagaacgct gccgatcaca ccttcaaggg tctccctatg | 7440 |
| gctaagatga tctggctctt ctacttctcc aagctgatgg agtttgtcga caccatgatc | 7500 |
| atggtcctca aaaagaacaa ccgacagatt cctttctgc acgtgtacca ccactcttcc | 7560 |
| atcttcacca tctggtggct ggtcaccttc gttgctccca acggtgaagc ctacttctct | 7620 |
| gctgccctga actcgttcat ccatgttatc atgtacggct actactttct gtctgccctg | 7680 |
| ggcttcaagc aggtgtcgtt catcaagttc tacatcactc gatcccagat gacccagttc | 7740 |
| tgcatgttgt ctgtccagtc ttcctgggac atgtacgcca tgaaggtcct ggccgacct | 7800 |
| ggataccct tcttcctgac cgctctgctc tggttctaca tgtgaccat gctcggtctc | 7860 |
| ttctacaact tttaccgaaa gaacgccaag ctcgccaagc aggccaaggc tgacgctgcc | 7920 |
| aaggagaagg ccagaaagct ccagtaagc | 7949 |

<210> SEQ ID NO 43
<211> LENGTH: 7949
<212> TYPE: DNA
<213> ORGANISM: Artificial sequence
<220> FEATURE:
<223> OTHER INFORMATION: plasmid 062-3.1b-c5/pY116

<400> SEQUENCE: 43

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgagccggaa gcataaagtg taaagcctgg ggtgcctaat | 360 |
| gagtgagcta actcacatta attgcgttgc gctcactgcc cgctttccag tcgggaaacc | 420 |
| tgtcgtgcca gctgcattaa tgaatcggcc aacgcgcggg gagaggcggt ttgcgtattg | 480 |
| ggcgctcttc cgcttcctcg ctcactgact cgctgcgctc ggtcgttcgg ctgcggcgag | 540 |
| cggtatcagc tcactcaaag gcggtaatac ggttatccac agaatcaggg gataacgcag | 600 |
| gaaagaacat gtgagcaaaa ggccagcaaa aggccaggaa ccgtaaaaag gccgcgttgc | 660 |
| tggcgttttt ccataggctc cgcccccctg acgagcatca caaaaatcga cgctcaagtc | 720 |
| agaggtggcg aaacccgaca ggactataaa gataccaggc gtttccccct ggaagctccc | 780 |
| tcgtgcgctc tcctgttccg accctgccgc ttaccggata cctgtccgcc tttctccctt | 840 |
| cgggaagcgt ggcgctttct catagctcac gctgtaggta tctcagttcg gtgtaggtcg | 900 |
| ttcgctccaa gctgggctgt gtgcacgaac ccccgttca gcccgaccgc tgcgccttat | 960 |

```
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaggatct tcacctagat ccttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg cttaccatc tggccccagt gctgcaatga    1560
taccgcgaga cccacgctca ccggctccag atttatcagc aataaccag ccagccggaa    1620 gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca agctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaatcgtg ttatataata    3240 ttatatgtat tatatatata catcatgatg atactgacag tcatgtccca ttgctaaata    3300
gacagactcc atctgccgcc tccaactgat gttctcaata tttaaggggt catctcgcat    3360
```

-continued

```
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttttg    4320 tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgt tgaagaggag actgaaataa atttagtctg cagaactttt tatcggaacc    5700
ttatctgggg cagtgaagta tatgttatgg taatagttac gagttagttg aacttataga    5760
```

```
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggagtcca ttgttccctt cctgccctcc    7020
aagatgcctc aggacctgtt catggacctc gccagcgcta tcggtgtccg agctgctccc    7080
tacgtcgatc ccctggaggc tgccctggtt gcccaggccg agaagtacat tcccaccatt    7140
gtccatcaca ctcgaggctt cctggttgcc gtggattctc ccctggctcg agagctgcct    7200
ctgatgaacc ccttccacgt gctcctgatt gtgctcgcct acctggtcac cgtgtttgtg    7260
ggtatgcaga tcatgaagaa cttgaacga ttcgaggtca agacgttctc gctcctgtac    7320
aacttctgtc tggtctcgct gagcgcctac atgtgcggtg gcattctgta cgaggctttt    7380
caggccaact atggactgtt tgagaacgct gccgatcaca ccttcaaggg tctccctatg    7440
gctaagatga tctggctctt ctacttctcc aagctgatgg agtttgtcga cacccttatc    7500
atggtcctca agaagaacaa ccgacagatt tcctttctgc acgtgtacca ccactcttcc    7560
atcttcacca tctggtggct ggtcaccttc gttgctccca acggtgaggc ctacttctct    7620
gctgccctga actcgttcat ccatgttatc atgtacggct actactttct gtctgccctg    7680
ggcttcaagc aggtgtcgtt catcaagttc tacatcactc gatcccagat gacccagttc    7740
tgcatgttgt ctgtccagtc ttcctgggac atgtacgcca tgaaggtcct tggccgacct    7800 ggataccct tcttcctgac cgctctgctc tggttctaca tgtggaccat gctcggtctc    7860
ttctacaact tttaccgacg aaacgccaag ctcgccaagc aggccaaggc tgacgctgcc    7920
aaggagaagg ccagaaagct ccagtaagc                                      7949
```

<210> SEQ ID NO 44
<211> LENGTH: 5213
<212> TYPE: DNA
<213> ORGANISM: Artificial sequence
<220> FEATURE:
<223> OTHER INFORMATION: plasmid KS366

<400> SEQUENCE: 44

| | | | | | |
|---|---|---|---|---|---|
| ctagaactag | tggatccttc | atccatgccc | ttcatttgcc | gcttattaat | taatttggta | 60 |
| acagtccgta | ctaatcagtt | acttatcctt | ccccatcat | aattaatctt | ggtagtctcg | 120 |
| aatgccacaa | cactgactag | tctcttggat | cataagaaaa | agccaaggaa | caaaagaaga | 180 |
| caaaacacaa | tgagagtatc | ctttgcatag | caatgtctaa | gttcataaaa | ttcaaacaaa | 240 |
| aacgcaatca | cacacagtgg | acatcactta | tccactagct | gatcaggatc | gccgcgtcaa | 300 |
| gaaaaaaaa | ctggaccccca | aaagccatgc | acaacaacac | gtactcacaa | aggtgtcaat | 360 |
| cgagcagccc | aaaacattca | ccaactcaac | ccatcatgag | ccctcacatt | tgttgtttct | 420 |
| aacccaacct | caaactcgta | ttctcttccg | ccacctcatt | tttgtttatt | tcaacacccg | 480 |
| tcaaactgca | tgccacccccg | tggccaaatg | tccatgcatg | ttaacaagac | ctatgactat | 540 |
| aaatagctgc | aatctcggcc | caggttttca | tcatcaagaa | ccagttcaat | atcctagtac | 600 |
| accgtattaa | agaatttaag | atatactcca | tggtgagagc | gcggttccca | ttactgttgc | 660 |
| tgggagttgt | tttcctagca | tcagtttctg | tctcatttgg | cattgcgtat | tgggaaaagc | 720 |
| agaaccccag | tcacaacaag | tgcctccgaa | gttgcaatag | cgagaaagac | tcctacagga | 780 |
| accaagcatg | ccacgctcgt | tgcaacctcc | ttaaggtgga | ggaaatggtt | gagaaagaga | 840 |
| aatgcaaacg | cggtaagatc | ccacgtccac | gtcctcgtcc | acagcaccca | gaacgtgaac | 900 |
| cacagcagcc | aggtgagaaa | gaacgtgata | aggatcgtca | gccacgtcca | atcccattcc | 960 |
| ctcgtccaca | gccacgtcag | aaagagaaac | atgaacagcg | tcgtgaacag | aaatggccac | 1020 |
| gtaaagaaga | gaaacgcggt | gagaaaggtt | ctgaacgtga | aaagaaagac | aaagatgagg | 1080 |
| aacaggatga | acgtcagttc | ccattcccgg | tggcggccgc | aagtatgaac | taaaatgcac | 1140 |
| gtaggtgtaa | gagctcatgg | agagcatgga | atattgtatc | cgaccatgta | acagtataat | 1200 |
| aactgagctc | catctcactt | cttctatgaa | taaacaaagg | atgttatgat | atattaacac | 1260 |
| tctatctatg | caccttattg | ttctatgata | aatttcctct | tattattata | aatcatctga | 1320 |
| atcgtgacgg | cttatggaat | gcttcaaata | gtacaaaaac | aaatgtgtac | tataagactt | 1380 |
| tctaaacaat | tctaactta | gcattgtgaa | cgagacataa | gtgttaagaa | gacataacaa | 1440 |
| ttataatgga | agaagtttgt | ctccatttat | atattatata | ttacccactt | atgtattata | 1500 |
| ttaggatgtt | aaggagacat | aacaattata | aagagagaag | tttgtatcca | tttatatatt | 1560 |
| atatactacc | catttatata | ttatacttat | ccacttattt | aatgtcttta | taaggtttga | 1620 |
| tccatgatat | ttctaatatt | ttagttgata | tgtatatgaa | agggtactat | ttgaactctc | 1680 |
| ttactctgta | taaaggttgg | atcatcctta | aagtgggtct | atttaatttt | attgcttctt | 1740 |
| acagataaaa | aaaaaattat | gagttggttt | gataaaatat | tgaaggattt | aaaataataa | 1800 |
| taaataacat | ataatatatg | tatataaatt | tattataata | taacatttat | ctataaaaaa | 1860 |
| gtaaatattg | tcataaatct | atacaatcgt | ttagccttgc | tggacgaatc | tcaattattt | 1920 |
| aaacgagagt | aaacatattt | gacttttttgg | ttatttaaca | aattattatt | taacactata | 1980 |
| tgaaattttt | tttttttatca | gcaaagaata | aaattaaatt | aaggaggaca | atggtgtccc | 2040 |
| aatccttata | caaccaactt | ccacaagaaa | gtcaagtcag | agacaacaaa | aaacaagca | 2100 |
| aaggaaattt | tttaatttga | gttgtcttgt | ttgctgcata | atttatgcag | taaaacacta | 2160 |
| cacataaccc | tttagcagt | aaagcaatgg | ttgaccgtgt | gcttagcttc | tttatttta | 2220 |
| ttttttttatc | agcaaagaat | aaataaaata | aaatgagaca | cttcagggat | gtttcaacgg | 2280 |

```
atcccccggg ctgcaggaat tcgatatcaa gcttatcgat accgtcgacc tcgagggggg    2340
gcccggtacc caattcgccc tatagtgagt cgtattacgc gcgctcactg gccgtcgttt    2400
tacaacgtcg tgactgggaa aaccctggcg ttacccaact taatcgcctt gcagcacatc    2460
cccctttcgc cagctggcgt aatagcgaag aggcccgcac cgatcgccct tcccaacagt    2520
tgcgcagcct gaatggcgaa tgggacgcgc cctgtagcgg cgcattaagc gcggcgggtg    2580
tggtggttac gcgcagcgtg accgctacac ttgccagcgc cctagcgccc gctcctttcg    2640
ctttcttccc ttcctttctc gccacgttcg ccggctttcc ccgtcaagct ctaaatcggg    2700
ggctcccttt agggttccga tttagtgctt tacggcacct cgaccccaaa aaacttgatt    2760
agggtgatgg ttcacgtagt gggccatcgc cctgatagac ggttttcgc cctttgacgt    2820 tggagtccac gttctttaat agtggactct tgttccaaac tggaacaaca ctcaaccta    2880 tctcggtcta ttcttttgat ttataaggga ttttgccgat tcggcctat tggttaaaaa    2940 atgagctgat ttaacaaaaa tttaacgcga attttaacaa aatattaacg cttacaattt    3000
aggtggcact tttcggggaa atgtgcgcgg aacccctatt tgtttatttt tctaaataca    3060
ttcaaatatg tatccgctca tgagacaata accctgataa atgcttcaat aatattgaaa    3120
aaggaagagt atgagtattc aacatttccg tgtcgccctt attcccttt ttgcggcatt    3180 ttgccttcct gttttgctc acccagaaac gctggtgaaa gtaaaagatg ctgaagatca    3240
gttgggtgca cgagtgggtt acatcgaact ggatctcaac agcggtaaga tccttgagag    3300
ttttcgcccc gaagaacgtt ttccaatgat gagcactttt aaagttctgc tatgtggcgc    3360
ggtattatcc cgtattgacg ccgggcaaga gcaactcggt cgccgcatac actattctca    3420
gaatgacttg gttgagtact caccagtcac agaaaagcat cttacggatg gcatgacagt    3480
aagagaatta tgcagtgctg ccataaccat gagtgataac actgcggcca acttacttct    3540
gacaacgatc ggaggaccga aggagctaac cgcttttttg cacaacatgg ggatcatgt    3600 aactcgcctt gatcgttggg aaccggagct gaatgaagcc ataccaaacg acgagcgtga    3660
caccacgatg cctgtagcaa tggcaacaac gttgcgcaaa ctattaactg gcgaactact    3720
tactctagct tcccggcaac aattaataga ctggatggag gcggataaag ttgcaggacc    3780
acttctgcgc tcggcccttc cggctggctg gtttattgct gataaatctg gagccggtga    3840
gcgtgggtct cgcggtatca ttgcagcact ggggccagat ggtaagccct cccgtatcgt    3900
agttatctac acgacgggga gtcaggcaac tatggatgaa cgaaatagac agatcgctga    3960
gataggtgcc tcactgatta agcattggta actgtcagac caagtttact catatatact    4020
ttagattgat ttaaaacttc atttttaatt taaaaggatc taggtgaaga tcctttttga    4080
taatctcatg accaaaatcc cttaacgtga gttttcgttc cactgagcgt cagacccgt    4140 agaaaagatc aaaggatctt cttgagatcc tttttttctg cgcgtaatct gctgcttgca    4200
aacaaaaaaa ccaccgctac cagcggtggt ttgtttgccg gatcaagagc taccaactct    4260
ttttccgaag gtaactggct tcagcagagc gcagatacca aatactgtcc ttctagtgta    4320
gccgtagtta ggccaccact tcaagaactc tgtagcaccg cctacatacc tcgctctgct    4380
aatcctgtta ccagtggctg ctgccagtgg cgataagtcg tgtcttaccg ggttggactc    4440
aagacgatag ttaccggata aggcgcagcg gtcgggctga acggggggtt cgtgcacaca    4500
gcccagcttg gagcgaacga cctacaccga actgagatac ctacagcgtg agctatgaga    4560
aagcgccacg cttcccgaag ggagaaaggc ggacaggtat ccggtaagcg gcagggtcgg    4620
aacaggagag cgcacgaggg agcttccagg gggaaacgcc tggtatcttt atagtcctgt    4680
```

| cgggtttcgc cacctctgac ttgagcgtcg attttgtgta tgctcgtcag ggggggcggag | 4740 |
| cctatggaaa aacgccagca acgcggcctt tttacggttc ctggccttttt gctggccttt | 4800 |
| tgctcacatg ttcttttcctg cgttatcccc tgattctgtg gataaccgta ttaccgcctt | 4860 |
| tgagtgagct gataccgctc gccgcagccg aacgaccgag cgcagcgagt cagtgagcga | 4920 |
| ggaagcggaa gagcgcccaa tacgcaaacc gcctctcccc gcgcgttggc cgattcatta | 4980 |
| atgcagctgg cacgacaggt ttcccgactg gaaagcgggc agtgagcgca acgcaattaa | 5040 |
| tgtgagttag ctcactcatt aggcacccca ggctttacac tttatgcttc cggctcgtat | 5100 |
| gttgtgtgga attgtgagcg gataacaatt tcacacagga aacagctatg accatgatta | 5160 |
| cgccaagcgc gcaattaacc ctcactaaag ggaacaaaag ctggagctcc acc | 5213 |

<210> SEQ ID NO 45
<211> LENGTH: 5267
<212> TYPE: DNA
<213> ORGANISM: Artificial sequence
<220> FEATURE:
<223> OTHER INFORMATION: plasmid KS120

<400> SEQUENCE: 45

| atctgatcaa cctgcattaa tgaatcggcc aacgcgcggg gagaggcggt ttgcgtattg | 60 |
| ggcgctcttc cgcttcctcg ctcactgact cgctgcgctc ggtcgttcgg ctgcggcgag | 120 |
| cggtatcagc tcactcaaag gcggtaatac ggttatccac agaatcaggg gataacgcag | 180 |
| gaaagaacat gtgagcaaaa ggccagcaaa aggccaggaa ccgtaaaaag gccgcgttgc | 240 |
| tggcgttttt ccataggctc cgcccccctg acgagcatca aaaaatcga cgctcaagtc | 300 |
| agaggtggcg aaacccgaca ggactataaa gataccaggc gtttccccct ggaagctccc | 360 |
| tcgtgcgctc tcctgttccg accctgccgc ttaccggata cctgtccgcc tttctccctt | 420 |
| cgggaagcgt ggcgctttct caatgctcac gctgtaggta tctcagttcg gtgtaggtcg | 480 |
| ttcgctccaa gctgggctgt gtgcacgaac cccccgttca gcccgaccgc tgcgccttat | 540 |
| ccggtaacta tcgtcttgag tccaacccgg taagacacga cttatcgcca ctggcagcag | 600 |
| ccactggtaa caggattagc agagcgaggt atgtaggcgg tgctacagag ttcttgaagt | 660 |
| ggtggcctaa ctacggctac actagaagga cagtatttgg tatctgcgct ctgctgaagc | 720 |
| cagttacctt cggaaaaaga gttggtagct cttgatccgg caaacaaacc accgctggta | 780 |
| gcggtggttt ttttgtttgc aagcagcaga ttacgcgcag aaaaaaagga tctcaagaag | 840 |
| atcctttgat cttttctacg gggtctgacg ctcagtggaa cgaaaactca cgttaaggga | 900 |
| ttttggtcat gacattaacc tataaaaata ggcgtatcac gaggcccttt cgtctcgcgc | 960 |
| gtttcggtga tgacggtgaa aacctctgac acatgcagct cccggagacg gtcacagctt | 1020 |
| gtctgtaagc ggatgccggg agcagacaag cccgtcaggg cgcgtcagcg ggtgttggcg | 1080 |
| ggtgtcgggg ctggcttaac tatgcggcat cagagcagat tgtactgaga gtgcaccata | 1140 |
| tggacatatt gtcgttagaa cgcggctaca attaatacat aacctatgt atcatacaca | 1200 |
| tacgatttag gtgacactat agaacggcgc gccaagcttg gatccgtcga cggcgcgccc | 1260 |
| gatcatccgg atatagttcc tcctttcagc aaaaaacccc tcaagacccg tttagaggcc | 1320 |
| ccaaggggtt atgctagtta ttgctcagcg gtggcagcag ccaactcagc ttcctttcgg | 1380 |
| gctttgttag cagccggatc gatccaagct gtacctcact attcctttgc cctcggacga | 1440 |
| gtgctggggc gtcggtttcc actatcgcg agtacttcta cacagccatc ggtccagacg | 1500 |
| gccgcgcttc tgcgggcgat ttgtgtacgc ccgacagtcc cggctccgga tcggacgatt | 1560 |

```
gcgtcgcatc gaccctgcgc ccaagctgca tcatcgaaat tgccgtcaac caagctctga   1620
tagagttggt caagaccaat gcggagcata tacgcccgga gccgcggcga tcctgcaagc   1680
tccggatgcc tccgctcgaa gtagcgcgtc tgctgctcca tacaagccaa ccacggcctc   1740
cagaagaaga tgttggcgac ctcgtattgg gaatccccga acatcgcctc gctccagtca   1800
atgaccgctg ttatgcggcc attgtccgtc aggacattgt tggagccgaa atccgcgtgc   1860
acgaggtgcc ggacttcggg gcagtcctcg gcccaaagca tcagctcatc gagagcctgc   1920
gcgacggacg cactgacggt gtcgtccatc acagtttgcc agtgatacac atggggatca   1980
gcaatcgcgc atatgaaatc acgccatgta gtgtattgac cgattccttg cggtccgaat   2040
gggccgaacc cgctcgtctg gctaagatcg gccgcagcga tcgcatccat agcctccgcg   2100
accggctgca gaacagcggg cagttcggtt tcaggcaggt cttgcaacgt gacaccctgt   2160
gcacggcggg agatgcaata ggtcaggctc tcgctgaatt ccccaatgtc aagcacttcc   2220
ggaatcggga gcgcggccga tgcaaagtgc cgataaacat aacgatcttt gtagaaacca   2280
tcggcgcagc tatttacccg caggacatat ccacgccctc ctacatcgaa gctgaaagca   2340
cgagattctt cgccctccga gagctgcatc aggtcggaga cgctgtcgaa cttttcgatc   2400
agaaacttct cgacagacgt cgcggtgagt tcaggctttt ccatgggtat atctccttct   2460
taaagttaaa caaaattatt tctagaggga accgttgtg gtctccctat agtgagtcgt    2520
attaatttcg cgggatcgag atcgatccaa ttccaatccc acaaaaatct gagcttaaca   2580
gcacagttgc tcctctcaga gcagaatcgg gtattcaaca ccctcatatc aactactacg   2640
ttgtgtataa cggtccacat gccggtatat acgatgactg gggttgtaca aaggcggcaa   2700
caaacggcgt tcccggagtt gcacacaaga aatttgccac tattacagag caagagcag    2760 cagctgacgc gtacacaaca agtcagcaaa cagacaggtt gaacttcatc cccaaggag    2820 aagctcaact caagcccaag agctttgcta aggccctaac aagcccacca aagcaaaaag   2880
cccactggct cacgctagga accaaaaggc ccagcagtga tccagcccca aaagagatct   2940
cctttgcccc ggagattaca atggacgatt tcctctatct ttacgatcta ggaaggaagt   3000
tcgaaggtga aggtgacgac actatgttca ccactgataa tgagaaggtt agcctcttca   3060
atttcagaaa gaatgctgac ccacagatgg ttagagaggc ctacgcagca ggtctcatca   3120
agacgatcta cccgagtaac aatctccagg agatcaaata ccttcccaag aaggttaaag   3180
atgcagtcaa aagattcagg actaattgca tcaagaacac agagaaagac atatttctca   3240
agatcagaag tactattcca gtatggacga ttcaaggctt gcttcataaa ccaaggcaag   3300
taatagagat tggagtctct aaaaaggtag ttcctactga atctaaggcc atgcatggag   3360
tctaagattc aaatcgagga tctaacagaa ctcgccgtga agactggcga acagttcata   3420
cagagtcttt tacgactcaa tgacaagaag aaaatcttcg tcaacatggt ggagcacgac   3480
actctggtct actccaaaaa tgtcaaagat acagtctcag aagaccaaag ggctattgag   3540
acttttcaac aaaggataat ttcgggaaac ctcctcggat tccattgccc agctatctgt   3600
cacttcatcg aaaggacagt agaaaaggaa ggtggctcct acaaatgcca tcattgcgat   3660
aaaggaaagg ctatcattca agatgcctct gccgacagtg gtcccaaaga tggacccca    3720 cccacgagga gcatcgtgga aaagaagac gttccaacca cgtcttcaaa gcaagtggat    3780
tgatgtgaca tctccactga cgtaagggat gacgcacaat cccactatcc ttcgcaagac   3840
ccttcctcta tataaggaag ttcatttcat ttggagagga cacgctcgag ctcatttctc   3900
tattacttca gccataacaa agaactcttt ttctcttctt attaaaccat gaaaaagcct   3960
```

```
gaactcaccg cgacgtctgt cgagaagttt ctgatcgaaa agttcgacag cgtctccgac    4020
ctgatgcagc tctcggaggg cgaagaatct cgtgctttca gcttcgatgt aggagggcgt    4080
ggatatgtcc tgcgggtaaa tagctgcgcc gatggtttct acaaagatcg ttatgtttat    4140
cggcactttg catcggccgc gctcccgatt ccggaagtgc ttgacattgg ggaattcagc    4200
gagagcctga cctattgcat ctcccgccgt gcacagggtg tcacgttgca agacctgcct    4260
gaaaccgaac tgcccgctgt tctgcagccg gtcgcggagg ccatggatgc gatcgctgcg    4320
gccgatctta gccagacgag cgggttcggc ccattcggac cgcaaggaat cggtcaatac    4380
actacatggc gtgatttcat atgcgcgatt gctgatcccc atgtgtatca ctggcaaact    4440
gtgatggacg acaccgtcag tgcgtccgtc gcgcaggctc tcgatgagct gatgctttgg    4500
gccgaggact gccccgaagt ccggcacctc gtgcacgcgg atttcggctc caacaatgtc    4560
ctgacggaca atggccgcat aacagcggtc attgactgga gcgaggcgat gttcggggat    4620
tcccaatacg aggtcgccaa catcttcttc tggaggccgt ggttggcttg tatggagcag    4680
cagacgcgct acttcgagcg gaggcatccg gagcttgcag gatcgccgcg gctccgggcg    4740
tatatgctcc gcattggtct tgaccaactc tatcagagct tggttgacgg caatttcgat    4800
gatgcagctt gggcgcaggg tcgatgcgac gcaatcgtcc gatccggagc cgggactgtc    4860
gggcgtacac aaatcgcccg cagaagcgcg gccgtctgga ccgatggctg tgtagaagta    4920
ctcgccgata gtggaaaccg acgccccagc actcgtccga gggcaaagga atagtgaggt    4980
acctaaagaa ggagtgcgtc gaagcagatc gttcaaacat ttggcaataa agtttcttaa    5040
gattgaatcc tgttgccggt cttgcgatga ttatcatata atttctgttg aattacgtta    5100
agcatgtaat aattaacatg taatgcatga cgttatttat gagatgggtt tttatgatta    5160
gagtcccgca attatacatt taatacgcga tagaaaacaa aatatagcgc gcaaactagg    5220
ataaattatc gcgcgcggtg tcatctatgt tactagatcg atgtcga                  5267
```

<210> SEQ ID NO 46
<211> LENGTH: 5687
<212> TYPE: DNA
<213> ORGANISM: Artificial sequence
<220> FEATURE:
<223> OTHER INFORMATION: plasmid KS367

<400> SEQUENCE: 46

```
ggccgcaagt atgaactaaa atgcacgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta actttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actacccatt tatatattat acttatccac     480
ttatttaatg tctttataag gtttgatcca tgatatttct aatatttag ttgatatgta      540 tatgaaaggg tactatttga actctcttac tctgtataaa ggttggatca tccttaaagt     600 gggtctatt aatttttattg cttcttacag ataaaaaaaa aattatgagt tggtttgata    660
aaatattgaa ggatttaaaa taataataaa taacatataa tatatgtata taaatttatt     720
ataatataac atttatctat aaaaaagtaa atattgtcat aaatctatac aatcgtttag     780
```

```
ccttgctgga cgaatctcaa ttatttaaac gagagtaaac atatttgact ttttggttat    840
ttaacaaatt attatttaac actatatgaa attttttttt ttatcagcaa agaataaaat    900
taaattaagg aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttttt agcagtaaag caatggttga   1080
ccgtgtgctt agcttctttt attttatttt tttatcagca aagaataaat aaaataaaat   1140
gagacacttc agggatgttt caacggatcc cccgggctgc aggaattcga tatcaagctt   1200
atcgataccg tcgacctcga ggggggggccc ggtacccaat cgccctata gtgagtcgta   1260
ttacgcgcgc tcactggccg tcgttttaca acgtcgtgac tgggaaaacc ctggcgttac   1320
ccaacttaat cgccttgcag cacatccccc tttcgccagc tggcgtaata gcgaagaggc   1380
ccgcaccgat cgcccttccc aacagttgcg cagcctgaat ggcgaatggg acgcgccctg   1440
tagcggcgca ttaagcgcgg cgggtgtggt ggttacgcgc agcgtgaccg ctacacttgc   1500
cagcgcccta gcgcccgctc ctttcgcttt cttcccttcc tttctcgcca cgttcgccgg   1560
ctttccccgt caagctctaa atcggggggct ccctttaggg ttccgattta gtgctttacg   1620
gcacctcgac cccaaaaaac ttgattaggg tgatggttca cgtagtgggc catcgccctg   1680
atagacggtt tttcgccctt tgacgttgga gtccacgttc tttaatagtg gactcttgtt   1740
ccaaactgga acaacactca accctatctc ggtctattct tttgatttat aagggatttt   1800
gccgatttcg gcctattggt taaaaaatga gctgatttaa caaaaattta acgcgaattt   1860
taacaaaata ttaacgctta caatttaggt ggcacttttc ggggaaatgt gcgcggaacc   1920
cctatttgtt tatttttcta aatacattca aatatgtatc cgctcatgag acaataaccc   1980
tgataaatgc ttcaataata ttgaaaaagg aagagtatga gtattcaaca tttccgtgtc   2040
gcccttattc cctttttttgc ggcattttgc cttcctgttt ttgctcaccc agaaacgctg   2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagc cggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tatactttag attgatttaa aacttcattt ttaatttaaa   2940
aggatctagg tgaagatcct ttttgataat ctcatgacca aaatccctta acgtgagttt   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactctttttt ccgaaggtaa ctggcttcag cagagcgcag   3180
```

```
ataccaaata ctgtccttct agtgtagccg tagttaggcc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccagggga    3540 aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg ccttttgct cacatgttct ttcctgcgtt atcccctgat     3720
tctgtggata accgtattac cgcctttgag tgagctgata ccgctcgccg cagccgaacg    3780
accgagcgca gcgagtcagt gagcgaggaa gcggaagagc gcccaatacg caaaccgcct    3840
ctccccgcgc gttggccgat tcattaatgc agctggcacg acaggtttcc cgactggaaa    3900
gcgggcagtg agcgcaacgc aattaatgtg agttagctca ctcattaggc accccaggct    3960
ttacacttta tgcttccggc tcgtatgttg tgtggaattg tgagcggata caatttcac     4020 acaggaaaca gctatgacca tgattacgcc aagcgcgcaa ttaaccctca ctaaagggaa    4080
caaaagctgg agctccaccc tagaactagt ggatccttca tccatgccct tcatttgccg    4140
cttattaatt aatttggtaa cagtccgtac taatcagtta cttatccttc ccccatcata    4200
attaatcttg gtagtctcga atgccacaac actgactagt ctcttggatc ataagaaaaa    4260
gccaaggaac aaaagaagac aaaacacaat gagagtatcc tttgcatagc aatgtctaag    4320
ttcataaaat tcaaacaaaa acgcaatcac acacagtgga catcacttat ccactagctg    4380
atcaggatcg ccgcgtcaag aaaaaaaaac tggacccccaa agccatgca caacaacacg     4440 tactcacaaa ggtgtcaatc gagcagccca aacattcac caactcaacc catcatgagc      4500
cctcacattt gttgtttcta acccaacctc aaactcgtat tctcttccgc cacctcattt    4560
ttgtttattt caacccccgt caaactgcat gccaccccgt ggccaaatgt ccatgcatgt    4620
taacaagacc tatgactata aatagctgca atctcggccc aggttttcat catcaagaac    4680
cagttcaata tcctagtaca ccgtattaaa gaatttaaga tatactccat ggagtccatt    4740
gctcccttcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggagtctccc    4920
ctggctcgag agctgcctct gatgaacccc ttccacgtgc tcctgatcgt gctcgcctac    4980
ctggtcaccg tgtttgtggg tatgcagatc atgaagaact tgaacgatt cgaggtcaag    5040 accttctccc tcctgcacaa cttctgtctg gtctccatct ccgcctacat gtgcggtggc    5100
atcctgtacg aggcttatca ggccaactat ggactgtttg agaacgctgc cgatcacacc    5160
ttcaagggtc tccctatggc taagatgatc tggctcttct acttctccaa gatcatggag    5220
tttgtcgaca ccatgatcat ggtcctcaag aagaacaacc gacagatttc ctttctgcac    5280
gtgtaccacc actcttccat cttcaccatc tggtggctgg tcaccttcgt tgctcccaac    5340
ggtgaagcct acttctctgc tgccctgaac tccttcatcc acgtcatcat gtacggctac    5400
tactttctgt ctgccctggg cttcaagcag gtgtcgttca tcaagttcta catcactcga    5460
tcccagatga cccagttctg catgatgtct gtccagtctt cctgggacat gtacgccatg    5520
aaggtccttg gccgacctgg ataccccttc ttcatcaccg ctctgctctg gttctacatg    5580
```

```
tggaccatgc tcggtctctt ctacaacttt taccgaaaga acgccaagct cgccaagcag    5640
gccaaggctg acgctgccaa ggagaaggcc agaaagctcc agtaagc                  5687

<210> SEQ ID NO 47
<211> LENGTH: 5687
<212> TYPE: DNA
<213> ORGANISM: Artificial sequence
<220> FEATURE:
<223> OTHER INFORMATION: plasmid KS374

<400> SEQUENCE: 47
ggccgcaagt atgaactaaa atgcacgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta actttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actacccatt tatatattat acttatccac     480
ttatttaatg tctttataag gtttgatcca tgatatttct aatatttag ttgatatgta      540 tatgaaaggg tactatttga actctcttac tctgtataaa ggttggatca tccttaaagt     600
gggtctattt aattttattg cttcttacag ataaaaaaaa aattatgagt tggtttgata     660
aaatattgaa ggatttaaaa taataataaa taacatataa tatatgtata taaatttatt     720
ataaataaac atttatctat aaaaaagtaa atattgtcat aaatctatac aatcgtttag     780
ccttgctgga cgaatctcaa ttatttaaac gagagtaaac atatttgact ttttggttat     840
ttaacaaatt attatttaac actatatgaa attttttttt ttatcagcaa agaataaaat     900
taaattaagg aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taaccctttt agcagtaaag caatggttga    1080
ccgtgtgctt agcttcttttt attttatttt tttatcagca aagaataaat aaaataaaat    1140
gagacacttc agggatgttt caacggatcc cccgggctgc aggaattcga tatcaagctt    1200
atcgataccg tcgacctcga ggggggggccc ggtacccaat tcgccctata gtgagtcgta    1260
ttacgcgcgc tcactggccg tcgttttaca acgtcgtgac tgggaaaacc ctggcgttac    1320
ccaacttaat cgccttgcag cacatccccc tttcgccagc tggcgtaata gcgaagaggc    1380
ccgcaccgat cgcccttccc aacagttgcg cagcctgaat ggcgaatggg acgcgccctg    1440
tagcggcgca ttaagcgcgg cgggtgtggt ggttacgcgc agcgtgaccg ctacacttgc    1500
cagcgcccta gcgcccgctc ctttcgcttt cttcccttcc tttctcgcca cgttcgccgg    1560
ctttccccgt caagctctaa atcgggggct ccctttaggg ttccgattta gtgctttacg    1620
gcacctcgac cccaaaaaac ttgattaggg tgatggttca cgtagtgggc catcgccctg    1680
atagacggtt tttcgccctt tgacgttgga gtccacgttc tttaatagtg gactcttgtt    1740
ccaaactgga acaacactca accctatctc ggtctattct tttgatttat aagggatttt    1800
gccgatttcg gcctattggt taaaaaatga gctgatttaa caaaaattta acgcgaattt    1860
taacaaaata ttaacgctta caatttaggt ggcacttttc ggggaaatgt gcgcggaacc    1920
cctatttgtt tatttttcta aatacattca aatatgtatc cgctcatgag acaataaccc    1980
```

```
tgataaatgc ttcaataata ttgaaaaagg aagagtatga gtattcaaca tttccgtgtc    2040
gcccttattc ccttttttgc ggcattttgc cttcctgttt ttgctcaccc agaaacgctg    2100
gtgaaagtaa aagatgctga agatcagttg ggtgcacgag tgggttacat cgaactggat    2160
ctcaacagcg gtaagatcct tgagagtttt cgccccgaag aacgttttcc aatgatgagc    2220
acttttaaag ttctgctatg tggcgcggta ttatcccgta ttgacgccgg gcaagagcaa    2280
ctcggtcgcc gcatacacta ttctcagaat gacttggttg agtactcacc agtcacagaa    2340
aagcatctta cggatggcat gacagtaaga gaattatgca gtgctgccat aaccatgagt    2400
gataacactg cggccaactt acttctgaca acgatcggag gaccgaagga gctaaccgct    2460
tttttgcaca acatggggga tcatgtaact cgccttgatc gttgggaacc ggagctgaat    2520
gaagccatac caaacgacga gcgtgacacc acgatgcctg tagcaatggc aacaacgttg    2580
cgcaaactat taactggcga actacttact ctagcttccc ggcaacaatt aatagactgg    2640
atggaggcgg ataaagttgc aggaccactt ctgcgctcgg cccttccggc tggctggttt    2700
attgctgata atctggagcc ggtgagcgt gggtctcgcg gtatcattgc agcactgggg    2760
ccagatggta agccctcccg tatcgtagtt atctacacga cggggagtca ggcaactatg    2820
gatgaacgaa atagacagat cgctgagata ggtgcctcac tgattaagca ttggtaactg    2880
tcagaccaag tttactcata tatactttag attgatttaa aacttcattt ttaatttaaa    2940
aggatctagg tgaagatcct ttttgataat ctcatgacca aaatccctta acgtgagttt    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
ataccaaata ctgtccttct agtgtagccg tagttaggcc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaagagc gcccaatacg caaaccgcct    3840
ctccccgcgc gttggccgat tcattaatgc agctggcacg acaggtttcc cgactggaaa    3900
gcgggcagtg agcgcaacgc aattaatgtg agttagctca ctcattaggc accccaggct    3960
ttacacttta tgcttccggc tcgtatgttg tgtggaattg tgagcggata acaatttcac    4020
acaggaaaca gctatgacca tgattacgcc aagcgcgcaa ttaaccctca ctaaagggaa    4080
caaaagctgg agctccaccc tagaactagt ggatccttca tccatgccct tcatttgccg    4140
cttattaatt aatttggtaa cagtccgtac taatcagtta cttatccttc ccccatcata    4200
attaatcttg gtagtctcga atgccacaac actgactagt ctcttggatc ataagaaaaa    4260 gccaggaac aaaagaagac aaaacacaat gagagtatcc tttgcatagc aatgtctaag    4320
ttcataaaat tcaaacaaaa acgcaatcac acacagtgga catcacttat ccactagctg    4380
```

```
atcaggatcg ccgcgtcaag aaaaaaaaac tggaccccaa aagccatgca caacaacacg   4440
tactcacaaa ggtgtcaatc gagcagccca aaacattcac caactcaacc catcatgagc   4500
cctcacattt gttgtttcta acccaacctc aaactcgtat tctcttccgc cacctcattt   4560
ttgtttattt caacacccgt caaactgcat gccacccgt ggccaaatgt ccatgcatgt   4620
taacaagacc tatgactata aatagctgca atctcggccc aggttttcat catcaagaac   4680
cagttcaata tcctagtaca ccgtattaaa gaatttaaga tatactccat ggagtccatt   4740
gctcccttcc tgccctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggagtctccc   4920
ctggctcgag agctgcctct gatgaacccc ttccacgtgc tcctgatcgt gctcgcctac   4980
ctggtcaccg tgtttgtggg tatgcagatc atgaagaact tgaacgatt cgaggtcaag   5040 acgtattcgc tcctgcacaa cttctgtctg gtctcgctga cgcctacat gtgcggtggc   5100 atcctgtacg aggctttcca ggccaactat ggactgtttg agaacgctgc cgatcacacc   5160
ttcaagggtc tccctatggc taagatgatc tggctcttct acttctccaa gatcatggag   5220
tttgtcgaca ccatgatcat ggtcctcaag aagaacaacc gacagatttc ctttctgcac   5280
gtgtaccacc actcttccat cttccaccatc tggtggctgg tcaccttcgt tgctcccaac   5340
ggtgaagcct acttctctgc tgccctgaac tcgttcatcc atgttatcat gtacggctac   5400
tactttctgt ctgccctggg cttcaagcag gtgtcgttca tcaagttcta catcactcga   5460
tcccagatga cccagttctg catgatgtct gtccagtctt cctgggacat gtacgccatg   5520
aaggtccttg ccgacctgg ataccccttc ttcatcgccg ctctgctctg gttctacatg   5580
tggaccatgc tcggtctctt ctacaacttt taccgaaaga cgccaagct cgccaagcag   5640 gccaaggctg acgctgccaa ggagaaggcc agaaagctcc agtaagc             5687
```

<210> SEQ ID NO 48
<211> LENGTH: 5687
<212> TYPE: DNA
<213> ORGANISM: Artificial sequence
<220> FEATURE:
<223> OTHER INFORMATION: plasmid KS375

<400> SEQUENCE: 48

```
catggagtcc attgttccct tcctgccctc caagatgcct caggacctgt tcatggacct     60
cgccagcgct atcggtgtcc gagctgctcc ctacgtcgat cccctggagg ctgccctggt    120
tgcccaggcc gagaagtaca ttcccaccat tgtccatcac actcgaggct tcctggttgc    180
cgtggattct cccctggctc gagagctgcc tctgatgaac ccccttccacg tgctcctgat    240 cgtgctcgcc tacctggtca ccgtgtttgt gggtatgcag atcatgaaga actttgaacg    300
attcgaggtc aagacgttct cgctcctgta caacttctgt ctggtctcgc tgagcgccta    360
catgtgcggt ggcattctgt acgaggcttt tcaggccaac tatggactgt ttgagaacgc    420
tgccgatcac accttcaagg gtctccctat ggctaagatg atctggctct tctacttctc    480
caagctgatg gagtttgtcg acaccatgat catggtcctc aaaaagaaca accgacagat    540
ttcctttctg cacgtgtacc accactcttc catcttcacc atctggtggc tggtcacctt    600
cgttgctccc aacggtgaag cctacttctc tgctgccctg aactcgttca tccatgttat    660
catgtacggc tactactttc tgtctgccct gggcttcaag caggtgtcgt tcatcaagtt    720
ctacatcact cgatcccaga tgacccagtt ctgcatgttg tctgtccagt cttcctggga    780
```

```
catgtacgcc atgaaggtcc ttggccgacc tggataccccc ttcttcctga ccgctctgct   840
ctggttctac atgtggacca tgctcggtct cttctacaac ttttaccgac gaaacgccaa   900
gctcgccaag caggccaagg ctgacgctgc caaggagaag gccagaaagc tccagtaagc   960
ggccgcaagt atgaactaaa atgcacgtag gtgtaagagc tcatggagag catggaatat  1020
tgtatccgac catgtaacag tataataact gagctccatc tcacttcttc tatgaataaa  1080
caaaggatgt tatgatatat taacactcta tctatgcacc ttattgttct atgataaatt  1140
tcctcttatt attataaatc atctgaatcg tgacggctta tggaatgctt caaatagtac  1200
aaaaacaaat gtgtactata agactttcta aacaattcta actttagcat tgtgaacgag  1260
acataagtgt taagaagaca taacaattat aatggaagaa gtttgtctcc atttatatat  1320
tatatattac ccacttatgt attatattag gatgttaagg agacataaca attataaaga  1380
gagaagtttg tatccattta tatattatat actacccatt tatatattat acttatccac  1440
ttatttaatg tctttataag gtttgatcca tgatatttct aatattttag ttgatatgta  1500
tatgaaaggg tactatttga actctcttac tctgtataaa ggttggatca tccttaaagt  1560
gggtctattt aattttattg cttcttacag ataaaaaaaa aattatgagt tggtttgata  1620
aaatattgaa ggatttaaaa taataataaa taacatataa tatatgtata taaatttatt  1680
ataaatataac atttatctat aaaaaagtaa atattgtcat aaatctatac aatcgtttag  1740
ccttgctgga cgaatctcaa ttatttaaac gagagtaaac atatttgact ttttggttat  1800
ttaacaaatt attatttaac actatatgaa attttttttt ttatcagcaa agaataaaat  1860
taaattaagg aggacaatgg tgtcccaatc cttatacaac caacttccac aagaaagtca  1920
agtcagagac aacaaaaaaa caagcaaagg aaatttttta atttgagttg tcttgtttgc  1980
tgcataattt atgcagtaaa acactacaca taacccttttt agcagtaaag caatggttga  2040
ccgtgtgctt agcttctttt attttatttt tttatcagca aagaataaat aaaataaaat  2100
gagacacttc agggatgttt caacggatcc cccgggctgc aggaattcga tatcaagctt  2160
atcgataccg tcgacctcga gggggggccc ggtacccaat tcgccctata gtgagtcgta  2220
ttacgcgcgc tcactggccg tcgttttaca acgtcgtgac tgggaaaacc ctggcgttac  2280
ccaacttaat cgccttgcag cacatccccc tttcgccagc tggcgtaata gcgaagaggc  2340
ccgcaccgat cgcccttccc aacagttgcg cagcctgaat ggcgaatggg acgcgccctg  2400
tagcggcgca ttaagcgcgg cgggtgtggt ggttacgcgc agcgtgaccg ctacacttgc  2460
cagcgcccta gcgcccgctc ctttcgcttt cttcccttcc tttctcgcca cgttcgccgg  2520
ctttccccgt caagctctaa atcggggggct cccctttaggg ttccgattta gtgctttacg  2580
gcacctcgac cccaaaaaac ttgattaggg tgatggttca cgtagtgggc catcgccctg  2640
atagacggtt tttcgccctt tgacgttgga gtccacgttc tttaatagtg gactcttgtt  2700
ccaaactgga acaacactca accctatctc ggtctattct tttgatttat aagggatttt  2760
gccgatttcg gcctattggt taaaaaatga gctgatttaa caaaaattta acgcgaattt  2820
taacaaaata ttaacgctta caatttaggt ggcactttte ggggaaatgt gcgcggaacc  2880
cctatttgtt tatttttcta aatacattca aatatgtatc cgctcatgag acaataaccc  2940
tgataaatgc ttcaataata ttgaaaaagg aagagtatga gtattcaaca tttccgtgtc  3000
gcccttattc cctttttttgc ggcattttgc cttcctgttt ttgctcaccc agaaacgctg  3060
gtgaaagtaa aagatgctga agatcagttg ggtgcacgag tgggttacat cgaactggat  3120
ctcaacagcg gtaagatcct tgagagtttt cgccccgaag aacgttttcc aatgatgagc  3180
```

```
acttttaaag ttctgctatg tggcgcggta ttatcccgta ttgacgccgg gcaagagcaa    3240
ctcggtcgcc gcatacacta ttctcagaat gacttggttg agtactcacc agtcacagaa    3300
aagcatctta cggatggcat gacagtaaga gaattatgca gtgctgccat aaccatgagt    3360
gataacactg cggccaactt acttctgaca acgatcggag gaccgaagga gctaaccgct    3420
tttttgcaca acatggggga tcatgtaact cgccttgatc gttgggaacc ggagctgaat    3480
gaagccatac caaacgacga gcgtgacacc acgatgcctg tagcaatggc aacaacgttg    3540
cgcaaactat taactggcga actacttact ctagcttccc ggcaacaatt aatagactgg    3600
atggaggcgg ataaagttgc aggaccactt ctgcgctcgg cccttccggc tggctggttt    3660
attgctgata atctggagc cggtgagcgt gggtctcgcg gtatcattgc agcactgggg    3720
ccagatggta agccctcccg tatcgtagtt atctacacga cggggagtca ggcaactatg    3780
gatgaacgaa atagacagat cgctgagata ggtgcctcac tgattaagca ttggtaactg    3840
tcagaccaag tttactcata tatactttag attgatttaa aacttcattt ttaatttaaa    3900
aggatctagg tgaagatcct ttttgataat ctcatgacca aaatccctta acgtgagttt    3960
tcgttccact gagcgtcaga ccccgtgaaa aagatcaaag gatcttcttg agatccttt    4020 tttctgcgcg taatctgctg cttgcaaaca aaaaaaccac cgctaccagc ggtggtttgt    4080
ttgccggatc aagagctacc aactctttt ccgaaggtaa ctggcttcag cagagcgcag    4140
ataccaaata ctgtccttct agtgtagccg tagttaggcc accacttcaa gaactctgta    4200
gcaccgccta catacctcgc tctgctaatc ctgttaccag tggctgctgc cagtggcgat    4260
aagtcgtgtc ttaccgggtt ggactcaaga cgatagttac cggataaggc gcagcggtcg    4320
ggctgaacgg ggggttcgtg cacacagccc agcttggagc gaacgaccta caccgaactg    4380
agatacctac agcgtgagct atgagaaagc gccacgcttc ccgaagggag aaaggcggac    4440
aggtatccgg taagcggcag ggtcggaaca ggagagcgca cgagggagct tccaggggga    4500
aacgcctggt atctttatag tcctgtcggg tttcgccacc tctgacttga gcgtcgattt    4560
ttgtgatgct cgtcaggggg gcggagccta tggaaaaacg ccagcaacgc ggcctttta    4620 cggttcctgg ccttttgctg gccttttgct cacatgttct ttcctgcgtt atcccctgat    4680
tctgtggata accgtattac cgcctttgag tgagctgata ccgctcgccg cagccgaacg    4740
accgagcgca gcgagtcagt gagcgaggaa gcggaagagc gcccaatacg caaaccgcct    4800
ctccccgcgc gttggccgat tcattaatgc agctggcacg acaggtttcc cgactggaaa    4860
gcgggcagtg agcgcaacgc aattaatgtg agttagctca ctcattaggc accccaggct    4920
ttacacttta tgcttccggc tcgtatgttg tgtggaattg tgagcggata acaatttcac    4980
acaggaaaca gctatgacca tgattacgcc aagcgcgcaa ttaaccctca ctaagggaa    5040 caaaagctgg agctccaccc tagaactagt ggatccttca tccatgccct tcatttgccg    5100
cttattaatt aatttggtaa cagtccgtac taatcagtta cttatccttc ccccatcata    5160
attaatcttg gtagtctcga atgccacaac actgactagt ctcttggatc ataagaaaaa    5220
gccaaggaac aaaagaagac aaaacacaat gagagtatcc tttgcatagc aatgtctaag    5280
ttcataaaat tcaaacaaaa acgcaatcac acacagtgga catcacttat ccactagctg    5340
atcaggatcg ccgcgtcaag aaaaaaaac tggaccccaa aagccatgca caacaacacg    5400
tactcacaaa ggtgtcaatc gagcagccca aaacattcac caactcaacc catcatgagc    5460
cctcacattt gttgtttcta acccaacctc aaactcgtat tctcttccgc cacctcattt    5520
ttgtttattt caacacccgt caaactgcat gccaccccgt ggccaaatgt ccatgcatgt    5580
```

-continued

| | |
|---|---|
| taacaagacc tatgactata aatagctgca atctcggccc aggttttcat catcaagaac | 5640 |
| cagttcaata tcctagtaca ccgtattaaa gaatttaaga tatactc | 5687 |

<210> SEQ ID NO 49
<211> LENGTH: 5687
<212> TYPE: DNA
<213> ORGANISM: Artificial sequence
<220> FEATURE:
<223> OTHER INFORMATION: plasmid KS380

<400> SEQUENCE: 49

| | |
|---|---|
| ggccgcaagt atgaactaaa atgcacgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta actttagcat tgtgaacgag | 300 |
| acataagtgt taagaagaca taacaattat aatggaagaa gtttgtctcc atttatatat | 360 |
| tatatattac ccactatgt attatattag gatgttaagg agacataaca attataaaga | 420 |
| gagaagtttg tatccattta tatattatat actacccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttccttacag ataaaaaaaa aattatgagt tggtttgata | 660 |
| aaatattgaa ggatttaaaa taataataaa taacatataa tatatgtata taaatttatt | 720 |
| ataatataac atttatctat aaaaaagtaa atattgtcat aaatctatac aatcgtttag | 780 |
| ccttgctgga cgaatctcaa ttatttaaac gagagtaaac atatttgact ttttggttat | 840 |
| ttaacaaatt attatttaac actatatgaa attttttttt ttatcagcaa agaataaaat | 900 |
| taaattaagg aggacaatgg tgtcccaatc cttatacaac caacttccac aagaaagtca | 960 |
| agtcagagac aacaaaaaaa caagcaaagg aaatttttta atttgagttg tcttgtttgc | 1020 |
| tgcataattt atgcagtaaa acactacaca taacccttt agcagtaaag caatggttga | 1080 |
| ccgtgtgctt agcttctttt atttttatttt tttatcagca aagaataaat aaaataaaat | 1140 |
| gagacacttc agggatgttt caacggatcc cccgggctgc aggaattcga tatcaagctt | 1200 |
| atcgataccg tcgacctcga ggggggggccc ggtacccaat tcgccctata gtgagtcgta | 1260 |
| ttacgcgcgc tcactggccg tcgttttaca acgtcgtgac tgggaaaacc ctggcgttac | 1320 |
| ccaacttaat cgccttgcag cacatccccc tttcgccagc tggcgtaata gcgaagaggc | 1380 |
| ccgcaccgat cgcccttccc aacagttgcg cagcctgaat ggcgaatggg acgcgccctg | 1440 |
| tagcggcgca ttaagcgcgg cgggtgtggt ggttacgcgc agcgtgaccg ctacacttgc | 1500 |
| cagcgcccta gcgcccgctc ctttcgcttt cttcccttcc tttctcgcca cgttcgccgg | 1560 |
| ctttccccgt caagctctaa atcgggggct ccctttaggg ttccgattta gtgctttacg | 1620 |
| gcacctcgac cccaaaaaac ttgattaggg tgatggttca cgtagtgggc catcgccctg | 1680 |
| atagacggtt tttcgccctt tgacgttgga gtccacgttc tttaatagtg gactcttgtt | 1740 |
| ccaaactgga acaacactca accctatctc ggtctattct tttgatttat aagggatttt | 1800 |
| gccgatttcg gcctattggt taaaaaatga gctgatttaa caaaaattta acgcgaattt | 1860 |
| taacaaaata ttaacgctta caatttaggt ggcacttttc ggggaaatgt gcgcggaacc | 1920 |
| cctatttgtt tatttttcta aatacattca aatatgtatc cgctcatgag acaataaccc | 1980 |

-continued

```
tgataaatgc ttcaataata ttgaaaaagg aagagtatga gtattcaaca tttccgtgtc    2040
gcccttattc ccttttttgc ggcattttgc cttcctgttt ttgctcaccc agaaacgctg    2100
gtgaaagtaa aagatgctga agatcagttg ggtgcacgag tgggttacat cgaactggat    2160
ctcaacagcg gtaagatcct tgagagtttt cgccccgaag aacgttttcc aatgatgagc    2220
acttttaaag ttctgctatg tggcgcggta ttatcccgta ttgacgccgg gcaagagcaa    2280
ctcggtcgcc gcatacacta ttctcagaat gacttggttg agtactcacc agtcacagaa    2340
aagcatctta cggatggcat gacagtaaga gaattatgca gtgctgccat aaccatgagt    2400
gataacactg cggccaactt acttctgaca acgatcggag gaccgaagga gctaaccgct    2460
tttttgcaca acatggggga tcatgtaact cgccttgatc gttgggaacc ggagctgaat    2520
gaagccatac caaacgacga gcgtgacacc acgatgcctg tagcaatggc aacaacgttg    2580
cgcaaactat taactggcga actacttact ctagcttccc ggcaacaatt aatagactgg    2640
atggaggcgg ataaagttgc aggaccactt ctgcgctcgg cccttccggc tggctggttt    2700
attgctgata atctggagcc ggtgagcgt gggtctcgcg gtatcattgc agcactgggg    2760
ccagatggta agccctcccg tatcgtagtt atctacacga cggggagtca ggcaactatg    2820
gatgaacgaa atagacagat cgctgagata ggtgcctcac tgattaagca ttggtaactg    2880
tcagaccaag tttactcata tactttag attgatttaa aacttcattt ttaatttaaa    2940
aggatctagg tgaagatcct ttttgataat ctcatgacca aaatcccctta acgtgagttt    3000 tcgttccact gagcgtcaga ccccgtagaa aagatcaaag gatcttcttg agatccttt    3060 tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgtccttct agtgtagccg tagttaggcc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaagagc gcccaatacg caaaccgcct    3840
ctccccgcgc gttggccgat tcattaatgc agctggcacg acaggtttcc cgactggaaa    3900
gcgggcagtg agcgcaacgc aattaatgtg agttagctca ctcattaggc accccaggct    3960
ttacacttta tgcttccggc tcgtatgttg tgtggaattg tgagcggata acaatttcac    4020
acaggaaaca gctatgacca tgattacgcc aagcgcgcaa ttaaccctca ctaaagggaa    4080
caaaagctgg agctccaccc tagaactagt ggatccttca tccatgccct tcatttgccg    4140
cttattaatt aatttggtaa cagtccgtac taatcagtta cttatccttc ccccatcata    4200
attaatcttg gtagtctcga atgccacaac actgactagt ctcttggatc ataagaaaaa    4260
gccaaggaac aaaagaagac aaaacacaat gagagtatcc tttgcatagc aatgtctaag    4320
ttcataaaat tcaaacaaaa acgcaatcac acacagtgga catcacttat ccactagctg    4380
```

```
atcaggatcg ccgcgtcaag aaaaaaaaac tggaccccaa aagccatgca caacaacacg   4440
tactcacaaa ggtgtcaatc gagcagccca aacattcac caactcaacc catcatgagc    4500
cctcacattt gttgtttcta acccaacctc aaactcgtat tctcttccgc cacctcattt   4560
ttgtttattt caacacccgt caaactgcat gccacccgt ggccaaatgt ccatgcatgt    4620
taacaagacc tatgactata aatagctgca atctcggccc aggttttcat catcaagaac   4680
cagttcaata tcctagtaca ccgtattaaa gaatttaaga tatactccat ggagtccatt   4740
gttcccttcc tgccctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggattctccc   4920
ctggctcgag agctgcctct gatgaacccc ttccacgtgc tcctgattgt gctcgcctac   4980
ctggtcaccg tgtttgtggg tatgcagatc atgaagaact ttgaacgatt cgaggtcaag   5040
acgttctcgc tcctgtacaa cttctgtctg gtctcgctga gcgcctacat gtgcggtggc   5100
attctgtacg aggcttttca ggccaactat ggactgtttg agaacgctgc cgatcacacc   5160
ttcaagggtc tccctatggc taagatgatc tggctcttct acttctccaa gctgatggag   5220
tttgtcgaca cccttatcat ggtcctcaag aagaacaacc gacagatttc ctttctgcac   5280
gtgtaccacc actcttccat cttccaccatc tggtggctgg tcaccttcgt tgctcccaac   5340
ggtgaggcct acttctctgc tgccctgaac tcgttcatcc atgttatcat gtacggctac   5400
tactttctgt ctgccctggg cttcaagcag gtgtcgttca tcaagttcta catcactcga   5460
tcccagatga cccagttctg catgttgtct gtccagtctt cctgggacat gtacgccatg   5520
aaggtccttg ccgacctgg ataccccttc ttcctgaccg ctctgctctg gttctacatg    5580
tggaccatgc tcggtctctt ctacaacttt taccgacgaa acgccaagct cgccaagcag   5640
gccaaggctg acgctgccaa ggagaaggcc agaaagctcc agtaagc                5687
```

<210> SEQ ID NO 50
<211> LENGTH: 5687
<212> TYPE: DNA
<213> ORGANISM: Artificial sequence
<220> FEATURE:
<223> OTHER INFORMATION: plasmid KS382

<400> SEQUENCE: 50

```
ggccgcaagt atgaactaaa atgcacgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta actttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatatttag ttgatatgta    540 tatgaaaggg tactatttga actctcttac tctgtataaa ggttggatca tccttaaagt    600
gggtctattt aatttttattg cttcttacag ataaaaaaaa aattatgagt tggtttgata   660
aaatattgaa ggatttaaaa taataataaa taacatataa tatatgtata taaatttatt    720
ataatataac atttatctat aaaaagtaa atattgtcat aaatctatac aatcgtttag    780
```

```
ccttgctgga cgaatctcaa ttatttaaac gagagtaaac atatttgact ttttggttat     840
ttaacaaatt attatttaac actatatgaa atttttttt ttatcagcaa agaataaaat     900
taaattaagg aggacaatgg tgtcccaatc cttatacaac caacttccac aagaaagtca     960
agtcagagac aacaaaaaaa caagcaaagg aaatttttta atttgagttg tcttgtttgc    1020
tgcataattt atgcagtaaa acactacaca taacccttt agcagtaaag caatggttga     1080
ccgtgtgctt agcttctttt attttatttt tttatcagca aagaataaat aaaataaaat    1140
gagacacttc agggatgttt caacggatcc cccgggctgc aggaattcga tatcaagctt    1200
atcgataccg tcgacctcga ggggggggccc ggtacccaat cgccctata gtgagtcgta    1260
ttacgcgcgc tcactggccg tcgttttaca acgtcgtgac tgggaaaacc ctggcgttac    1320
ccaacttaat cgccttgcag cacatccccc tttcgccagc tggcgtaata gcgaagaggc    1380
ccgcaccgat cgcccttccc aacagttgcg cagcctgaat ggcgaatggg acgcgcctg     1440
tagcggcgca ttaagcgcgg cgggtgtggt ggttacgcgc agcgtgaccg ctacacttgc    1500
cagcgcccta gcgcccgctc ctttcgcttt cttcccttcc tttctcgcca cgttcgccgg    1560
ctttccccgt caagctctaa atcggggggct ccctttaggg ttccgattta gtgctttacg    1620
gcacctcgac cccaaaaaac ttgattaggg tgatggttca cgtagtgggc catcgccctg    1680
atagacggtt tttcgccctt tgacgttgga gtccacgttc tttaatagtg gactcttgtt    1740
ccaaactgga acaacactca accctatctc ggtctattct tttgatttat aagggatttt    1800
gccgatttcg gcctattggt taaaaaatga gctgatttaa caaaaattta acgcgaattt    1860
taacaaaata ttaacgctta caatttaggt ggcacttttc ggggaaatgt gcgcggaacc    1920
cctatttgtt tatttttcta aatacattca aatatgtatc cgctcatgag acaataaccc    1980
tgataaatgc ttcaataata ttgaaaaagg aagagtatga gtattcaaca tttccgtgtc    2040
gcccttattc ccttttttgc ggcatttttgc cttcctgttt ttgctcaccc agaaacgctg    2100
gtgaaagtaa aagatgctga agatcagttg ggtgcacgag tgggttacat cgaactggat    2160
ctcaacagcg gtaagatcct tgagagtttt cgccccgaag aacgttttcc aatgatgagc    2220
acttttaaag ttctgctatg tggcgcggta ttatcccgta ttgacgccgg gcaagagcaa    2280
ctcggtcgcc gcatacacta ttctcagaat gacttggttg agtactcacc agtcacagaa    2340
aagcatctta cggatggcat gacagtaaga gaattatgca gtgctgccat aaccatgagt    2400
gataacactg cggccaactt acttctgaca acgatcggag gaccgaagga gctaaccgct    2460
tttttgcaca acatggggga tcatgtaact cgccttgatc gttgggaacc ggagctgaat    2520
gaagccatac caaacgacga gcgtgacacc acgatgcctg tagcaatggc aacaacgttg    2580
cgcaaactat taactggcga actacttact ctagcttccc ggcaacaatt aatagactgg    2640
atggaggcgg ataaagttgc aggaccactt ctgcgctcgg cccttccggc tggctggttt    2700
attgctgata atctggagc cggtgagcgt gggtctcgcg gtatcattgc agcactgggg    2760
ccagatggta agccctcccg tatcgtagtt atctacacga cggggagtca ggcaactatg    2820
gatgaacgaa atagacagat cgctgagata ggtgcctcac tgattaagca ttggtaactg    2880
tcagaccaag tttactcata tatactttag attgatttaa aacttcattt ttaatttaaa    2940
aggatctagg tgaagatcct ttttgataat ctcatgacca aaatccctta acgtgagttt    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactctttt ccgaaggtaa ctggcttcag cagagcgcag    3180
```

```
ataccaaata ctgtccttct agtgtagccg tagttaggcc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggccttttta    3660
cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaagagc gcccaatacg caaaccgcct    3840
ctccccgcgc gttggccgat tcattaatgc agctggcacg acaggtttcc cgactggaaa    3900
gcgggcagtg agcgcaacgc aattaatgtg agttagctca ctcattaggc accccaggct    3960
ttacacttta tgcttccggc tcgtatgttg tgtggaattg tgagcggata acaatttcac    4020
acaggaaaca gctatgacca tgattacgcc aagcgcgcaa ttaaccctca ctaagggaa    4080 caaaagctgg agctccaccc tagaactagt ggatccttca tccatgccct tcatttgccg    4140
cttattaatt aatttggtaa cagtccgtac taatcagtta cttatccttc ccccatcata    4200
attaatcttg gtagtctcga atgccacaac actgactagt ctcttggatc ataagaaaaa    4260
gccaaggaac aaaagaagac aaaacacaat gagagtatcc tttgcatagc aatgtctaag    4320
ttcataaaat tcaaacaaaa acgcaatcac acacagtgga catcacttat ccactagctg    4380
atcaggatcg ccgcgtcaag aaaaaaaaac tggaccccaa aagccatgca caacaacacg    4440
tactcacaaa ggtgtcaatc gagcagccca aaacattcac caactcaacc catcatgagc    4500
cctcacattt gttgtttcta acccaacctc aaactcgtat tctcttccgc cacctcattt    4560
ttgtttattt caacccccgt caaactgcat gccaccccgt ggccaaatgt ccatgcatgt    4620
taacaagacc tatgactata aatagctgca atctcggccc aggttttcat catcaagaac    4680
cagttcaata tccagtaca ccgtattaaa gaatttaaga tatactccat ggagtccatt    4740
gttcccttcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggattctccc    4920
ctggctcgag agctgcctct gatgaacccc ttccacgtgc tcctgatcgt gctcgcctac    4980
ctggtcaccg tgtttgtggg tatgcagatc atgaagaact ttgaacgatt cgaggtcaag    5040
acgttctcgc tcctgtacaa cttctgtctg gtctcgctga gcgcctacat gtgcggtggc    5100
attctgtacg aggcttatca ggccaactat ggactgtttc agaacgctgc cgatcacacc    5160
ttcaagggtc tccctatggc taagatgatc tggctcttct acttctccaa gctgatggag    5220
tttgtcgaca ccatgatcat ggtcctcaaa aagaacaacc gacagatttc ctttctgcac    5280
gtgtaccacc actcttccat cttcaccatc tggtggctgg tcaccttcgt tgctcccaac    5340
ggtgaagcct acttctctgc tgccctgaac tcgttcatcc atgttatcat gtacggctac    5400
tactttctgt ctgccctggg cttcaagcag gtgtcgttca tcaagttcta catcactcga    5460
tcccagatga cccagttctg catgttgtct gtccagtctt cctgggacat gtacgccatg    5520
aaggtccttg gccgacctgg ataccccttc ttcctgaccg ctctgctctg gttctacatg    5580
```
tggaccatgc tcggtctctt ctacaacttt taccgaaaga acgccaagct cgccaagcag  5640
gccaaggctg acgctgccaa ggagaaggcc agaaagctcc agtaagc  5687

<210> SEQ ID NO 51
<211> LENGTH: 5687
<212> TYPE: DNA
<213> ORGANISM: Artificial sequence
<220> FEATURE:
<223> OTHER INFORMATION: plasmid KS383

<400> SEQUENCE: 51

| | | | | | |
|---|---|---|---|---|---|
| ggccgcaagt | atgaactaaa | atgcacgtag | gtgtaagagc | tcatggagag | catggaatat | 60 |
| tgtatccgac | catgtaacag | tataataact | gagctccatc | tcacttcttc | tatgaataaa | 120 |
| caaaggatgt | tatgatatat | taacactcta | tctatgcacc | ttattgttct | atgataaatt | 180 |
| tcctcttatt | attataaatc | atctgaatcg | tgacggctta | tggaatgctt | caaatagtac | 240 |
| aaaaacaaat | gtgtactata | agactttcta | aacaattcta | actttagcat | tgtgaacgag | 300 |
| acataagtgt | taagaagaca | taacaattat | aatggaagaa | gtttgtctcc | atttatatat | 360 |
| tatatattac | ccactatgt | attatattag | gatgttaagg | agacataaca | attataaaga | 420 |
| gagaagtttg | tatccattta | tatattat | actacccatt | tatatattat | acttatccac | 480 |
| ttatttaatg | tctttataag | gtttgatcca | tgatatttct | aatatttag | ttgatatgta | 540 |
| tatgaaaggg | tactatttga | actctcttac | tctgtataaa | ggttggatca | tccttaaagt | 600 |
| gggtctattt | aatttattg | cttccttacag | ataaaaaaaa | aattatgagt | tggtttgata | 660 |
| aaatattgaa | ggatttaaaa | taataataaa | taacatataa | tatatgtata | taaatttatt | 720 |
| ataaatataac | atttatctat | aaaaaagtaa | atattgtcat | aaatctatac | aatcgtttag | 780 |
| ccttgctgga | cgaatctcaa | ttatttaaac | gagagtaaac | atatttgact | ttttggttat | 840 |
| ttaacaaatt | attatttaac | actatatgaa | attttttttt | ttatcagcaa | agaataaaat | 900 |
| taaattaagg | aggacaatgg | tgtcccaatc | cttatacaac | caacttccac | aagaaagtca | 960 |
| agtcagagac | aacaaaaaaa | caagcaaagg | aaattttta | atttgagttg | tcttgtttgc | 1020 |
| tgcataattt | atgcagtaaa | acactacaca | taacccttt | agcagtaaag | caatggttga | 1080 |
| ccgtgtgctt | agcttctttt | atttatttt | tttatcagca | aagaataaat | aaaataaat | 1140 |
| gagacacttc | agggatgttt | caacggatcc | cccgggctgc | aggaattcga | tatcaagctt | 1200 |
| atcgataccg | tcgacctcga | gggggggccc | ggtacccaat | tcgccctata | gtgagtcgta | 1260 |
| ttacgcgcgc | tcactggccg | tcgttttaca | acgtcgtgac | tgggaaaacc | ctggcgttac | 1320 |
| ccaacttaat | cgccttgcag | cacatccccc | tttcgccagc | tggcgtaata | gcgaagaggc | 1380 |
| ccgcaccgat | cgcccttccc | aacagttgcg | cagcctgaat | ggcgaatggg | acgcgccctg | 1440 |
| tagcggcgca | ttaagcgcgg | cgggtgtggt | ggttacgcgc | agcgtgaccg | ctacacttgc | 1500 |
| cagcgcccta | gcgcccgctc | ctttcgcttt | cttcccttcc | tttctcgcca | cgttcgccgg | 1560 |
| ctttccccgt | caagctctaa | atcgggggct | ccctttaggg | ttccgattta | gtgctttacg | 1620 |
| gcacctcgac | cccaaaaaac | ttgattaggg | tgatggttca | cgtagtgggc | catcgccctg | 1680 |
| atagacggtt | tttcgccctt | tgacgttgga | gtccacgttc | tttaatagtg | gactcttgtt | 1740 |
| ccaaactgga | acaacactca | accctatctc | ggtctattct | tttgatttat | aagggatttt | 1800 |
| gccgatttcg | gcctattggt | taaaaaatga | gctgatttaa | caaaaattta | acgcgaattt | 1860 |
| taacaaaata | ttaacgctta | caatttaggt | ggcacttttc | ggggaaatgt | gcgcggaacc | 1920 |
| cctatttgtt | tattttccta | aatacattca | aatatgtatc | cgctcatgag | acaataaccc | 1980 |

```
tgataaatgc ttcaataata ttgaaaaagg aagagtatga gtattcaaca tttccgtgtc   2040
gcccttattc cctttttgc ggcattttgc cttcctgttt ttgctcaccc agaaacgctg    2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagc cggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tactttag attgatttaa aacttcattt ttaatttaaa    2940
aggatctagg tgaagatcct ttttgataat ctcatgacca aaatccctta acgtgagttt   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactcttttt ccgaaggtaa ctggcttcag cagagcgcag   3180
ataccaaata ctgtccttct agtgtagccg tagttaggcc accacttcaa gaactctgta   3240
gcaccgccta catacctcgc tctgctaatc ctgttaccag tggctgctgc cagtggcgat   3300
aagtcgtgtc ttaccgggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcaggggg gcggagccta tggaaaaacg ccagcaacgc ggccttttta   3660
cggttcctgg ccttttgctg ccttttgct cacatgttct ttcctgcgtt atcccctgat   3720
tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900
gcgggcagtg agcgcaacgc aattaatgtg agttagctca ctcattaggc accccaggct   3960
ttacacttta tgcttccggc tcgtatgttg tgtggaattg tgagcggata caatttcac    4020 acaggaaaca gctatgacca tgattacgcc aagcgcgcaa ttaaccctca ctaaagggaa   4080
caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
```

```
atcaggatcg ccgcgtcaag aaaaaaaaac tggaccccaa aagccatgca caacaacacg    4440
tactcacaaa ggtgtcaatc gagcagccca aacattcac caactcaacc catcatgagc     4500
cctcacattt gttgtttcta acccaacctc aaactcgtat tctcttccgc cacctcattt    4560
ttgtttattt caacacccgt caaactgcat gccaccccgt ggccaaatgt ccatgcatgt    4620
taacaagacc tatgactata aatagctgca atctcggccc aggttttcat catcaagaac    4680
cagttcaata tcctagtaca ccgtattaaa gaatttaaga tatactccat ggagtccatt    4740
gttcccttcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggagtctccc    4920
ctggctcgag agctgcctct gatgaacccc ttccacgtgc tcatgcttgt gctcgcctac    4980
ctggtcaccg tgtttgtggg tatgcagatc atgaagaact ttgaacgatt cgaggtcaag    5040
acgttctcgc tcctgtacaa cttctgtctg gtctcgctga gcgcctacat gtgcggtggc    5100
attctgtacg aggcttttca ggccaactat ggactgtttg agaacgctgc cgatcacacc    5160
ttcaagggtc tccctatggc taagatgatc tggctcttct acttctccaa gctgatggag    5220
tttgtcgaca ccatgatcat ggtcctcaaa agaacaacc gacagatttc ctttctgcac     5280
gtgtaccacc actcttccat cttcaccatc tggtggctgg tcaccttcgt tgctcccaac    5340
ggtgaagcct ggttctctgc tgccctgaac tcgttcatcc atgttatcat gtacggctac    5400
tactttctgt ctgccctggg cttcaagcag gtgtcgctga tcaagttcta cctgactcga    5460
tcccagatga cccagttctg catgttgtct gtccagtctt cctgggacat gtacgccatg    5520
aaggtccttg gccgacctgg ataccccttc ttcctgaccg ctctgctctg gttctacatg    5580
tggaccatgc tcggtctctt ctacaacttt taccgacgaa acgccaagct cgccaagcag    5640
gccaaggctg acgctgccaa ggagaaggcc agaaagctcc agtaagc                  5687

<210> SEQ ID NO 52
<211> LENGTH: 5687
<212> TYPE: DNA
<213> ORGANISM: Artificial sequence
<220> FEATURE:
<223> OTHER INFORMATION: plasmid KS384

<400> SEQUENCE: 52
ggccgcaagt atgaactaaa atgcacgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta actttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatatttag ttgatatgta     540 tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaagtaa atattgtcat aaatctatac aatcgtttag     780
```

```
ccttgctgga cgaatctcaa ttatttaaac gagagtaaac atatttgact ttttggttat    840
ttaacaaatt attatttaac actatatgaa attttttttt ttatcagcaa agaataaaat    900
taaattaagg aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttt agcagtaaag caatggttga   1080
ccgtgtgctt agcttctttt atttatttt tttatcagca aagaataaat aaaataaaat   1140
gagacacttc agggatgttt caacggatcc cccgggctgc aggaattcga tatcaagctt   1200
atcgataccg tcgacctcga gggggggccc ggtacccaat tcgccctata gtgagtcgta   1260
ttacgcgcgc tcactggccg tcgttttaca acgtcgtgac tgggaaaacc ctggcgttac   1320
ccaacttaat cgccttgcag cacatccccc tttcgccagc tggcgtaata gcgaagaggc   1380
ccgcaccgat cgcccttccc aacagttgcg cagcctgaat ggcgaatggg acgcgcctg   1440
tagcggcgca ttaagcgcgg cgggtgtggt ggttacgcgc agcgtgaccg ctacacttgc   1500
cagcgcccta gcgcccgctc ctttcgcttt cttcccttcc tttctcgcca cgttcgccgg   1560
ctttccccgt caagctctaa atcggggct cctttaggg ttccgattta gtgctttacg   1620
gcacctcgac cccaaaaaac ttgattaggg tgatggttca cgtagtgggc catcgccctg   1680
atagacggtt tttcgccctt tgacgttgga gtccacgttc tttaatagtg gactcttgtt   1740
ccaaactgga acaacactca accctatctc ggtctattct tttgatttat aagggatttt   1800
gccgatttcg gcctattggt taaaaaatga gctgatttaa caaaaattta acgcgaattt   1860
taacaaaata ttaacgctta caatttaggt ggcacttttc ggggaaatgt gcgcggaacc   1920
cctatttgtt tatttttcta aatacattca aatatgtatc cgctcatgag acaataaccc   1980
tgataaatgc ttcaataata ttgaaaaagg aagagtatga gtattcaaca tttccgtgtc   2040
gcccttattc cctttttgc ggcattttgc cttcctgttt ttgctcaccc agaaacgctg   2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagc cggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tatactttag attgatttaa aacttcattt ttaatttaaa   2940
aggatctagg tgaagatcct ttttgataat ctcatgacca aaatccctta acgtgagttt   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactcttttt ccgaaggtaa ctggcttcag cagagcgcag   3180
```

```
ataccaaata ctgtccttct agtgtagccg tagttaggcc accacttcaa gaactctgta   3240
gcaccgccta catacctcgc tctgctaatc ctgttaccag tggctgctgc cagtggcgat   3300
aagtcgtgtc ttaccggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcagggg gcggagccta tggaaaaacg ccagcaacgc ggccttttta   3660
cggttcctgg ccttttgctg ccttttgct cacatgttct ttcctgcgtt atcccctgat   3720
tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900 gcggcagtg agcgcaacgc aattaatgtg agttagctca ctcattaggc accccaggct   3960 ttacactta tgcttccggc tcgtatgttg tgtggaattg tgagcggata caatttcac   4020 acaggaaaca gctatgacca tgattacgcc aagcgcgcaa ttaaccctca ctaagggaa   4080 caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
atcaggatcg ccgcgtcaag aaaaaaaaac tggaccccaa aagccatgca caacaacacg   4440
tactcacaaa ggtgtcaatc gagcagccca aaacattcac caactcaacc catcatgagc   4500
cctcacattt gttgtttcta acccaacctc aaactcgtat tctcttccgc cacctcatt   4560 ttgtttattt caacccccgt caaactgcat gccaccccgt ggccaaatgt ccatgcatgt   4620
taacaagacc tatgactata aatagctgca atctcggccc aggttttcat catcaagaac   4680
cagttcaata tccagtaca ccgtattaaa gaatttaaga tatactccat ggagtccatt   4740 gttccccttcc tgccctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggattctccc   4920
ctggctcgag agctgcctct gatgaacccc ttccacgtgc tcctgatcgt gctcgcctac   4980
ctggtcaccg tgtttgtggg tatgcagatc atgaagaact ttgaacgatt cgaggtcaag   5040
acgtattcgc tcctgtacaa cttctgtctg gtctcgctga gcgcctacat gtgcggtggc   5100
attctgtacg aggcttatca ggccaactat ggactgtttg agaacgctgc cgatcacacc   5160
ttcaagggtc tccctatggc taagatgatc tggctcttct acttctccaa gctgatggag   5220
tttgtcgaca ccatgatcat ggtcctcaaa aagaacaacc gacagatttc ctttctgcac   5280
gtgtaccacc actcttccat cttccaccatc tggtggctgg tcaccttcgt tgctcccaac   5340
ggtgaagcct acttctctgc tgccctgaac tcgttcatcc atgttatcat gtacggctac   5400
tactttctgt ctgccctggg cttcaagcag gtgtcgttca tcaagttcta catcactcga   5460
tcccagatga cccagttctg catgttgtct gtccagtctt cctgggacat gtacgccatg   5520
aaggtccttg gccgacctgg ataccccttc ttcctgaccg ctctgctctg gttctacatg   5580
```

| | |
|---|---|
| tggaccatgc tcggtctctt ctacaacttt taccgacgaa acgccaagct cgccaagcag | 5640 |
| gccaaggctg acgctgccaa ggagaaggcc agaaagctcc agtaagc | 5687 |

<210> SEQ ID NO 53
<211> LENGTH: 5687
<212> TYPE: DNA
<213> ORGANISM: Artificial sequence
<220> FEATURE:
<223> OTHER INFORMATION: plasmid KS385

<400> SEQUENCE: 53

| | |
|---|---|
| ggccgcaagt atgaactaaa atgcacgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta actttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccattta tatattatat actacccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttccttacag ataaaaaaaa aattatgagt tggtttgata | 660 |
| aaatattgaa ggatttaaaa taataataaa taacatataa tatatgtata taaatttatt | 720 |
| ataatataac atttatctat aaaaaagtaa atattgtcat aaatctatac aatcgtttag | 780 |
| ccttgctgga cgaatctcaa ttatttaaac gagagtaaac atatttgact ttttggttat | 840 |
| ttaacaaatt attatttaac actatatgaa atttttttt ttatcagcaa agaataaaat | 900 |
| taaattaagg aggacaatgg tgtcccaatc cttatacaac caacttccac aagaaagtca | 960 |
| agtcagagac aacaaaaaaa caagcaaagg aaattttta atttgagttg tcttgtttgc | 1020 |
| tgcataattt atgcagtaaa acactacaca taacccttt agcagtaaag caatggttga | 1080 |
| ccgtgtgctt agcttctttt attttatttt tttatcagca aagaataaat aaaataaaat | 1140 |
| gagacacttc agggatgttt caacggatcc cccgggctgc aggaattcga tatcaagctt | 1200 |
| atcgataccg tcgacctcga ggggggggccc ggtacccaat cgccctata gtgagtcgta | 1260 |
| ttacgcgcgc tcactggccg tcgttttaca acgtcgtgac tgggaaaacc ctggcgttac | 1320 |
| ccaacttaat cgccttgcag cacatcccccc tttcgccagc tggcgtaata gcgaagaggc | 1380 |
| ccgcaccgat cgcccttccc aacagttgcg cagcctgaat ggcgaatggg acgcgccctg | 1440 |
| tagcggcgca ttaagcgcgg cgggtgtggt ggttacgcgc agcgtgaccg ctacacttgc | 1500 |
| cagcgcccta gcgcccgctc ctttcgcttt cttcccttcc tttctcgcca cgttcgccgg | 1560 |
| ctttccccgt caagctctaa atcgggggct ccctttaggg ttccgattta gtgctttacg | 1620 |
| gcacctcgac cccaaaaaac ttgattaggg tgatggttca cgtagtgggc catcgccctg | 1680 |
| atagacggtt tttcgccctt tgacgttgga gtccacgttc tttaatagtg gactcttgtt | 1740 |
| ccaaactgga acaacactca accctatctc ggtctattct tttgatttat aagggatttt | 1800 |
| gccgatttcg gcctattggt taaaaaatga gctgatttaa caaaaattta acgcgaattt | 1860 |
| taacaaaata ttaacgctta caatttaggt ggcacttttc ggggaaatgt gcgcggaacc | 1920 |
| cctatttgtt tatttttcta aatacattca aatatgtatc cgctcatgag acaataaccc | 1980 |

```
tgataaatgc ttcaataata ttgaaaaagg aagagtatga gtattcaaca tttccgtgtc  2040
gcccttattc ccttttttgc ggcattttgc cttcctgttt ttgctcaccc agaaacgctg  2100
gtgaaagtaa aagatgctga agatcagttg ggtgcacgag tgggttacat cgaactggat  2160
ctcaacagcg gtaagatcct tgagagtttt cgccccgaag aacgttttcc aatgatgagc  2220
acttttaaag ttctgctatg tggcgcggta ttatcccgta ttgacgccgg gcaagagcaa  2280
ctcggtcgcc gcatacacta ttctcagaat gacttggttg agtactcacc agtcacagaa  2340
aagcatctta cggatggcat gacagtaaga gaattatgca gtgctgccat aaccatgagt  2400
gataacactg cggccaactt acttctgaca acgatcggag gaccgaagga gctaaccgct  2460
tttttgcaca acatggggga tcatgtaact cgccttgatc gttgggaacc ggagctgaat  2520
gaagccatac caaacgacga gcgtgacacc acgatgcctg tagcaatggc aacaacgttg  2580
cgcaaactat taactggcga actacttact ctagcttccc ggcaacaatt aatagactgg  2640
atggaggcgg ataaagttgc aggaccactt ctgcgctcgg cccttccggc tggctggttt  2700
attgctgata atctggagcc ggtgagcgt gggtctcgcg gtatcattgc agcactgggg  2760
ccagatggta agccctcccg tatcgtagtt atctacacga cggggagtca ggcaactatg  2820
gatgaacgaa atagacagat cgctgagata ggtgcctcac tgattaagca ttggtaactg  2880
tcagaccaag tttactcata tactttag attgatttaa aacttcattt ttaatttaaa  2940
aggatctagg tgaagatcct ttttgataat ctcatgacca aaatccctta acgtgagttt  3000
tcgttccact gagcgtcaga ccccgtagaa aagatcaaag gatcttcttg agatcctttt  3060
tttctgcgcg taatctgctg cttgcaaaca aaaaaaccac cgctaccagc ggtggtttgt  3120
ttgccggatc aagagctacc aactctttt ccgaaggtaa ctggcttcag cagagcgcag  3180
ataccaaata ctgtccttct agtgtagccg tagttaggcc accacttcaa gaactctgta  3240
gcaccgccta catacctcgc tctgctaatc ctgttaccag tggctgctgc cagtggcgat  3300
aagtcgtgtc ttaccgggtt ggactcaaga cgatagttac cggataaggc gcagcggtcg  3360
ggctgaacgg ggggttcgtg cacacagccc agcttggagc gaacgaccta caccgaactg  3420
agatacctac agcgtgagct atgagaaagc gccacgcttc ccgaagggag aaaggcggac  3480
aggtatccgg taagcggcag ggtcggaaca ggagagcgca cgagggagct tccaggggga  3540
aacgcctggt atctttatag tcctgtcggg tttcgccacc tctgacttga gcgtcgattt  3600
ttgtgatgct cgtcaggggg gcggagccta tggaaaaacg ccagcaacgc ggccttttta  3660
cggttcctgg ccttttgctg gccttttgct cacatgttct ttcctgcgtt atcccctgat  3720
tctgtggata accgtattac cgcctttgag tgagctgata ccgctcgccg cagccgaacg  3780
accgagcgca gcgagtcagt gagcgaggaa gcggaagagc gcccaatacg caaaccgcct  3840
ctccccgcgc gttggccgat tcattaatgc agctggcacg acaggtttcc cgactggaaa  3900
gcgggcagtg agcgcaacgc aattaatgtg agttagctca ctcattaggc accccaggct  3960
ttacacttta tgcttccggc tcgtatgttg tgtggaattg tgagcggata acaatttcac  4020
acaggaaaca gctatgacca tgattacgcc aagcgcgcaa ttaaccctca ctaaagggaa  4080
caaaagctgg agctccaccc tagaactagt ggatccttca tccatgccct tcatttgccg  4140
cttattaatt aatttggtaa cagtccgtac taatcagtta cttatccttc ccccatcata  4200
attaatcttg gtagtctcga atgccacaac actgactagt ctcttggatc ataagaaaaa  4260
gccaaggaac aaaagaagac aaaacacaat gagagtatcc tttgcatagc aatgtctaag  4320
ttcataaaat tcaaacaaaa acgcaatcac acacagtgga catcacttat ccactagctg  4380
```

-continued

```
atcaggatcg ccgcgtcaag aaaaaaaaac tggaccccaa aagccatgca caacaacacg    4440
tactcacaaa ggtgtcaatc gagcagccca aaacattcac caactcaacc catcatgagc    4500
cctcacattt gttgtttcta acccaacctc aaactcgtat tctcttccgc cacctcattt    4560
ttgtttattt caacacccgt caaactgcat gccacccgt ggccaaatgt ccatgcatgt     4620
taacaagacc tatgactata aatagctgca atctcggccc aggttttcat catcaagaac    4680
cagttcaata tcctagtaca ccgtattaaa gaatttaaga tatactccat ggagtccatt    4740
gctcccttcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggattctccc    4920
ctggctcgag agctgcctct gatgaacccc ttccacgtgc tcctgattgt gctcgcctac    4980
ctggtcaccg tgtttgtggg tatgcagatc atgaagaact ttgaacgatt cgaggtcaag    5040
acgtattcgc tcctgtacaa cttctgtctg gtctcgctga gcgcctacat gtgcggtggc    5100
attctgtacg aggcttttca ggccaactat ggactgtttg agaacgctgc cgatcacacc    5160
ttcaagggtc tccctatggc taagatgatc tggctcttct acttctccaa gctgatggag    5220
tttgtcgaca ccatgatcct ggtcctcaaa agaacaacc gacagatttc ctttctgcac     5280
gtgtaccacc actcttccct gttcaccatc tggtggctgg tcaccttcgt tgctcccaac    5340
ggtgaagcct acttctctgc tgccatgaac tcgttcatcc atgttatcat gtacggctac    5400
tactttctgt ctgccctggg cttcaagcag gtgtcgttca tcaagttcta cctgactcga    5460
tcccagatga cccagttctg catgttgtct gtccagtctt cctgggacat gtacgccatg    5520
aaggtccttg gccgacctgg ataccccttc ttcctgaccg ctctgctctg gttctacatg    5580
tggacccttc tcggtctctt ctacaacttt taccgacgaa acgccaagct cgccaagcag    5640
gccaaggctg acgctgccaa ggagaaggcc agaaagctcc agtaagc                  5687
```

<210> SEQ ID NO 54
<211> LENGTH: 5687
<212> TYPE: DNA
<213> ORGANISM: Artificial sequence
<220> FEATURE:
<223> OTHER INFORMATION: plasmid KS386

<400> SEQUENCE: 54

```
ggccgcaagt atgaactaaa atgcacgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta aacaattcta actttagcat tgtgaacgag     300
acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actacccatt tatatattat acttatccac     480
ttatttaatg tctttataag gtttgatcca tgatatttct aatatttag ttgatatgta      540 tatgaaaggg tactatttga actctcttac tctgtataaa ggttggatca tccttaaagt     600 gggtctatt aatttattg cttcttacag ataaaaaaaa aattatgagt tggtttgata       660
aaatattgaa ggatttaaaa taataataaa taacatataa tatatgtata taaatttatt     720
ataatataac atttatctat aaaaagtaa atattgtcat aaatctatac aatcgtttag     780
```

```
ccttgctgga cgaatctcaa ttatttaaac gagagtaaac atatttgact ttttggttat    840
ttaacaaatt attatttaac actatatgaa attttttttt ttatcagcaa agaataaaat    900
taaattaagg aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taacccttttt agcagtaaag caatggttga   1080
ccgtgtgctt agcttctttt attttatttt tttatcagca aagaataaat aaaataaaat   1140
gagacacttc agggatgttt caacggatcc cccgggctgc aggaattcga tatcaagctt   1200
atcgataccg tcgacctcga ggggggggccc ggtacccaat cgccctata gtgagtcgta   1260
ttacgcgcgc tcactggccg tcgttttaca acgtcgtgac tgggaaaacc ctggcgttac   1320
ccaacttaat cgccttgcag cacatccccc tttcgccagc tggcgtaata gcgaagaggc   1380
ccgcaccgat cgcccttccc aacagttgcg cagcctgaat ggcgaatggg acgcgccctg   1440
tagcggcgca ttaagcgcgg cgggtgtggt ggttacgcgc agcgtgaccg ctacacttgc   1500
cagcgcccta gcgcccgctc ctttcgcttt cttcccttcc tttctcgcca cgttcgccgg   1560
ctttccccgt caagctctaa atcggggggct ccctttaggg ttccgattta gtgctttacg   1620
gcacctcgac cccaaaaaac ttgattaggg tgatggttca cgtagtgggc catcgccctg   1680
atagacggtt tttcgccctt tgacgttgga gtccacgttc tttaatagtg gactcttgtt   1740
ccaaactgga acaacactca accctatctc ggtctattct tttgatttat aagggatttt   1800
gccgatttcg gcctattggt taaaaaatga gctgatttaa caaaaattta acgcgaattt   1860
taacaaaata ttaacgctta caatttaggt ggcacttttc ggggaaatgt gcgcggaacc   1920
cctatttgtt tattttttcta aatacattca aatatgtatc cgctcatgag acaataaccc   1980
tgataaatgc ttcaataata ttgaaaaagg aagagtatga gtattcaaca tttccgtgtc   2040
gcccttattc cctttttttgc ggcattttgc cttcctgttt ttgctcaccc agaaacgctg   2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagc cggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tatactttag attgatttaa aacttcattt ttaatttaaa   2940
aggatctagg tgaagatcct ttttgataat ctcatgacca aaatccctta acgtgagttt   3000
tcgttccact gagcgtcaga cccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactcttttt ccgaaggtaa ctggcttcag cagagcgcag   3180
```

```
ataccaaata ctgtccttct agtgtagccg tagttaggcc accacttcaa gaactctgta   3240
gcaccgccta catacctcgc tctgctaatc ctgttaccag tggctgctgc cagtggcgat   3300
aagtcgtgtc ttaccggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcagggg gcggagccta tggaaaacg ccagcaacgc ggcctttta   3660 cggttcctgg ccttttgctg ccttttgct cacatgttct ttcctgcgtt atccctgat   3720 tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900
gcgggcagtg agcgcaacgc aattaatgtg agttagctca ctcattaggc accccaggct   3960
ttacacttta tgcttccggc tcgtatgttg tgtggaattg tgagcggata acaatttcac   4020
acaggaaaca gctatgacca tgattacgcc aagcgcgcaa ttaaccctca ctaagggaa   4080 caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
atcaggatcg ccgcgtcaag aaaaaaaaac tggaccccaa aagccatgca caacaacacg   4440
tactcacaaa ggtgtcaatc gagcagccca aaacattcac caactcaacc catcatgagc   4500
cctcacattt gttgtttcta acccaacctc aaactcgtat tctcttccgc cacctcattt   4560
ttgtttattt caacaccccgt caaactgcat gccaccccgt ggccaaatgt ccatgcatgt   4620
taacaagacc tatgactata aatagctgca atctcggccc aggttttcat catcaagaac   4680
cagttcaata tccagtacac ccgtattaaa gaatttaaga tatactccat ggagtccatt   4740
gttcccttcc tgccctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggattctccc   4920
ctggctcgag agctgcctct gatgaacccc ttccacgtgc tcatgcttgt gctcgcctac   4980
ctggtcaccg tgtttgtggg tatgcagatc atgaagaact tgaacgatt cgaggtcaag   5040 acgttctcgc tcctgtacaa cttctgtctg gtctcgctga gcgcctacat gtgcggtggc   5100
attctgtacg aggcttttca ggccaactat ggactgtttg agaacgctgc cgatcacacc   5160
ttcaagggtc tccctatggc taagatgatc tggctcttct acttctccaa gctgatggag   5220
tttgtcgaca ccatgatcat ggtcctcaga aagaacaacc gacagatttc ctttctgcac   5280
gtgtaccacc actcttccat cttcaccatc tggtggctgg tcaccttcgt tgctcccaac   5340
ggtgaagcct acttctctgc tgccctgaac tcgttcatcc atgttatcat gtacggctac   5400
tactttctgt ctgccctggg cttcaagcag gtgtcgctga tcaagttcta catcactcga   5460
tcccagatga cccagttctg catgttgtct gtccagtctt cctgggacat gtacgccatg   5520
aaggtccttg gccgacctgg ataccccttc ttcctgaccg ctctgctctg gttctacatg   5580
```

```
tggaccatgc tcggtctctt ctacaacttt taccgacgaa acgccaagct cgccaagcag   5640
gccaaggctg acgctgccaa ggagaaggcc agaaagctcc agtaagc               5687
```

<210> SEQ ID NO 55
<211> LENGTH: 5687
<212> TYPE: DNA
<213> ORGANISM: Artificial sequence
<220> FEATURE:
<223> OTHER INFORMATION: plasmid pLF128)

<400> SEQUENCE: 55

```
gtacaacttc tgtctggtct cgctgagcgc ctacatgtgc ggtggcattc tgtacgaggc     60
ttatcaggcc aactatggac tgtttcagaa cgctgccgat cacaccttca agggtctccc    120
tatggctaag atgatctggc tcttctactt ctccaagctg atggagtttg tcgacaccat    180
gatcatggtc ctcaaaaaga caaccgaca gatttccttt ctgcacgtgt accaccactc    240
ttccatcttc accatctggt ggctggtcac cttcgttgct cccaacggtg aagcctactt    300
ctctgctgcc ctgaactcgt tcatccatgt tatcatgtac ggctactact ttctgtctgc    360
cctgggcttc aagcaggtgt cgttcatcaa gttctacatc actcgatccc agatgaccca    420
gttctgcatg ttgtctgtcc agtcttcctg ggacatgtac gccatgaagg tccttggccg    480
acctggatac cccttcttcc tgaccgctct gctctggttc tacatgtgga ccatgctcgg    540
tctcttctac aacttttacc gaagaacgc caagctcgcc aagcaggcca aggctgacgc    600
tgccaaggag aaggccagaa agctccagta agcggccgca agtatgaact aaaatgcacg    660
taggtgtaag agctcatgga gagcatggaa tattgtatcc gaccatgtaa cagtataata    720
actgagctcc atctcacttc ttctatgaat aaacaaagga tgttatgata tattaacact    780
ctatctatgc accttattgt tctatgataa atttcctctt attattataa atcatctgaa    840
tcgtgacggc ttatggaatg cttcaaatag tacaaaaaca aatgtgtact ataagacttt    900
ctaaacaatt ctaactttag cattgtgaac gagacataag tgttaagaag acataacaat    960
tataatggaa gaagtttgtc tccatttata tattatatat tacccactta tgtattatat   1020
taggatgtta aggagacata acaattataa agagagaagt ttgtatccat ttatatatta   1080
tatactaccc atttatatat tacttatc cacttattta atgtctttat aaggtttgat    1140
ccatgatatt tctaatattt tagttgatat gtatatgaaa gggtactatt tgaactctct   1200
tactctgtat aaaggttgga tcatcctaa agtgggtcta tttaatttta ttgcttctta   1260
cagataaaaa aaaattatg agttggtttg ataaaatatt gaaggattta aaataataat   1320
aaataacata taatatatgt atataaattt attataatat aacatttatc tataaaaaag   1380
taaatattgt cataaatcta tacaatcgtt tagccttgct ggacgaatct caattattta   1440
aacgagagta acatatttg acttttggt tatttaacaa attattattt aacactatat    1500 gaaattttt tttttatcag caagaataa aattaaatta aggaggacaa tggtgtccca    1560
atccttatac aaccaacttc cacaagaaag tcaagtcaga gacaacaaaa aacaagcaa    1620 aggaaatttt ttaatttgag ttgtcttgtt tgctgcataa tttatgcagt aaaacactac   1680
acataaccct tttagcagta aagcaatggt tgaccgtgtg cttagcttct tttatttttat   1740 ttttttatca gcaaagaata aataaaataa aatgagacac ttcagggatg tttcaacgga   1800
tcccccgggc tgcaggaatt cgatatcaag cttatcgata ccgtcgacct cgagggggg    1860 cccggtaccc aattcgccct atagtgagtc gtattacgcg cgctcactgg ccgtcgtttt   1920
acaacgtcgt gactgggaaa accctggcgt tacccaactt aatcgccttg cagcacatcc   1980
```

```
cccttttcgcc agctggcgta atagcgaaga ggcccgcacc gatcgccctt cccaacagtt   2040
gcgcagcctg aatggcgaat gggacgcgcc ctgtagcggc gcattaagcg cggcgggtgt   2100
ggtggttacg cgcagcgtga ccgctacact tgccagcgcc ctagcgcccg ctcctttcgc   2160
tttcttccct tcctttctcg ccacgttcgc cggctttccc cgtcaagctc taaatcgggg   2220
gctcccttta gggttccgat ttagtgcttt acggcacctc gaccccaaaa aacttgatta   2280
gggtgatggt tcacgtagtg gccatcgccc tgatagacg gtttttcgcc ctttgacgtt   2340
ggagtccacg ttctttaata gtggactctt gttccaaact ggaacaacac tcaaccctat   2400
ctcggtctat tcttttgatt tataagggat tttgccgatt tcggcctatt ggttaaaaaa   2460
tgagctgatt taacaaaaat ttaacgcgaa ttttaacaaa atattaacgc ttacaattta   2520
ggtggcactt ttcggggaaa tgtgcgcgga acccctattt gtttattttt ctaaatacat   2580
tcaaatatgt atccgctcat gagacaataa ccctgataaa tgcttcaata atattgaaaa   2640
aggaagagta tgagtattca acatttccgt gtcgccctta ttcccttttt tgcggcattt   2700
tgccttcctg tttttgctca cccagaaacg ctggtgaaag taaaagatgc tgaagatcag   2760
ttgggtgcac gagtgggtta catcgaactg gatctcaaca gcggtaagat ccttgagagt   2820
tttcgccccg aagaacgttt tccaatgatg agcacttttta aagttctgct atgtggcgcg   2880
gtattatccc gtattgacgc cgggcaagag caactcggtc gccgcataca ctattctcag   2940
aatgacttgg ttgagtactc accagtcaca gaaaagcatc ttacggatgg catgacagta   3000
agagaattat gcagtgctgc cataaccatg agtgataaca ctgcggccaa cttacttctg   3060
acaacgatcg gaggaccgaa ggagctaacc gcttttttgc acaacatggg ggatcatgta   3120
actcgccttg atcgttggga accggagctg aatgaagcca taccaaacga cgagcgtgac   3180
accacgatgc ctgtagcaat ggcaacaacg ttgcgcaaac tattaactgg cgaactactt   3240
actctagctt cccggcaaca attaatagac tggatggagg cggataaagt tgcaggacca   3300
cttctgcgct cggcccttcc ggctggctgg tttattgctg ataaatctgg agccggtgag   3360
cgtgggtctc gcggtatcat tgcagcactg gggccagatg gtaagccctc ccgtatcgta   3420
gttatctaca cgacggggag tcaggcaact atggatgaac gaaatagaca gatcgctgag   3480
ataggtgcct cactgattaa gcattggtaa ctgtcagacc aagtttactc atatatactt   3540
tagattgatt taaaacttca ttttaattt aaaaggatct aggtgaagat cctttttgat   3600
aatctcatga ccaaaatccc ttaacgtgag ttttcgttcc actgagcgtc agaccccgta   3660
gaaaagatca aaggatcttc ttgagatcct ttttttctgc gcgtaatctg ctgcttgcaa   3720
acaaaaaaac caccgctacc agcggtggtt tgtttgccgg atcaagagct accaactctt   3780
tttccgaagg taactggctt cagcagagcg cagataccaa atactgtcct tctagtgtag   3840
ccgtagttag gccaccactt caagaactct gtagcaccgc ctacatacct cgctctgcta   3900
atcctgttac cagtggctgc tgccagtggc gataagtcgt gtcttaccgg gttggactca   3960
agacgatagt taccggataa ggcgcagcgg tcgggctgaa cggggggttc gtgcacacag   4020
cccagcttgg agcgaacgac ctacaccgaa ctgagatacc tacagcgtga gctatgagaa   4080
agcgccacgc ttcccgaagg gagaaaggcg gacaggtatc cggtaagcgg cagggtcgga   4140
acaggagagc gcacgaggga gcttccaggg ggaaacgcct ggtatcttta tagtcctgtc   4200
gggtttcgcc acctctgact tgagcgtcga tttttgtgat gctcgtcagg ggggcggagc   4260
ctatggaaaa acgccagcaa cgcggccttt ttacggttcc tggccttttg ctggccttttg   4320
gctcacatgt tctttcctgc gttatcccct gattctgtgg ataaccgtat taccgccttt   4380
```

```
gagtgagctg ataccgctcg ccgcagccga acgaccgagc gcagcgagtc agtgagcgag    4440
gaagcggaag agcgcccaat acgcaaaccg cctctccccg cgcgttggcc gattcattaa    4500
tgcagctggc acgacaggtt tcccgactgg aaagcgggca gtgagcgcaa cgcaattaat    4560
gtgagttagc tcactcatta ggcaccccag gctttacact ttatgcttcc ggctcgtatg    4620
ttgtgtggaa ttgtgagcgg ataacaattt cacacaggaa acagctatga ccatgattac    4680
gccaagcgcg caattaaccc tcactaaagg gaacaaaagc tggagctcca ccctagaact    4740
agtggatcct tcatccatgc ccttcatttg ccgcttatta attaatttgg taacagtccg    4800
tactaatcag ttacttatcc ttcccccatc ataattaatc ttggtagtct cgaatgccac    4860
aacactgact agtctcttgg atcataagaa aaagccaagg aacaaaagaa gacaaaacac    4920
aatgagagta tcctttgcat agcaatgtct aagttcataa aattcaaaca aaaacgcaat    4980
cacacacagt ggacatcact tatccactag ctgatcagga tcgccgcgtc aagaaaaaaa    5040
aactggaccc caaaagccat gcacaacaac acgtactcac aaaggtgtca atcgagcagc    5100
ccaaaacatt caccaactca acccatcatg agccctcaca tttgttgttt ctaacccaac    5160
ctcaaactcg tattctcttc cgccacctca tttttgttta tttcaacacc cgtcaaactg    5220
catgccaccc cgtggccaaa tgtccatgca tgttaacaag acctatgact ataaatagct    5280
gcaatctcgg cccaggtttt catcatcaag aaccagttca atatcctagt acaccgtatt    5340
aaagaattta agatatactc catggagtcc attgttccct tcctgccctc aagatgcct     5400 caggacctgt tcatggacct cgccagcgct atcggtgtcc gagctgctcc ctacgtcgat    5460
cccctggagg ctgccctggt tgcccaggcc gagaagtaca ttcccaccat tgtccatcac    5520
actcgaggct tcctggttgc cgtggattct ccctggctc gagagctgcc tctgatgaac    5580
cccttccacg tgctcatgct tgtgctcgcc tacctggtca ccgtgtttgt gggtatgcag    5640
atcatgaaga actttgaacg attcgaggtc aagacgttct cgctcct             5687

<210> SEQ ID NO 56
<211> LENGTH: 957
<212> TYPE: DNA
<213> ORGANISM: Artificial sequence
<220> FEATURE:
<223> OTHER INFORMATION: MaD9elSHFL-4 nucleotide

<400> SEQUENCE: 56
atggagtcca ttgttccctt cctgccctcc aagatgcctc aggacctgtt catggacctc      60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggattctc ccctggctcg agagctgcct ctgatgaacc ccttccacgt gctcatgctt    240
gtgctcgcct acctggtcac cgtgtttgtg ggtatgcaga tcatgaagaa ctttgaacga    300
ttcgaggtca agacgttctc gctcctgtac aacttctgtc tggtctcgct gagcgcctac    360
atgtgcggtg gcattctgta cgaggcttat caggccaact atggactgtt tcagaacgct    420
gccgatcaca ccttcaaggg tctccctatg ctaagatga tctggctctt ctacttctcc    480
aagctgatgg agtttgtcga caccatgatc atggtcctca aaagaacaa ccgacagatt    540 tcctttctgc acgtgtacca ccactcttcc atcttcacca tctggtggct ggtcaccttc    600
gttgctccca cggtgaagc ctacttctct gctgccctga actcgttcat ccatgttatc    660
atgtacggct actactttct gtctgccctg ggcttcaagc aggtgtcgtt catcaagttc    720
tacatcactc gatcccagat gacccagttc tgcatgttgt ctgtccagtc ttcctgggac    780
```

```
atgtacgcca tgaaggtcct tggccgacct ggatacccct tcttcctgac cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaa       957
```

<210> SEQ ID NO 57
<211> LENGTH: 318
<212> TYPE: PRT
<213> ORGANISM: Artificial sequence
<220> FEATURE:
<223> OTHER INFORMATION: MaD9elSHFL-4 amino acid sequence
<400> SEQUENCE: 57

```
Met Glu Ser Ile Val Pro Phe Leu Pro Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Asp Ser Pro
    50                  55                  60

Leu Ala Arg Glu Leu Pro Leu Met Asn Pro Phe His Val Leu Met Leu
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu Tyr Asn Phe
            100                 105                 110

Cys Leu Val Ser Leu Ser Ala Tyr Met Cys Gly Gly Ile Leu Tyr Glu
        115                 120                 125

Ala Tyr Gln Ala Asn Tyr Gly Leu Phe Gln Asn Ala Ala Asp His Thr
    130                 135                 140

Phe Lys Gly Leu Pro Met Ala Lys Met Ile Trp Leu Pro Tyr Phe Ser
145                 150                 155                 160

Lys Leu Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Leu Ser Val Gln
                245                 250                 255

Ser Ser Trp Asp Met Tyr Ala Met Lys Val Leu Gly Arg Pro Gly Tyr
            260                 265                 270

Pro Phe Phe Leu Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 58
<211> LENGTH: 7948

<212> TYPE: DNA
<213> ORGANISM: Artificial sequence
<220> FEATURE:
<223> OTHER INFORMATION: plasmid pY183

<400> SEQUENCE: 58

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | ggcaacggtt | tcacttgagt | gcagtggcta | 240 |
| gtgctcttac | tcgtacagtg | tgcaatactg | cgtatcatag | tctttgatgt | atatcgtatt | 300 |
| cattcatgtt | agttgcgtac | gagccggaag | cataaagtgt | aaagcctggg | gtgcctaatg | 360 |
| agtgagctaa | ctcacattaa | ttgcgttgcg | ctcactgccc | gctttccagt | cgggaaacct | 420 |
| gtcgtgccag | ctgcattaat | gaatcggcca | acgcgcgggg | agaggcggtt | tgcgtattgg | 480 |
| gcgctcttcc | gcttcctcgc | tcactgactc | gctgcgctcg | tcgttcggc | tgcggcgagc | 540 |
| ggtatcagct | cactcaaagg | cggtaatacg | gttatccaca | gaatcagggg | ataacgcagg | 600 |
| aaagaacatg | tgagcaaaag | gccagcaaaa | ggccaggaac | cgtaaaaagg | ccgcgttgct | 660 |
| ggcgtttttc | cataggctcc | gcccccctga | cgagcatcac | aaaaatcgac | gctcaagtca | 720 |
| gaggtggcga | aacccgacag | gactataaag | ataccaggcg | tttccccctg | gaagctccct | 780 |
| cgtgcgctct | cctgttccga | ccctgccgct | taccggatac | ctgtccgcct | ttctcccttc | 840 |
| gggaagcgtg | gcgctttctc | atagctcacg | ctgtaggtat | ctcagttcgg | tgtaggtcgt | 900 |
| tcgctccaag | ctgggctgtg | tgcacgaacc | ccccgttcag | cccgaccgct | gcgccttatc | 960 |
| cggtaactat | cgtcttgagt | ccaacccggt | aagacacgac | ttatcgccac | tggcagcagc | 1020 |
| cactggtaac | aggattagca | gagcgaggta | tgtaggcggt | gctacagagt | tcttgaagtg | 1080 |
| gtggcctaac | tacggctaca | ctagaaggac | agtatttggt | atctgcgctc | tgctgaagcc | 1140 |
| agttaccttc | ggaaaaagag | ttggtagctc | ttgatccggc | aaacaaacca | ccgctggtag | 1200 |
| cggtggtttt | tttgtttgca | agcagcagat | tacgcgcaga | aaaaaaggat | ctcaagaaga | 1260 |
| tcctttgatc | ttttctacgg | ggtctgacgc | tcagtggaac | gaaaactcac | gttaagggat | 1320 |
| tttggtcatg | agattatcaa | aaaggatctt | cacctagatc | cttttaaatt | aaaaatgaag | 1380 |
| ttttaaatca | atctaaagta | tatatgagta | aacttggtct | gacagttacc | aatgcttaat | 1440 |
| cagtgaggca | cctatctcag | cgatctgtct | atttcgttca | tccatagttg | cctgactccc | 1500 |
| cgtcgtgtag | ataactacga | tacgggaggg | cttaccatct | ggccccagtg | ctgcaatgat | 1560 |
| accgcgagac | ccacgctcac | cggctccaga | tttatcagca | ataaaccagc | cagccggaag | 1620 |
| ggccgagcgc | agaagtggtc | ctgcaacttt | atccgcctcc | atccagtcta | ttaattgttg | 1680 |
| ccgggaagct | agagtaagta | gttcgccagt | taatagtttg | cgcaacgttg | ttgccattgc | 1740 |
| tacaggcatc | gtggtgtcac | gctcgtcgtt | tggtatggct | tcattcagct | ccggttccca | 1800 |
| acgatcaagg | cgagttacat | gatcccccat | gttgtgcaaa | aaagcggtta | gctccttcgg | 1860 |
| tcctccgatc | gttgtcagaa | gtaagttggc | cgcagtgtta | tcactcatgg | ttatggcagc | 1920 |
| actgcataat | tctcttactg | tcatgccatc | cgtaagatgc | ttttctgtga | ctggtgagta | 1980 |
| ctcaaccaag | tcattctgag | aatagtgtat | gcggcgaccg | agttgctctt | gcccggcgtc | 2040 |
| aatacgggat | aataccgcgc | cacatagcag | aactttaaaa | gtgctcatca | ttggaaaacg | 2100 |
| ttcttcgggg | cgaaaactct | caaggatctt | accgctgttg | agatccagtt | cgatgtaacc | 2160 |
| cactcgtgca | cccaactgat | cttcagcatc | ttttactttc | accagcgttt | ctgggtgagc | 2220 |

```
aaaaacagga aggcaaaatg ccgcaaaaaa gggaataagg gcgacacgga aatgttgaat      2280
actcatactc ttccttttc aatattattg aagcatttat cagggttatt gtctcatgag       2340
cggatacata tttgaatgta tttagaaaaa taaacaaata ggggttccgc gcacatttcc      2400
ccgaaaagtg ccacctgacg cgccctgtag cggcgcatta agcgcggcgg gtgtggtggt      2460
tacgcgcagc gtgaccgcta cacttgccag cgccctagcg cccgctcctt tcgctttctt     2520
cccttccttt ctcgccacgt tcgccggctt tccccgtcaa gctctaaatc ggggctccc      2580 tttagggttc cgatttagtg ctttacggca cctcgacccc aaaaaacttg attagggtga     2640
tggttcacgt agtgggccat cgccctgata gacggttttt cgcccttga cgttggagtc      2700 cacgttcttt aatagtggac tcttgttcca aactggaaca acactcaacc ctatctcggt    2760 ctattcttt gatttataag ggattttgcc gatttcggcc tattggttaa aaaatgagct      2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc     2940
cagctggcga aaggggatg tgctgcaagg cgattaagtt gggtaacgcc agggttttcc      3000
cagtcacgac gttgtaaaac gacggccagt gaattgtaat acgactcact atagggcgaa    3060
ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag   3300
acagactcca tctgccgcct ccaactgatg ttctcaatat ttaaggggtc atctcgcatt   3360
gtttaataat aaacgactc catctaccgc ctccaaatga tgttctcaaa atatattgta    3420
tgaacttatt tttattactt agtattatta gacaacttac ttgctttatg aaaaacactt   3480
cctatttagg aaacaattta taatggcagt tcgttcattt aacaatttat gtagaataaa   3540
tgttataaat gcgtatggga aatcttaaat atggatagca taaatgatat ctgcattgcc   3600
taattcgaaa tcaacagcaa cgaaaaaaat cccttgtaca acataaatag tcatcgagaa   3660
atatcaacta tcaaagaaca gctattcaca cgttactatt gagattatta ttggacgaga   3720
atcacacact caactgtctt tctctcttct agaaatacag gtacaagtat gtactattct    3780
cattgttcat acttctagtc atttcatccc acatattcct tggatttctc tccaatgaat   3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaatc     4140 gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt ttttttttgt    4320 tttttttt tctaatgatt cattaccgct atgtatacct acttgtactt gtagtaagcc     4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
```

```
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160 gagagggac taggaactcc ttgtactggg agttctcgta gtcagagacg tcctccttct    5220
tctgttcaga cacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactaggggg gggcctttt atatggccaa gccaagctct    6180
ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttaac    6480
aaaaagtgag ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agcccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca tggagtccat tgttcccttc ctgccctcca    7020
```

```
agatgcctca ggacctgttc atggacctcg ccagcgctat cggtgtccga gctgctccct    7080
acgtcgatcc cctggaggct gccctggttg cccaggccga gaagtacatt cccaccattg    7140
tccatcacac tcgaggcttc ctggttgccg tggattctcc cctggctcga gagctgcctc    7200
tgatgaaccc cttccacgtg ctcatgcttg tgctcgccta cctggtcacc gtgtttgtgg    7260
gtatgcagat catgaagaac tttgaacgat tcgaggtcaa gacgttctcg ctcctgtaca    7320
acttctgtct ggtctcgctg agcgcctaca tgtgcggtgg cattctgtac gaggcttatc    7380
aggccaacta tggactgttt cagaacgctg ccgatcacac cttcaagggt ctccctatgg    7440
ctaagatgat ctggctcttc tacttctcca agctgatgga gtttgtcgac accatgatca    7500
tggtcctcaa aaagaacaac cgacagattt cctttctgca cgtgtaccac cactcttcca    7560
tcttcaccat ctggtggctg gtcaccttcg ttgctcccaa cggtgaagcc tacttctctg    7620
ctgccctgaa ctcgttcatc catgttatca tgtacggcta ctactttctg tctgccctgg    7680
gcttcaagca ggtgtcgttc atcaagttct acatcactcg atcccagatg acccagttct    7740
gcatgttgtc tgtccagtct tcctgggaca tgtacgccat gaaggtcctt ggccgacctg    7800
gatacccctt cttcctgacc gctctgctct ggttctacat gtggaccatg ctcggtctct    7860
tctacaactt ttaccgaaag aacgccaagc tcgccaagca ggccaaggct gacgctgcca    7920
aggagaaggc cagaaagctc cagtaagc                                       7948
```

<210> SEQ ID NO 59
<211> LENGTH: 1266
<212> TYPE: DNA
<213> ORGANISM: Euglena gracilis
<220> FEATURE:
<221> NAME/KEY: misc_feature
<222> LOCATION: (1)..(1266)
<223> OTHER INFORMATION: EgD8

<400> SEQUENCE: 59

```
atgaagtcaa agcgccaagc gcttcccctt acaattgatg gaacaacata tgatgtgtct      60
gcctgggtca atttccaccc tggtggtgcg gaaattatag agaattacca aggaagggat     120
gccactgatg ccttcatggt tatgcactct caagaagcct tcgacaagct caagcgcatg     180
cccaaaatca atcccagttc tgagttgcca ccccaggctg cagtgaatga agctcaagag     240
gatttccgga agctccgaga agagttgatc gcaactggca tgtttgatgc ctcccccctc     300
tggtactcat acaaaatcag caccacactg ggccttggag tgctgggtta tttcctgatg     360
gttcagtatc agatgtattt cattggggca gtgttgcttg ggatgcacta tcaacagatg     420
ggctggcttt tcatgacat tgccaccac cagactttca agaaccggaa ctggaacaac      480
ctcgtgggac tggtatttgg caatggtctg caaggttttt ccgtgacatg gtggaaggac    540
agacacaatg cacatcattc ggcaaccaat gttcaagggc acgaccctga tattgacaac    600 ctcccctct tagcctggtc tgaggatgac gtcacacggg cgtcaccgat ttcccgcaag     660
ctcattcagt tccagcagta ctatttcttg gtcatctgta tcttgttgcg gttcatttgg    720
tgtttccaga gcgtgttgac cgtgcgcagt ttgaaggaca gagataacca attctatcgc    780
tctcagtata agaaggaggc cattggcctc gccctgcact ggaccttgaa gaccctgttc    840
cacttattct ttatgcccag catcctcaca tgctgttgg tgtttttcgt ttcggagctg     900
gttggcggct tcggcattgc gatcgtggtg ttcatgaacc actacccact ggagaagatc    960
ggggactcag tctgggatgg ccatggattc tcggttggcc agatccatga gaccatgaac   1020
attcggcgag ggattatcac agattggttt ttcggaggct tgaattacca gattgagcac   1080
```

-continued

```
catttgtggc cgaccctccc tcgccacaac ctgacagcgg ttagctacca ggtggaacag    1140
ctgtgccaga agcacaacct gccgtatcgg aacccgctgc cccatgaagg gttggtcatc    1200
ctgctgcgct atctggcggt gttcgcccgg atggcggaga agcaacccgc ggggaaggct    1260
ctataa                                                               1266
```

<210> SEQ ID NO 60
<211> LENGTH: 1341
<212> TYPE: DNA
<213> ORGANISM: Mortierella alpina
<220> FEATURE:
<221> NAME/KEY: misc_feature
<222> LOCATION: (1)..(1341)
<223> OTHER INFORMATION: MaD5

<400> SEQUENCE: 60

```
atgggaacgg accaaggaaa aaccttcacc tgggaagagc tggcggccca taacaccaag     60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
gagatgtatc acgcgtttgg ggctgcagat gccattatga agaagtacta tgtcggtaca    240
ctggtctcga atgagctgcc catcttcccg gagccaacgg tgttccacaa aaccatcaag    300
acgagagtcg agggctactt tacgatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcactttc agtgacccac    540 aaccccactg tctggaagat tctgggagcc acgcacgact ttttcaacgg agcatcgtac    600
ctggtgtgga tgtaccaaca tatgctcggc catcacccct acaccaacat gctggagca    660 gatcccgacg tgtcgacgtc tgagcccgat gttcgtcgta tcaagcccaa ccaaaagtgg    720
tttgtcaacc acatcaacca gcacatgttt gttcctttcc tgtacggact gctggcgttc    780
aaggtgcgca ttcaggacat caacattttg tactttgtca agaccaatga cgctattcgt    840
gtcaatccca tctcgacatg gcacactgtg atgttctggg gcggcaaggc ttttcttgtc    900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccatacctt    1260
gtcaaggata cgttttggca agcatttgct tcacatttgg agcacttgcg tgttcttgga    1320
ctccgtccca aggaagagta g                                              1341
```

<210> SEQ ID NO 61
<211> LENGTH: 1077
<212> TYPE: DNA
<213> ORGANISM: Saprolegnia diclina
<220> FEATURE:
<221> NAME/KEY: misc_feature
<222> LOCATION: (1)..(1077)
<223> OTHER INFORMATION: SdD17

<400> SEQUENCE: 61

```
atgactgagg ataagacgaa ggtcgagttc ccgacgctca cggagctcaa gcactcgatc     60
```

```
ccgaacgcgt gctttgagtc gaacctcggc ctctcgctct actacacggc ccgcgcgatc      120
ttcaacgcgt cggcctcggc ggcgctgctc tacgcggcgc gctcgacgcc gttcattgcc      180
gataacgttc tgctccacgc gctcgtttgc gccacctaca tctacgtgca gggcgtcatc      240
ttctggggct tcttcacggt cggccacgac tgcggccact cggccttctc gcgctaccac      300
agcgtcaact ttatcatcgg ctgcatcatg cactctgcga ttttgacgcc gttcgagagc      360
tggcgcgtga cgcaccgcca ccaccacaag aacacgggca acattgataa ggacgagatc      420
ttttacccgc accggtcggt caaggacctc caggacgtgc gccaatgggg ctacacgctc      480
ggcggtgcgt ggtttgtcta cttgaaggtc gggtatgccc cgcgcacgat gagccacttt      540
gacccgtggg acccgctcct ccttcgccgc gcgtcggccg tcatcgtgtc gctcggcgtc      600
tgggccgcct tcttcgccgc gtacgcgtac ctcacatact cgctcggctt tgccgtcatg      660
ggcctctact actatgcgcc gctctttgtc tttgcttcgt tcctcgtcat tacgaccttc      720
ttgcaccaca acgacgaagc gacgccgtgg tacggcgact cggagtggac gtacgtcaag      780
ggcaacctct cgagcgtcga ccgctcgtac ggcgcgttcg tggacaacct gagccaccac      840
attggcacgc accaggtcca ccacttgttc ccgatcattc cgcactacaa gctcaacgaa      900
gccaccaagc actttgcggc cgcgtacccg cacctcgtgc gcaggaacga cgagcccatc      960
atcacggcct tcttcaagac cgcgcacctc tttgtcaact acggcgctgt gcccgagacg     1020
gcgcagatct tcacgctcaa agagtcggcc gcggccgcca aggccaagtc ggactaa        1077
```

<210> SEQ ID NO 62
<211> LENGTH: 1209
<212> TYPE: DNA
<213> ORGANISM: Fusarium monoliforme
<220> FEATURE:
<221> NAME/KEY: misc_feature
<222> LOCATION: (1)..(1209)
<223> OTHER INFORMATION: FmD15

<400> SEQUENCE: 62

```
atggcgactc gacagcgaac tgccaccact gttgtggtcg aggaccttcc caaggtcact       60
cttgaggcca agtctgaacc tgtgttcccc gatatcaaga ccatcaagga tgccattccc      120
gcgcactgct tccagccctc gctcgtcacc tcattctact acgtcttccg cgattttgcc      180
atggtctctg ccctcgtctg ggctgctctc acctacatcc ccagcatccc cgaccagacc      240
ctccgcgtcg cagcttggat ggtctacggc ttcgtccagg gtctgttctg caccggtgtc      300
tggattctcg gccatgagtg cggccacggt gctttctctc tccacggaaa ggtcaacaat      360
gtgaccggct ggttcctcca ctcgttcctc ctcgtcccct acttcagctg gaagtactct      420
caccaccgcc accaccgctt caccggccac atggatctcg acatggcttt cgtccccaag      480
actgagccca gccctccaa gtcgctcatg attgctggca ttgacgtcgc cgagcttgtt      540
gaggacaccc ccgctgctca gatggtcaag ctcatcttcc accagctttt cggatggcag      600
gcgtacctct tcttcaacgc tagctctggc aagggcagca agcagtggga gcccaagact      660
ggcctctcca gtggttccg agtcagtcac ttcgagccta ccagcgctgt cttccgcccc      720
aacgaggcca tcttcatcct catctccgat atcggtcttg ctctaatggg aactgctctg      780
tactttgctt ccaagcaagt tggtgtttcg accattctct tcctctacct tgttccctac      840
ctgtgggttc accactggct cgttgccatt acctacctcc accaccacca caccgagctc      900
cctcactaca ccgctgaggg ctggacctac gtcaagggag ctctcgccac tgtcgaccgt      960
gagtttggct tcatcggaaa gcacctcttc cacggtatca ttgagaagca cgttgttcac     1020
```

```
catctcttcc ctaagatccc cttctacaag gctgacgagg ccaccgaggc catcaagccc    1080
gtcattggcg accactactg ccacgacgac cgaagcttcc tgggccagct gtggaccatc    1140
ttcggcacgc tcaagtacgt cgagcacgac cctgcccgac ccggtgccat gcgatggaac    1200
aaggactag                                                            1209

<210> SEQ ID NO 63
<211> LENGTH: 11988
<212> TYPE: DNA
<213> ORGANISM: Artificial sequence
<220> FEATURE:
<223> OTHER INFORMATION: plasmid pKR1230
<220> FEATURE:
<221> NAME/KEY: misc_feature
<222> LOCATION: (7997)..(7997)
<223> OTHER INFORMATION: n is unknown

<400> SEQUENCE: 63
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaagc caaggaacaa agaagacaa      180 aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg accccaaaa gccatgcaca acaacgta ctcacaaagg tgtcaatcga       360
gcagcccaaa acattcacca actcaaccca tcatgagccc tcacatttgt tgtttctaac    420
ccaacctcaa actcgtattc tcttccgcca cctcattttt gtttatttca cacccgtca    480 aactgcatgc caccccgtgg ccaaatgtcc atgcatgtta acaagaccta tgactataaa    540
tagctgcaat ctcggcccag ttttcatca tcaagaacca gttcaatatc ctagtacacc     600
gtattaaaga atttaagata tactgcggcc gccccttca ccatggagtc cattgctccc    660
ttcctgccct ccaagatgcc tcaggacctg ttcatggacc tcgccagcgc tatcggtgtc    720
cgagctgctc cctacgtcga tcccctggag gctgccctgg ttgcccaggc cgagaagtac    780
attcccacca ttgtccatca cactcgaggc ttcctggttg ccgtggagtc tcccctggct    840
cgagagctgc ctctgatgaa ccccttccac gtgctcctga tcgtgctcgc ctacctggtc    900
accgtgtttg tgggtatgca gatcatgaag aactttgaac gattcgaggt caagaccttc    960
tccctcctgc acaacttctg tctggtctcc atctccgcct acatgtgcgg tggcatcctg   1020
tacgaggctt atcaggccaa ctatggactg tttgagaacg ctgccgatca caccttcaag   1080
ggtctcccta tggctaagat gatctggctc ttctacttct ccaagatcat ggagtttgtc   1140
gacaccatga tcatggtcct caagaagaac aaccgacaga tttcctttct gcacgtgtac   1200
caccactctt ccatcttcac catctggtgg ctggtcacct tcgttgctcc caacggtgaa   1260
gcctacttct ctgctgccct gaactccttc atccacgtca tcatgtacgg ctactacttt   1320
ctgtctgccc tgggcttcaa gcaggtgtcg ttcatcaagt tctacatcac tcgatcccag   1380
atgacccagt tctgcatgat gtctgtccag tcttcctggg acatgtacgc catgaaggtc   1440
cttggccgac ctggatacccc cttcttcatc accgctctgc tctggttcta catgtggacc   1500
atgctcggtc tcttctacaa cttttaccga agaacgcca agctcgccaa gcaggccaag   1560
gctgacgctg ccaaggagaa ggccagaaag ctccagtaag cggccgcaag tatgaactaa   1620
aatgcatgta ggtgtaagag ctcatggaga gcatggaata ttgtatccga ccatgtaaca   1680
gtataataac tgagctccat ctcacttctt ctatgaataa acaaggatg ttatgatata    1740
```

```
ttaacactct atctatgcac cttattgttc tatgataaat ttcctcttat tattataaat    1800
catctgaatc gtgacggctt atggaatgct tcaaatagta caaaaacaaa tgtgtactat    1860
aagactttct aaacaattct aaccttagca ttgtgaacga gacataagtg ttaagaagac    1920
ataacaatta taatggaaga agtttgtctc catttatata ttatatatta cccacttatg    1980
tattatatta ggatgttaag gagacataac aattataaag agagaagttt gtatccattt    2040
atatattata tactacccat ttatatatta tacttatcca cttatttaat gtctttataa    2100
ggtttgatcc atgatatttc taatattttta gttgatatgt atatgaaagg gtactatttg    2160
aactctctta ctctgtataa aggttggatc atccttaaag tgggtctatt taattttatt    2220
gcttcttaca gataaaaaaa aaattatgag ttggtttgat aaaatattga aggatttaaa    2280
ataataataa ataacatata atatatgtat ataaattttat tataatataa catttatcta    2340
taaaaaagta aatattgtca taaatctata caatcgttta gccttgctgg acgaatctca    2400
attatttaaa cgagagtaaa catatttgac tttttggtta tttaacaaat tattatttaa    2460
cactatatga aattttttt ttatcagca aagaataaaa ttaaattaag aaggacaatg    2520
gtgtcccaat cctatacaa ccaacttcca caagaaagtc aagtcagaga caacaaaaaa    2580
acaagcaaag gaaattttt aatttgagtt gtcttgtttg ctgcataatt tatgcagtaa    2640
aacactacac ataacccttt tagcagtaga gcaatggttg accgtgtgct tagcttcttt    2700
tattttattt ttttatcagc aaagaataaa taaaataaaa tgagacactt cagggatgtt    2760
tcaacaagct tggcgcgccg ttctatagtg tcacctaaat cgtatgtgta tgatacataa    2820
ggttatgtat taattgtagc cgcgttctaa cgacaatatg tccatatggt gcactctcag    2880
tacaatctgc tctgatgccg catagttaag ccagccccga cacccgccaa cacccgctga    2940
cgcgccctga cgggcttgtc tgctcccggc atccgcttac agacaagctg tgaccgtctc    3000
cgggagctgc atgtgtcaga ggttttcacc gtcatcaccg aaacgcgcga gacgaaaggg    3060
cctcgtgata cgcctatttt tataggttaa tgtcatgacc aaaatcccttt aacgtgagtt    3120 ttcgttccac tgagcgtcag accccgtaga aagatcaaa ggatcttctt gagatccttt    3180
ttttctgcgc gtaatctgct gcttgcaaac aaaaaaacca ccgctaccag cggtggtttg    3240
tttgccggat caagagctac caactctttt tccgaaggta actggcttca gcagagcgca    3300
gataccaaat actgtccttc tagtgtagcc gtagttaggc caccacttca agaactctgt    3360
agcaccgcct acatacccg ctctgctaat cctgttacca gtggctgctg ccagtggcga    3420
taagtcgtgt cttaccgggt tggactcaag acgatagtta ccggataagg cgcagcggtc    3480
gggctgaacg gggggttcgt gcacacagcc cagcttggag cgaacgacct acaccgaact    3540
gagataccta cagcgtgagc attgagaaag cgccacgctt cccgaaggga gaaggcgga    3600 caggtatccg gtaagcggca gggtcggaac aggagagcgc acgagggagc ttccaggggg    3660
aaacgcctgg tatctttata gtcctgtcgg gtttcgccac ctctgacttg agcgtcgatt    3720
tttgtgatgc tcgtcagggg ggcggagcct atggaaaaac gccagcaacg cggcctttt    3780 acggttcctg gccttttgct ggccttttgc tcacatgttc tttcctgcgt tatccctga    3840 ttctgtggat aaccgtatta ccgcctttga gtgagctgat accgctcgcc gcagccgaac    3900
gaccgagcgc agcgagtcag tgagcgagga agcggaagag cgcccaatac gcaaaccgcc    3960
tctccccgcg cgttggccga ttcattaatg caggttgatc agatctcgat cccgcgaaat    4020
taatacgact cactatagg g agaccacaac ggtttccctc tagaaataat tttgtttaac    4080
tttaagaagg agatataccc atggaaaagc ctgaactcac cgcgacgtct gtcgagaagt    4140
```

```
ttctgatcga aaagttcgac agcgtctccg acctgatgca gctctcggag ggcgaagaat    4200
ctcgtgcttt cagcttcgat gtaggagggc gtggatatgt cctgcgggta aatagctgcg    4260
ccgatggttt ctacaaagat cgttatgttt atcggcactt tgcatcggcc gcgctcccga    4320
ttccggaagt gcttgacatt ggggaattca gcgagagcct gacctattgc atctcccgcc    4380
gtgcacaggg tgtcacgttg caagacctgc ctgaaaccga actgcccgct gttctgcagc    4440
cggtcgcgga ggctatggat gcgatcgctg cggccgatct tagccagacg agcgggttcg    4500
gcccattcgg accgcaagga atcggtcaat acactacatg gcgtgatttc atatgcgcga    4560
ttgctgatcc ccatgtgtat cactggcaaa ctgtgatgga cgacaccgtc agtgcgtccg    4620
tcgcgcaggc tctcgatgag ctgatgcttt gggccgagga ctgccccgaa gtccggcacc    4680
tcgtgcacgc ggatttcggc tccaacaatg tcctgacgga caatggccgc ataacagcgg    4740
tcattgactg gagcgaggcg atgttcgggg attcccaata cgaggtcgcc aacatcttct    4800
tctggaggcc gtggttggct tgtatggagc agcagacgcg ctacttcgag cggaggcatc    4860
cggagcttgc aggatcgccg cggctccggg cgtatatgct ccgcattggt cttgaccaac    4920
tctatcagag cttggttgac ggcaatttcg atgatgcagc ttgggcgcag ggtcgatgcg    4980
acgcaatcgt ccgatccgga gccgggactg tcgggcgtac acaaatcgcc cgcagaagcg    5040
cggccgtctg gaccgatggc tgtgtagaag tactcgccga tagtggaaac cgacgccccca   5100
gcactcgtcc gagggcaaag gaatagtgag gtacagcttg gatcgatccg gctgctaaca    5160
aagcccgaaa ggaagctgag ttggctgctg ccaccgctga gcaataacta gcataacccc    5220
ttggggcctc taaacgggtc ttgaggggtt ttttgctgaa aggaggaact atatccggat    5280
gatcgggcgc gccgtcgacg gatccgtacg caaaggcaaa gatttaaact cgaaaacatt    5340
acaaaagtct caaaacagag gcaaggccat gcacaaagca cactctaagt gcttccattg    5400
cctactaagt agggtacgta cacgatcacc attcaccagt gatgatcttt attaatatac    5460
aacacactca gagacagctt atgttatagc tagctagcat aaactatcac atcatgtgtt    5520
agtacgacaa gtgacaacat tgcttttaac ttcgcggcct tggatcctct agaccggata    5580
taatgagccg taaacaaaga tgattaagta gtaattaata cgtactagta aaagtggcaa    5640
aagataacga gaaagaacca atttctttgc attcggcctt agcggaaggc atatataagc    5700
tttgattatt ttatttagtg taatgatttc gtacaaccaa agcatttatt tagtactctc    5760
acacttgtgt cgcggccgcg aattcactag tgattcctta tagagccttc cccgcgggtt    5820
gcttctccgc catccgggcg aacaccgcca gatagcgcag caggatgacc aacccttcat    5880
ggggcagcgg gttccgatac ggcaggttgt gcttctggca cagctgttcc acctggtagc    5940
taaccgctgt caggttgtgg cgagggaggg tcggccacaa atggtgctca atctggtaat    6000
tcaagcctcc gaaaaccaa tctgtgataa tccctcgccg aatgttcatg gtctcatgga    6060
tctggccaac cgagaatcca tggccatccc agactgagtc cccgatcttc tccagtgggt    6120
agtggttcat gaacaccacg atcgcaatgc cgaagccgcc aaccagctcc gaaacgaaaa    6180
acaccaacag cgatgtgagg atgctgggca taaagaataa gtggaacagg gtcttcaagg    6240
tccagtgcag ggcgaggcca atggcctcct tcttatactg agagcgatag aattggttat    6300
ctctgtcctt caaactgcgc acggtcaaca cgctctggaa acaccaaatg aaccgcaaca    6360
agatacagat gaccaagaaa tagtactgct ggaactgaat gagcttgcgg gaaatcggtg    6420
acgcccgtgt gacgtcatcc tcagaccagg ctaagagggg gaggttgtca atatcagggt    6480
cgtgcccttg aacattggtt gccgaatgat gtgcattgtg tctgtccttc caccatgtca    6540
```

```
cggaaaaacc ttgcagacca ttgccaaata ccagtcccac gaggttgttc cagttccggt   6600
tcttgaaagt ctggtggtgg caaatgtcat gagaaagcca gcccatctgt tgatagtgca   6660
tcccaagcaa cactgcccca atgaaataca tctgatactg aaccatcagg aaataaccca   6720
gcactccaag gcccagtgtg gtgctgattt tgtatgagta ccagaggggg gaggcatcaa   6780
acatgccagt tgcgatcaac tcttctcgga gcttccggaa atcctcttga gcttcattca   6840
ctgcagcctg gggtggcaac tcagaactgg gattgatttt gggcatgcgc ttgagcttgt   6900
cgaaggcttc ttgagagtgc ataaccatga aggcatcagt ggcatcccct ccttggtaat   6960
tctctataat ttccgcacca ccagggtgga aattgaccca ggcagacaca tcatatgttg   7020
ttccatcaat tgtaagggga agcgcttggc gctttgactt catttcaatc gaattcccgc   7080
ggccgcttgg ggggctatgg aagactttct tagttagttt tgtgaataag caatgttggg   7140
agaatcggga ctacttatag gataggaata aaacagaaaa gtattaagtg ctaatgaaat   7200
atttagactg ataattaaaa tcttcacgta tgtccacttg atataaaaac gtcaggaata   7260
aaggaagtac agtagaattt aaaggtactc ttttatata tacccgtgtt ctcttttggg   7320
ctagctagtt gcataaaaaa taatctatat ttttatcatt attttaaata tcttatgaga   7380
tggtaaatat ttatcataat ttttttact attatttatt atttgtgtgt gtaatacata   7440
tagaagttaa ttcaaatttt tatttacttt ttcattattt tgatatgatt caccattaat   7500
ttagtgttat tatttataat agttcatttt aatcttttg tatatattat gcgtgcagta   7560
cttttttcct acatataact actattacat tttatttata taatattttt attaatgaat   7620
tttcgtgata atatgtaata ttgttcatta ttatttcaga ttttttaaaa atatttgtgt   7680 tattattat gaaatatgta attttttag tatttgattt tatgatgata aagtgttcta   7740
aattcaaaag aaggggaaa gcgtaaacat taaaaaacgt catcaaacaa aaacaaaatc   7800
ttgttaataa agataaaaact gtttgttttg atcactgtta tttcgtaata taaaaacatt   7860
atttatattt atattgttga caaccaaatt tgcctatcaa atctaaccaa tataatgcat   7920
gcgtggcagg taatgtacta ccatgaactt aagtcatgac ataataaacc gtgaatctga   7980
ccaatgcatg tacctancta aattgtattt gtgacacgaa gcaaatgatt caattcacaa   8040
tggagatggg aaacaaataa tgaagaaccc agaactaaga aagcttttct gaaaaataaa   8100
ataaaggcaa tgtcaaaagt atactgcatc atcagtccag aaagcacatg atatttttt   8160 atcagtatca atgcagctag ttttattta caatatcgat atagctagtt taaatatatt   8220
gcagctagat ttataaatat ttgtgttatt atttatcatt tgtgtaatcc tgttttagt   8280 attttagttt atatatgatg ataatgtatt ccaaatttaa aagaagggaa ataaatttaa   8340
acaagaaaaa aagtcatcaa acaaaaaaca aatgaaaggg tggaaagatg ttaccatgta   8400
atgtgaatgt tacagtattt cttttattat agagttaaca aattaactaa tatgattttg   8460
ttaataatga taaatatttt ttttattat tatttcataa tataaaaata gtttacttaa   8520
tataaaaaaa attctatcgt tcacaacaaa gttggccacc taatttaacc atgcatgtac   8580
ccatggacca tattaggtaa ccatcaaacc tgatgaagag ataaagagat gaagacttaa   8640
gtcataacac aaaaccataa aaaacaaaaa tacaatcaac cgtcaatctg accaatgcat   8700
gaaaaagctg caatagtgag tggcgacaca aagcacatga ttttcttaca acggagataa   8760
aaccaaaaaa atatttcatg aacaacctag aacaaataaa gcttttatat aataaatata   8820
taaataaata aaggctatgg aataaatatac ttcaatatat ttggattaaa taaattgttg   8880
gcggggttga tatatttata cacacctaaa gtcacttcaa tctcattttc acttaacttt   8940
```

```
tatttttttt ttctttttat ttatcataaa gagaatattg ataatatact ttttaacata   9000
tttttatgac atttttatt ggtgaaaact tattaaaaat cataaatttt gtaagttaga    9060
tttatttaaa gagttcctct tcttatttta aatttttta taaatttta ataactaaa     9120
atttgtgtta aaaatgttaa aaaatgtgtt attaacccctt ctcttcgagg acgtacgtga  9180
aggttaaaca tggtgaatat gttaccacta gctgggatgc ccattagatc aaaactgtaa  9240
aattctcccg tttccttct attcacatgt gagcccctc ccttttcttt ctttctcaat    9300
tttgattgag ttaaagtcac cagcaatgca tcactcaccc tccaaaaaat ttcttgtaca  9360
acttctcgga ctatcccaaa gctccttttc ctgagatgga tggtcctgtc tcttgccctt  9420
gatgtcttcc ttgttcgatt ttggcttcct ctaatgtctt tcttgctagg aatcaccacc  9480
tcactcatct atgttgtcgt agcttctgaa agtctcatac atatccttag tgttgcactc  9540
atcttgtatt gaagtgaaaa agaatgttgt tctcctatcc aaatctccat tgaatctctt  9600
tctcccaatg ttgtcccatc ggttggtcct cctctccaac caattgtaag gtgtttaaca  9660
taaacatggt acaattaaga ttttcattt cattaagaaa agattgagat ttgtggttct   9720
aaagtttcaa ttagagtttg atgatattga acaaccgta gaacacatta agtattacta   9780
acttatacat agagcattgg aatttcacct tttatttatt ctgtttccgc caaaggtaca  9840
tgactcaagt tattttacac aagtaacaaa ggcatctaag cctaagtatt cttattcaga  9900
cttttcatta ttactttcat tgatttggtg cgaaatgcgg ccgcctactc ttccttggga  9960
cggagtccaa gaacacgcaa gtgctccaaa tgtgaagcaa atgcttgcca aaacgtatcc  10020
ttgacaaggt atggaaccctt gtactcgctg caggtgttct tgatgatggc cagaatatcg 10080
ggataatggt gctgcgacac gttggggaac agatggtgca cagcctggta gttcaagctg 10140
ccagtgatgc tggtccagag gtgcgaatcg tgtgcgtaat cctgcgtagt ctcgacctgc  10200
atagctgccc agtccttttg gatgatcccg ttctcgtcag gcaacggcca ctgaacttcc  10260
tcaacaacgt ggttcgcctg gaaggtcagc gccagccagt aagacgacac catgtccgcg  10320
accgtgaaca agagcagcac cttgcccagg ggcagatact gcaggggaac aatcaggcga  10380
taccagacaa agaaagcctt gccgccccag aacatcacag tgtgccatgt cgagatggga  10440
ttgacacgaa tagcgtcatt ggtcttgaca aagtacaaaa tgttgatgtc ctgaatgcgc  10500
accttgaacg ccagcagtcc gtacaggaaa ggaacaaaca tgtgctggtt gatgtggttg  10560
acaaaccact tttggttggg cttgatacga cgaacatcgg gctcagacgt cgacacgtcg  10620
ggatctgctc cagcaatgtt ggtgtagggg tgatggccga gcatatgttg gtacatccac  10680
accaggtacg atgctccgtt gaaaaagtcg tgcgtggctc ccagaatctt ccagacagtg  10740
gggttgtggg tcactgaaaa gtgagacgca tcatgaagag ggttgagtcc gacttgtgcg  10800
cacgcaaatc ccatgatgat tgcaaacacc acctgaagcc atgtgcgttc gacaacgaaa  10860
ggcacaaaga gctgcgcgta gtaggaagcg atcaaggatc caaagataag agcgtatcgt  10920
ccccagatct ctggtctatt cttgggatca atgttccgat ccgtaaagta gccctcgact  10980
ctcgtcttga tggttttgtg gaacaccgtt ggctccggga agatgggcag ctcattcgag  11040
accagtgtac cgacatagta cttcttcata atggcatctg cagccccaaa cgcgtgatac  11100
atctcaaaga ccggagtaac atctcggcca gctccgagca ggagagtgtc cactccacca  11160
ggatggcggc tcaagaactt tgtgacatcg tacaccctgc cgcggatggc caagagtagg  11220
tcgtccttgg tgttatgggc cgccagctct tcccagtgta aggttttttcc ttggtccgtt  11280
cccatgcggc cgcggtgatg actgatgagt gtttaaggac caatggagag aatgtttgag  11340
```

-continued

| | |
|---|---|
| ttgtgaagcg gagaacctga ggcgtggtta tttataggga agagaggaag gtgaatgagg | 11400 |
| gacacgtcac agaagtaggg tgctgagctt gagacattct tcagtatgca tggctatgga | 11460 |
| agccttgggt gctacacctc atgaagttca tggtgtgagg tggcttcggc atctcaatta | 11520 |
| agtgacaaag agaaaggtgt ttcagtgttt ctattgcaaa tggcagaaac tcgtgatgac | 11580 |
| gaggggacca tgcatggttt catttctttt cttcctggat tctttcttc cttttatata | 11640 |
| tgcaggttca taatttaaaa attagactcg ctttcaattt cttaatttct cattttcctc | 11700 |
| ttatattact gtactaatgt taaccacgta cacttatttt ttttttagtt taattttgat | 11760 |
| agattgtgtt gatttaaaca tattaatatt ttcaaccaaa taaaaatcat tttagtagat | 11820 |
| acggcttttt aaataattat taaaaatatt aactatttat cctaaatggc acattttaat | 11880 |
| taaaaaaaat ccggtgttgt aagtgtttta ttaatttgtt ttggcattat taaagcaact | 11940 |
| tttttttat ttgttggcat tttgagtacg tacttaggct agcctgca | 11988 |

<210> SEQ ID NO 64
<211> LENGTH: 11983
<212> TYPE: DNA
<213> ORGANISM: Artificial sequence
<220> FEATURE:
<223> OTHER INFORMATION: plasmid pKR1231
<220> FEATURE:
<221> NAME/KEY: misc_feature
<222> LOCATION: (7992)..(7992)
<223> OTHER INFORMATION: n is unknown

<400> SEQUENCE: 64

| | |
|---|---|
| ggagatccaa gcttttgatc catgcccttc atttgccgct tattaattaa tttggtaaca | 60 |
| gtccgtacta atcagttact tatccttccc ccatcataat taatcttggt agtctcgaat | 120 |
| gccacaacac tgactagtct cttggatcat aagaaaaagc caaggaacaa aagaagacaa | 180 |
| aacacaatga gagtatcctt tgcatagcaa tgtctaagtt cataaaattc aaacaaaaac | 240 |
| gcaatcacac acagtggaca tcacttatcc actagctgat caggatcgcc gcgtcaagaa | 300 |
| aaaaaaactg accccaaaa gccatgcaca acaacacgta ctcacaaagg tgtcaatcga | 360 |
| gcagcccaaa acattcacca actcaaccca tcatgagccc tcacatttgt tgtttctaac | 420 |
| ccaacctcaa actcgtattc tcttccgcca cctcattttt gtttatttca acaccgtca | 480 |
| aactgcatgc caccccgtgg ccaaatgtcc atgcatgtta acaagaccta tgactataaa | 540 |
| tagctgcaat ctcggcccag gttttcatca tcaagaacca gttcaatatc ctagtacacc | 600 |
| gtattaaaga atttaagata tactgcggcc gcaaaccatg gagtccattg ttcccttcct | 660 |
| gccctccaag atgcctcagg acctgttcat ggacctcgcc agcgctatcg gtgtccgagc | 720 |
| tgctccctac gtcgatcccc tggaggctgc cctggttgcc caggccgaga agtacattcc | 780 |
| caccattgtc catcacactc gaggcttcct ggttgccgtg gattctcccc tggctcgaga | 840 |
| gctgcctctg atgaaccct tccacgtgct catgcttgtg ctcgcctacc tggtcaccgt | 900 |
| gtttgtgggt atgcagatca tgaagaactt tgaacgattc gaggtcaaga cgttctcgct | 960 |
| cctgtacaac ttctgtctgg tctcgctgag cgcctacatg tgcggtggca ttctgtacga | 1020 |
| ggcttatcag gccaactatg gactgtttca gaacgctgcc gatcacacct tcaagggtct | 1080 |
| ccctatggct aagatgatct ggctcttcta cttctccaag ctgatggagt tgtcgacac | 1140 |
| catgatcatg gtcctcaaaa agaacaaccg acagatttcc ttctgcacg tgtaccacca | 1200 |
| ctcttccatc ttcaccatct ggtggctggt caccttcgtt gctcccaacg gtgaagccta | 1260 |
| cttctctgct gccctgaact cgttcatcca tgttatcatg tacggctact actttctgtc | 1320 |

```
tgccctgggc ttcaagcagg tgtcgttcat caagttctac atcactcgat cccagatgac  1380
ccagttctgc atgttgtctg tccagtcttc ctgggacatg tacgccatga aggtccttgg  1440
ccgacctgga tacccttcct tcctgaccgc tctgctctgg ttctacatgt ggaccatgct  1500
cggtctcttc tacaactttt accgaaagaa cgccaagctc gccaagcagg ccaaggctga  1560
cgctgccaag gagaaggcca gaaagctcca gtaagcggcc gcaagtatga actaaaatgc  1620
atgtaggtgt aagagctcat ggagagcatg gaatattgta tccgaccatg taacagtata  1680
ataactgagc tccatctcac ttcttctatg aataaacaaa ggatgttatg atatattaac  1740
actctatcta tgcaccttat tgttctatga taaatttcct cttattatta taaatcatct  1800
gaatcgtgac ggcttatgga atgcttcaaa tagtacaaaa acaaatgtgt actataagac  1860
tttctaaaca attctaacct tagcattgtg aacgagacat aagtgttaag aagacataac  1920
aattataatg gaagaagttt gtctccattt atatattata tattacccac ttatgtatta  1980
tattaggatg ttaaggagac ataacaatta taaagagaga agtttgtatc catttatata  2040
ttatatacta cccatttata tattatactt atccacttat ttaatgtctt tataaggttt  2100
gatccatgat atttctaata ttttagttga tatgtatatg aaagggtact attttgaactc 2160
tcttactctg tataaaggtt ggatcatcct taaagtgggt ctatttaatt ttattgcttc  2220
ttacagataa aaaaaaatt atgagttggt ttgataaaat attgaaggat ttaaaataat  2280
aataaataac atataatata tgtatataaa tttattataa tataacattt atctataaaa  2340
aagtaaatat tgtcataaat ctatacaatc gtttagcctt gctggacgaa tctcaattat  2400
ttaaacgaga gtaaacatat ttgactttt ggttatttaa caaattatta tttaacacta   2460
tatgaaattt ttttttttat cagcaaagaa taaaattaaa ttaagaagga caatggtgtc  2520
ccaatcctta tacaaccaac ttccacaaga aagtcaagtc agagacaaca aaaaaacaag  2580
caaaggaaat tttttaattt gagttgtctt gtttgctgca taatttatgc agtaaaacac  2640
tacacataac ccttttagca gtagagcaat ggttgaccgt gtgcttagct tcttttatt   2700
tatttttta tcagcaaaga ataaataaaa taaaatgaga cacttcaggg atgtttcaac  2760
aagcttggcg cgccgttcta tagtgtcacc taaatcgtat gtgtatgata cataaggtta  2820
tgtattaatt gtagccgcgt tctaacgaca atatgtccat atggtgcact ctcagtacaa  2880
tctgctctga tgccgcatag ttaagccagc cccgacaccc gccaacaccc gctgacgcgc  2940
cctgacgggc ttgtctgctc ccggcatccg cttacagaca agctgtgacc gtctccggga  3000
gctgcatgtg tcagaggttt tcaccgtcat caccgaaacg cgcgagacga aagggcctcg  3060
tgatacgcct atttttatag gttaatgtca tgaccaaaat cccttaacgt gagttttcgt  3120
tccactgagc gtcagacccc gtagaaaaga tcaaaggatc ttcttgagat cctttttttc  3180
tgcgcgtaat ctgctgcttg caaacaaaaa aaccaccgct accagcggtg gtttgtttgc  3240
cggatcaaga gctaccaact cttttttccga aggtaactgg cttcagcaga gcgcagatac  3300
caaatactgt ccttctagtg tagccgtagt taggccacca cttcaagaac tctgtagcac  3360
cgcctacata cctcgctctg ctaatcctgt taccagtggc tgctgccagt ggcgataagt  3420
cgtgtcttac cgggttggac tcaagacgat agttaccgga taaggcgcag cggtcgggct  3480
gaacgggggg ttcgtgcaca cagcccagct tggagcgaac gacctacacc gaactgagat  3540
acctacagcg tgagcattga gaaagcgcca cgcttcccga agggagaaag gcggacaggt  3600
atccggtaag cggcagggtc ggaacaggag agcgcacgag ggagcttcca gggggaaacg  3660
cctggtatct ttatagtcct gtcgggtttc gccacctctg acttgagcgt cgatttttgt  3720
```

```
gatgctcgtc agggggggcgg agcctatgga aaaacgccag caacgcggcc ttttttacggt    3780 tcctggcctt ttgctggcct tttgctcaca tgttctttcc tgcgttatcc cctgattctg    3840
tggataaccg tattaccgcc tttgagtgag ctgataccgc tcgccgcagc cgaacgaccg    3900
agcgcagcga gtcagtgagc gaggaagcgg aagagcgccc aatacgcaaa ccgcctctcc    3960
ccgcgcgttg gccgattcat taatgcaggt tgatcagatc tcgatcccgc gaaattaata    4020
cgactcacta tagggagacc acaacggttt ccctctagaa ataattttgt ttaactttaa    4080
gaaggagata tacccatgga aaagcctgaa ctcaccgcga cgtctgtcga agtttctg    4140 atcgaaaagt tcgacagcgt ctccgacctg atgcagctct cggagggcga agaatctcgt    4200
gctttcagct tcgatgtagg agggcgtgga tatgtcctgc gggtaaatag ctgcgccgat    4260
ggtttctaca aagatcgtta tgtttatcgg cactttgcat cggccgcgct cccgattccg    4320
gaagtgcttg acattgggga attcagcgag agcctgacct attgcatctc ccgccgtgca    4380
cagggtgtca cgttgcaaga cctgcctgaa accgaactgc ccgctgttct gcagccggtc    4440
gcggaggcta tggatgcgat cgctgcggcc gatcttagcc agacgagcgg gttcggccca    4500
ttcggaccgc aaggaatcgg tcaatacact acatggcgtg atttcatatg cgcgattgct    4560
gatccccatg tgtatcactg gcaaactgtg atggacgaca ccgtcagtgc gtccgtcgcg    4620
caggctctcg atgagctgat gctttgggcc gaggactgcc ccgaagtccg gcacctcgtg    4680
cacgcggatt tcggctccaa caatgtcctg acggacaatg gccgcataac agcggtcatt    4740
gactggagcg aggcgatgtt cggggattcc caatacgagg tcgccaacat cttcttctgg    4800
aggccgtggt tggcttgtat ggagcagcag acgcgctact tcgagcggag gcatccggag    4860
cttgcaggat cgccgcggct ccgggcgtat atgctccgca ttggtcttga ccaactctat    4920
cagagcttgg ttgacggcaa tttcgatgat gcagcttggg cgcagggtcg atgcgacgca    4980
atcgtccgat ccggagccgg gactgtcggg cgtacacaaa tcgcccgcag aagcgcggcc    5040
gtctggaccg atggctgtgt agaagtactc gccgatagtg gaaaccgacg ccccagcact    5100
cgtccgaggc aaaggaata gtgaggtaca gcttggatcg atccggctgc taacaaagcc    5160
cgaaaggaag ctgagttggc tgctgccacc gctgagcaat aactagcata ccccttgggg    5220
gcctctaaac gggtcttgag gggttttttg ctgaaaggag gaactatatc cggatgatcg    5280
ggcgcgccgt cgacggatcc gtacgcaaag gcaaagattt aaactcgaaa acattacaaa    5340
agtctcaaaa cagaggcaag gccatgcaca aagcacactc taagtgcttc cattgcctac    5400
taagtagggt acgtacacga tcaccattca ccagtgatga tctttattaa tatacaacac    5460
actcagagac agcttatgtt atagctagct agcataaact atcacatcat gtgttagtac    5520
gacaagtgac aacattgctt ttaacttcgc ggccttggat cctctagacc ggatataatg    5580
agccgtaaac aaagatgatt aagtagtaat taatacgtac tagtaaaagt ggcaaaagat    5640
aacgagaaag aaccaatttc tttgcattcg gccttagcgg aaggcatata taagctttga    5700
ttattttatt tagtgtaatg atttcgtaca accaaagcat ttatttagta ctctcacact    5760
tgtgtcgcgg ccgcgaattc actagtgatt ccttatagag ccttcccgc gggttgcttc    5820 tccgccatcc gggcgaacac cgccagatag cgcagcagga tgaccaaccc ttcatggggc    5880
agcgggttcc gatacggcag gttgtgcttc tggcacagct gttccacctg gtagctaacc    5940
gctgtcaggt tgtggcgagg gagggtcggc cacaaatggt gctcaatctg gtaattcaag    6000
cctccgaaaa accaatctgt gataatccct cgccgaatgt tcatggtctc atggatctgg    6060
ccaaccgaga atccatggcc atcccagact gagtccccga tcttctccag tgggtagtgg    6120
```

-continued

| | |
|---|---|
| ttcatgaaca ccacgatcgc aatgccgaag ccgccaacca gctccgaaac gaaaaacacc | 6180 |
| aacagcgatg tgaggatgct gggcataaag aataagtgga acagggtctt caaggtccag | 6240 |
| tgcagggcga ggccaatggc ctccttctta tactgagagc gatagaattg gttatctctg | 6300 |
| tccttcaaac tgcgcacggt caacacgctc tggaaacacc aaatgaaccg caacaagata | 6360 |
| cagatgacca agaaatagta ctgctggaac tgaatgagct tgcgggaaat cggtgacgcc | 6420 |
| cgtgtgacgt catcctcaga ccaggctaag agggggaggt tgtcaatatc agggtcgtgc | 6480 |
| ccttgaacat tggttgccga atgatgtgca ttgtgtctgt ccttccacca tgtcacggaa | 6540 |
| aaaccttgca gaccattgcc aaataccagt cccacgaggt gttccagtt ccggttcttg | 6600 |
| aaagtctggt ggtggcaaat gtcatgagaa agccagccca tctgttgata gtgcatccca | 6660 |
| agcaacactg ccccaatgaa atacatctga tactgaacca tcaggaaata acccagcact | 6720 |
| ccaaggccca gtgtggtgct gattttgtat gagtaccaga ggggggaggc atcaaacatg | 6780 |
| ccagttgcga tcaactcttc tcggagcttc cggaaatcct cttgagcttc attcactgca | 6840 |
| gcctggggtg gcaactcaga actgggattg attttgggca tgcgcttgag cttgtcgaag | 6900 |
| gcttcttgag agtgcataac catgaaggca tcagtgcat cccttcctg gtaattctct | 6960 |
| ataatttccg caccaccagg gtggaaattg acccaggcag acacatcata tgttgttcca | 7020 |
| tcaattgtaa ggggaagcgc ttggcgcttt gacttcattt caatcgaatt cccgcggccg | 7080 |
| cttgggggc tatggaagac tttcttagtt agttgtgtga ataagcaatg ttgggagaat | 7140 |
| cgggactact tataggatag gaataaaaca gaaaagtatt aagtgctaat gaaatattta | 7200 |
| gactgataat taaaatcttc acgtatgtcc acttgatata aaacgtcag gaataaagga | 7260 |
| agtacagtag aatttaaagg tactctttt atatataccc gtgttctctt tttggctagc | 7320 |
| tagttgcata aaaaataatc tatatttta tcattatttt aaatatctta tgagatggta | 7380 |
| aatatttatc ataattttt ttactattat ttattattg tgtgtgtaat acatatagaa | 7440 |
| gttaattaca aatttatt acttttcat tattttgata tgattcacca ttaatttagt | 7500 |
| gttattattt ataatagttc attttaatct ttttgtatat attatgcgtg cagtacttt | 7560 |
| ttcctacata taactactat tacatttat ttatataata ttttattaa tgaattttcg | 7620 |
| tgataatatg taatattgtt cattattatt tcagatttt taaaaatatt tgtgttatta | 7680 |
| tttatgaaat atgtaatttt tttagtattt gattttatga tgataaagtg ttctaaattc | 7740 |
| aaaagaaggg ggaaagcgta aacattaaaa aacgtcatca aacaaaaaca aaatcttgtt | 7800 |
| aataaagata aaactgtttg ttttgatcac tgttatttcg taatataaaa acattattta | 7860 |
| tatttatatt gttgacaacc aaatttgcct atcaaatcta accaatataa tgcatgcgtg | 7920 |
| gcaggtaatg tactaccatg aacttaagtc atgacataat aaaccgtgaa tctgaccaat | 7980 |
| gcatgtacct anctaaattg tatttgtgac acgaagcaaa tgattcaatt cacaatggag | 8040 |
| atgggaaaca aataatgaag aacccagaac taagaaagct tttctgaaaa ataaaataaa | 8100 |
| ggcaatgtca aaagtatact gcatcatcag tccagaaagc acatgatatt ttttatcag | 8160 |
| tatcaatgca gctagtttta ttttacaata tcgatatagc tagtttaaat atattgcagc | 8220 |
| tagatttata aatatttgtg ttattattta tcatttgtgt aatcctgttt ttagtatttt | 8280 |
| agtttatata tgatgataat gtattccaaa tttaaagaa gggaaataaa tttaaacaag | 8340 |
| aaaaaaagtc atcaaacaaa aaacaaatga agggtggaa agatgttacc atgtaatgtg | 8400 |
| aatgttacag tatttctttt attatagagt taacaaatta actaatatga ttttgttaat | 8460 |
| aatgataaaa tattttttt attattattt cataatataa aaatagttta cttaatataa | 8520 |

```
aaaaaattct atcgttcaca acaaagttgg ccacctaatt taaccatgca tgtacccatg    8580
gaccatatta ggtaaccatc aaacctgatg aagagataaa gagatgaaga cttaagtcat    8640
aacacaaaac cataaaaaac aaaaatacaa tcaaccgtca atctgaccaa tgcatgaaaa    8700
agctgcaata gtgagtggcg acacaaagca catgattttc ttacaacgga gataaaacca    8760
aaaaaatatt tcatgaacaa cctagaacaa ataaagcttt tatataataa atatataaat    8820
aaataaaggc tatggaataa tatacttcaa tatatttgga ttaaataaat tgttggcggg    8880
gttgatatat ttatacacac ctaaagtcac ttcaatctca ttttcactta actttttattt   8940
tttttttctt tttatttatc ataaagagaa tattgataat atacttttta acatatttt    9000
atgacatttt ttattggtga aaacttatta aaaatcataa attttgtaag ttagatttat    9060
ttaaagagtt cctcttctta ttttaaattt tttaataaat ttttaaataa ctaaaatttg    9120
tgttaaaaat gttaaaaaat gtgttattaa cccttctctt cgaggacgta cgtgaaggtt    9180
aaacatggtg aatatgttac cactagctgg gatgcccatt agatcaaaac tgtaaaattc    9240
tcccgtttcc cttctattca catgtgagcc ccctcccttt tctttctttc tcaattttga    9300
ttgagttaaa gtcaccagca atgcatcact caccctccaa aaaatttctt gtacaacttc    9360
tcggactatc ccaaagctcc ttttcctgag atggatggtc ctgtctcttg cccttgatgt    9420
cttccttgtt cgattttggc ttcctctaat gtctttcttg ctaggaatca ccacctcact    9480
catctatgtt gtcgtagctt ctgaaagtct catacatatc cttagtgttg cactcatctt    9540
gtattgaagt gaaaagaat gttgttctcc tatccaaatc tccattgaat ctctttctcc    9600
caatgttgtc ccatcggttg gtcctcctct ccaaccaatt gtaaggtgtt taacataaac    9660
atggtacaat taagattttt catttcatta agaaaagatt gagatttgtg ttctaaagt    9720
ttcaattaga gtttgatgat attgaaacaa ccgtagaaca cattaagtat tactaactta    9780
tacatagagc attggaattt caccttttat ttattctgtt tccgccaaag gtacatgact   9840
caagttattt tacacaagta acaaaggcat ctaagcctaa gtattcttat tcagacttt    9900
cattattact ttcattgatt tggtgcgaaa tgcggccgcc tactcttcct tgggacggag    9960
tccaagaaca cgcaagtgct ccaaatgtga agcaaatgct tgccaaaacg tatccttgac   10020
aaggtatgga accttgtact cgctgcaggt gttcttgatg atggccagaa tatcgggata   10080
atggtgctgc gacacgttgg ggaacagatg gtgcacagcc tggtagttca agctgccagt   10140
gatgctggtc cagaggtgcg aatcgtgtgc gtaatcctgc gtagtctcga cctgcatagc   10200
tgcccagtcc ttttggatga tcccgttctc gtcaggcaac ggccactgaa cttcctcaac   10260
aacgtggttc gcctggaagg tcagcgccag ccagtaagac gacaccatgt ccgcgaccgt   10320
gaacaagagc agcaccttgc ccaggggcag atactgcagg ggaacaatca ggcgatacca   10380
gacaaagaaa gccttgccgc cccagaacat cacagtgtgc catgtcgaga tgggattgac   10440
acgaatagcg tcattggtct tgacaaagta caaaatgttg atgtcctgaa tgcgcacctt   10500
gaacgccagc agtccgtaca ggaaaggaac aaacatgtgc tggttgatgt ggttgacaaa   10560
ccacttttgg ttgggcttga tacgacgaac atcgggctca gacgtcgaca cgtcgggatc   10620
tgctccagca atgttggtgt aggggtgatg gccgagcata tgttggtaca tccacaccag   10680
gtacgatgct ccgttgaaaa agtcgtgcgt ggctcccaga atcttccaga cagtgggtt    10740
gtgggtcact gaaagtgag acgcatcatg aagagggttg agtccgactt gtgcgcacgc   10800
aaatcccatg atgattgcaa acaccacctg aagccatgtg cgttcgacaa cgaaaggcac   10860
aaagagctgc gcgtagtagg aagcgatcaa ggatccaaag ataagagcgt atcgtcccca   10920
```

```
gatctctggt ctattcttgg gatcaatgtt ccgatccgta aagtagccct cgactctcgt    10980
cttgatggtt ttgtggaaca ccgttggctc cgggaagatg ggcagctcat tcgagaccag    11040
tgtaccgaca tagtacttct tcataatggc atctgcagcc ccaaacgcgt gatacatctc    11100
aaagaccgga gtaacatctc ggccagctcc gagcaggaga gtgtccactc caccaggatg    11160
gcggctcaag aactttgtga catcgtacac cctgccgcgg atggccaaga gtaggtcgtc    11220
cttggtgtta tgggccgcca gctcttccca ggtgaaggtt tttccttggt ccgttcccat    11280
gcggccgcgg tgatgactga tgagtgttta aggaccaatg gagagaatgt ttgagttgtg    11340
aagcggagaa cctgaggcgt ggttatttat agggaagaga ggaaggtgaa tgagggacac    11400
gtcacagaag tagggtgctg agcttgagac attcttcagt atgcatggct atggaagcct    11460
tgggtgctac acctcatgaa gttcatggtg tgaggtggct tcggcatctc aattaagtga    11520
caaagagaaa ggtgtttcag tgtttctatt gcaaatggca gaaactcgtg atgacgaggg    11580
gaccatgcat ggtttcattt ctttcttcc tggattcttt ctttccttttt atatatgcag    11640 gttcataatt taaaaattag actcgctttc aatttcttaa tttctcattt cctcttata    11700 ttactgtact aatgttaacc acgtacactt atttttttt tagtttaatt ttgatagatt    11760
gtgttgattt aaacatatta atattttcaa ccaaataaaa atcatttag tagatacggc    11820 tttttaaata attattaaaa atattaacta tttatcctaa atggcacatt ttaattaaaa    11880
aaaatccggt gttgtaagtg ttttattaat ttgttttggc attattaaag caactttttt    11940
tttatttgtt ggcattttga gtacgtactt aggctagcct gca                     11983

<210> SEQ ID NO 65
<211> LENGTH: 11198
<212> TYPE: DNA
<213> ORGANISM: Artificial sequence
<220> FEATURE:
<223> OTHER INFORMATION: plasmid pKR1232

<400> SEQUENCE: 65
gatccgtcga cggcgcgccc gatcatccgg atatagttcc tcctttcagc aaaaaacccc      60
tcaagacccg tttagaggcc caaggggtt atgctagtta ttgctcagcg gtggcagcag     120
ccaactcagc ttccttcgg gctttgttag cagccggatc gatccaagct gtacctcact     180
attcctttgc cctcggacga gtgctgggc gtcggtttcc actatcggcg agtacttcta     240
cacagccatc ggtccagacg gccgcgcttc tgcgggcgat ttgtgtacgc ccgacagtcc     300
cggctccgga tcggacgatt gcgtcgcatc gaccctgcgc ccaagctgca tcatcgaaat     360
tgccgtcaac caagctctga tagagttggt caagaccaat gcggagcata tacgcccgga     420
gccgcggcga tcctgcaagc tccggatgcc tccgctcgaa gtagcgcgtc tgctgctcca     480
tacaagccaa ccacggcctc cagaagaaga tgttggcgac ctcgtattgg gaatccccga     540
acatcgcctc gctccagtca atgaccgctg ttatgcggcc attgtccgtc aggacattgt     600
tggagccgaa atccgcgtgc acgaggtgcc ggacttcggg gcagtcctcg gcccaaagca     660
tcagctcatc gagagcctgc gcgacggacg cactgacggt gtcgtccatc acagtttgcc     720
agtgatacac atggggatca gcaatcgcgc atatgaaatc acgccatgta gtgtattgac     780
cgattccttg cggtccgaat gggccgaacc cgctcgtctg gctaagatcg gccgcagcga     840
tcgcatccat agcctccgcg accggctgca gaacagcggg cagttcggtt tcaggcaggt     900
cttgcaacgt gacaccctgt gcacggcggg agatgcaata ggtcaggctc tcgctgaatt     960
ccccaatgtc aagcacttcc ggaatcggga gcgcggccga tgcaaagtgc cgataaacat    1020
```

```
aacgatcttt gtagaaacca tcggcgcagc tatttacccg caggacatat ccacgccctc    1080
ctacatcgaa gctgaaagca cgagattctt cgccctccga gagctgcatc aggtcggaga    1140
cgctgtcgaa cttttcgatc agaaacttct cgacagacgt cgcggtgagt tcaggctttt    1200
ccatgggtat atctccttct taaagttaaa caaaattatt tctagaggga aaccgttgtg    1260
gtctccctat agtgagtcgt attaatttcg cgggatcgag atcgatccaa ttccaatccc    1320
acaaaaatct gagcttaaca gcacagttgc tcctctcaga gcagaatcgg gtattcaaca    1380
ccctcatatc aactactacg ttgtgtataa cggtccacat gccggtatat acgatgactg    1440
gggttgtaca aaggcggcaa caaacggcgt tcccggagtt gcacacaaga aatttgccac    1500
tattacagag gcaagagcag cagctgacgc gtacacaaca agtcagcaaa cagacaggtt    1560
gaacttcatc cccaaaggag aagctcaact caagcccaag agctttgcta aggccctaac    1620
aagcccacca aagcaaaaag cccactggct cacgctagga accaaaaggc ccagcagtga    1680
tccagcccca aaagagatct cctttgcccc ggagattaca atggacgatt tcctctatct    1740
ttacgatcta ggaaggaagt tcgaaggtga aggtgacgac actatgttca ccactgataa    1800
tgagaaggtt agcctcttca atttcagaaa gaatgctgac ccacagatgg ttagagaggc    1860
ctacgcagca ggtctcatca agacgatcta cccgagtaac aatctccagg agatcaaata    1920
ccttcccaag aaggttaaag atgcagtcaa aagattcagg actaattgca tcaagaacac    1980
agagaaagac atatttctca agatcagaag tactattcca gtatggacga ttcaaggctt    2040
gcttcataaa ccaaggcaag taatagagat tggagtctct aaaaaggtag ttcctactga    2100
atctaaggcc atgcatggag tctaagattc aaatcgagga tctaacagaa ctcgccgtga    2160
agactggcga acagttcata cagagtcttt tacgactcaa tgacaagaag aaaatcttcg    2220
tcaacatggt ggagcacgac actctggtct actccaaaaa tgtcaaagat acagtctcag    2280
aagaccaaag ggctattgag acttttcaac aaaggtataa ttcgggaaac ctcctcggat    2340
tccattgccc agctatctgt cacttcatcg aaaggacagt agaaaggaa ggtggctcct    2400 acaaatgcca tcattgcgat aaaggaaagg ctatcattca agatgcctct gccgacagtg    2460
gtcccaaaga tggaccccca cccacgagga gcatcgtgga aaaagaagac gttccaacca    2520
cgtcttcaaa gcaagtggat tgatgtgaca tctccactga cgtaagggat gacgcacaat    2580
cccactatcc ttcgcaagac ccttcctcta tataaggaag ttcatttcat ttggagagga    2640
cacgctcgag ctcatttctc tattacttca gccataacaa aagaactctt ttctcttctt    2700
attaaaccat gaaaaagcct gaactcaccg cgacgtctgt cgagaagttt ctgatcgaaa    2760
agttcgacag cgtctccgac ctgatgcagc tctcggaggg cgaagaatct cgtgctttca    2820
gcttcgatgt aggagggcgt ggatatgtcc tgcgggtaaa tagctgcgcc gatggtttct    2880
acaaagatcg ttatgtttat cggcactttg catcggccgc gctcccgatt ccggaagtgc    2940
ttgacattgg ggaattcagc gagagcctga cctattgcat ctcccgccgt gcacagggtg    3000
tcacgttgca agacctgcct gaaaccgaac tgcccgctgt tctgcagccg gtcgcggagg    3060
ccatggatgc gatcgctgcg gccgatctta gccagacgag cgggttcggc ccattcggac    3120
cgcaaggaat cggtcaatac actacatggc gtgatttcat atgcgcgatt gctgatcccc    3180
atgtgtatca ctggcaaact gtgatggacg acaccgtcag tgcgtccgtc gcgcaggctc    3240
tcgatgagct gatgctttgg gccgaggact gccccgaagt ccggcacctc gtgcacgcgg    3300
atttcggctc caacaatgtc ctgacggaca atggccgcat aacagcggtc attgactgga    3360
gcgaggcgat gttcggggat tcccaatacg aggtcgccaa catcttcttc tggaggccgt    3420
```

```
ggttggcttg tatggagcag cagacgcgct acttcgagcg gaggcatccg gagcttgcag    3480
gatcgccgcg gctccgggcg tatatgctcc gcattggtct tgaccaactc tatcagagct    3540
tggttgacgg caatttcgat gatgcagctt gggcgcaggg tcgatgcgac gcaatcgtcc    3600
gatccggagc cgggactgtc gggcgtacac aaatcgcccg cagaagcgcg gccgtctgga    3660
ccgatggctg tgtagaagta ctcgccgata gtggaaaccg acgccccagc actcgtccga    3720
gggcaaagga atagtgaggt acctaaagaa ggagtgcgtc gaagcagatc gttcaaacat    3780
ttggcaataa agtttcttaa gattgaatcc tgttgccggt cttgcgatga ttatcatata    3840
atttctgttg aattacgtta agcatgtaat aattaacatg taatgcatga cgttatttat    3900
gagatgggtt tttatgatta gagtcccgca attatacatt taatacgcga tagaaaacaa    3960
aatatagcgc gcaaactagg ataaattatc gcgcgcggtg tcatctatgt tactagatcg    4020
atgtcgaatc gatcaacctg cattaatgaa tcggccaacg cgcggggaga ggcggttttgc   4080 gtattgggcg ctcttccgct tcctcgctca ctgactcgct gcgctcggtc gttcggctgc    4140
ggcgagcggt atcagctcac tcaaaggcgg taatacggtt atccacagaa tcaggggata    4200
acgcaggaaa gaacatgtga gcaaaaggcc agcaaaaggc caggaaccgt aaaaaggccg    4260
cgttgctggc gtttttccat aggctccgcc ccctgacga gcatcacaaa aatcgacgct     4320
caagtcagag gtggcgaaac ccgacaggac tataaagata ccaggcgttt ccccctggaa    4380
gctccctcgt gcgctctcct gttccgaccc tgccgcttac cggatacctg tccgcctttc    4440
tcccttcggg aagcgtggcg ctttctcaat gctcacgctg taggtatctc agttcggtgt    4500
aggtcgttcg ctccaagctg ggctgtgtgc acgaaccccc cgttcagccc gaccgctgcg    4560
ccttatccgg taactatcgt cttgagtcca acccggtaag acgacttta tcgccactgg     4620 cagcagccac tggtaacagg attagcagag cgaggtatgt aggcggtgct acagagttct    4680
tgaagtggtg gcctaactac ggctacacta aaggacagt atttggtatc tgcgctctgc     4740
tgaagccagt taccttcgga aaaagagttg gtagctcttg atccggcaaa caaaccaccg    4800
ctggtagcgg tggttttttt gtttgcaagc agcagattac gcgcagaaaa aaaggatctc    4860
aagaagatcc tttgatcttt tctacggggt ctgacgctca gtggaacgaa aactcacgtt    4920
aagggatttt ggtcatgaca ttaacctata aaaataggcg tatcacgagg ccctttcgtc    4980
tcgcgcgttt cggtgatgac ggtgaaaacc tctgacacat gcagctcccg gagacggtca    5040
cagcttgtct gtaagcggat gccgggagca gacaagcccg tcagggcgcg tcagcgggtg    5100
ttggcgggtg tcggggctgg cttaactatg cggcatcaga gcagattgta ctgagagtgc    5160
accatatgga catattgtcg ttagaacgcg gctacaatta atacataacc ttatgtatca    5220
tacacatacg atttaggtga cactatagaa cggcgcgcca agcttggatc tcctgcagga    5280
tctggccggc cggatctcgt acggatcctc tagacgtacg caaaggcaaa gatttaaact    5340
cgaaaacatt acaaaagtct caaaacagag gcaaggccat gcacaaagca cactctaagt    5400
gcttccattg cctactaagt agggtacgta cacgatcacc attcaccagt gatgatcttt    5460
attaatatac aacacactca gagacagctt atgttatagc tagctagcat aaactatcac    5520
atcatgtgtt agtacgacaa gtgacaacat tgcttttaac ttcgcggccg cctagcctag    5580
tccttgttcc atcgcatggc accgggtcgg gcagggtcgt gctcgacgta cttgagcgtg    5640
ccgaagatgg tccacagctg gcccaggaag cttcggtcgt cgtggcagta gtggtcgcca    5700
atgacgggct tgatgcctcc ggtggcctcg tcagccttgt agaaggggat cttagggaag    5760
agatggtgaa caacgtgctt ctcaatgata ccgtggaaga ggtgctttcc gatgaagcca    5820
```

```
aactcacggt cgacagtggc gagagctccc ttgacgtagg tccagccctc agcggtgtag    5880
tgagggagct cggtgtggtg gtggtggagg taggtaatgg caacgagcca gtggtgaacc    5940
cacaggtagg gaacaaggta gaggaagaga atggtcgaaa caccaacttg cttggaagca    6000
aagtacagag cagttcccat tagagcaaga ccgatatcgg agatgaggat gaagatggcc    6060 tcgttgggc ggaagacagc gctggtaggc tcgaagtgac tgactcggaa ccacttggag    6120
aggccagtct tgggctccca ctgcttgctg cccttgccag agctagcgtt gaagaagagg    6180
tacgcctgcc atccgaaaag ctggtggaag atgagcttga ccatctgagc agcggggtg    6240 tcctcaacaa gctcggcgac gtcaatgcca gcaatcatga gcgacttgga gggcttgggc    6300
tcagtcttgg ggacgaaagc catgtcgaga tccatgtggc cggtgaagcg gtggtggcgg    6360
tggtgagagt acttccagct gaagtagggg acgaggagga acgagtggag gaaccagccg    6420
gtcacattgt tgacctttcc gtggagagag aaagcaccgt ggccgcactc atggccgaga    6480
atccagacac cggtgcagaa cagaccctgg acgaagccgt agaccatcca agctgcgacg    6540
cggagggtct ggtcggggat gctggggatg taggtgagag cagcccagac gagggcagag    6600
accatggcaa aatcgcggaa gacgtagtag aatgaggtga cgagcgaggg ctggaagcag    6660
tgcgcgggaa tggcatcctt gatggtcttg atatcgggga acacaggttc agacttggcc    6720
tcaagagtga ccttgggaag gtcctcgacc acaacagtgg tggcagttcg ctgtcgagtc    6780
gccattgtgc ggccgcttgc tattgatggg tgaagtgaag tgaaggtggg ggcatttatt    6840
gaagttttag ggtgttgtag ttgcatggaa tatggtacgt ggaagtgaag tggggtggtt    6900
ttggtgcggt ggctgcattt gcttcaatgc ttgttaattt acgtgcttcc acgtaacatt    6960
tccatgcatt tggtttataa actgattact atcaaacatt atatatcatt agtataaccc    7020
acttggcttc acgtaatcat ataagatcta gtataaaaaa attatttatc ttaaaagaa    7080 ttatgtgtaa aattttctta ttcaacggta aatatatgcg gtgagtggaa ttaatactca    7140
ataaattagg aaacactgat ttctaacaaa agggaaaaat attcattagc atagagaata    7200
ataagacaag ttgtgtaatt gtttttttc ctactctagt ataataagac taataggatt    7260
gcgggccaat taatgtgaaa ttttttgct tataggtttg gaaattacct tgatgaggtt    7320
taatttgtca atggagcaaa aaattgtctt tttttggtac atcacgttga atattattaa    7380
ttaatctaaa ttaaccgagc agatattgat cacttcgcag tttgcaccat atctttaggg    7440
gattgaaatc gccagtgtga caaggcagca ccagatacaa cagatcaatt tgagtagaat    7500
catactttct gtaacaaata atgaaagtgg ttaaagcaca ttttttgtat ttttacttt    7560 ttttgttctt tcattttagt ttttaaaat aaagtaaata taagttctgt tcttttgtaa    7620
ttatttcctt caaaatttat tatttgcacc gcatctattt gtaattatcg cctacttgtc    7680
aaactagggt gcacttagta aatatctggt gcaaataaca aatgccttta ttttttgggc    7740
acagacagaa acgacatcgt taagccgtga agcgaaagga acgaaacggc gtcgtttaat    7800
ctggagcccc aaacgcagtt ggtttcgtac gtcgagtcga cctgcaggtc gactcgacgt    7860
acgatcccac atgcaagttt ttatttcaat ccctttcct ttgaataact gaccaagaac    7920
aacaagaaaa aaaaaaaaaa agaaaaggat catttttgaaa ggatattttt cgctcctatt    7980
caaatactgt atttttacca aaaaaactgt attttttccta cactctcaag cttttgttttt    8040 cgcttcgact ctcatgattt ccttcatatg ccaatcactc tatttataaa tggcataagg    8100
tagtgtgaac aattgcaaag cttgtcatca aaagcttgca atgtacaaat taatgttttt    8160
catgcctttc aaaattatct gcacccccta gctattaatc taacatctaa gtaaggctag    8220
```

```
tgaatttttt cgaatagtca tgcagtgcat taatttcccc gtgactattt tggctttgac    8280
tccaacactg gccccgtaca tccgtccctc attacatgaa aagaaatatt gtttatattc    8340
ttaattaaaa atattgtccc ttctaaattt tcatatagtt aattattata ttactttttt    8400
ctctattcta ttagttctat tttcaaatta ttatttatgc atatgtaaag tacattatat    8460
ttttgctata tacttaaata tttctaaatt attaaaaaaa gactgatatg aaaaatttat    8520 tcttttaaa gctatatcat tttatatata cttttctttt tcttttcttt cattttctat     8580
tcaatttaat aagaaataaa ttttgtaaat ttttatttat caatttataa aaatatttta    8640
ctttatatgt ttttcacat ttttgttaaa caaatcatat cattatgatt gaaagagagg     8700
aaattgacag tgagtaataa gtgatgagaa aaaatgtgt tatttcctaa aaaaaccta      8760 aacaaacatg tatctactct ctatttcatc tatctctcat ttcattttc tctttatctc     8820 tttcttatt ttttatcat atcatttcac attaattatt tttactctct ttattttttc      8880
tctctatccc tctcttattt ccactcatat atacactcca aaattggggc atgcctttat    8940
cactactcta tctcctccac taaatcattt aaatgaaact gaaaagcatt ggcaagtctc    9000
ctcccctcct caagtgattt ccaactcagc attggcatct aattgattca gtatatctat    9060
tgcatgtgta aaagtctttc cacaatacat aactattaat taatcttaaa taaataaagg    9120
ataaaatatt ttttttcttt cataaaatta aaatatgtta ttttttgttt agatgtatat    9180
tcgaataaat ctaaatatat gataatgatt tttatattg attaaacata taatcaatat     9240
taaatatgat atttttttat ataggttgta cacataattt tataaggata aaaaatatga    9300
taaaaataaa ttttaaatat tttatattt acgagaaaaa aaaatatttt agccataaat     9360
aaatgaccag catattttac aaccttagta attcataaat tcctatatgt atatttgaaa    9420
ttaaaaacag ataatcgtta agggaaggaa tcctacgtca tctcttgcca tttgttttc     9480 atgcaaacag aaagggacga aaaccacct caccatgaat cactcttcac accattttta    9540
ctagcaaaca agtctcaaca actgaagcca gctctctttc cgtttctttt tacaacactt    9600
tctttgaaat agtagtattt tttttcaca tgatttatta acgtgccaaa agatgcttat     9660
tgaatagagt gcacatttgt aatgtactac taattagaac atgaaaaagc attgttctaa    9720
cacgataatc ctgtgaaggc gttaactcca aagatccaat ttcactatat aaattgtgac    9780
gaaagcaaaa tgaattcaca tagctgagag agaaaggaaa ggttaactaa gaagcaatac    9840
ttcagcggcc gcatgactga ggataagacg aaggtcgagt tcccgacgct cacggagctc    9900
aagcactcga tcccgaacgc gtgctttgag tcgaacctcg gcctctcgct ctactacacg    9960
gcccgcgcga tcttcaacgc gtcggcctcg gcggcgctgc tctacgcggc gcgctcgacg    10020
ccgttcattg ccgataacgt tctgctccac gcgctcgttt gcgccaccta catctacgtg    10080
cagggcgtca tcttctgggg cttcttcacg gtcggccacg actgcggcca ctcggccttc    10140
tcgcgctacc acagcgtcaa ctttatcatc ggctgcatca tgcactctgc gattttgacg    10200
ccgttcgaga gctggcgcgt gacgcaccgc caccaccaca agaacacggg caacattgat    10260
aaggacgaga tcttttaccc gcaccggtcg gtcaaggacc tccaggacgt gcgccaatgg    10320
gtctacacgc tcggcggtgc gtggtttgtc tacttgaagg tcgggtatgc cccgcgcacg    10380
atgagccact tgacccgtg ggacccgctc tccttcgcc gcgcgtcggc cgtcatcgtg      10440
tcgctcggcg tctgggccgc cttcttcgcc gcgtacgcgt acctcacata tcgctcggc     10500 tttgccgtca tgggcctcta ctactatgcg ccgctctttg tctttgcttc gttcctcgtc    10560
attacgacct tcttgcacca caacgacgaa gcgacgccgt ggtacggcga ctcggagtgg    10620
```

```
acgtacgtca agggcaacct ctcgagcgtc gaccgctcgt acggcgcgtt cgtggacaac    10680
ctgagccacc acattggcac gcaccaggtc caccacttgt tcccgatcat tccgcactac    10740
aagctcaacg aagccaccaa gcactttgcg gccgcgtacc cgcacctcgt gcgcaggaac    10800
gacgagccca tcatcacggc cttcttcaag accgcgcacc tctttgtcaa ctacggcgct    10860
gtgcccgaga cggcgcagat cttcacgctc aaagagtcgg ccgcggccgc caaggccaag    10920
tcggactaag cggccgcgaa ttcaatcact agtgaattcg cggccgcatg agccgtaaag    10980
gttcaataca acgagtgctt gttttcttag ggacaagcat tgtacttatg tatgattctg    11040
tgtaaccatg agtcttccac gttgtactaa tgtgaagggc aaaaataaaa cacagaacaa    11100
gttcgttttt ctcaaataat gtgaaggtag aaaatggaac catgcctcct ctcttgcatg    11160
tgatttaaaa tattagcaga tggtaccgta cgtgggcg                           11198
```

<210> SEQ ID NO 66
<211> LENGTH: 9231
<212> TYPE: DNA
<213> ORGANISM: Artificial sequence
<220> FEATURE:
<223> OTHER INFORMATION: plasmid pKR954
<220> FEATURE:
<221> NAME/KEY: misc_feature
<222> LOCATION: (6544)..(6544)
<223> OTHER INFORMATION: n is unknown

<400> SEQUENCE: 66

```
gtacggatcc gtcgacggcg cgcccgatca tccggatata gttcctcctt tcagcaaaaa     60 accccctcaag acccgtttag aggccccaag gggttatgct agttattgct cagcggtggc    120
agcagccaac tcagcttcct ttcgggcttt gttagcagcc ggatcgatcc aagctgtacc    180
tcactattcc tttgccctcg gacgagtgct ggggcgtcgg tttccactat cggcgagtac    240
ttctacacag ccatcggtcc agacggccgc gcttctgcgg gcgatttgtg tacgcccgac    300
agtcccggct ccggatcgga cgattgcgtc gcatcgaccc tgcgcccaag ctgcatcatc    360
gaaattgccg tcaaccaagc tctgatagag ttggtcaaga ccaatgcgga gcatatacgc    420
ccggagccgc ggcgatcctg caagctccgg atgcctccgc tcgaagtagc gcgtctgctg    480
ctccatacaa gccaaccacg gcctccagaa gaagatgttg gcgacctcgt attgggaatc    540
cccgaacatc gcctcgctcc agtcaatgac cgctgttatg cggccattgt ccgtcaggac    600
attgttggag ccgaaatccg cgtgcacgag gtgccggact cggggcagt cctcggccca    660 aagcatcagc tcatcgagag cctgcgcgac ggacgcactg acggtgtcgt ccatcacagt    720
ttgccagtga tacacatggg gatcagcaat cgcgcatatg aaatcacgcc atgtagtgta    780
ttgaccgatt ccttgcggtc cgaatgggcc gaacccgctc gtctggctaa gatcggccgc    840
agcgatcgca tccatagcct ccgcgaccgg ctgcagaaca gcgggcagtt cggtttcagg    900
caggtcttgc aacgtgacac cctgtgcacg gcgggagatg caataggtca ggctctcgct    960
gaattcccca tgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga aagcacgaga ttcttcgccc tccgagagct gcatcaggtc   1140
ggagacgctg tcgaactttt cgatcagaaa cttctcgaca gacgtcgcgg tgagttcagg   1200 ctttttccatg ggtatatctc cttcttaaag ttaaacaaaa ttatttctag agggaaaccg   1260
ttgtggtctc cctatagtga gtcgtattaa tttcgcggga tcgagatctg atcaacctgc   1320
attaatgaat cggccaacgc gcggggagag gcggtttgcg tattgggcgc tcttccgctt   1380
```

```
cctcgctcac tgactcgctg cgctcggtcg ttcggctgcg gcgagcgta tcagctcact    1440 caaaggcggt aatacggtta tccacagaat caggggataa cgcaggaaag aacatgtgag    1500
caaaaggcca gcaaaaggcc aggaaccgta aaaaggccgc gttgctggcg tttttccata    1560
ggctccgccc ccctgacgag catcacaaaa atcgacgctc aagtcagagg tggcgaaacc    1620
cgacaggact ataaagatac caggcgtttc ccctggaag ctccctcgtg cgctctcctg    1680
ttccgaccct gccgcttacc ggatacctgt ccgcctttct cccttcggga agcgtggcgc    1740
tttctcaatg ctcacgctgt aggtatctca gttcggtgta ggtcgttcgc tccaagctgg    1800
gctgtgtgca cgaaccccc gttcagcccg accgctgcgc cttatccggt aactatcgtc    1860
ttgagtccaa cccggtaaga cacgacttat cgccactggc agcagccact ggtaacagga    1920
ttagcagagc gaggtatgta ggcggtgcta cagagttctt gaagtggtgg cctaactacg    1980
gctacactag aaggacagta tttggtatct gcgctctgct gaagccagtt accttcggaa    2040
aaagagttgg tagctcttga tccggcaaac aaaccaccgc tggtagcggt ggttttttg     2100 tttgcaagca gcagattacg cgcagaaaaa aaggatctca agaagatcct ttgatctttt    2160
ctacggggtc tgacgctcag tggaacgaaa actcacgtta agggattttg gtcatgacat    2220
taacctataa aaataggcgt atcacgaggc cctttcgtct cgcgcgtttc ggtgatgacg    2280
gtgaaaacct ctgacacatg cagctcccgg agacggtcac agcttgtctg taagcggatg    2340
ccgggagcag acaagcccgt cagggcgcgt cagcgggtgt tggcgggtgt cggggctggc    2400
ttaactatgc ggcatcagag cagattgtac tgagagtgca ccatatggac atattgtcgt    2460
tagaacgcgg ctacaattaa tacataacct tatgtatcat acacatacga tttaggtgac    2520
actatagaac ggcgcgccaa gcttggatct cctgcaggct agcctaagta cgtactcaaa    2580
atgccaacaa ataaaaaaaa agttgcttta ataatgccaa acaaattaa taaaacactt    2640 acaacaccgg attttttta attaaaatgt gccatttagg ataaatagtt aatatttta     2700 ataattattt aaaaagccgt atctactaaa atgatttta tttggttgaa aatattaata    2760
tgtttaaatc aacacaatct atcaaaatta aactaaaaaa aaaataagtg tacgtggtta    2820
acattagtac agtaatataa gaggaaaatg agaaattaag aaattgaaag cgagtctaat    2880
ttttaaatta tgaacctgca tatataaaag gaaagaaaga atccaggaag aaaagaaatg    2940
aaaccatgca tggtcccctc gtcatcacga gtttctgcca tttgcaatag aaacactgaa    3000
acacctttct ctttgtcact taattgagat gccgaagcca cctcacacca tgaacttcat    3060
gaggtgtagc acccaaggct tccatagcca tgcatactga agaatgtctc aagctcagca    3120
ccctacttct gtgacgtgtc cctcattcac cttcctctct tccctataaa taaccacgcc    3180
tcaggttctc cgcttcacaa ctcaaacatt ctctccattg gtccttaaac actcatcagt    3240
catcaccgcg gccgcatggg aacggaccaa ggaaaaacct tcacctggga agagctggcg    3300
gcccataaca ccaaggacga cctactcttg gccatccgcg gcagggtgta cgatgtcaca    3360
aagttcttga gccgccatcc tggtggagtg gacactctcc tgctcggagc tggccgagat    3420
gttactccgg tctttgagat gtatcacgcg tttgggctg cagatgccat tatgaagaag    3480
tactatgtcg gtacactggt ctcgaatgag ctgcccatct tcccggagcc aacggtgttc    3540
cacaaaacca tcaagacgag agtcgagggc tactttacgg atcggaacat tgatcccaag    3600
aatagaccag agatctgggg acgatacgct cttatctttg gatccttgat cgcttcctac    3660
tacgcgcagc tctttgtgcc tttcgttgtc gaacgcacat ggcttcaggt ggtgtttgca    3720
atcatcatgg gatttgcgtg cgcacaagtc ggactcaacc ctcttcatga tgcgtctcac    3780
```

```
ttttcagtga cccacaaccc cactgtctgg aagattctgg gagccacgca cgacttttc    3840 aacggagcat cgtacctggt gtggatgtac aacatatgc tcggccatca ccctacacc    3900 aacattgctg gagcagatcc cgacgtgtcg acgtctgagc ccgatgttcg tcgtatcaag    3960
cccaaccaaa agtggtttgt caaccacatc aaccagcaca tgtttgttcc tttcctgtac    4020
ggactgctgg cgttcaaggt gcgcattcag gacatcaaca ttttgtactt tgtcaagacc    4080
aatgacgcta ttcgtgtcaa tcccatctcg acatggcaca ctgtgatgtt ctggggcggc    4140
aaggctttct tgtctggta tcgcctgatt gttccctgc agtatctgcc cctgggcaag    4200
gtgctgctct tgttcacggt cgcggacatg gtgtcgtctt actggctggc gctgaccttc    4260
caggcgaacc acgttgttga ggaagttcag tggccgttgc ctgacagaaa cgggatcatc    4320
caaaaggact gggcagctat gcaggtcgag actacgcagg attacgcaca cgattcgcac    4380
ctctggacca gcatcactgg cagcttgaac taccaggctg tgcaccatct gttccccaac    4440
gtgtcgcagc accattatcc cgatattctg gccatcatca agaacacctg cagcgagtac    4500
aaggttccat accttgtcaa ggatacgttt tggcaagcat tgcttcaca tttggagcac    4560 ttgcgtgttc ttggactccg tcccaaggaa gagtaggcgg ccgcatttcg caccaaatca    4620
atgaaagtaa taatgaaaag tctgaataag aatacttagg cttagatgcc tttgttactt    4680
gtgtaaaata acttgagtca tgtacctttg gcggaaacag aataaataaa aggtgaaatt    4740
ccaatgctct atgtataagt tagtaatact taatgtgttc tacggttgtt tcaatatcat    4800
caaactctaa ttgaaacttt agaaccacaa atctcaatct tttcttaatg aaatgaaaaa    4860
tcttaattgt accatgttta tgttaaacac cttacaattg gttggagagg aggaccaacc    4920
gatgggacaa cattgggaga aagagattca atggagattt ggataggaga acaacattct    4980
ttttcacttc aatacaagat gagtgcaaca ctaaggatat gtatgagact ttcagaagct    5040
acgacaacat agatgagtga ggtggtgatt cctagcaaga aagacattag aggaagccaa    5100
aatcgaacaa ggaagacatc aagggcaaga gacaggacca tccatctcag gaaaggagc    5160 tttgggatag tccgagaagt tgtacaagaa attttttgga gggtgagtga tgcattgctg    5220
gtgactttaa ctcaatcaaa attgagaaag aaagaaaagg gaggggctc acatgtgaat    5280 agaagggaaa cgggagaatt ttacagtttt gatctaatgg gcatcccagc tagtggtaac    5340
atattcacca tgtttaacct tcacgtacgt cctcgaagag aagggttaat aacacatttt    5400
ttaacatttt taacacaaat tttagttatt taaaaattta ttaaaaaatt taaaataaga    5460
agaggaactc tttaaataaa tctaacttac aaaatttatg attttttaata agttttcacc    5520 aataaaaaat gtcataaaaa tatgttaaaa agtatattat caatattctc tttatgataa    5580
ataaaaagaa aaaaaaata aaagttaagt gaaaatgaga ttgaagtgac tttaggtgtg    5640
tataaatata tcaaccccgc caacaattta tttaatccaa atatattgaa gtatattat    5700 ccatagcctt tatttattta tatatttatt atataaaagc tttatttgtt ctaggttgtt    5760
catgaaatat ttttttggtt ttatctccgt tgtaagaaaa tcatgtgctt tgtgtcgcca    5820
ctcactattg cagcttttc atgcattggt cagattgacg gttgattgta ttttgttttt    5880
ttatggtttt tgttatgac ttaagtcttc atctctttat ctcttcatca ggtttgatgg    5940
ttacctaata tggtccatgg gtacatgcat ggttaaatta ggtggccaac tttgttgtga    6000
acgatagaat ttttttttata ttaagtaaac tattttatta ttatgaaata ataataaaaa    6060
aaatatttta tcattattaa caaaatcata ttagttaatt tgttaactct ataataaaag    6120
aaatactgta acattcacat tacatggtaa catctttcca cccttttcatt tgtttttttgt    6180
```

```
ttgatgactt tttttcttgt ttaaatttat ttcccttctt ttaaatttgg aatacattat    6240
catcatatat aaactaaaat actaaaaaca ggattacaca aatgataaat aataacacaa    6300
atatttataa atctagctgc aatatattta aactagctat atcgatattg taaaataaaa    6360
ctagctgcat tgatactgat aaaaaaatat catgtgcttt ctggactgat gatgcagtat    6420
acttttgaca ttgcctttat tttattttc agaaaagctt tcttagttct gggttcttca     6480
ttatttgttt cccatctcca ttgtgaattg aatcatttgc ttcgtgtcac aaatacaatt    6540
tagntaggta catgcattgg tcagattcac ggtttattat gtcatgactt aagttcatgg    6600
tagtacatta cctgccacgc atgcattata ttggttagat ttgataggca aatttggttg    6660
tcaacaatat aaatataaat aatgttttta tattacgaaa taacagtgat caaaacaaac    6720
agttttatct ttattaacaa gattttgttt ttgtttgatg acgttttta atgtttacgc     6780 tttccccctt cttttgaatt tagaacactt tatcatcata aaatcaaata ctaaaaaaat    6840
tacatatttc ataaataata acacaaatat ttttaaaaaa tctgaaataa taatgaacaa    6900
tattacatat tatcacgaaa attcattaat aaaaatatta tataaataaa atgtaatagt    6960
agttatatgt aggaaaaaag tactgcacgc ataatatata caaaaagatt aaaatgaact    7020 attataaaata ataacactaa attaatggtg aatcatatca aaataatgaa aaagtaaata   7080
aaatttgtaa ttaacttcta tatgtattac acacacaaat aataaataat agtaaaaaaa    7140
attatgataa atatttacca tctcataaga tatttaaaat aatgataaaa atatagatta    7200
ttttttatgc aactagctag ccaaaaagag aacacgggta tatataaaaa gagtaccttt    7260
aaattctact gtacttcctt tattcctgac gttttttatat caagtggaca tacgtgaaga    7320
ttttaattat cagtctaaat atttcattag cacttaatac ttttctgttt tattcctatc    7380
ctataagtag tcccgattct cccaacattg cttattcaca caactaacta agaaagtctt    7440
ccatagcccc ccaagcggcc gcgggaattc gattgaaatg aagtcaaagc gccaagcgct    7500 tcccttaca attgatggaa caacatatga tgtgtctgcc tgggtcaatt ccaccctgg     7560 tggtgcggaa attatagaga attaccaagg aagggatgcc actgatgcct tcatggttat    7620
gcactctcaa gaagccttcg acaagctcaa gcgcatgccc aaaatcaatc ccagttctga    7680
gttgccaccc caggctgcag tgaatgaagc tcaagaggat ttccggaagc tccgagaaga    7740
gttgatcgca actggcatgt tgatgcctc ccccctctgg tactcataca aaatcagcac     7800
cacactgggc cttggagtgc tgggttattt cctgatggtt cagtatcaga tgtatttcat    7860
tggggcagtg ttgcttggga tgcactatca acagatgggc tggctttctc atgacatttg    7920
ccaccaccag actttcaaga accggaactg gaacaacctc gtgggactgg tatttggcaa    7980
tggtctgcaa ggttttccg tgacatggtg gaaggacaga cacaatgcac atcattcggc     8040
aaccaatgtt caagggcacg accctgtatat tgacaacctc cccctcttag cctggtctga    8100
ggatgacgtc acacgggcgt caccgatttc ccgcaagctc attcagttcc agcagtacta    8160
tttcttggtc atctgtatct tgttgcggtt catttggtgt ttccagagcg tgttgaccgt    8220
gcgcagtttg aaggacagag ataaccaatt ctatcgctct cagtataaga aggaggccat    8280
tggcctcgcc ctgcactgga ccttgaagac cctgttccac ttattcttta tgcccagcat    8340
cctcacatcg ctgttggtgt ttttcgtttc ggagctggtt ggcggcttcg gcattgcgat    8400
cgtggtgttc atgaaccact acccactgga aagatcgggg actcagtct gggatggcca     8460 tggattctcg gttggccaga tccatgagac catgaacatt cggcgaggga ttatcacaga    8520 ttggttttc ggaggcttga attaccagat tgagcaccat ttgtggccga ccctccctcg     8580
```

| | |
|---|---|
| ccacaacctg acagcggtta gctaccaggt ggaacagctg tgccagaagc acaacctgcc | 8640 |
| gtatcggaac ccgctgcccc atgaagggtt ggtcatcctg ctgcgctatc tggcggtgtt | 8700 |
| cgcccgatg gcggagaagc aacccgcggg gaaggctcta taaggaatca ctagtgaatt | 8760 |
| cgcggccgcg acacaagtgt gagagtacta aataaatgct ttggttgtac gaaatcatta | 8820 |
| cactaaataa aataatcaaa gcttatatat gccttccgct aaggccgaat gcaagaaat | 8880 |
| tggttctttc tcgttatctt tgccactttt tactagtacg tattaattac tacttaatca | 8940 |
| tctttgttta cggctcatta tatccggtct agaggatcca aggccgcgaa gttaaaagca | 9000 |
| atgttgtcac ttgtcgtact aacacatgat gtgatagttt atgctagcta gctataacat | 9060 |
| aagctgtctc tgagtgtgtt gtatattaat aaagatcatc actggtgaat ggtgatcgtg | 9120 |
| tacgtaccct acttagtagg caatggaagc acttagagtg tgctttgtgc atggccttgc | 9180 |
| ctctgttttg agacttttgt aatgttttcg agtttaaatc tttgcctttg c | 9231 |

<210> SEQ ID NO 67
<211> LENGTH: 7949
<212> TYPE: DNA
<213> ORGANISM: Artificial sequence
<220> FEATURE:
<223> OTHER INFORMATION: plasmid 004-3.1b-f2/pY116

<400> SEQUENCE: 67

| | |
|---|---|
| atggagtcca ttgctcccct cctgccctcc aagatgcctc aggacctgtt catggacctc | 60 |
| gccagcgcta tcggtgtccg agctgctccc tacgtcgatc ccctggaggc tgccctggtt | 120 |
| gcccaggccg agaagtacat tcccaccatt gtccatcaca ctcgaggctt cctggttgcc | 180 |
| gtggattctc ccctggctcg agagctgcct ctgatgaacc ccttccacgt gctcctgatt | 240 |
| gtgctcgcct acctggtcac cgtgtttgtg gtatgcaga tcatgaagaa ctttgaacga | 300 |
| tcgaggtca agacgttctc gctcctgtac aacttctgtc tggtctcgct gagcgcctac | 360 |
| atgtgcggtg gcatcctgta cgaggctttc caggccaact atggactgtt tgagaacgct | 420 |
| gccgatcaca ccttcaaggg tctccctatg gctaagatga tctggctctt ctacttctcc | 480 |
| aagctgatgg agtttgtcga caccatgatc atggtcctca aaaagaacaa ccgacagatt | 540 |
| tcctttctgc acgtgtacca ccactctcc atcttcacca tctggtggct ggtcaccttc | 600 |
| gttgctccca acggtgaagc ctacttctct gctgccctga actcgttcat ccatgttatc | 660 |
| atgtacggct actactttct gtctgccctg ggcttcaagc aggtgtcgtt catcaagttc | 720 |
| tacatcactc gatcccagat gacccagttc tgcatgatgt ctgtccagtc ttcctgggac | 780 |
| atgtacgcca tgaaggtcct tggccgacct ggatacccct tcttcctgac cgctctgctc | 840 |
| tggttctaca tgtggaccat gctcggtctc ttctacaact tttaccgaaa gaacgccaag | 900 |
| ctcgccaagc aggccaaggc tgacgctgcc aaggagaagg ccagaaagct ccagtaagcg | 960 |
| gccgcaagtg tggatgggga agtgagtgcc cggttctgtg tgcacaattg gcaatccaag | 1020 |
| atggatggat tcaacacagg gatatagcga gctacgtggt ggtgcgagga tatagcaacg | 1080 |
| gatatttatg tttgacactt gagaatgtac gatacaagca ctgtccaagt acaatactaa | 1140 |
| acatactgta catactcata ctcgtacccg gcaacggtt tcacttgagt gcagtggcta | 1200 |
| gtgctcttac tcgtacagtg tgcaatactg cgtatcatag tctttgatgt atatcgtatt | 1260 |
| cattcatgtt agttgcgtac gagccggaag cataaagtgt aaagcctggg gtgcctaatg | 1320 |
| agtgagctaa ctcacattaa ttgcgttgcg ctcactgccc gctttccagt cgggaaacct | 1380 |
| gtcgtgccag ctgcattaat gaatcggcca acgcgcgggg agaggcggtt tgcgtattgg | 1440 |

```
gcgctcttcc gcttcctcgc tcactgactc gctgcgctcg gtcgttcggc tgcggcgagc    1500
ggtatcagct cactcaaagg cggtaatacg gttatccaca gaatcagggg ataacgcagg    1560
aaagaacatg tgagcaaaag gccagcaaaa ggccaggaac cgtaaaaagg ccgcgttgct    1620 ggcgttttc catagg ctcc gcccccctga cgagcatcac aaaaatcgac gctcaagtca    1680
gaggtggcga acccgacag gactataaag ataccaggcg tttccccctg gaagctccct    1740
cgtgcgctct cctgttccga ccctgccgct taccggatac ctgtccgcct ttctcccttc    1800
gggaagcgtg cgctttctc atagctcacg ctgtaggtat ctcagttcgg tgtaggtcgt    1860
tcgctccaag ctgggctgtg tgcacgaacc ccccgttcag cccgaccgct gcgccttatc    1920
cggtaactat cgtcttgagt ccaacccggt aagacacgac ttatcgccac tggcagcagc    1980
cactggtaac aggattagca gagcgaggta tgtaggcggt gctacagagt tcttgaagtg    2040
gtggcctaac tacggctaca ctagaaggac agtatttggt atctgcgctc tgctgaagcc    2100
agttaccttc ggaaaaagag ttggtagctc ttgatccggc aaacaaacca ccgctggtag    2160
cggtggtttt tttgtttgca agcagcagat tacgcgcaga aaaaaggat ctcaagaaga    2220 tcctttgatc ttttctacgg ggtctgacgc tcagtggaac gaaaactcac gttaagggat    2280
tttggtcatg agattatcaa aaaggatctt cacctagatc cttttaaatt aaaaatgaag    2340
ttttaaatca atctaaagta tatatgagta aacttggtct gacagttacc aatgcttaat    2400
cagtgaggca cctatctcag cgatctgtct atttcgttca tccatagttg cctgactccc    2460
cgtcgtgtag ataactacga tacggggagg cttaccatct ggccccagtg ctgcaatgat    2520
accgcgagac ccacgctcac cggctccaga tttatcagca ataaaccagc cagccggaag    2580
ggccgagcgc agaagtggtc ctgcaacttt atccgcctcc atccagtcta ttaattgttg    2640
ccgggaagct agagtaagta gttcgccagt taatagtttg cgcaacgttg ttgccattgc    2700
tacaggcatc gtggtgtcac gctcgtcgtt tggtatggct tcattcagct ccggttccca    2760
acgatcaagg cgagttacat gatccccat gttgtgcaaa aaagcggtta gctccttcgg    2820
tcctccgatc gttgtcagaa gtaagttggc cgcagtgtta tcactcatgg ttatggcagc    2880
actgcataat tctcttactg tcatgccatc cgtaagatgc ttttctgtga ctggtgagta    2940
ctcaaccaag tcattctgag aatagtgtat gcggcgaccg agttgctctt gcccggcgtc    3000
aatacgggat aataccgcgc cacatagcag aactttaaaa gtgctcatca ttggaaaacg    3060
ttcttcgggg cgaaaactct caaggatctt accgctgttg agatccagtt cgatgtaacc    3120
cactcgtgca cccaactgat cttcagcatc ttttactttc accagcgttt ctgggtgagc    3180
aaaaacagga aggcaaaatg ccgcaaaaaa gggaataagg gcgacacgga aatgttgaat    3240
actcatactc ttccttttc aatattattg aagcatttat cagggttatt gtctcatgag    3300
cggatacata tttgaatgta tttagaaaaa taaacaaata ggggttccgc gcacatttcc    3360
ccgaaaagtg ccacctgacg cgccctgtag cggcgcatta agcgcggcgg gtgtggtggt    3420
tacgcgcagc gtgaccgcta cacttgccag cgccctagcg cccgctcctt tcgctttctt    3480
cccttccttt ctcgccacgt tcgccggctt tccccgtcaa gctctaaatc ggggctccc    3540 tttagggttc cgatttagtg ctttacggca cctcgacccc aaaaaacttg attagggtga    3600
tggttcacgt agtgggccat cgccctgata cgttttt cgccctttga cgttggagtc    3660
cacgttcttt aatagtggac tcttgttcca aactggaaca acactcaacc ctatctcggt    3720
ctattctttt gatttataag ggattttgcc gatttcggcc tattggttaa aaaatgagct    3780
gatttaacaa aaatttaacg cgaattttaa caaaatatta acgcttacaa ttccattcg    3840
```

```
ccattcaggc tgcgcaactg ttgggaaggg cgatcggtgc gggcctcttc gctattacgc    3900
cagctggcga aggggggatg tgctgcaagg cgattaagtt gggtaacgcc agggttttcc    3960
cagtcacgac gttgtaaaac gacggccagt gaattgtaat acgactcact atagggcgaa    4020
ttgggtaccg ggccccccct cgaggtcgat ggtgtcgata agcttgatat cgaattcatg    4080
tcacacaaac cgatcttcgc ctcaaggaaa cctaattcta catccgagag actgccgaga    4140
tccagtctac actgattaat tttcgggcca ataatttaaa aaaatcgtgt tatataatat    4200
tatatgtatt atatatatac atcatgatga tactgacagt catgtcccat tgctaaatag    4260
acagactcca tctgccgcct ccaactgatg ttctcaatat ttaaggggtc atctcgcatt    4320
gtttaataat aaacagactc catctaccgc ctccaaatga tgttctcaaa atatattgta    4380
tgaacttatt tttattactt agtattatta gacaacttac ttgctttatg aaaaacactt    4440
cctatttagg aaacaattta taatggcagt tcgttcattt aacaatttat gtagaataaa    4500
tgttataaat gcgtatggga atcttaaat atggatagca taaatgatat ctgcattgcc    4560
taattcgaaa tcaacagcaa cgaaaaaaat cccttgtaca acataaatag tcatcgagaa    4620
atatcaacta tcaagaaca gctattcaca cgttactatt gagattatta ttggacgaga    4680
atcacacact caactgtctt tctctcttct agaaatacag gtacaagtat gtactattct    4740
cattgttcat acttctagtc atttcatccc acatattcct tggatttctc tccaatgaat    4800
gacattctat cttgcaaatt caacaattat aataagatat accaaagtag cggtatagtg    4860
gcaatcaaaa agcttctctg gtgtgcttct cgtatttatt tttattctaa tgatccatta    4920
aaggtatata tttatttctt gttatataat ccttttgttt attacatggg ctggatacat    4980
aaaggtattt tgatttaatt ttttgcttaa attcaatccc ccctcgttca gtgtcaactg    5040
taatggtagg aaattaccat acttttgaag aagcaaaaaa aatgaaagaa aaaaaaaatc    5100
gtatttccag gttagacgtt ccgcagaatc tagaatgcgg tatgcggtac attgttcttc    5160
gaacgtaaaa gttgcgctcc ctgagatatt gtacattttt gcttttacaa gtacaagtac    5220
atcgtacaac tatgtactac tgttgatgca tccacaacag tttgttttgt ttttttttgt    5280
tttttttttt tctaatgatt cattaccgct atgtatacct acttgtactt gtagtaagcc    5340
gggttattgg cgttcaatta atcatagact tatgaatctg cacggtgtgc gctgcgagtt    5400
acttttagct tatgcatgct acttgggtgt aatattggga tctgttcgga aatcaacgga    5460
tgctcaatcg atttcgacag taattaatta agtcatacac aagtcagctt tcttcgagcc    5520
tcatataagt ataagtagtt caacgtatta gcactgtacc cagcatctcc gtatcgagaa    5580
acacaacaac atgccccatt ggacagatca tgcggataca caggttgtgc agtatcatac    5640
atactcgatc agacaggtcg tctgaccatc atacaagctg aacaagcgct ccatacttgc    5700
acgctctcta tatacacagt taaattacat atccatagtc taacctctaa cagttaatct    5760
tctggtaagc ctcccagcca gccttctggt atcgcttggc ctcctcaata ggatctcggt    5820
tctggccgta cagacctcgg ccgacaatta tgatatccgt tccggtagac atgcatcct    5880 caacagttcg gtactgctgt ccgagagcgt ctcccttgtc gtcaagaccc accccggggg    5940
tcagaataag ccagtcctca gagtcgccct taggtcggtt ctgggcaatg aagccaacca    6000
caaactcggg gtcggatcgg gcaagctcaa tggtctgctt ggagtactcg ccagtggcca    6060
gagagccctt gcaagacagc tcggccagca tgagcagacc tctggccagc ttctcgttgg    6120
gagaggggac taggaactcc ttgtactggg agttctcgta gtcagagacg tcctccttct    6180
tctgttcaga gacagtttcc tcggcaccag ctcgcaggcc agcaatgatt ccggttccgg    6240
```

```
gtacaccgtg ggcgttggtg atatcggacc actcggcgat tcggtgacac cggtactggt    6300
gcttgacagt gttgccaata tctgcgaact ttctgtcctc gaacaggaag aaaccgtgct    6360
taagagcaag ttccttgagg gggagcacag tgccggcgta ggtgaagtcg tcaatgatgt    6420
cgatatgggt tttgatcatg cacacataag gtccgacctt atcggcaagc tcaatgagct    6480
ccttggtggt ggtaacatcc agagaagcac acaggttggt tttcttggct gccacgagct    6540
tgagcactcg agcggcaaag gcggacttgt ggacgttagc tcgagcttcg taggagggca    6600
ttttggtggt gaagaggaga ctgaaataaa tttagtctgc agaacttttt atcggaacct    6660
tatctggggc agtgaagtat atgttatggt aatagttacg agttagttga acttatagat    6720
agactggact atacggctat cggtccaaat tagaaagaac gtcaatggct ctctgggcgt    6780
cgcctttgcc gacaaaaatg tgatcatgat gaaagccagc aatgacgttg cagctgatat    6840
tgttgtcggc caaccgcgcc gaaaacgcag ctgtcagacc cacagcctcc aacgaagaat    6900
gtatcgtcaa agtgatccaa gcacactcat agttggagtc gtactccaaa ggcggcaatg    6960
acgagtcaga cagatactcg tcgacgttta acagtgtac gcagatctac tatagaggaa    7020
catttaaatt gccccggaga agacggccag gccgcctaga tgacaaattc aacaactcac    7080
agctgacttt ctgccattgc cactaggggg gggccttttt atatggccaa gccaagctct    7140
ccacgtcggt tgggctgcac ccaacaataa atgggtaggg ttgcaccaac aaagggatgg    7200 gatgggggt agaagatacg aggataacgg ggctcaatgg cacaaataag aacgaatact    7260
gccattaaga ctcgtgatcc agcgactgac accattgcat catctaaggg cctcaaaact    7320
acctcggaac tgctgcgctg atctggacac cacagaggtt ccgagcactt taggttgcac    7380
caaatgtccc accaggtgca ggcagaaaac gctggaacag cgtgtacagt ttgtcttaac    7440
aaaaagtgag ggcgctgagg tcgagcaggg tggtgtgact tgttatagcc tttagagctg    7500
cgaaagcgcg tatggatttg gctcatcagg ccagattgag ggtctgtgga cacatgtcat    7560
gttagtgtac ttcaatcgcc ccctggatat agccccgaca ataggccgtg gcctcatttt    7620
tttgccttcc gcacatttcc attgctcgat acccacacct tgcttctcct gcacttgcca    7680
accttaatac tggtttacat tgaccaacat cttacaagcg gggggcttgt ctagggtata    7740
tataaacagt ggctctccca atcggttgcc agtctctttt ttcctttctt tccccacaga    7800
ttcgaaatct aaactacaca tcacagaatt ccgagccgtg agtatccacg acaagatcag    7860
tgtcgagacg acgcgttttg tgtaatgaca caatccgaaa gtcgctagca acacacactc    7920
tctacacaaa ctaacccagc tctggtacc                                       7949

<210> SEQ ID NO 68
<211> LENGTH: 7949
<212> TYPE: DNA
<213> ORGANISM: Artificial sequence
<220> FEATURE:
<223> OTHER INFORMATION: plasmid 006-2.1b-e11/pY116

<400> SEQUENCE: 68
atggagtcca ttgccccctt cctgccctcc aagatgcctc aggacctgtt catggacctc      60
gccagcgcta tcggtgtccg agctgctccc tacgtcgatc ccctggaggc tgccctggtt     120
gcccaggcca gaagtacat tcccaccatt gtccatcaca ctcgaggctt cctgttgcc       180
```

Hmm, line 180 — "gcccaggcca gaagtacat tcccaccatt" — the original has "agaagtacat" which is 10 chars. Let me trust original.

```
gcccaggcca gaagtacat  tcccaccatt gtccatcaca ctcgaggctt cctgttgcc      180 gtggagtctc ccctggctcg agagctgcct ctgatgaacc ccttccacgt gctcctgatc     240
gtgctcgcct acctggtcac cgtgtttgtg ggtatgcaga tcatgaagaa ctttgaacgg     300
ttcgaggtca agacgttctc gctcctgcac aacttctgtc tggtctcgat tagcgcctac     360
```

```
atgtgcggtg gcatcctgta cgaggctttc caggccaact atggactgtt tgagaacgct      420
gccgatcaca ccttcaaggg tctccctatg gctaagatga tctggctctt ctacttctcc      480
aagatcatgg agtttgtcga caccatgatc atggtcctca agaagaacaa ccgacagatt      540
tcctttctgc acgtgtacca ccactcttcc atcttcacca tctggtggct ggtcaccttc      600
gttgctccca acggtgaagc ctacttctct gctgccctga actcgttcat ccatgttatc      660
atgtacggct actactttct gtctgccctg ggcttcaagc aggtgtcgct gatcaagttc      720
tacatcactc gatcccagat gacccagttc tgcatgatgt ctgtccagtc ttcctgggac      780
atgtacgcca tgaaggtcct tggccgacct ggataccccct tcttcatcac cgctctgctc      840
tggttctaca tgtggaccat gctcggtctc ttctacaact tttaccgaaa gaacgccaag      900
ctcgccaagc aggccaaggc tgacgctgcc aaggagaagg ccagaaagct ccagtaagcg      960
gccgcaagtg tggatgggga agtgagtgcc cggttctgtg tgcacaattg gcaatccaag     1020
atggatggat tcaacacagg gatatagcga gctacgtggt ggtgcgagga tatagcaacg     1080
gatatttatg tttgacactt gagaatgtac gatacaagca ctgtccaagt acaatactaa     1140
acatactgta catactcata ctcgtacccg gcaacggtt tcacttgagt gcagtggcta      1200
gtgctcttac tcgtacagtg tgcaatactg cgtatcatag tctttgatgt atatcgtatt     1260
cattcatgtt agttgcgtac gagccggaag cataaagtgt aaagcctggg gtgcctaatg     1320
agtgagctaa ctcacattaa ttgcgttgcg ctcactgccc gctttccagt cgggaaacct     1380
gtcgtgccag ctgcattaat gaatcggcca acgcgcgggg agaggcggtt tgcgtattgg     1440
gcgctcttcc gcttcctcgc tcactgactc gctgcgctcg gtcgttcggc tgcggcgagc     1500
ggtatcagct cactcaaagg cggtaatacg gttatccaca gaatcagggg ataacgcagg     1560
aaagaacatg tgagcaaaag gccagcaaaa ggccaggaac cgtaaaaagg ccgcgttgct     1620 ggcgttttttc cataggctcc gcccccctga cgagcatcac aaaaatcgac gctcaagtca     1680
gaggtggcga aacccgacag gactataaag ataccaggcg tttccccctg gaagctccct     1740
cgtgcgctct cctgttccga ccctgccgct taccggatac ctgtccgcct ttctcccttc     1800
gggaagcgtg gcgctttctc atagctcacg ctgtaggtat ctcagttcgg tgtaggtcgt     1860
tcgctccaag ctgggctgtg tgcacgaacc ccccgttcag cccgaccgct gcgccttatc     1920
cggtaactat cgtcttgagt ccaacccggt aagacacgac ttatcgccac tggcagcagc     1980
cactggtaac aggattagca gagcgaggta tgtaggcggt gctacagagt tcttgaagtg     2040
gtggcctaac tacggctaca ctagaaggac agtatttggt atctgcgctc tgctgaagcc     2100
agttaccttc ggaaaaagag ttggtagctc ttgatccggc aaacaaacca ccgctggtag     2160
cggtggtttt tttgtttgca agcagcagat tacgcgcaga aaaaaaggat ctcaagaaga     2220
tcctttgatc ttttctacgg ggtctgacgc tcagtggaac gaaaactcac gttaagggat     2280
tttggtcatg agattatcaa aaaggatctt cacctagatc cttttaaatt aaaaatgaag     2340
ttttaaatca atctaaagta tatatgagta aacttggtct gacagttacc aatgcttaat     2400
cagtgaggca cctatctcag cgatctgtct atttcgttca tccatagttg cctgactccc     2460
cgtcgtgtag ataactacga tacgggaggg cttaccatct ggccccagtg ctgcaatgat     2520
accgcgagac ccacgctcac cggctccaga tttatcagca ataaaccagc cagccggaag     2580
ggccgagcgc agaagtggtc ctgcaacttt atccgcctcc atccagtcta ttaattgttg     2640
ccgggaagct agagtaagta gttcgccagt taatagtttg cgcaacgttg ttgccattgc     2700
tacaggcatc gtggtgtcac gctcgtcgtt tggtatggct tcattcagct ccggttccca     2760
```

```
acgatcaagg cgagttacat gatcccccat gttgtgcaaa aaagcggtta gctccttcgg   2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
aatacgggat aataccgcgc cacatagcag aactttaaaa gtgctcatca ttggaaaacg   3060
ttcttcgggg cgaaaactct caaggatctt accgctgttg agatccagtt cgatgtaacc   3120
cactcgtgca cccaactgat cttcagcatc ttttactttc accagcgttt ctgggtgagc   3180
aaaaacagga aggcaaaatg ccgcaaaaaa gggaataagg gcgacacgga aatgttgaat   3240
actcatactc ttcctttttc aatattattg aagcatttat cagggttatt gtctcatgag   3300
cggatacata tttgaatgta tttagaaaaa taaacaaata ggggttccgc gcacatttcc   3360
ccgaaaagtg ccacctgacg cgccctgtag cggcgcatta agcgcggcgg gtgtggtggt   3420
tacgcgcagc gtgaccgcta cacttgccag cgccctagcg cccgctcctt tcgctttctt   3480
cccttccttt ctcgccacgt tcgccggctt tccccgtcaa gctctaaatc ggggctccc   3540 tttagggttc cgatttagtg ctttacggca cctcgacccc aaaaaacttg attagggtga   3600
tggttcacgt agtgggccat cgccctgata cggttttt cgccctttga cgttggagtc   3660
cacgttcttt aatagtggac tcttgttcca aactggaaca cactcaacc ctatctcggt   3720 ctattctttt gatttataag ggattttgcc gatttcggcc tattggttaa aaaatgagct   3780
gatttaacaa aaatttaacg cgaattttaa caaaatatta cgcttacaa tttccattcg   3840 ccattcaggc tgcgcaactg ttgggaaggg cgatcggtgc gggcctcttc gctattacgc   3900
cagctggcga aggggggatg tgctgcaagg cgattaagtt gggtaacgcc agggttttcc   3960
cagtcacgac gttgtaaaac gacggccagt gaattgtaat acgactcact atagggcgaa   4020
ttgggtaccg gcccccccct cgaggtcgat ggtgtcgata agcttgatat cgaattcatg   4080
tcacacaaac cgatcttcgc ctcaaggaaa cctaattcta catccgagag actgccgaga   4140
tccagtctac actgattaat tttcgggcca ataatttaaa aaaatcgtgt tatataatat   4200
tatatgtatt atatatatac atcatgatga tactgacagt catgtcccat tgctaaatag   4260
acagactcca tctgccgcct ccaactgatg ttctcaatat ttaagggtc atctcgcatt   4320 gtttaataat aaacagactc catctaccgc ctccaaatga tgttctcaaa atatattgta   4380
tgaacttatt tttattactt agtattatta gacaacttac ttgctttatg aaaaacactt   4440
cctatttagg aaacaattta taatggcagt tcgttcattt aacaattat gtagaataaa   4500 tgttataaat gcgtatggga atcttaaat atggatagca taaatgatat ctgcattgcc   4560
taattcgaaa tcaacagcaa cgaaaaaaat cccttgtaca acataaatag tcatcgagaa   4620
atatcaacta tcaaagaaca gctattcaca cgttactatt gagattatta ttggacgaga   4680
atcacacact caactgtctt tctctcttct agaaatacag gtacaagtat gtactattct   4740
cattgttcat acttctagtc atttcatccc acatattcct tggatttctc tccaatgaat   4800
gacattctat cttgcaaatt caacaattat aataagatat accaaagtag cggtatagtg   4860
gcaatcaaaa agcttctctg gtgtgcttct cgtatttatt tttattctaa tgatccatta   4920
aaggtatata tttatttctt gttatataat ccttttgttt attacatggg ctggatacat   4980
aaaggtattt tgatttaatt ttttgcttaa attcaatccc cctcgttca gtgtcaactg   5040 taatggtagg aaattaccat acttttgaag aagcaaaaaa aatgaaagaa aaaaaaatc   5100 gtatttccag gttagacgtt ccgcagaatc tagaatgcgg tatgcggtac attgttcttc   5160
```

```
gaacgtaaaa gttgcgctcc ctgagatatt gtacattttt gcttttacaa gtacaagtac   5220
atcgtacaac tatgtactac tgttgatgca tccacaacag tttgttttgt tttttttttgt   5280 tttttttttt tctaatgatt cattaccgct atgtatacct acttgtactt gtagtaagcc   5340
gggttattgg cgttcaatta atcatagact tatgaatctg cacggtgtgc gctgcgagtt   5400
acttttagct tatgcatgct acttgggtgt aatattggga tctgttcgga atcaacgga    5460 tgctcaatcg atttcgacag taattaatta agtcatacac aagtcagctt tcttcgagcc   5520
tcatataagt ataagtagtt caacgtatta gcactgtacc cagcatctcc gtatcgagaa    5580
acacaacaac atgccccatt ggacagatca tgcggataca caggttgtgc agtatcatac    5640
atactcgatc agacaggtcg tctgaccatc atacaagctg aacaagcgct ccatacttgc    5700
acgctctcta tatacacagt taaattacat atccatagtc taacctctaa cagttaatct    5760
tctggtaagc ctcccagcca gccttctggt atcgcttggc ctcctcaata ggatctcggt    5820
tctggccgta cagacctcgg ccgacaatta tgatatccgt tccggtagac atgacatcct   5880
caacagttcg gtactgctgt ccgagagcgt ctcccttgtc gtcaagaccc accccggggg    5940
tcagaataag ccagtcctca gagtcgccct taggtcggtt ctgggcaatg aagccaacca    6000
caaactcggg gtcggatcgg gcaagctcaa tggtctgctt ggagtactcg ccagtggcca    6060
gagagccctt gcaagacagc tcggccagca tgagcagacc tctggccagc ttctcgttgg    6120
gagaggggac taggaactcc ttgtactggg agttctcgta gtcagagacg tcctccttct   6180
tctgttcaga gacagtttcc tcggcaccag ctcgcaggcc agcaatgatt ccggttccgg    6240
gtacaccgtg ggcgttggtg atatcggacc actcggcgat tcggtgacac cggtactggt   6300
gcttgacagt gttgccaata tctgcgaact ttctgtcctc gaacaggaag aaaccgtgct   6360
taagagcaag ttccttgagg gggagcacag tgccggcgta ggtgaagtcg tcaatgatgt   6420
cgatatgggt tttgatcatg cacacataag gtccgacctt atcggcaagc tcaatgagct   6480
ccttggtggt ggtaacatcc agagaagcac acaggttggt tttcttggct gccacgagct    6540
tgagcactcg agcggcaaag gcggacttgt ggacgttagc tcgagcttcg taggagggca    6600
ttttggtggt gaagaggaga ctgaaataaa tttagtctgc agaacttttt atcggaacct    6660
tatctggggc agtgaagtat atgttatggt aatagttacg agttagttga acttatagat    6720
agactggact atacggctat cggtccaaat tagaaagaac gtcaatggct ctctgggcgt    6780
cgcctttgcc gacaaaaatg tgatcatgat gaaagccagc aatgacgttg cagctgatat    6840
tgttgtcggc caaccgcgcc gaaaacgcag ctgtcagacc cacagcctcc aacgaagaat    6900
gtatcgtcaa agtgatccaa gcacactcat agttggagtc gtactccaaa ggcggcaatg   6960
acgagtcaga cagatactcg tcgacgttta aacagtgtac gcagatctac tatagaggaa    7020
catttaaatt gccccggaga agacggccag gccgcctaga tgacaaattc aacaactcac    7080
agctgacttt ctgccattgc cactaggggg gggcctttt atatggccaa gccaagctct    7140
ccacgtcggt tgggctgcac ccaacaataa atgggtaggg ttgcaccaac aaagggatgg    7200 gatgggggt agaagatacg aggataacgg ggctcaatgg cacaaataag aacgaatact    7260
gccattaaga ctcgtgatcc agcgactgac accattgcat catctaaggg cctcaaaact    7320
acctcggaac tgctgcgctg atctggacac cacagaggtt ccgagcactt taggttgcac   7380
caaatgtccc accaggtgca ggcagaaaac gctggaacag cgtgtacagt ttgtcttaac    7440
aaaaagtgag ggcgctgagg tcgagcaggg tggtgtgact tgtttatagcc tttagagctg   7500 cgaaagcgcg tatggatttg gctcatcagg ccagattgag ggtctgtgga cacatgtcat    7560
```

-continued

```
gttagtgtac ttcaatcgcc ccctggatat agccccgaca ataggccgtg gcctcatttt    7620
tttgccttcc gcacatttcc attgctcgat acccacacct tgcttctcct gcacttgcca    7680
accttaatac tggtttacat tgaccaacat cttacaagcg ggggcttgt ctagggtata     7740 tataaacagt ggctctccca atcggttgcc agtctctttt ttcctttctt tccccacaga    7800
ttcgaaatct aaactacaca tcacagaatt ccgagccgtg agtatccacg acaagatcag    7860
tgtcgagacg acgcgttttg tgtaatgaca caatccgaaa gtcgctagca acacacactc    7920
tctacacaaa ctaacccagc tctggtacc                                      7949
```

<210> SEQ ID NO 69
<211> LENGTH: 7949
<212> TYPE: DNA
<213> ORGANISM: Artificial sequence
<220> FEATURE:
<223> OTHER INFORMATION: plasmid 009-2.1b-h9/pY116

<400> SEQUENCE: 69

```
atggagtcca ttgctccctt cctgccctcc aagatgcctc aggacctgtt catggacctc      60
gccagcgcta tcggtgtccg agctgctccc tacgtcgatc ccctggaggc tgccctggtt     120
gcccaggccg agaagtacat tcccaccatt gtccatcaca ctcgaggctt cctggttgcc     180
gtggagtctc ccctggctcg agagctgcct ctgatgaacc ccttccacgt gctcctgatc     240
gtgctcgcct acctggtcac cgtgtttgtg ggtatgcaga tcatgaagaa cttgaacga      300 ttcgaggtca agacgtattc gctcctgcac aacttctgtc tggtctcgat tagcgcctac    360
atgtgcggtg gcatcctgta cgaggctttc caggccaact atggactgtt tgagaacgct    420
gccgatcaca ccttcaaggg tctccctatg gctaagatga tctggctctt ctacttctcc    480
aagatcatgg agtttgtcga caccttatc atggtcctca agaagaacaa ccgacagatt    540
tcctttctgc acgtgtacca ccactcttcc atcttcacca tctggtggct ggtcaccttc    600
gttgctccca acggtgaagc ctacttctct gctgccctga actcgttcat ccatgttatc    660
atgtacggct actactttct gtctgccctg ggcttcaagc aggtgtcgct gatcaagttc    720
tacatcactc gatcccagat gacccagttc tgcatgatgt ctgtccagtc ttcctgggac    780
atgtacgcca tgaaggtcct tggccgacct ggataccct tcttcatcgc cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaagcg    960
gccgcaagtg tggatgggga agtgagtgcc cggttctgtg tgcacaattg gcaatccaag   1020
atggatggat tcaacacagg gatatagcga gctacgtggt ggtgcgagga tatagcaacg   1080
gatatttatg tttgacactt gagaatgtac gatacaagca ctgtccaagt acaatactaa   1140
acatactgta catactcata ctcgtacccg ggcaacggtt tcacttgagt gcagtggcta   1200
gtgctcttac tcgtacagtg tgcaatactg cgtatcatag tctttgatgt atatcgtatt   1260
cattcatgtt agttgcgtac gagccggaag cataaagtgt aaagcctggg gtgcctaatg    1320
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg gtcgttcggc tgcggcgagc   1500
ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620
ggcgtttttc cataggctcc gcccccctga cgagcatcac aaaaatcgac gctcaagtca   1680
```

```
gaggtggcga aacccgacag gactataaag ataccaggcg tttcccsctg gaagctccct   1740
cgtgcgctct cctgttccga ccctgccgct taccggatac ctgtccgcct ttctcccttc   1800
gggaagcgtg gcgctttctc atagctcacg ctgtaggtat ctcagttcgg tgtaggtcgt   1860
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaaggac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaggat ctcaagaaga   2220
tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacggagggg cttaccatct ggccccagtg ctgcaatgat   2520
accgcgagac ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatcccccat gttgtgcaaa aaagcggtta gctccttcgg   2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
aatacgggat aataccgcgc cacatagcag aactttaaaa gtgctcatca ttggaaaacg   3060
ttcttcgggg cgaaaactct caaggatctt accgctgttg agatccagtt cgatgtaacc   3120
cactcgtgca cccaactgat cttcagcatc ttttactttc accagcgttt ctgggtgagc   3180
aaaaacagga aggcaaaatg ccgcaaaaaa gggaataagg gcgacacgga aatgttgaat   3240
actcatactc ttcctttttc aatattattg aagcatttat cagggttatt gtctcatgag   3300
cggatacata tttgaatgta tttagaaaaa taaacaaata ggggttccgc gcacatttcc   3360
ccgaaaagtg ccacctgacg cgccctgtag cggcgcatta agcgcggcgg gtgtggtggt   3420
tacgcgcagc gtgaccgcta cacttgccag cgccctagcg cccgctcctt tcgctttctt   3480
cccttccttt ctcgccacgt tcgccggctt tccccgtcaa gctctaaatc ggggctccc   3540
tttagggttc cgatttagtg ctttacggca cctcgacccc aaaaaacttg attagggtga   3600
tggttcacgt agtgggccat cgccctgata gacggttttt cgccctttga cgttggagtc   3660
cacgttcttt aatagtggac tcttgttcca aactggaaca acactcaacc ctatctcggt   3720
ctattctttt gatttataag ggattttgcc gatttcggcc tattggttaa aaaatgagct   3780
gatttaacaa aaatttaacg cgaattttaa caaatatta cgcttacaa tttccattcg   3840
ccattcaggc tgcgcaactg ttgggaaggg cgatcggtgc gggcctcttc gctattacgc   3900
cagctggcga aagggggatg tgctgcaagg cgattaagtt gggtaacgcc agggttttcc   3960
cagtcacgac gttgtaaaac gacggccagt gaattgtaat acgactcact ataggggcgaa   4020
ttgggtaccg ggccccccct cgaggtcgat ggtgtcgata agcttgatat cgaattcatg   4080
```

-continued

| | |
|---|---|
| tcacacaaac cgatcttcgc ctcaaggaaa cctaattcta catccgagag actgccgaga | 4140 |
| tccagtctac actgattaat tttcgggcca ataatttaaa aaaatcgtgt tatataatat | 4200 |
| tatatgtatt atatatatac atcatgatga tactgacagt catgtcccat tgctaaatag | 4260 |
| acagactcca tctgccgcct ccaactgatg ttctcaatat ttaaggggtc atctcgcatt | 4320 |
| gtttaataat aaacagactc catctaccgc ctccaaatga tgttctcaaa atatattgta | 4380 |
| tgaacttatt tttattactt agtattatta gacaacttac ttgctttatg aaaaacactt | 4440 |
| cctatttagg aaacaattta taatggcagt tcgttcattt aacaatttat gtagaataaa | 4500 |
| tgttataaat gcgtatggga atcttaaat atggatagca taaatgatat ctgcattgcc | 4560 |
| taattcgaaa tcaacagcaa cgaaaaaaat cccttgtaca acataaatag tcatcgagaa | 4620 |
| atatcaacta tcaaagaaca gctattcaca cgttactatt gagattatta ttggacgaga | 4680 |
| atcacacact caactgtctt tctctcttct agaaatacag gtacaagtat gtactattct | 4740 |
| cattgttcat acttctagtc atttcatccc acatattcct tggatttctc tccaatgaat | 4800 |
| gacattctat cttgcaaatt caacaattat aataagatat accaaagtag cggtatagtg | 4860 |
| gcaatcaaaa agcttctctg gtgtgcttct cgtatttatt tttattctaa tgatccatta | 4920 |
| aaggtatata tttatttctt gttatataat ccttttgttt attacatggg ctggatacat | 4980 |
| aaaggtattt tgatttaatt ttttgcttaa attcaatccc ccctcgttca gtgtcaactg | 5040 |
| taatggtagg aaattaccat acttttgaag aagcaaaaaa aatgaaagaa aaaaaaaatc | 5100 |
| gtatttccag gttagacgtt ccgcagaatc tagaatgcgg tatgcggtac attgttcttc | 5160 |
| gaacgtaaaa gttgcgctcc ctgagatatt gtacattttt gcttttacaa gtacaagtac | 5220 |
| atcgtacaac tatgtactac tgttgatgca tccacaacag tttgtttgt ttttttttgt | 5280 |
| ttttttttt tctaatgatt cattaccgct atgtatacct acttgtactt gtagtaagcc | 5340 |
| gggttattgg cgttcaatta atcatagact tatgaatctg cacggtgtgc gctgcgagtt | 5400 |
| actttagct tatgcatgct acttgggtgt aatattggga tctgttcgga aatcaacgga | 5460 |
| tgctcaatcg atttcgacag taattaatta agtcatacac aagtcagctt tcttcgagcc | 5520 |
| tcatataagt ataagtagtt caacgtatta gcactgtacc cagcatctcc gtatcgagaa | 5580 |
| acacaacaac atgccccatt ggacagatca tgcggataca caggttgtgc agtatcatac | 5640 |
| atactcgatc agacaggtcg tctgaccatc atacaagctg aacaagcgct ccatacttgc | 5700 |
| acgctctcta tatacacagt taaattacat atccatagtc taacctctaa cagttaatct | 5760 |
| tctggtaagc ctcccagcca gccttctggt atcgcttggc ctcctcaata ggatctcggt | 5820 |
| tctggccgta cagacctcgg ccgacaatta tgatatccgt tccggtagac atgcatcct | 5880 |
| caacagttcg gtactgctgt ccgagagcgt ctcccttgtc gtcaagaccc accccggggg | 5940 |
| tcagaataag ccagtcctca gagtcgccct taggtcggtt ctgggcaatg aagccaacca | 6000 |
| caaactcggg gtcggatcgg gcaagctcaa tggtctgctt ggagtactcg ccagtggcca | 6060 |
| gagagccctt gcaagacagc tcggccagca tgagcagacc tctggccagc ttctcgttgg | 6120 |
| gagagggac taggaactcc ttgtactggg agttctcgta gtcagagacg tcctccttct | 6180 |
| tctgttcaga gacagtttcc tcggcaccag ctcgcaggcc agcaatgatt ccggttccgg | 6240 |
| gtacaccgtg ggcgttggtg atatcggacc actcggcgat tcggtgacac cggtactggt | 6300 |
| gcttgacagt gttgccaata tctgcgaact ttctgtcctc gaacaggaag aaaccgtgct | 6360 |
| taagagcaag ttccttgagg gggagcacag tgccggcgta ggtgaagtcg tcaatgatgt | 6420 |
| cgatatgggt tttgatcatg cacacataag gtccgacctt atcggcaagc tcaatgagct | 6480 |

```
cccttggtggt ggtaacatcc agagaagcac acaggttggt tttcttggct gccacgagct    6540
tgagcactcg agcggcaaag gcggacttgt ggacgttagc tcgagcttcg taggagggca    6600
ttttggtggt gaagaggaga ctgaaataaa tttagtctgc agaactttt atcggaacct     6660 tatctggggc agtgaagtat atgttatggt aatagttacg agttagttga acttatagat    6720
agactggact atacggctat cggtccaaat tagaaagaac gtcaatggct ctctgggcgt    6780
cgcctttgcc gacaaaaatg tgatcatgat gaaagccagc aatgacgttg cagctgatat    6840
tgttgtcggc caaccgcgcc gaaaacgcag ctgtcagacc cacagcctcc aacgaagaat    6900
gtatcgtcaa agtgatccaa gcacactcat agttggagtc gtactccaaa ggcggcaatg    6960
acgagtcaga cagatactcg tcgacgttta acagtgtac gcagatctac tatagaggaa     7020
catttaaatt gccccggaga agacggccag gccgcctaga tgacaaattc aacaactcac    7080
agctgacttt ctgccattgc cactaggggg gggcctttt atatggccaa gccaagctct     7140
ccacgtcggt tgggctgcac ccaacaataa atgggtaggg ttgcaccaac aaagggatgg    7200 gatgggggt agaagatacg aggataacgg ggctcaatgg cacaaataag aacgaatact     7260
gccattaaga ctcgtgatcc agcgactgac accattgcat catctaaggg cctcaaaact    7320
acctcggaac tgctgcgctg atctggacac acagaggtt ccgagcactt taggttgcac     7380
caaatgtccc accaggtgca ggcagaaaac gctggaacag cgtgtacagt ttgtcttaac    7440
aaaaagtgag ggcgctgagg tcgagcaggg tggtgtgact tgttatagcc tttagagctg    7500
cgaaagcgcg tatggatttg gctcatcagg ccagattgag ggtctgtgga cacatgtcat    7560
gttagtgtac ttcaatcgcc ccctggatat agccccgaca ataggccgtg gcctcatttt    7620
tttgccttcc gcacatttcc attgctcgat acccacacct tgcttctcct gcacttgcca    7680
accttaatac tggtttacat tgaccaacat cttacaagcg gggggcttgt ctagggtata    7740
tataaacagt ggctctccca atcggttgcc agtctctttt ttccttttct tccccacaga    7800
ttcgaaatct aaactacaca tcacagaatt ccgagccgtg agtatccacg acaagatcag    7860
tgtcgagacg acgcgttttg tgtaatgaca caatccgaaa gtcgctagca acacacactc    7920
tctacacaaa ctaacccagc tctggtacc                                      7949
```

<210> SEQ ID NO 70
<211> LENGTH: 7949
<212> TYPE: DNA
<213> ORGANISM: Artificial sequence
<220> FEATURE:
<223> OTHER INFORMATION: plasmid 010-2.1b-c3/pY116

<400> SEQUENCE: 70

```
atggagtcca ttgttcccctt cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctgttgcc     180 gtggagtctc ccctggctcg agagctgcct ctgatgaacc ccttccacgt gctcctgatc    240
gtgctcgcct acctggtcac cgtgtttgtg ggtatgcaga tcatgaagaa ctttgaacga    300
ttcgaggtca agacgtattc gctcctgcac aacttctgtc tggtctcgct gagcgcctac    360
atgtgcggtg gcattctgta cgaggcttat caggccaact atggactgtt tgagaacgct    420
gccgatcaca ccttcaaggg tctccctatg gctaagatga tctggctctt ctacttctcc    480
aagatcatgg agtttgtcga caccatgatc atggtcctca agaagaacaa ccgacagatt    540 tccttttctgc acgtgtacca ccactcttcc atcttcacca tctggtggct ggtcaccttc    600
```

```
gttgctccca acggtgaagc ctacttctct gctgccctga actcgttcat ccatgttatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggataccct tcttcatcac cgctctgctc    840
tggttctaca tgtggaccat gctcggtctc ttctacaact tttaccgaaa gaacgccaag    900
ctcgccaagc aggccaaggc tgacgctgcc aaggagaagg ccagaaagct ccagtaagcg    960
gccgcaagtg tggatgggga agtgagtgcc cggttctgtg tgcacaattg gcaatccaag   1020
atggatggat tcaacacagg gatatagcga gctacgtggg ggtgcgagga tatagcaacg   1080
gatatttatg tttgacactt gagaatgtac gatacaagca ctgtccaagt acaatactaa   1140
acatactgta catactcata ctcgtacccg ggcaacggtt tcacttgagt gcagtggcta   1200
gtgctcttac tcgtacagtg tgcaatactg cgtatcatag tctttgatgt atatcgtatt   1260
cattcatgtt agttgcgtac gagccggaag cataaagtgt aaagcctggg gtgcctaatg   1320
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg gtcgttcggc tgcggcgagc   1500
ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620
ggcgtttttc cataggctcc gcccccctga cgagcatcac aaaaatcgac gctcaagtca   1680
gaggtggcga aacccgacag gactataaag ataccaggcg tttccccctg gaagctccct   1740
cgtgcgctct cctgttccga ccctgccgct taccggatac ctgtccgcct ttctcccttc   1800
gggaagcgtg gcgctttctc atagctcacg ctgtaggtat ctcagttcgg tgtaggtcgt   1860
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaaggac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaggat ctcaagaaga   2220 tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacgggaggg cttaccatct ggccccagtg ctgcaatgat   2520
accgcgagac ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatccccat gttgtgcaaa aaagcggtta gctccttcgg   2820
tcctccgatc gttgtcagaa gtaagttggc cgcagtgtta tcactcatgg ttatggcagc   2880
actgcataat tctcttactg tcatgccatc cgtaagatgc ttttctgtga ctggtgagta   2940
ctcaaccaag tcattctgag aatagtgtat gcggcgaccg agttgctctt gcccggcgtc   3000
```

```
aatacgggat aataccgcgc cacatagcag aactttaaaa gtgctcatca ttggaaaacg    3060
ttcttcgggg cgaaaactct caaggatctt accgctgttg agatccagtt cgatgtaacc    3120
cactcgtgca cccaactgat cttcagcatc ttttactttc accagcgttt ctgggtgagc    3180
aaaaacagga aggcaaaatg ccgcaaaaaa gggaataagg gcgacacgga aatgttgaat    3240
actcatactc ttccttttc aatattattg aagcatttat cagggttatt gtctcatgag    3300
cggatacata tttgaatgta tttagaaaaa taaacaaata ggggttccgc gcacatttcc    3360
ccgaaaagtg ccacctgacg cgccctgtag cggcgcatta agcgcggcgg gtgtggtggt    3420
tacgcgcagc gtgaccgcta cacttgccag cgccctagcg cccgctcctt tcgctttctt    3480
cccttccttt ctcgccacgt tcgccggctt tccccgtcaa gctctaaatc ggggctccc    3540 tttagggttc cgatttagtg ctttacggca cctcgacccc aaaaaacttg attagggtga    3600
tggttcacgt agtgggccat cgccctgata cggtttttt cgcccttga cgttggagtc    3660 cacgttcttt aatagtggac tcttgttcca aactggaaca acactcaacc ctatctcggt    3720
ctattctttt gatttataag gattttgcc gatttcggcc tattggttaa aaaatgagct    3780
gatttaacaa aaatttaacg cgaattttaa caaaatatta acgcttacaa tttccattcg    3840
ccattcaggc tgcgcaactg ttgggaaggg cgatcggtgc gggcctcttc gctattacgc    3900
cagctggcga aggggggatg tgctgcaagg cgattaagtt gggtaacgcc agggttttcc    3960
cagtcacgac gttgtaaaac gacggccagt gaattgtaat acgactcact atagggcgaa    4020
ttgggtaccg ggccccccct cgaggtcgat ggtgtcgata agcttgatat cgaattcatg    4080
tcacacaaac cgatcttcgc ctcaaggaaa cctaattcta catccgagag actgccgaga    4140
tccagtctac actgattaat tttcgggcca ataatttaaa aaaatcgtgt tatataatat    4200
tatatgtatt atatatatac atcatgatga tactgacagt catgtcccat tgctaaatag    4260
acagactcca tctgccgcct ccaactgatg ttctcaatat ttaaggggtc atctcgcatt    4320
gtttaataat aaacagactc catctaccgc ctccaaatga tgttctcaaa atatattgta    4380
tgaacttatt tttattactt agtattatta gacaacttac ttgctttatg aaaaacactt    4440
cctatttagg aaacaattta taatggcagt tcgttcattt aacaatttat gtagaataaa    4500
tgttataaat gcgtatggga aatcttaaat atggatagca taaatgatat ctgcattgcc    4560
taattcgaaa tcaacagcaa cgaaaaaaat cccttgtaca acataaatag tcatcgagaa    4620
atatcaacta tcaaagaaca gctattcaca cgttactatt gagattatta ttggacgaga    4680
atcacacact caactgtctt tctctcttct agaaatacag gtacaagtat gtactattct    4740
cattgttcat acttctagtc atttcatccc acatattcct tggatttctc tccaatgaat    4800
gacattctat cttgcaaatt caacaattat aataagatat accaaagtag cggtatagtg    4860
gcaatcaaaa agcttctctg gtgtgcttct cgtatttatt tttattctaa tgatccatta    4920
aaggtatata tttatttctt gttatataat cctttgttt attacatggg ctggatacat    4980
aaaggtattt tgatttaatt ttttgcttaa attcaatccc ccctcgttca gtgtcaactg    5040
taatggtagg aaattaccat acttttgaag aagcaaaaaa aatgaaagaa aaaaaaaatc    5100
gtatttccag gttagacgtt ccgcagaatc tagaatgcgg tatgcggtac attgttcttc    5160
gaacgtaaaa gttgcgctcc ctgagatatt gtacatttt gcttttacaa gtacaagtac    5220
atcgtacaac tatgtactac tgttgatgca tccacaacag tttgttttgt tttttttgt     5280 tttttttttt tctaatgatt cattaccgct atgtatacct acttgtactt gtagtaagcc    5340
gggttattgg cgttcaatta atcatagact tatgaatctg cacggtgtgc gctgcgagtt    5400
```

```
acttttagct tatgcatgct acttgggtgt aatattggga tctgttcgga aatcaacgga   5460
tgctcaatcg atttcgacag taattaatta agtcatacac aagtcagctt tcttcgagcc   5520
tcatataagt ataagtagtt caacgtatta gcactgtacc cagcatctcc gtatcgagaa   5580
acacaacaac atgccccatt ggacagatca tgcggataca caggttgtgc agtatcatac   5640
atactcgatc agacaggtcg tctgaccatc atacaagctg aacaagcgct ccatacttgc   5700
acgctctcta tatacacagt taaattacat atccatagtc taacctctaa cagttaatct   5760
tctggtaagc ctcccagcca gccttctggt atcgcttggc ctcctcaata ggatctcggt   5820
tctggccgta cagacctcgg ccgacaatta tgatatccgt tccggtagac atgacatcct   5880
caacagttcg gtactgctgt ccgagagcgt ctcccttgtc gtcaagaccc accccggggg   5940
tcagaataag ccagtcctca gagtcgccct taggtcggtt ctgggcaatg aagccaacca   6000
caaactcggg gtcggatcgg gcaagctcaa tggtctgctt ggagtactcg ccagtggcca   6060
gagagccctt gcaagacagc tcggccagca tgagcagacc tctggccagc ttctcgttgg   6120
gagaggggac taggaactcc ttgtactggg agttctcgta gtcagagacg tcctccttct   6180
tctgttcaga gacagtttcc tcggcaccag ctcgcaggcc agcaatgatt ccggttccgg   6240
gtacaccgtg ggcgttggtg atatcggacc actcggcgat tcggtgacac cggtactggt   6300
gcttgacagt gttgccaata tctgcgaact ttctgtcctc gaacaggaag aaaccgtgct   6360
taagagcaag ttccttgagg gggagcacag tgccggcgta ggtgaagtcg tcaatgatgt   6420
cgatatgggt tttgatcatg cacacataag gtccgacctt atcggcaagc tcaatgagct   6480
ccttggtggt ggtaacatcc agagaagcac acaggttggt tttcttggct gccacgagct   6540
tgagcactcg agcggcaaag gcggacttgt ggacgttagc tcgagcttcg taggagggca   6600
ttttggtggt gaagaggaga ctgaaataaa tttagtctgc agaacttttt atcggaacct   6660
tatctggggc agtgaagtat atgttatggt aatagttacg agttagttga acttatagat   6720
agactggact atacggctat cggtccaaat tagaaagaac gtcaatggct ctctgggcgt   6780
cgcctttgcc gacaaaaatg tgatcatgat gaaagccagc aatgacgttg cagctgatat   6840
tgttgtcggc caaccgcgcc gaaaacgcag ctgtcagacc cacagcctcc aacgaagaat   6900
gtatcgtcaa agtgatccaa gcacactcat agttggagtc gtactccaaa ggcggcaatg   6960
acgagtcaga cagatactcg tcgacgttta acagtgtac gcagatctac tatagaggaa   7020
catttaaatt gccccggaga agacggccag gccgcctaga tgacaaattc aacaactcac   7080
agctgacttt ctgccattgc cactaggggg gggccttttt atatggccaa gccaagctct   7140
ccacgtcggt tgggctgcac ccaacaataa atgggtaggg ttgcaccaac aaagggatgg   7200 gatgggggt agaagatacg aggataacgg ggctcaatgg cacaaataag aacgaatact   7260
gccattaaga ctcgtgatcc agcgactgac accattgcat catctaaggg cctcaaaact   7320
acctcggaac tgctgcgctg atctggacac cacagaggtt ccgagcactt taggttgcac   7380
caaatgtccc accaggtgca ggcagaaaac gctggaacag cgtgtacagt ttgtcttaac   7440
aaaaagtgag ggcgctgagg tcgagcaggg tggtgtgact tgtttatagcc tttagagctg   7500 cgaaagcgcg tatggatttg gctcatcagg ccagattgag ggtctgtgga cacatgtcat   7560
gttagtgtac ttcaatcgcc ccctggatat agccccgaca ataggccgtg gcctcatttt   7620
tttgccttcc gcacatttcc attgctcgat acccacacct tgcttctcct gcacttgcca   7680
accttaatac tggtttacat tgaccaacat cttacaagcg gggggcttgt ctagggtata   7740
tataaacagt ggctctccca atcggttgcc agtctctttt ttcctttctt tccccacaga   7800
```

-continued

| | |
|---|---|
| ttcgaaatct aaactacaca tcacagaatt ccgagccgtg agtatccacg acaagatcag | 7860 |
| tgtcgagacg acgcgttttg tgtaatgaca caatccgaaa gtcgctagca acacacactc | 7920 |
| tctacacaaa ctaacccagc tctggtacc | 7949 |

<210> SEQ ID NO 71
<211> LENGTH: 7949
<212> TYPE: DNA
<213> ORGANISM: Artificial sequence
<220> FEATURE:
<223> OTHER INFORMATION: plasmid 012-2.1b-d5/pY116

<400> SEQUENCE: 71

| | |
|---|---|
| atggagtcca ttgctccctt cctgctctcc aagatgcctc aggacctgtt catggacctc | 60 |
| gccagcgcta tcggtgtccg agctgctccc tacgtcgatc ccctggaggc tgccctggtt | 120 |
| gcccaggccg agaagtacat tcccaccatt gtccatcaca ctcgaggctt cctggttgcc | 180 |
| gtggagtctc ccctggctcg agagctgcct ctgatgaacc ccttccacgt gctcctgatc | 240 |
| gtgctcgcct acctggtcac cgtgtttgtg ggtatgcaga tcatgaagaa ctttgaacga | 300 |
| ttcgaggtca gacgtattc gctcctgcac aacttctgtc tggtctcgct gagcgcctac | 360 |
| atgtgcggtg gcattctgta cgaggctttt caggccaact atggactgtt tgagaacgct | 420 |
| gccgatcaca ccttcaaggg tctccctatg ctaagatga tctggctctt ctacttctcc | 480 |
| aagatcatgg agtttgtcga caccatgatc atggtcctca gaagaacaa ccgacagatt | 540 |
| tcctttctgc acgtgtacca ccactcttcc atcttcacca tctggtggct ggtcaccttc | 600 |
| gttgctccca acggtgaagc ctacttctct gctgccctga actcgttcat ccatgttatc | 660 |
| atgtacggct actactttct gtctgccctg ggcttcaagc aggtgtcgct gatcaagttc | 720 |
| tacatcactc gatcccagat gacccagttc tgcatgttgt ctgtccagtc ttcctgggac | 780 |
| atgtacgcca tgaaggtcct tggccgacct ggatacccct tcttcatcac cgctctgctc | 840 |
| tggttctaca tgtggaccat gctcggtctc ttctacaact tttaccgaaa gaacgccaag | 900 |
| ctcgccaagc aggccaaggc tgacgctgcc aaggagaagg ccagaaagct ccagtaagcg | 960 |
| gccgcaagtg tggatgggga agtgagtgcc cggttctgtg tgcacaattg gcaatccaag | 1020 |
| atggatggat tcaacacagg gatatagcga gctacgtggt ggtgcgagga tatagcaacg | 1080 |
| gatatttatg tttgacactt gagaatgtac gatacaagca ctgtccaagt acaatactaa | 1140 |
| acatactgta catactcata ctcgtacccg ggcaacggtt tcacttgagt gcagtggcta | 1200 |
| gtgctcttac tcgtacagtg tgcaatactg cgtatcatag tctttgatgt atatcgtatt | 1260 |
| cattcatgtt agttgcgtac gagccggaag cataaagtgt aaagcctggg gtgcctaatg | 1320 |
| agtgagctaa ctcacattaa ttgcgttgcg ctcactgccc gctttccagt cgggaaacct | 1380 |
| gtcgtgccag ctgcattaat gaatcggcca acgcgcgggg agaggcggtt tgcgtattgg | 1440 |
| gcgctcttcc gcttcctcgc tcactgactc gctgcgctcg tcgttcggc tgcggcgagc | 1500 |
| ggtatcagct cactcaaagg cggtaatacg gttatccaca gaatcagggg ataacgcagg | 1560 |
| aaagaacatg tgagcaaaag gccagcaaaa ggccaggaac cgtaaaaagg ccgcgttgct | 1620 |
| ggcgtttttc cataggctcc gcccccctga cgagcatcac aaaaatcgac gctcaagtca | 1680 |
| gaggtggcga aacccgacag gactataaag ataccaggcg tttccccctg gaagctccct | 1740 |
| cgtgcgctct cctgttccga ccctgccgct taccggatac ctgtccgcct ttctcccttc | 1800 |
| gggaagcgtg gcgctttctc atagctcacg ctgtaggtat ctcagttcgg tgtaggtcgt | 1860 |
| tcgctccaag ctgggctgtg tgcacgaacc ccccgttcag cccgaccgct gcgccttatc | 1920 |

```
cggtaactat cgtcttgagt ccaacccggt aagacacgac ttatcgccac tggcagcagc    1980
cactggtaac aggattagca gagcgaggta tgtaggcggt gctacagagt tcttgaagtg    2040
gtggcctaac tacggctaca ctagaaggac agtatttggt atctgcgctc tgctgaagcc    2100
agttaccttc ggaaaaagag ttggtagctc ttgatccggc aaacaaacca ccgctggtag    2160
cggtggtttt tttgtttgca agcagcagat tacgcgcaga aaaaaggat ctcaagaaga     2220 tcctttgatc ttttctacgg ggtctgacgc tcagtggaac gaaaactcac gttaagggat    2280
tttggtcatg agattatcaa aaaggatctt cacctagatc cttttaaatt aaaaatgaag    2340
ttttaaatca atctaaagta tatatgagta aacttggtct gacagttacc aatgcttaat    2400
cagtgaggca cctatctcag cgatctgtct atttcgttca tccatagttg cctgactccc    2460
cgtcgtgtag ataactacga tacgggaggg cttaccatct ggccccagtg ctgcaatgat    2520
accgcgagac ccacgctcac cggctccaga tttatcagca ataaaccagc cagccggaag    2580
ggccgagcgc agaagtggtc ctgcaacttt atccgcctcc atccagtcta ttaattgttg    2640
ccgggaagct agagtaagta gttcgccagt taatagtttg cgcaacgttg ttgccattgc    2700
tacaggcatc gtggtgtcac gctcgtcgtt tggtatggct tcattcagct ccggttccca    2760
acgatcaagg cgagttacat gatccccat gttgtgcaaa aaagcggtta gctccttcgg      2820
tcctccgatc gttgtcagaa gtaagttggc cgcagtgtta tcactcatgg ttatggcagc    2880
actgcataat tctcttactg tcatgccatc cgtaagatgc ttttctgtga ctggtgagta    2940
ctcaaccaag tcattctgag aatagtgtat gcggcgaccg agttgctctt gcccggcgtc    3000
aatacgggat aataccgcgc cacatagcag aactttaaaa gtgctcatca ttggaaaacg    3060
ttcttcgggg cgaaaactct caaggatctt accgctgttg agatccagtt cgatgtaacc    3120
cactcgtgca cccaactgat cttcagcatc ttttactttc accagcgttt ctgggtgagc    3180
aaaaacagga aggcaaaatg ccgcaaaaaa gggaataagg gcgacacgga aatgttgaat    3240
actcatactc ttcctttttc aatattattg aagcatttat cagggttatt gtctcatgag    3300
cggatacata tttgaatgta tttagaaaaa taaacaaata ggggttccgc gcacatttcc    3360
ccgaaaagtg ccacctgacg cgccctgtag cggcgcatta agcgcggcgg gtgtggtggt    3420
tacgcgcagc gtgaccgcta cacttgccag cgccctagcg cccgctcctt tcgctttctt    3480
cccttccttt ctcgccacgt tcgccggctt tccccgtcaa gctctaaatc ggggggctccc    3540 tttagggttc cgatttagtg ctttacggca cctcgacccc aaaaaacttg attagggtga    3600
tggttcacgt agtgggccat cgccctgata acggttttt cgccctttga cgttggagtc     3660
cacgttcttt aatagtggac tcttgttcca aactggaaca acactcaacc ctatctcggt    3720
ctattctttt gatttataag ggattttgcc gatttcggcc tattggttaa aaaatgagct    3780
gatttaacaa aaatttaacg cgaattttaa caaaatatta acgcttacaa tttccattcg    3840
ccattcaggc tgcgcaactg ttgggaaggg cgatcggtgc gggcctcttc gctattacgc    3900
cagctggcga aaggggatg tgctgcaagg cgattaagtt gggtaacgcc agggttttcc     3960
cagtcacgac gttgtaaaac gacggccagt gaattgtaat acgactcact ataggcgaa     4020 ttgggtaccg gccccccct cgaggtcgat ggtgtcgata agcttgatat cgaattcatg      4080
tcacacaaac cgatcttcgc ctcaaggaaa cctaattcta catccgagag actgccgaga    4140
tccagtctac actgattaat tttcgggcca ataatttaaa aaaatcgtgt tatataatat     4200
tatatgtatt atatatatac atcatgatga tactgacagt catgtcccat tgctaaatag    4260
acagactcca tctgccgcct ccaactgatg ttctcaatat ttaaggggtc atctcgcatt    4320
```

```
gtttaataat aaacagactc catctaccgc ctccaaatga tgttctcaaa atatattgta   4380
tgaacttatt tttattactt agtattatta gacaacttac ttgctttatg aaaaacactt   4440
cctatttagg aaacaattta taatggcagt tcgttcattt aacaatttat gtagaataaa   4500
tgttataaat gcgtatggga aatcttaaat atggatagca taaatgatat ctgcattgcc   4560
taattcgaaa tcaacagcaa cgaaaaaaat cccttgtaca acataaatag tcatcgagaa   4620
atatcaacta tcaaagaaca gctattcaca cgttactatt gagattatta ttggacgaga   4680
atcacacact caactgtctt tctctcttct agaaatacag gtacaagtat gtactattct   4740
cattgttcat acttctagtc atttcatccc acatattcct tggatttctc tccaatgaat   4800
gacattctat cttgcaaatt caacaattat aataagatat accaaagtag cggtatagtg   4860
gcaatcaaaa agcttctctg gtgtgcttct cgtatttatt tttattctaa tgatccatta   4920
aaggtatata tttatttctt gttatataat cctttttgttt attacatggg ctggatacat   4980
aaaggtattt tgatttaatt ttttgcttaa attcaatccc ccctcgttca gtgtcaactg   5040
taatggtagg aaattaccat acttttgaag aagcaaaaaa aatgaaagaa aaaaaaaatc   5100
gtatttccag gttagacgtt ccgcagaatc tagaatgcgg tatgcggtac attgttcttc   5160
gaacgtaaaa gttgcgctcc ctgagatatt gtacattttt gcttttacaa gtacaagtac   5220
atcgtacaac tatgtactac tgttgatgca tccacaacag tttgttttgt tttttttgt    5280 tttttttttt tctaatgatt cattaccgct atgtatacct acttgtactt gtagtaagcc   5340
gggttattgg cgttcaatta atcatagact tatgaatctg cacggtgtgc gctgcgagtt   5400
acttttagct tatgcatgct acttgggtgt aatattggga tctgttcgga aatcaacgga   5460
tgctcaatcg atttcgacag taattaatta agtcatacac aagtcagctt tcttcgagcc   5520
tcatataagt ataagtagtt caacgtatta gcactgtacc cagcatctcc gtatcgagaa   5580
acacaacaac atgccccatt ggacagatca tgcggataca caggttgtgc agtatcatac   5640
atactcgatc agacaggtcg tctgaccatc atacaagctg aacaagcgct ccatacttgc   5700
acgctctcta tatacacagt taaattacat atccatagtc taacctctaa cagttaatct   5760
tctggtaagc ctcccagcca gccttctggt atcgcttggc ctcctcaata ggatctcggt   5820
tctggccgta cagacctcgg ccgacaatta tgatatccgt tccggtagac atgcatcct    5880 caacagttcg gtactgctgt ccgagagcgt ctcccttgtc gtcaagaccc accccgggg    5940 tcagaataag ccagtcctca gagtcgccct taggtcggtt ctgggcaatg aagccaacca   6000
caaactcggg gtcggatcgg gcaagctcaa tggtctgctt ggagtactcg ccagtggcca   6060
gagagccctt gcaagacagc tcggccagca tgagcagacc tctggccagc ttctcgttgg   6120
gagaggggac taggaactcc ttgtactggg agttctcgta gtcagagacg tcctccttct   6180
tctgttcaga gacagtttcc tcggcaccag ctcgcaggcc agcaatgatt ccggttccgg   6240
gtacaccgtg ggcgttggtg atatcggacc actcggcgat tcggtgacac cggtactggt   6300
gcttgacagt gttgccaata tctgcgaact ttctgtcctc gaacaggaag aaaccgtgct   6360
taagagcaag ttccttgagg gggagcacag tgccggcgta ggtgaagtcg tcaatgatgt   6420
cgatatgggt tttgatcatg cacacataag gtccgacctt atcggcaagc tcaatgagct   6480
ccttggtggt ggtaacatcc agagaagcac acaggttggt tttcttggct gccacgagct   6540
tgagcactcg agcggcaaag gcggacttgt ggacgttagc tcgagcttcg taggagggca   6600
ttttggtggt gaagaggaga ctgaaataaa tttagtctgc agaactttt atcggaacct    6660 tatctggggc agtgaagtat atgttatggt aatagttacg agttagttga acttatagat   6720
```

| | |
|---|---|
| agactggact atacggctat cggtccaaat tagaaagaac gtcaatggct ctctgggcgt | 6780 |
| cgcctttgcc gacaaaaatg tgatcatgat gaaagccagc aatgacgttg cagctgatat | 6840 |
| tgttgtcggc caaccgcgcc gaaaacgcag ctgtcagacc cacagcctcc aacgaagaat | 6900 |
| gtatcgtcaa agtgatccaa gcacactcat agttggagtc gtactccaaa ggcggcaatg | 6960 |
| acgagtcaga cagatactcg tcgacgttta acagtgtac gcagatctac tatagaggaa | 7020 |
| catttaaatt gccccggaga agacggccag gccgcctaga tgacaaattc aacaactcac | 7080 |
| agctgacttt ctgccattgc cactagggg gggccttttt atatggccaa gccaagctct | 7140 |
| ccacgtcggt tgggctgcac ccaacaataa atgggtaggg ttgcaccaac aaagggatgg | 7200 |
| gatgggggt agaagatacg aggataacgg ggctcaatgg cacaaataag aacgaatact | 7260 |
| gccattaaga ctcgtgatcc agcgactgac accattgcat catctaaggg cctcaaaact | 7320 |
| acctcggaac tgctgcgctg atctggacac cacagaggtt ccgagcactt taggttgcac | 7380 |
| caaatgtccc accaggtgca ggcagaaaac gctggaacga cgtgtacagt ttgtcttaac | 7440 |
| aaaaagtgag ggcgctgagg tcgagcaggg tggtgtgact tgttatagcc tttagagctg | 7500 |
| cgaaagcgcg tatggatttg gctcatcagg ccagattgag ggtctgtgga cacatgtcat | 7560 |
| gttagtgtac ttcaatcgcc ccctggatat agccccgaca ataggccgtg gcctcatttt | 7620 |
| tttgccttcc gcacatttcc attgctcgat acccacacct tgcttctcct gcacttgcca | 7680 |
| accttaatac tggtttacat tgaccaacat cttacaagcg gggggcttgt ctagggtata | 7740 |
| tataaacagt ggctctccca atcggttgcc agtctctttt ttccttctt tccccacaga | 7800 |
| ttcgaaatct aaactacaca tcacagaatt ccgagccgtg agtatccacg acaagatcag | 7860 |
| tgtcgagacg acgcgttttg tgtaatgaca caatccgaaa gtcgctagca acacacactc | 7920 |
| tctacacaaa ctaacccagc tctggtacc | 7949 |

<210> SEQ ID NO 72
<211> LENGTH: 5687
<212> TYPE: DNA
<213> ORGANISM: Artificial sequence
<220> FEATURE:
<223> OTHER INFORMATION: plasmid KS369

<400> SEQUENCE: 72

| | |
|---|---|
| ggccgcaagt atgaactaaa atgcacgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta actttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccatttta tatattatat actaccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttcttacag ataaaaaaaa aattatgagt tggtttgata | 660 |
| aaatattgaa ggatttaaaa taataataaa taacatataa tatatgtata taaatttatt | 720 |
| ataatataac atttatctat aaaaaagtaa atattgtcat aaatctatac aatcgtttag | 780 |
| ccttgctgga cgaatctcaa ttatttaaac gagagtaaac atatttgact ttttggttat | 840 |

```
ttaacaaatt attatttaac actatatgaa attttttttt ttatcagcaa agaataaaat      900
taaattaagg aggacaatgg tgtcccaatc cttatacaac caacttccac aagaaagtca      960
agtcagagac aacaaaaaaa caagcaaagg aaattttta atttgagttg tcttgtttgc      1020
tgcataattt atgcagtaaa acactacaca taacccttt agcagtaaag caatggttga      1080
ccgtgtgctt agcttctttt attttatttt tttatcagca aagaataaat aaaataaaat      1140
gagacacttc agggatgttt caacggatcc cccgggctgc aggaattcga tatcaagctt      1200
atcgataccg tcgacctcga gggggggccc ggtacccaat cgccctata gtgagtcgta      1260
ttacgcgcgc tcactggccg tcgttttaca acgtcgtgac tgggaaaacc ctggcgttac      1320
ccaacttaat cgccttgcag cacatccccc tttcgccagc tggcgtaata gcgaagaggc      1380
ccgcaccgat cgcccttccc aacagttgcg cagcctgaat ggcgaatggg acgcgccctg      1440
tagcggcgca ttaagcgcgg cgggtgtggt ggttacgcgc agcgtgaccg ctacacttgc      1500
cagcgcccta gcgcccgctc ctttcgcttt cttcccttcc tttctcgcca cgttcgccgg      1560
ctttccccgt caagctctaa atcgggggct ccctttaggg ttccgattta gtgctttacg      1620
gcacctcgac cccaaaaaac ttgattaggg tgatggttca cgtagtgggc catcgccctg      1680
atagacggtt tttcgccctt tgacgttgga gtccacgttc tttaatagtg gactcttgtt      1740
ccaaactgga acaacactca accctatctc ggtctattct tttgatttat aagggatttt      1800
gccgatttcg gcctattggt taaaaaatga gctgatttaa caaaaattta acgcgaattt      1860
taacaaaata ttaacgctta caatttaggt ggcacttttc ggggaaatgt gcgcggaacc      1920
cctatttgtt tatttttcta aatacattca aatatgtatc cgctcatgag acaataaccc      1980
tgataaatgc ttcaataata ttgaaaaagg aagagtatga gtattcaaca tttccgtgtc      2040
gcccttattc cctttttgc ggcattttgc cttcctgttt ttgctcaccc agaaacgctg      2100
gtgaaagtaa aagatgctga agatcagttg ggtgcacgag tgggttacat cgaactggat      2160
ctcaacagcg gtaagatcct tgagagtttt cgccccgaag aacgttttcc aatgatgagc      2220
acttttaaag ttctgctatg tggcgcggta ttatcccgta ttgacgccgg gcaagagcaa      2280
ctcggtcgcc gcatacacta ttctcagaat gacttggttg agtactcacc agtcacagaa      2340
aagcatctta cggatggcat gacagtaaga gaattatgca gtgctgccat aaccatgagt      2400
gataacactg cggccaactt acttctgaca acgatcggag gaccgaagga gctaaccgct      2460
tttttgcaca acatggggga tcatgtaact cgccttgatc gttgggaacc ggagctgaat      2520
gaagccatac caaacgacga gcgtgacacc acgatgcctg tagcaatggc aacaacgttg      2580
cgcaaactat taactggcga actacttact ctagcttccc ggcaacaatt aatagactgg      2640
atggaggcgg ataaagttgc aggaccactt ctgcgctcgg cccttccggc tggctggttt      2700
attgctgata atctggagc cggtgagcgt gggtctcgcg gtatcattgc agcactgggg      2760
ccagatggta agccctcccg tatcgtagtt atctacacga cggggagtca ggcaactatg      2820
gatgaacgaa atagacagat cgctgagata ggtgcctcac tgattaagca ttggtaactg      2880
tcagaccaag tttactcata tatactttag attgatttaa aacttcattt ttaatttaaa      2940
aggatctagg tgaagatcct ttttgataat ctcatgacca aaatccctta acgtgagttt      3000
tcgttccact gagcgtcaga ccccgtagaa aagatcaaag gatcttcttg agatcctttt      3060
tttctgcgcg taatctgctg cttgcaaaca aaaaaaccac cgctaccagc ggtggtttgt      3120
ttgccggatc aagagctacc aactcttttt ccgaaggtaa ctggcttcag cagagcgcag      3180
ataccaaata ctgtccttct agtgtagccg tagttaggcc accacttcaa gaactctgta      3240
```

```
gcaccgccta catacctcgc tctgctaatc ctgttaccag tggctgctgc cagtggcgat   3300
aagtcgtgtc ttaccgggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcagggtg gcggagccta tggaaaaacg ccagcaacgc ggccttttta   3660
cggttcctgg ccttttgctg gccttttgct cacatgttct ttcctgcgtt atcccctgat   3720
tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900
gcgggcagtg agcgcaacgc aattaatgtg agttagctca ctcattaggc accccaggct   3960
ttacacttta tgcttccggc tcgtatgttg tgtggaattg tgagcggata acaatttcac   4020
acaggaaaca gctatgacca tgattacgcc aagcgcgcaa ttaaccctca ctaagggaa    4080 caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
atcaggatcg ccgcgtcaag aaaaaaaaac tggaccccaa aagccatgca caacaacacg   4440
tactcacaaa ggtgtcaatc gagcagccca aaacattcac caactcaacc catcatgagc   4500
cctcacattt gttgtttcta acccaacctc aaactcgtat tctcttccgc cacctcattt   4560
ttgtttattt caacacccgt caaactgcat gccaccccgt ggccaaatgt ccatgcatgt   4620
taacaagacc tatgactata aatagctgca atctcggccc aggttttcat catcaagaac   4680
cagttcaata tcctagtaca ccgtattaaa gaatttaaga tatactccat ggagtccatt   4740
gctcccttcc tgccctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggagtctccc   4920
ctggctcgag agctgcctct gatgaacccc ttccacgtgc tcctgatcgt gctcgcctac   4980
ctggtcaccg tgtttgtggg tatgcagatc atgaagaact tgaacgatt cgaggtcaag    5040 acgtattcgc tcctgcacaa cttctgtctg gtctcgatta gcgcctacat gtgcggtggc   5100
atcctgtacg aggcttttcca ggccaactat ggactgtttg agaacgctgc cgatcacacc   5160
ttcaagggtc tccctatggc taagatgatc tggctcttct acttctccaa gatcatggag   5220
tttgtcgaca cccttatcat ggtcctcaag aagaacaacc gacagatttc ctttctgcac   5280
gtgtaccacc actcttccat cttcaccatc tggtggctgg tcaccttcgt tgctcccaac   5340
ggtgaagcct acttctctgc tgccctgaac tcgttcatcc atgttatcat gtacggctac   5400
tactttctgt ctgccctggg cttcaagcag gtgtcgctga tcaagttcta catcactcga   5460
tcccagatga cccagttctg catgatgtct gtccagtctt cctgggacat gtacgccatg   5520
aaggtccttg gccgacctgg ataccccttc ttcatcgccg ctctgctctg gttctacatg   5580
tggaccatgc tcggtctctt ctacaacttt taccgaaaga acgccaagct cgccaagcag   5640
```

```
gccaaggctg acgctgccaa ggagaaggcc agaaagctcc agtaagc              5687

<210> SEQ ID NO 73
<211> LENGTH: 5687
<212> TYPE: DNA
<213> ORGANISM: Artificial sequence
<220> FEATURE:
<223> OTHER INFORMATION: plasmid KS370

<400> SEQUENCE: 73
ggccgcaagt atgaactaaa atgcacgtag gtgtaagagc tcatggagag catggaatat    60
tgtatccgac catgtaacag tataataact gagctccatc tcacttcttc tatgaataaa   120
caaaggatgt tatgatatat taacactcta tctatgcacc ttattgttct atgataaatt   180
tcctcttatt attataaatc atctgaatcg tgacggctta tggaatgctt caaatagtac   240
aaaaacaaat gtgtactata agactttcta aacaattcta actttagcat tgtgaacgag   300
acataagtgt taagaagaca taacaattat aatggaagaa gtttgtctcc atttatatat   360
tatatattac ccacttatgt attatattag gatgttaagg agacataaca attataaaga   420
gagaagtttg tatccattta tatattatat actacccatt tatatattat acttatccac   480
ttatttaatg tctttataag gtttgatcca tgatatttct aatattttag ttgatatgta   540
tatgaaaggg tactatttga actctcttac tctgtataaa ggttggatca tccttaaagt   600
gggtctattt aattttattg cttcttacag ataaaaaaaa aattatgagt tggtttgata   660
aaatattgaa ggatttaaaa taataataaa taacatataa tatatgtata taaatttatt   720
ataatataac atttatctat aaaaaagtaa atattgtcat aaatctatac aatcgtttag   780
ccttgctgga cgaatctcaa ttatttaaac gagagtaaac atatttgact ttttggttat   840
ttaacaaatt attatttaac actatatgaa attttttttt ttatcagcaa agaataaaat   900
taaattaagg aggacaatgg tgtcccaatc cttatacaac caacttccac aagaaagtca   960
agtcagagac aacaaaaaaa caagcaaagg aaattttta atttgagttg tcttgtttgc   1020
tgcataattt atgcagtaaa acactacaca taacccttt agcagtaaag caatggttga   1080
ccgtgtgctt agcttctttt attttatttt tttatcagca aagaataaat aaaataaaat   1140
gagacacttc agggatgttt caacggatcc cccgggctgc aggaattcga tatcaagctt   1200
atcgataccg tcgacctcga gggggggccc ggtacccaat cgccctata gtgagtcgta   1260
ttacgcgcgc tcactggccg tcgttttaca acgtcgtgac tgggaaaacc ctggcgttac   1320
ccaacttaat cgccttgcag cacatccccc tttcgccagc tggcgtaata gcgaagaggc   1380
ccgcaccgat cgcccttccc aacagttgcg cagcctgaat ggcgaatggg acgcgcctg   1440
tagcggcgca ttaagcgcgg cgggtgtggt ggttacgcgc agcgtgaccg ctacacttgc   1500
cagcgcccta gcgcccgctc ctttcgcttt cttcccttcc tttctcgcca cgttcgccgg   1560
ctttccccgt caagctctaa atcggggggct ccctttaggg ttccgattta gtgctttacg   1620
gcacctcgac cccaaaaaac ttgattaggg tgatggttca cgtagtgggc catcgccctg   1680
atagacggtt tttcgccctt tgacgttgga gtccacgttc tttaatagtg gactcttgtt   1740
ccaaactgga acaacactca acccctatctc ggtctattct tttgatttat aagggatttt   1800
gccgatttcg gcctattggt taaaaaatga gctgatttaa caaaaattta acgcgaattt   1860
taacaaaata ttaacgctta caatttaggt ggcacttttc ggggaaatgt gcgcggaacc   1920
cctatttgtt tatttttcta aatacattca aatatgtatc cgctcatgag acaataaccc   1980
tgataaatgc ttcaataata ttgaaaaagg aagagtatga gtattcaaca tttccgtgtc   2040
```

```
gcccttattc cctttttgc ggcattttgc cttcctgttt ttgctcaccc agaaacgctg   2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagcc ggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tatactttag attgatttaa aacttcattt ttaatttaaa   2940
aggatctagg tgaagatcct tttgataat ctcatgacca aaatccctta acgtgagttt   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactctttt ccgaaggtaa ctggcttcag cagagcgcag   3180
ataccaaata ctgtccttct agtgtagccg tagttaggcc accacttcaa gaactctgta   3240
gcaccgccta catacctcgc tctgctaatc ctgttaccag tggctgctgc cagtggcgat   3300
aagtcgtgtc ttaccgggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag ggtcggaaca ggagagcgca cgagggagct tccaggggga   3540
aacgcctggt atctttatag tcctgtcggg tttcgccacc tctgacttga gcgtcgattt   3600
ttgtgatgct cgtcaggggg gcggagccta tggaaaaacg ccagcaacgc ggccttttta   3660
cggttcctgg ccttttgctg gccttttgct cacatgttct ttcctgcgtt atccctgat   3720 tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900
gcgggcagtg agcgcaacgc aattaatgtg agttagctca ctcattaggc accccaggct   3960
ttacacttta tgcttccggc tcgtatgttg tgtggaattg tgagcggata acaatttcac   4020
acaggaaaca gctatgacca tgattacgcc aagcgcgcaa ttaaccctca ctaagggaa    4080 caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
atcaggatcg ccgcgtcaag aaaaaaaaac tggacccca aagccatgca caacaacacg   4440
```

```
tactcacaaa ggtgtcaatc gagcagccca aaacattcac caactcaacc catcatgagc    4500
cctcacattt gttgtttcta acccaacctc aaactcgtat tctcttccgc cacctcattt    4560
ttgtttattt caacacccgt caaactgcat gccaccccgt ggccaaatgt ccatgcatgt    4620
taacaagacc tatgactata aatagctgca atctcggccc aggttttcat catcaagaac    4680
cagttcaata tcctagtaca ccgtattaaa gaatttaaga tatactccat ggagtccatt    4740
gttcccttcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggagtctccc    4920
ctggctcgag agctgcctct gatgaacccc ttccacgtgc tcctgatcgt gctcgcctac    4980
ctggtcaccg tgtttgtggg tatgcagatc atgaagaact ttgaacgatt cgaggtcaag    5040
acgtattcgc tcctgcacaa cttctgtctg gtctcgctga gcgcctacat gtgcggtggc    5100
attctgtacg aggcttatca ggccaactat ggactgtttg agaacgctgc cgatcacacc    5160
ttcaagggtc tccctatggc taagatgatc tggctcttct acttctccaa gatcatggag    5220
tttgtcgaca ccatgatcat ggtcctcaag aagaacaacc gacagatttc ctttctgcac    5280
gtgtaccacc actcttccat cttcaccatc tggtggctgg tcaccttcgt tgctcccaac    5340
ggtgaagcct acttctctgc tgccctgaac tcgttcatcc atgttatcat gtacggctac    5400
tactttctgt ctgccctggg cttcaagcag gtgtcgttca tcaagttcta catcactcga    5460
tcccagatga cccagttctg catgatgtct gtccagtctt cctgggacat gtacgccatg    5520
aaggtccttg ccgacctggg ataccccttc ttcatcaccg ctctgctctg gttctacatg    5580
tggaccatgc tcggtctctt ctacaacttt taccgaaaga acgccaagct cgccaagcag    5640
gccaaggctg acgctgccaa ggagaaggcc agaaagctcc agtaagc                  5687

<210> SEQ ID NO 74
<211> LENGTH: 5687
<212> TYPE: DNA
<213> ORGANISM: Artificial sequence
<220> FEATURE:
<223> OTHER INFORMATION: plasmid KS371

<400> SEQUENCE: 74
ggccgcaagt atgaactaaa atgcacgtag gtgtaagagc tcatggagag catggaatat     60
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta actttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccatttta tatattatat actacccatt tatatattat acttatccac    480
ttatttaatg tctttataag gtttgatcca tgatatttct aatatttag ttgatatgta     540 tatgaaaggg tactatttga actctcttac tctgtataaa ggttggatca tccttaaagt    600
gggtctattt aatttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
```

```
ttaacaaatt attatttaac actatatgaa attttttttt ttatcagcaa agaataaaat    900
taaattaagg aggacaatgg tgtcccaatc cttatacaac caacttccac aagaaagtca    960
agtcagagac aacaaaaaaa caagcaaagg aaattttta atttgagttg tcttgtttgc   1020
tgcataattt atgcagtaaa acactacaca taaccctttt agcagtaaag caatggttga   1080
ccgtgtgctt agcttctttt attttatttt tttatcagca aagaataaat aaaataaaat   1140
gagacacttc agggatgttt caacggatcc cccgggctgc aggaattcga tatcaagctt   1200
atcgataccg tcgacctcga gggggggccc ggtacccaat cgccctata gtgagtcgta   1260
ttacgcgcgc tcactggccg tcgttttaca acgtcgtgac tgggaaaacc ctggcgttac   1320
ccaacttaat cgccttgcag cacatccccc tttcgccagc tggcgtaata gcgaagaggc   1380
ccgcaccgat cgcccttccc aacagttgcg cagcctgaat ggcgaatggg acgcgccctg   1440
tagcggcgca ttaagcgcgg cgggtgtggt ggttacgcgc agcgtgaccg ctacacttgc   1500
cagcgcccta gcgcccgctc ctttcgcttt cttcccttcc tttctcgcca cgttcgccgg   1560
ctttccccgt caagctctaa atcggggggct ccctttaggg ttccgattta gtgctttacg   1620
gcacctcgac cccaaaaaac ttgattaggg tgatggttca cgtagtgggc catcgccctg   1680
atagacggtt tttcgccctt tgacgttgga gtccacgttc tttaatagtg gactcttgtt   1740
ccaaactgga caacactca accctatctc ggtctattct tttgatttat aagggatttt   1800
gccgatttcg gcctattggt taaaaaatga gctgatttaa caaaaattta acgcgaattt   1860
taacaaaata ttaacgctta caatttaggt ggcacttttc ggggaaatgt gcgcggaacc   1920
cctatttgtt tatttttcta aatacattca aatatgtatc cgctcatgag acaataaccc   1980
tgataaatgc ttcaataata ttgaaaaagg aagagtatga gtattcaaca tttccgtgtc   2040
gcccttattc ccttttttgc ggcattttgc cttcctgttt ttgctcaccc agaaacgctg   2100
gtgaaagtaa aagatgctga agatcagttg ggtgcacgag tgggttacat cgaactggat   2160
ctcaacagcg gtaagatcct tgagagtttt cgccccgaag aacgttttcc aatgatgagc   2220
acttttaaag ttctgctatg tggcgcggta ttatcccgta ttgacgccgg gcaagagcaa   2280
ctcggtcgcc gcatacacta ttctcagaat gacttggttg agtactcacc agtcacagaa   2340
aagcatctta cggatggcat gacagtaaga gaattatgca gtgctgccat aaccatgagt   2400
gataacactg cggccaactt acttctgaca acgatcggag gaccgaagga gctaaccgct   2460
tttttgcaca acatggggga tcatgtaact cgccttgatc gttgggaacc ggagctgaat   2520
gaagccatac caaacgacga gcgtgacacc acgatgcctg tagcaatggc aacaacgttg   2580
cgcaaactat taactggcga actacttact ctagcttccc ggcaacaatt aatagactgg   2640
atggaggcgg ataaagttgc aggaccactt ctgcgctcgg cccttccggc tggctggttt   2700
attgctgata atctggagc cggtgagcgt gggtctcgcg gtatcattgc agcactgggg   2760
ccagatggta agccctcccg tatcgtagtt atctacacga cggggagtca ggcaactatg   2820
gatgaacgaa atagacagat cgctgagata ggtgcctcac tgattaagca ttggtaactg   2880
tcagaccaag tttactcata tatactttag attgatttaa aacttcattt ttaatttaaa   2940
aggatctagg tgaagatcct ttttgataat ctcatgacca aaatccctta acgtgagttt   3000
tcgttccact gagcgtcaga ccccgtagaa aagatcaaag gatcttcttg agatcctttt   3060
tttctgcgcg taatctgctg cttgcaaaca aaaaaaccac cgctaccagc ggtggtttgt   3120
ttgccggatc aagagctacc aactcttttt ccgaaggtaa ctggcttcag cagagcgcag   3180
ataccaaata ctgtccttct agtgtagccg tagttaggcc accacttcaa gaactctgta   3240
```

```
gcaccgccta catacctcgc tctgctaatc ctgttaccag tggctgctgc cagtggcgat   3300
aagtcgtgtc ttaccgggtt ggactcaaga cgatagttac cggataaggc gcagcggtcg   3360
ggctgaacgg ggggttcgtg cacacagccc agcttggagc gaacgaccta caccgaactg   3420
agatacctac agcgtgagct atgagaaagc gccacgcttc ccgaagggag aaaggcggac   3480
aggtatccgg taagcggcag gtcggaaca ggagagcgca cgagggagct tccaggggga    3540
aacgcctggt atctttatag tcctgtcggg tttcgccacc tctgacttga gcgtcgattt   3600
ttgtgatgct cgtcagggg gcggagccta tggaaaaacg ccagcaacgc ggccttttta    3660
cggttcctgg cctttttgctg gccttttgct cacatgttct ttcctgcgtt atccctgat   3720 tctgtggata accgtattac cgcctttgag tgagctgata ccgctcgccg cagccgaacg   3780
accgagcgca gcgagtcagt gagcgaggaa gcggaagagc gcccaatacg caaaccgcct   3840
ctccccgcgc gttggccgat tcattaatgc agctggcacg acaggtttcc cgactggaaa   3900
gcgggcagtg agcgcaacgc aattaatgtg agttagctca ctcattaggc accccaggct   3960
ttacacttta tgcttccggc tcgtatgttg tgtggaattg tgagcggata acaatttcac   4020
acaggaaaca gctatgacca tgattacgcc aagcgcgcaa ttaaccctca ctaagggaa    4080 caaaagctgg agctccaccc tagaactagt ggatccttca tccatgccct tcatttgccg   4140
cttattaatt aatttggtaa cagtccgtac taatcagtta cttatccttc ccccatcata   4200
attaatcttg gtagtctcga atgccacaac actgactagt ctcttggatc ataagaaaaa   4260
gccaaggaac aaaagaagac aaaacacaat gagagtatcc tttgcatagc aatgtctaag   4320
ttcataaaat tcaaacaaaa acgcaatcac acacagtgga catcacttat ccactagctg   4380
atcaggatcg ccgcgtcaag aaaaaaaaac tggaccccaa aagccatgca caacaacacg   4440
tactcacaaa ggtgtcaatc gagcagccca aaacattcac caactcaacc catcatgagc   4500
cctcacattt gttgtttcta acccaacctc aaactcgtat tctcttccgc cacctcattt   4560
ttgtttattt caacacccgt caaactgcat gccaccccgt ggccaaatgt ccatgcatgt   4620
taacaagacc tatgactata aatagctgca atctcggccc aggttttcat catcaagaac   4680
cagttcaata tcctagtaca ccgtattaaa gaatttaaga tatactccat ggagtccatt   4740
gctcccttcc tgctctccaa gatgcctcag gacctgttca tggacctcgc cagcgctatc   4800
ggtgtccgag ctgctcccta cgtcgatccc ctggaggctg ccctggttgc ccaggccgag   4860
aagtacattc ccaccattgt ccatcacact cgaggcttcc tggttgccgt ggagtctccc   4920
ctggctcgag agctgcctct gatgaacccc ttccacgtgc tcctgatcgt gctcgcctac   4980
ctggtcaccg tgtttgtggg tatgcagatc atgaagaact tgaacgatt cgaggtcaag    5040 acgtattcgc tcctgcacaa cttctgtctg gtctcgctga gcgcctacat gtgcggtggc   5100
attctgtacg aggcttttca ggccaactat ggactgtttg agaacgctgc cgatcacacc   5160
ttcaagggtc tccctatggc taagatgatc tggctcttct acttctccaa gatcatggag   5220
tttgtcgaca ccatgatcat ggtcctcaag aagaacaacc gacagatttc ctttctgcac   5280
gtgtaccacc actcttccat cttccaccat tggtggctgg tcaccttcgt tgctcccaac   5340
ggtgaagcct acttctctgc tgccctgaac tcgttcatcc atgttatcat gtacggctac   5400
tactttctgt ctgccctggg cttcaagcag gtgtcgctga tcaagttcta catcactcga   5460
tcccagatga cccagttctg catgttgtct gtccagtctt cctgggacat gtacgccatg   5520
aaggtccttg gccgacctgg ataccccttc ttcatcaccg ctctgctctg gttctacatg   5580
tggaccatgc tcggtctctt ctacaacttt taccgaaaga acgccaagct cgccaagcag   5640
```

```
gccaaggctg acgctgccaa ggagaaggcc agaaagctcc agtaagc          5687

<210> SEQ ID NO 75
<211> LENGTH: 5687
<212> TYPE: DNA
<213> ORGANISM: Artificial sequence
<220> FEATURE:
<223> OTHER INFORMATION: plasmid KS372

<400> SEQUENCE: 75
ggccgcaagt atgaactaaa atgcacgtag gtgtaagagc tcatggagag catggaatat    60
tgtatccgac catgtaacag tataataact gagctccatc tcacttcttc tatgaataaa   120
caaaggatgt tatgatatat taacactcta tctatgcacc ttattgttct atgataaatt   180
tcctcttatt attataaatc atctgaatcg tgacggctta tggaatgctt caaatagtac   240
aaaaacaaat gtgtactata agactttcta aacaattcta actttagcat tgtgaacgag   300
acataagtgt taagaagaca taacaattat aatggaagaa gtttgtctcc atttatatat   360
tatatattac ccacttatgt attatattag gatgttaagg agacataaca attataaaga   420
gagaagtttg tatccatttta tatattatat actacccatt tatatattat acttatccac   480
ttatttaatg tctttataag gtttgatcca tgatatttct aatattttag ttgatatgta   540
tatgaaaggg tactatttga actctcttac tctgtataaa ggttggatca tccttaaagt   600
gggtctattt aattttattg cttcttacag ataaaaaaaa aattatgagt tggtttgata   660
aaatattgaa ggatttaaaa taataataaa taacatataa tatatgtata taaatttatt   720
ataatataac atttatctat aaaaaagtaa atattgtcat aaatctatac aatcgtttag   780
ccttgctgga cgaatctcaa ttatttaaac gagagtaaac atatttgact ttttggttat   840
ttaacaaatt attatttaac actatatgaa attttttttt ttatcagcaa agaataaaat   900
taaattaagg aggacaatgg tgtcccaatc cttatacaac caacttccac aagaaagtca   960
agtcagagac aacaaaaaaa caagcaaagg aaattttttta atttgagttg tcttgtttgc  1020
tgcataattt atgcagtaaa acactacaca taaccctttt agcagtaaag caatggttga  1080
ccgtgtgctt agcttctttt atttttattttt tttatcagca aagaataaat aaaataaaat  1140
gagacacttc agggatgttt caacggatcc cccgggctgc aggaattcga tatcaagctt  1200
atcgataccg tcgacctcga ggggggggccc ggtacccaat tcgccctata gtgagtcgta  1260
ttacgcgcgc tcactggccg tcgttttaca acgtcgtgac tgggaaaacc ctggcgttac  1320
ccaacttaat cgccttgcag cacatccccc tttcgccagc tggcgtaata gcgaagaggc  1380
ccgcaccgat cgcccttccc aacagttgcg cagcctgaat ggcgaatggg acgcgcctg   1440
tagcggcgca ttaagcgcgg cgggtgtggt ggttacgcgc agcgtgaccg ctacacttgc  1500
cagcgcccta gcgcccgctc ctttcgcttt cttcccttcc tttctcgcca cgttcgccgg  1560
ctttccccgt caagctctaa atcggggggct cccttttaggg ttccgattta gtgctttacg  1620
gcacctcgac cccaaaaaac ttgattaggg tgatggttca cgtagtgggc catcgccctg  1680
atagacggtt tttcgccctt tgacgttgga gtccacgttc tttaatagtg gactcttgtt  1740
ccaaactgga acaacactca accctatctc ggtctattct tttgatttat aagggatttt  1800
gccgatttcg gcctattggt taaaaaatga gctgatttaa caaaaattta acgcgaattt  1860
taacaaaata ttaacgctta caatttaggt ggcacttttc ggggaaatgt gcgcggaacc  1920
cctatttgtt tatttttcta aatacattca aatatgtatc cgctcatgag acaataaccc  1980
tgataaatgc ttcaataata ttgaaaaagg aagagtatga gtattcaaca tttccgtgtc  2040
```

```
gcccttattc cctttttgc ggcattttgc cttcctgttt ttgctcaccc agaaacgctg    2100
gtgaaagtaa aagatgctga agatcagttg ggtgcacgag tgggttacat cgaactggat    2160
ctcaacagcg gtaagatcct tgagagtttt cgccccgaag aacgttttcc aatgatgagc    2220
acttttaaag ttctgctatg tggcgcggta ttatcccgta ttgacgccgg gcaagagcaa    2280
ctcggtcgcc gcatacacta ttctcagaat gacttggttg agtactcacc agtcacagaa    2340
aagcatctta cggatggcat gacagtaaga gaattatgca gtgctgccat aaccatgagt    2400
gataacactg cggccaactt acttctgaca acgatcggag gaccgaagga gctaaccgct    2460
tttttgcaca acatggggga tcatgtaact cgccttgatc gttgggaacc ggagctgaat    2520
gaagccatac caaacgacga gcgtgacacc acgatgcctg tagcaatggc aacaacgttg    2580
cgcaaactat taactggcga actacttact ctagcttccc ggcaacaatt aatagactgg    2640
atggaggcgg ataaagttgc aggaccactt ctgcgctcgg cccttccggc tggctggttt    2700
attgctgata atctggagcc ggtgagcgt gggtctcgcg gtatcattgc agcactgggg    2760
ccagatggta agccctcccg tatcgtagtt atctacacga cggggagtca ggcaactatg    2820
gatgaacgaa atagacagat cgctgagata ggtgcctcac tgattaagca ttggtaactg    2880
tcagaccaag tttactcata tatactttag attgatttaa aacttcattt ttaatttaaa    2940
aggatctagg tgaagatcct tttgataat ctcatgacca aaatccctta acgtgagttt    3000
tcgttccact gagcgtcaga ccccgtagaa aagatcaaag gatcttcttg agatcctttt    3060
tttctgcgcg taatctgctg cttgcaaaca aaaaaaccac cgctaccagc ggtggtttgt    3120
ttgccggatc aagagctacc aactcttttt ccgaaggtaa ctggcttcag cagagcgcag    3180
ataccaaata ctgtccttct agtgtagccg tagttaggcc accacttcaa gaactctgta    3240
gcaccgccta catacctcgc tctgctaatc ctgttaccag tggctgctgc cagtggcgat    3300
aagtcgtgtc ttaccgggtt ggactcaaga cgatagttac cggataaggc gcagcggtcg    3360
ggctgaacgg ggggttcgtg cacacagccc agcttggagc gaacgaccta caccgaactg    3420
agatacctac agcgtgagct atgagaaagc gccacgcttc ccgaagggag aaaggcggac    3480
aggtatccgg taagcggcag ggtcggaaca ggagagcgca cgagggagct tccaggggga    3540
aacgcctggt atctttatag tcctgtcggg tttcgccacc tctgacttga gcgtcgattt    3600
ttgtgatgct cgtcaggggg gcggagccta tggaaaaacg ccagcaacgc ggcctttta    3660 cggttcctgg ccttttgctg gccttttgct cacatgttct ttcctgcgtt atcccctgat    3720
tctgtggata accgtattac cgcctttgag tgagctgata ccgctcgccg cagccgaacg    3780
accgagcgca gcgagtcagt gagcgaggaa gcggaagagc gcccaatacg caaaccgcct    3840
ctccccgcgc gttggccgat tcattaatgc agctggcacg acaggtttcc cgactggaaa    3900
gcgggcagtg agcgcaacgc aattaatgtg agttagctca ctcattaggc acccccaggct   3960 ttacacttta tgcttccggc tcgtatgttg tgtggaattg tgagcggata acaatttcac    4020
acaggaaaca gctatgacca tgattacgcc aagcgcgcaa ttaaccctca ctaaagggaa    4080
caaaagctgg agctccaccc tagaactagt ggatccttca tccatgccct tcatttgccg    4140
cttattaatt aatttggtaa cagtccgtac taatcagtta cttatccttc ccccatcata    4200
attaatcttg gtagtctcga atgccacaac actgactagt ctcttggatc ataagaaaaa    4260
gccaaggaac aaaagaagac aaaacacaat gagagtatcc tttgcatagc aatgtctaag    4320
ttcataaaat tcaaacaaaa acgcaatcac acacagtgga catcacttat ccactagctg    4380
atcaggatcg ccgcgtcaag aaaaaaaaac tggaccccaa aagccatgca caacaacacg    4440
```

```
tactcacaaa ggtgtcaatc gagcagccca aaacattcac caactcaacc catcatgagc    4500
cctcacattt gttgtttcta acccaacctc aaactcgtat tctcttccgc cacctcattt    4560
ttgtttattt caacacccgt caaactgcat gccaccccgt ggccaaatgt ccatgcatgt    4620
taacaagacc tatgactata aatagctgca atctcggccc aggttttcat catcaagaac    4680
cagttcaata tcctagtaca ccgtattaaa gaatttaaga tatactccat ggagtccatt    4740 gccccctcc tgccctccaa gatgcctcag gacctgttca tggacctcgc cagcgctatc    4800
ggtgtccgag ctgctcccta cgtcgatccc ctggaggctg ccctggttgc ccaggccgag    4860
aagtacattc ccaccattgt ccatcacact cgaggcttcc tggttgccgt ggagtctccc    4920
ctggctcgag agctgcctct gatgaacccc ttccacgtgc tcctgatcgt gctcgcctac    4980
ctggtcaccg tgtttgtggg tatgcagatc atgaagaact ttgaacggtt cgaggtcaag    5040
acgttctcgc tcctgcacaa cttctgtctg gtctcgatta gcgcctacat gtgcggtggc    5100
atcctgtacg aggctttcca ggccaactat ggactgtttg agaacgctgc cgatcacacc    5160
ttcaagggtc tccctatggc taagatgatc tggctcttct acttctccaa gatcatggag    5220
tttgtcgaca ccatgatcat ggtcctcaag aagaacaacc gacagatttc ctttctgcac    5280
gtgtaccacc actcttccat cttcaccatc tggtggctgg tcaccttcgt tgctcccaac    5340
ggtgaagcct acttctctgc tgccctgaac tcgttcatcc atgttatcat gtacggctac    5400
tactttctgt ctgccctggg cttcaagcag gtgtcgctga tcaagttcta catcactcga    5460
tcccagatga cccagttctg catgatgtct gtccagtctt cctgggacat gtacgccatg    5520
aaggtccttg gccgacctgg atacccttc ttcatcaccg ctctgctctg gttctacatg    5580
tggaccatgc tcggtctctt ctacaacttt taccgaaaga cgccaagct cgccaagcag    5640 gccaaggctg acgctgccaa ggagaaggcc agaaagctcc agtaagc                 5687
```

<210> SEQ ID NO 76
<211> LENGTH: 5687
<212> TYPE: DNA
<213> ORGANISM: Artificial sequence
<220> FEATURE:
<223> OTHER INFORMATION: plasmid KS376

<400> SEQUENCE: 76

```
catggagtcc attgctccct tcctgccctc caagatgcct caggacctgt tcatggacct      60
cgccagcgct atcggtgtcc gagctgctcc ctacgtcgat cccctggagg ctgccctggt     120
tgcccaggcc gagaagtaca ttcccaccat tgtccatcac actcgaggct tcctggttgc     180
cgtggattct cccctggctc gagagctgcc tctgatgaac cccttccacg tgctcctgat     240
tgtgctcgcc tacctggtca ccgtgtttgt gggtatgcag atcatgaaga actttgaacg     300
attcgaggtc aagacgttct cgctcctgta caacttctgt ctggtctcgc tgagcgccta     360
catgtgcggt ggcatcctgt acgaggcttt ccaggccaac tatggactgt ttgagaacgc     420
tgccgatcac accttcaagg gtctccctat ggctaagatg atctggctct tctacttctc     480
caagctgatg gagtttgtcg acaccatgat catggtcctc aaaaagaaca accgacagat     540
ttcctttctg cacgtgtacc accactcttc catcttcacc atctggtggc tggtcacctt     600
cgttgctccc aacggtgaag cctacttctc tgctgccct aactcgttca tccatgttat     660
catgtacggc tactactttc tgtctgccct gggcttcaag caggtgtcgt tcatcaagtt     720
ctacatcact cgatcccaga tgacccagtt ctgcatgatg tctgtccagt cttcctggga     780
catgtacgcc atgaaggtcc ttggccgacc tggataccc ttcttcctga ccgctctgct     840
```

```
ctggttctac atgtggacca tgctcggtct cttctacaac ttttaccgaa agaacgccaa    900
gctcgccaag caggccaagg ctgacgctgc caaggagaag gccagaaagc tccagtaagc    960
ggccgcaagt atgaactaaa atgcacgtag gtgtaagagc tcatggagag catggaatat   1020
tgtatccgac catgtaacag tataataact gagctccatc tcacttcttc tatgaataaa   1080
caaaggatgt tatgatatat taacactcta tctatgcacc ttattgttct atgataaatt   1140
tcctcttatt attataaatc atctgaatcg tgacggctta tggaatgctt caaatagtac   1200
aaaaacaaat gtgtactata agactttcta aacaattcta actttagcat tgtgaacgag   1260
acataagtgt taagaagaca taacaattat aatggaagaa gtttgtctcc atttatatat   1320
tatatattac ccacttatgt attatattag gatgttaagg agacataaca attataaaga   1380
gagaagtttg tatccattta tatattatat actacccatt tatatattat acttatccac   1440
ttatttaatg tctttataag gtttgatcca tgatatttct aatattttag ttgatatgta   1500
tatgaaaggg tactatttga actctcttac tctgtataaa ggttggatca tccttaaagt   1560
gggtctattt aattttattg cttcttacag ataaaaaaaa aattatgagt tggtttgata   1620
aaatattgaa ggatttaaaa taataataaa taacatataa tatatgtata taaatttatt   1680
ataatataac atttatctat aaaaaagtaa atattgtcat aaatctatac aatcgtttag   1740
ccttgctgga cgaatctcaa ttatttaaac gagagtaaac atatttgact ttttggttat   1800
ttaacaaatt attatttaac actatatgaa attttttttt ttatcagcaa agaataaaat   1860
taaattaagg aggacaatgg tgtcccaatc cttatacaac caacttccac aagaaagtca   1920
agtcagagac aacaaaaaaa caagcaaagg aaatttttta atttgagttg tcttgtttgc   1980
tgcataattt atgcagtaaa acactacaca taacccttttt agcagtaaag caatggttga   2040
ccgtgtgctt agcttctttt attttatttt tttatcagca aagaataaat aaaataaaat   2100
gagacacttc agggatgttt caacggatcc cccgggctgc aggaattcga tatcaagctt   2160
atcgataccg tcgacctcga ggggggggccc ggtacccaat tcgccctata gtgagtcgta   2220
ttacgcgcgc tcactggccg tcgttttaca acgtcgtgac tgggaaaacc ctggcgttac   2280
ccaacttaat cgccttgcag cacatccccc tttcgccagc tggcgtaata gcgaagaggc   2340
ccgcaccgat cgcccttccc aacagttgcg cagcctgaat ggcgaatggg acgcgccctg   2400
tagcggcgca ttaagcgcgg cgggtgtggt ggttacgcgc agcgtgaccg ctacacttgc   2460
cagcgcccta gcgcccgctc ctttcgcttt cttcccttcc tttctcgcca cgttcgccgg   2520
ctttccccgt caagctctaa atcggggggct cccttagggg ttccgattta gtgctttacg   2580
gcacctcgac cccaaaaaac ttgattaggg tgatggttca cgtagtgggc catcgccctg   2640
atagacggtt tttcgccctt tgacgttgga gtccacgttc tttaatagtg gactcttgtt   2700
ccaaactgga acaacactca accctatctc ggtctattct tttgatttat aagggatttt   2760
gccgatttcg gcctattggt taaaaaatga gctgatttaa caaaaattta cgcgaatttt   2820
taacaaaata ttaacgctta caatttaggt ggcactttc ggggaaatgt gcgcggaacc   2880
cctatttgtt tatttttcta aatacattca aatatgtatc cgctcatgag acaataaccc   2940
tgataaatgc ttcaataata ttgaaaaagg aagagtatga gtattcaaca tttccgtgtc   3000
gcccttattc cctttttgc ggcattttgc cttcctgttt ttgctcaccc agaaacgctg   3060
gtgaaagtaa aagatgctga agatcagttg ggtgcacgag tgggttacat cgaactggat   3120
ctcaacagcg gtaagatcct tgagagtttt cgccccgaag aacgttttcc aatgatgagc   3180
acttttaaag ttctgctatg tggcgcggta ttatcccgta ttgacgccgg caagagcaa    3240
```

```
ctcggtcgcc gcatacacta ttctcagaat gacttggttg agtactcacc agtcacagaa  3300
aagcatctta cggatggcat gacagtaaga gaattatgca gtgctgccat aaccatgagt  3360
gataacactg cggccaactt acttctgaca acgatcggag gaccgaagga gctaaccgct  3420
tttttgcaca acatggggga tcatgtaact cgccttgatc gttgggaacc ggagctgaat  3480
gaagccatac caaacgacga gcgtgacacc acgatgcctg tagcaatggc aacaacgttg  3540
cgcaaactat taactggcga actacttact ctagcttccc ggcaacaatt aatagactgg  3600
atggaggcgg ataaagttgc aggaccactt ctgcgctcgg cccttccggc tggctggttt  3660
attgctgata atctggagcc ggtgagcgt gggtctcgcg gtatcattgc agcactgggg  3720
ccagatggta agccctcccg tatcgtagtt atctacacga cggggagtca ggcaactatg  3780
gatgaacgaa atagacagat cgctgagata ggtgcctcac tgattaagca ttggtaactg  3840
tcagaccaag tttactcata tatactttag attgatttaa aacttcattt ttaatttaaa  3900
aggatctagg tgaagatcct ttttgataat ctcatgacca aaatccctta acgtgagttt  3960
tcgttccact gagcgtcaga ccccgtagaa aagatcaaag gatcttcttg agatcctttt  4020
tttctgcgcg taatctgctg cttgcaaaca aaaaaaccac cgctaccagc ggtggtttgt  4080
ttgccggatc aagagctacc aactcttttt ccgaaggtaa ctggcttcag cagagcgcag  4140
ataccaaata ctgtccttct agtgtagccg tagttaggcc accacttcaa gaactctgta  4200
gcaccgccta catacctcgc tctgctaatc ctgttaccag tggctgctgc cagtggcgat  4260
aagtcgtgtc ttaccgggtt ggactcaaga cgatagttac cggataaggc gcagcggtcg  4320
ggctgaacgg ggggttcgtg cacacagccc agcttggagc gaacgaccta caccgaactg  4380
agatacctac agcgtgagct atgagaaagc gccacgcttc ccgaagggag aaaggcggac  4440
aggtatccgg taagcggcag ggtcggaaca ggagagcgca cgagggagct ccaggggga  4500
aacgcctggt atctttatag tcctgtcggg tttcgccacc tctgacttga gcgtcgattt  4560
ttgtgatgct cgtcaggggg gcggagccta tggaaaaacg ccagcaacgc ggcctttta  4620
cggttcctgg ccttttgctg gccttttgct cacatgttct ttcctgcgtt atcccctgat  4680
tctgtggata accgtattac cgcctttgag tgagctgata ccgctcgccg cagccgaacg  4740
accgagcgca gcgagtcagt gagcgaggaa gcggaagagc gcccaatacg caaaccgcct  4800
ctccccgcgc gttggccgat tcattaatgc agctggcacg acaggtttcc cgactggaaa  4860
gcgggcagtg agcgcaacgc aattaatgtg agttagctca ctcattaggc accccaggct  4920
ttacacttta tgcttccggc tcgtatgttg tgtggaattg tgagcggata acaatttcac  4980
acaggaaaca gctatgacca tgattacgcc aagcgcgcaa ttaaccctca ctaaagggaa  5040
caaaagctgg agctccaccc tagaactagt ggatccttca tccatgccct tcatttgccg  5100
cttattaatt aatttggtaa cagtccgtac taatcagtta cttatccttc ccccatcata  5160
attaatcttg gtagtctcga atgccacaac actgactagt ctcttggatc ataagaaaaa  5220
gccaaggaac aaaagaagac aaaacacaat gagagtatcc tttgcatagc aatgtctaag  5280
ttcataaaat tcaaacaaaa acgcaatcac acacagtgga catcacttat ccactagctg  5340
atcaggatcg ccgcgtcaag aaaaaaaaac tggaccccaa aagccatgca caacaacacg  5400
tactcacaaa ggtgtcaatc gagcagccca aacattcac caactcaacc catcatgagc  5460
cctcacattt gttgtttcta acccaacctc aaactcgtat tctcttccgc cacctcattt  5520
ttgtttattt caacacccgt caaactgcat gccaccccgt ggccaaatgt ccatgcatgt  5580
taacaagacc tatgactata aatagctgca atctcggccc aggttttcat catcaagaac  5640
```
cagttcaata tcctagtaca ccgtattaaa gaatttaaga tatactc            5687

<210> SEQ ID NO 77
<211> LENGTH: 318
<212> TYPE: PRT
<213> ORGANISM: Artificial Sequence
<220> FEATURE:
<223> OTHER INFORMATION: M. alpina delta-6 elongase with possible
      modifications noted
<220> FEATURE:
<221> NAME/KEY: MISC_FEATURE
<222> LOCATION: (5)..(5)
<223> OTHER INFORMATION: Xaa is Ala or Val
<220> FEATURE:
<221> NAME/KEY: MISC_FEATURE
<222> LOCATION: (9)..(9)
<223> OTHER INFORMATION: Xaa is Pro or Leu
<220> FEATURE:
<221> NAME/KEY: MISC_FEATURE
<222> LOCATION: (62)..(62)
<223> OTHER INFORMATION: Xaa is Glu or Asp
<220> FEATURE:
<221> NAME/KEY: MISC_FEATURE
<222> LOCATION: (79)..(79)
<223> OTHER INFORMATION: Xaa is Leu or Met
<220> FEATURE:
<221> NAME/KEY: MISC_FEATURE
<222> LOCATION: (80)..(80)
<223> OTHER INFORMATION: Xaa is Ile or Leu
<220> FEATURE:
<221> NAME/KEY: MISC_FEATURE
<222> LOCATION: (106)..(106)
<223> OTHER INFORMATION: Xaa is Phe or Tyr
<220> FEATURE:
<221> NAME/KEY: MISC_FEATURE
<222> LOCATION: (110)..(110)
<223> OTHER INFORMATION: Xaa is His or Tyr
<220> FEATURE:
<221> NAME/KEY: MISC_FEATURE
<222> LOCATION: (117)..(117)
<223> OTHER INFORMATION: Xaa is Ile or Leu
<220> FEATURE:
<221> NAME/KEY: MISC_FEATURE
<222> LOCATION: (130)..(130)
<223> OTHER INFORMATION: Xaa is Tyr or Phe
<220> FEATURE:
<221> NAME/KEY: MISC_FEATURE
<222> LOCATION: (138)..(138)
<223> OTHER INFORMATION: Xaa is Glu or Gln
<220> FEATURE:
<221> NAME/KEY: MISC_FEATURE
<222> LOCATION: (162)..(162)
<223> OTHER INFORMATION: Xaa is Ile or Leu
<220> FEATURE:
<221> NAME/KEY: MISC_FEATURE
<222> LOCATION: (169)..(169)
<223> OTHER INFORMATION: Xaa is Met or Leu
<220> FEATURE:
<221> NAME/KEY: MISC_FEATURE
<222> LOCATION: (171)..(171)
<223> OTHER INFORMATION: Xaa is Met or Leu
<220> FEATURE:
<221> NAME/KEY: MISC_FEATURE
<222> LOCATION: (174)..(174)
<223> OTHER INFORMATION: Xaa is Lys or Arg
<220> FEATURE:
<221> NAME/KEY: MISC_FEATURE
<222> LOCATION: (191)..(191)
<223> OTHER INFORMATION: Xaa is Ile or Leu
<220> FEATURE:
<221> NAME/KEY: MISC_FEATURE
<222> LOCATION: (208)..(208)
<223> OTHER INFORMATION: Xaa is Tyr or Trp
<220> FEATURE:
<221> NAME/KEY: MISC_FEATURE
<222> LOCATION: (213)..(213)
<223> OTHER INFORMATION: Xaa is Leu or Met
<220> FEATURE:

```
<221> NAME/KEY: MISC_FEATURE
<222> LOCATION: (237)..(237)
<223> OTHER INFORMATION: Xaa is Phe or Leu
<220> FEATURE:
<221> NAME/KEY: MISC_FEATURE
<222> LOCATION: (242)..(242)
<223> OTHER INFORMATION: Xaa is Ile or Leu
<220> FEATURE:
<221> NAME/KEY: MISC_FEATURE
<222> LOCATION: (253)..(253)
<223> OTHER INFORMATION: Xaa is Met or Leu
<220> FEATURE:
<221> NAME/KEY: MISC_FEATURE
<222> LOCATION: (276)..(276)
<223> OTHER INFORMATION: Xaa is Ile or Leu
<220> FEATURE:
<221> NAME/KEY: MISC_FEATURE
<222> LOCATION: (277)..(277)
<223> OTHER INFORMATION: Xaa is Thr or Ala
<220> FEATURE:
<221> NAME/KEY: MISC_FEATURE
<222> LOCATION: (287)..(287)
<223> OTHER INFORMATION: Xaa is Met or Leu
<220> FEATURE:
<221> NAME/KEY: MISC_FEATURE
<222> LOCATION: (297)..(297)
<223> OTHER INFORMATION: Xaa is Lys or Arg

<400> SEQUENCE: 77
```

```
Met Glu Ser Ile Xaa Pro Phe Leu Xaa Ser Lys Met Pro Gln Asp Leu
1               5                   10                  15

Phe Met Asp Leu Ala Ser Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Xaa Ser Pro
50                  55                  60

Leu Ala Arg Glu Leu Pro Leu Met Asn Pro Phe His Val Leu Xaa Xaa
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Xaa Ser Leu Leu Xaa Asn Phe
            100                 105                 110

Cys Leu Val Ser Xaa Ser Ala Tyr Met Cys Gly Gly Ile Leu Tyr Glu
        115                 120                 125

Ala Xaa Gln Ala Asn Tyr Gly Leu Phe Xaa Asn Ala Ala Asp His Thr
    130                 135                 140

Phe Lys Gly Leu Pro Met Ala Lys Met Ile Trp Leu Phe Tyr Phe Ser
145                 150                 155                 160

Lys Xaa Met Glu Phe Val Asp Thr Xaa Ile Xaa Val Leu Xaa Lys Asn
                165                 170                 175

Asn Arg Gln Ile Ser Phe Leu His Val Tyr His His Ser Ser Xaa Phe
            180                 185                 190

Thr Ile Trp Trp Leu Val Thr Phe Val Ala Pro Asn Gly Glu Ala Xaa
        195                 200                 205

Phe Ser Ala Ala Xaa Asn Ser Phe Ile His Val Ile Met Tyr Gly Tyr
    210                 215                 220

Tyr Phe Leu Ser Ala Leu Gly Phe Lys Gln Val Ser Xaa Ile Lys Phe
225                 230                 235                 240

Tyr Xaa Thr Arg Ser Gln Met Thr Gln Phe Cys Met Xaa Ser Val Gln
                245                 250                 255

Ser Ser Trp Asp Met Tyr Ala Met Lys Val Leu Gly Arg Pro Gly Tyr
            260                 265                 270
```

```
Pro Phe Phe Xaa Xaa Ala Leu Leu Trp Phe Tyr Met Trp Thr Xaa Leu
        275                 280                 285

Gly Leu Phe Tyr Asn Phe Tyr Arg Xaa Asn Ala Lys Leu Ala Lys Gln
        290                 295                 300

Ala Lys Ala Asp Ala Ala Lys Glu Lys Ala Arg Lys Leu Gln
305                 310                 315

<210> SEQ ID NO 78
<211> LENGTH: 5364
<212> TYPE: DNA
<213> ORGANISM: Artificial Sequence
<220> FEATURE:
<223> OTHER INFORMATION: plasmid pKR952

<400> SEQUENCE: 78
ggctagccta agtacgtact caaaatgcca acaaataaaa aaaagttgc tttaataatg      60 ccaaaacaaa ttaataaaac acttacaaca ccggattttt tttaattaaa atgtgccatt    120
taggataaat agttaatatt tttaataatt atttaaaaag ccgtatctac taaaatgatt    180
tttatttggt tgaaaatatt aatatgttta aatcaacaca atctatcaaa attaaactaa    240
aaaaaaaata agtgtacgtg gttaacatta gtacagtaat ataagaggaa aatgagaaat    300
taagaaattg aaagcgagtc taattttaa attatgaacc tgcatatata aaaggaaaga     360
aagaatccag gaagaaaaga atgaaaccca tgcatggtcc cctcgtcatc acgagtttct    420
gccatttgca atagaaacac tgaaacacct ttctctttgt cacttaattg agatgccgaa    480
gccacctcac accatgaact tcatgaggtg tagcacccaa ggcttccata gccatgcata    540
ctgaagaatg tctcaagctc agcaccctac ttctgtgacg tgtccctcat tcaccttcct    600
ctcttcccta taaataacca cgcctcaggt tctccgcttc acaactcaaa cattctctcc    660
attggtcctt aaacactcat cagtcatcac cgcggccgca tgggaacgga ccaaggaaaa    720
accttcacct gggaagagct ggcggcccat aacaccaagg acgacctact cttggccatc    780
cgcggcaggg tgtacgatgt cacaaagttc ttgagccgcc atcctggtgg agtggacact    840
ctcctgctcg gagctggccg agatgttact ccggtctttg agatgtatca cgcgtttggg    900
gctgcagatg ccattatgaa gaagtactat gtcggtacac tggtctcgaa tgagctgccc    960
atcttcccgg agccaacggt gttccacaaa accatcaaga cgagagtcga gggctacttt   1020
acggatcgga acattgatcc caagaataga ccagagatct ggggacgata cgctcttatc   1080
tttggatcct tgatcgcttc ctactacgcg cagctctttg tgcctttcgt tgtcgaacgc   1140
acatggcttc aggtggtgtt tgcaatcatc atgggatttg cgtgcgcaca agtcggactc   1200
aaccctcttc atgatgcgtc tcactttca gtgacccaca accccactgt ctggaagatt    1260
ctgggagcca cgcacgactt tttcaacgga gcatcgtacc tggtgtggat gtaccaacat   1320
atgctcggcc atcaccccta ccaacattgc tggagcag atcccgacgt gtcgacgtct    1380
gagcccgatg ttcgtcgtat caagcccaac caaaagtggt tgtcaaccaa catcaaccag   1440
cacatgtttg ttcctttcct gtacggactg ctggcgttca aggtgcgcat tcaggacatc   1500
aacattttgt actttgtcaa gaccaatgac gctattcgtg tcaatcccat ctcgacatgg   1560
cacactgtga tgttctgggg cggcaaggct ttctttgtct ggtatcgcct gattgttccc   1620
ctgcagtatc tgcccctggg caaggtgctg ctcttgttca cggtcgcgga catggtgtcg   1680
tcttactggc tggcgctgac cttccaggcg aaccacgttg ttgaggaagt tcagtggccg   1740
ttgcctgacg agaacgggat catccaaaag gactgggcag ctatgcaggt cgagactacg   1800
```

```
caggattacg cacacgattc gcacctctgg accagcatca ctggcagctt gaactaccag    1860
gctgtgcacc atctgttccc caacgtgtcg cagcaccatt atcccgatat tctggccatc    1920
atcaagaaca cctgcagcga gtacaaggtt ccataccttg tcaaggatac gttttggcaa    1980
gcatttgctt cacatttgga gcacttgcgt gttcttggac tccgtcccaa ggaagagtag    2040
gcggccgcat ttcgcaccaa atcaatgaaa gtaataatga aaagtctgaa taagaatact    2100
taggcttaga tgcctttgtt acttgtgtaa ataacttga gtcatgtacc tttggcggaa    2160
acagaataaa taaaaggtga aattccaatg ctctatgtat aagttagtaa tacttaatgt    2220
gttctacggt tgtttcaata tcatcaaact ctaattgaaa ctttagaacc acaaatctca    2280
atcttttctt aatgaaatga aaatcttaa ttgtaccatg tttatgttaa acaccttaca    2340
attggttgga gaggaggacc aaccgatggg acaacattgg gagaaagaga ttcaatggag    2400
atttggatag gagaacaaca ttcttttca cttcaataca agatgagtgc aacactaagg    2460
atatgtatga gactttcaga agctacgaca acatagatga gtgaggtggt gattcctagc    2520
aagaaagaca ttagaggaag ccaaaatcga acaaggaaga catcaagggc aagagacagg    2580
accatccatc tcaggaaaag gagctttggg atagtccgag aagttgtaca agaaattttt    2640
tggagggtga gtgatgcatt gctggtgact ttaactcaat caaaattgag aaagaaagaa    2700
aagggagggg gctcacatgt gaatagaagg gaaacgggag aattttacag ttttgatcta    2760
atgggcatcc cagctagtgg taacatattc accatgttta accttcacgt acggatccgt    2820
cgacggcgcg cccgatcatc cggatatagt tcctcctttc agcaaaaaac ccctcaagac    2880
ccgtttagag gccccaaggg gttatgctag ttattgctca gcggtggcag cagccaactc    2940
agcttccttt cgggctttgt tagcagccgg atcgatccaa gctgtacctc actattcctt    3000
tgccctcgga cgagtgctgg ggcgtcggtt tccactatcg gcgagtactt ctacacagcc    3060
atcggtccag acggccgcgc ttctgcgggc gatttgtgta cgcccgacag tcccggctcc    3120
ggatcggacg attgcgtcgc atcgaccctg cgcccaagct gcatcatcga aattgccgtc    3180
aaccaagctc tgatagagtt ggtcaagacc aatgcggagc atatacgccc ggagccgcgg    3240
cgatcctgca agctccggat gcctccgctc gaagtagcgc gtctgctgct ccatacaagc    3300
caaccacggc ctccagaaga agatgttggc gacctcgtat tgggaatccc cgaacatcgc    3360
ctcgctccag tcaatgaccg ctgttatgcg gccattgtcc gtcaggacat gttggagcc     3420 gaaatccgcg tgcacgaggt gccggacttc ggggcagtcc tcggcccaaa gcatcagctc    3480
atcgagagcc tgcgcgacgg acgcactgac ggtgtcgtcc atcacagttt gccagtgata    3540
cacatgggga tcagcaatcg cgcatatgaa atcacgccat gtagtgtatt gaccgattcc    3600
ttgcggtccg aatgggccga acccgctcgt ctggctaaga tcggccgcag cgatcgcatc    3660
catagcctcc gcgaccggct gcagaacagc gggcagttcg gtttcaggca ggtcttgcaa    3720
cgtgacaccc tgtgcacggc gggagatgca ataggtcagg ctctcgctga attccccaat    3780
gtcaagcact tccggaatcg ggagcgcggc cgatgcaaag tgccgataaa cataacgatc    3840
tttgtagaaa ccatcggcgc agctatttac ccgcaggaca tatccacgcc ctcctacatc    3900
gaagctgaaa gcacgagatt cttcgccctc cgagagctgc atcaggtcgg agacgctgtc    3960
gaacttttcg atcagaaact ctctgacaga cgtcgcggtg agttcaggct tttccatggg    4020
tatatctcct tcttaaagtt aaacaaaatt atttctagag ggaaaccgtt gtggtctccc    4080
tatagtgagt cgtattaatt tcgcgggatc gagatctgat caacctgcat taatgaatcg    4140
gccaacgcgc ggggagaggc ggtttgcgta ttgggcgctc ttccgcttcc tcgctcactg    4200
```

| | |
|---|---:|
| actcgctgcg ctcggtcgtt cggctgcggc gagcggtatc agctcactca aaggcggtaa | 4260 |
| tacggttatc cacagaatca ggggataacg caggaaagaa catgtgagca aaaggccagc | 4320 |
| aaaaggccag gaaccgtaaa aaggccgcgt tgctggcgtt tttccatagg ctccgccccc | 4380 |
| ctgacgagca tcacaaaaat cgacgctcaa gtcagaggtg gcgaaacccg acaggactat | 4440 |
| aaagatacca ggcgtttccc cctggaagct ccctcgtgcg ctctcctgtt ccgaccctgc | 4500 |
| cgcttaccgg atacctgtcc gcctttctcc cttcgggaag cgtggcgctt tctcaatgct | 4560 |
| cacgctgtag gtatctcagt tcggtgtagg tcgttcgctc caagctgggc tgtgtgcacg | 4620 |
| aaccccccgt tcagcccgac cgctgcgcct tatccggtaa ctatcgtctt gagtccaacc | 4680 |
| cggtaagaca cgacttatcg ccactggcag cagccactgg taacaggatt agcagagcga | 4740 |
| ggtatgtagg cggtgctaca gagttcttga agtggtggcc taactacggc tacactagaa | 4800 |
| ggacagtatt tggtatctgc gctctgctga agccagttac cttcggaaaa agagttggta | 4860 |
| gctcttgatc cggcaaacaa accaccgctg gtagcggtgg tttttttgtt tgcaagcagc | 4920 |
| agattacgcg cagaaaaaaa ggatctcaag aagatccttt gatcttttct acggggtctg | 4980 |
| acgctcagtg gaacgaaaac tcacgttaag ggattttggt catgacatta acctataaaa | 5040 |
| ataggcgtat cacgaggccc tttcgtctcg cgcgtttcgg tgatgacggt gaaaacctct | 5100 |
| gacacatgca gctcccggag acggtcacag cttgtctgta gcggatgcc gggagcagac | 5160 |
| aagcccgtca gggcgcgtca gcgggtgttg gcgggtgtcg gggctggctt aactatgcgg | 5220 |
| catcagagca gattgtactg agagtgcacc atatggacat attgtcgtta gaacgcggct | 5280 |
| acaattaata cataaccta tgtatcatac acatacgatt taggtgacac tatagaacgg | 5340 |
| cgcgccaagc ttggatctcc tgca | 5364 |

<210> SEQ ID NO 79
<211> LENGTH: 5303
<212> TYPE: DNA
<213> ORGANISM: Artificial Sequence
<220> FEATURE:
<223> OTHER INFORMATION: plasmid pKR325

<400> SEQUENCE: 79

| | |
|---|---:|
| agcttggatc tcctgcagga tctggccggc cggatctcgt acggatccgt cgacggcgcg | 60 |
| cccgatcatc cggatatagt tcctcctttc agcaaaaaac ccctcaagac ccgtttagag | 120 |
| gccccaaggg gttatgctag ttattgctca gcggtggcag cagccaactc agcttccttt | 180 |
| cgggctttgt tagcagccgg atcgatccaa gctgtacctc actattcctt tgccctcgga | 240 |
| cgagtgctgg ggcgtcggtt tccactatcg gcgagtactt ctacacagcc atcggtccag | 300 |
| acggccgcgc ttctgcgggc gatttgtgta cgcccgacag tcccggctcc ggatcggacg | 360 |
| attgcgtcgc atcgaccctg cgcccaagct gcatcatcga aattgccgtc aaccaagctc | 420 |
| tgatagagtt ggtcaagacc aatgcggagc atatacgccc ggagccgcgg cgatcctgca | 480 |
| agctccggat gcctccgctc gaagtagcgc gtctgctgct ccatacaagc caaccacggc | 540 |
| ctccagaaga agatgttggc gacctcgtat tgggaatccc cgaacatcgc ctcgctccag | 600 |
| tcaatgaccg ctgttatgcg gccattgtcc gtcaggacat tgttggagcc gaaatccgcg | 660 |
| tgcacgaggt gccggacttc ggggcagtcc tcggcccaaa gcatcagctc atcgagagcc | 720 |
| tgcgcgacgg acgcactgac ggtgtcgtcc atcacagttt gccagtgata cacatgggga | 780 |
| tcagcaatcg cgcatatgaa atcacgccat gtagtgtatt gaccgattcc ttgcggtccg | 840 |
| aatgggccga acccgctcgt ctggctaaga tcggccgcag cgatcgcatc catagcctcc | 900 |

-continued

```
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca cacccctcat atcaactact   1440
acgttgtgta taacggtcca catgccgta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
aagatgcagt caaaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaaggat aatttcggga acctcctcg gattccattg cccagctatc   2400
tgtcacttca tcgaaaggac agtagaaaag gaaggtggct cctacaaatg ccatcattgc   2460
gataaaggaa aggctatcat tcaagatgcc tctgccgaca gtggtcccaa agatggaccc   2520
ccacccacga ggagcatcgt ggaaaaagaa gacgttccaa ccacgtcttc aaagcaagtg   2580
gattgatgtg acatctccac tgacgtaagg gatgacgcac aatcccacta tccttcgcaa   2640
gacccttcct ctatataagg aagttcattt catttggaga ggacacgctc gagctcattt   2700
ctctattact tcagccataa caaaagaact ctttttctctt cttattaaac catgaaaaag   2760
cctgaactca ccgcgacgtc tgtcgagaag tttctgatcg aaaagttcga cagcgtctcc   2820
gacctgatgc agctctcgga gggcgaagaa tctcgtgctt tcagcttcga tgtaggaggg   2880
cgtggatatg tcctgcgggt aaatagctgc gccgatggtt tctacaaaga tcgttatgtt   2940
tatcggcact ttgcatcggc cgcgctcccg attccggaag tgcttgacat tggggaattc   3000
agcgagagcc tgacctattg catctcccgc cgtgcacagg gtgtcacgtt gcaagacctg   3060
cctgaaaccg aactgcccgc tgttctgcag ccggtcgcgg aggccatgga tgcgatcgct   3120
gcggccgatc ttagccagac gagcgggttc ggcccattcg gaccgcaagg aatcggtcaa   3180
tacactacat ggcgtgattt catatgcgcg attgctgatc cccatgtgta tcactggcaa   3240
actgtgatgg acgacaccgt cagtgcgtcc gtcgcgcagg ctctcgatga gctgatgctt   3300
```

```
tgggccgagg actgccccga agtccggcac ctcgtgcacg cggatttcgg ctccaacaat    3360
gtcctgacgg acaatggccg cataacagcg gtcattgact ggagcgaggc gatgttcggg    3420
gattcccaat acgaggtcgc caacatcttc ttctggaggc cgtggttggc ttgtatggag    3480
cagcagacgc gctacttcga gcggaggcat ccggagcttg caggatcgcc gcggctccgg    3540
gcgtatatgc tccgcattgg tcttgaccaa ctctatcaga gcttggttga cggcaatttc    3600
gatgatgcag cttgggcgca gggtcgatgc gacgcaatcg tccgatccgg agccgggact    3660
gtcgggcgta cacaaatcgc ccgcagaagc gcggccgtct ggaccgatgg ctgtgtagaa    3720
gtactcgccg atagtggaaa ccgacgcccc agcactcgtc cgagggcaaa ggaatagtga    3780
ggtacctaaa gaaggagtgc gtcgaagcag atcgttcaaa catttggcaa taaagtttct    3840
taagattgaa tcctgttgcc ggtcttgcga tgattatcat ataatttctg ttgaattacg    3900
ttaagcatgt aataattaac atgtaatgca tgacgttatt tatgagatgg gttttatga    3960 ttagagtccc gcaattatac atttaatacg cgatagaaaa caaatatag cgcgcaaact    4020 aggataaatt atcgcgcgcg gtgtcatcta tgttactaga tcgatgtcga atcgatcaac    4080
ctgcattaat gaatcggcca acgcgcgggg agaggcggtt tgcgtattgg gcgctcttcc    4140
gcttcctcgc tcactgactc gctgcgctcg gtcgttcggc tgcggcgagc ggtatcagct    4200
cactcaaagg cggtaatacg gttatccaca gaatcagggg ataacgcagg aaagaacatg    4260
tgagcaaaag gccagcaaaa ggccaggaac cgtaaaaagg ccgcgttgct ggcgtttttc    4320
cataggctcc gccccctga cgagcatcac aaaaatcgac gctcaagtca gaggtggcga    4380
aacccgacag gactataaag ataccaggcg tttccccctg gaagctccct cgtgcgctct    4440
cctgttccga ccctgccgct taccggatac ctgtccgcct ttctccttc gggaagcgtg    4500 gcgctttctc aatgctcacg ctgtaggtat ctcagttcgg tgtaggtcgt tcgctccaag    4560
ctgggctgtg tgcacgaacc ccccgttcag cccgaccgct gcgccttatc cggtaactat    4620
cgtcttgagt ccaacccggt aagacacgac ttatcgccac tggcagcagc cactggtaac    4680
aggattagca gagcgaggta tgtaggcggt gctacagagt tcttgaagtg gtggcctaac    4740
tacggctaca ctagaaggac agtatttggt atctgcgctc tgctgaagcc agttaccttc    4800
ggaaaaagag ttggtagctc ttgatccggc aaacaaacca ccgctggtag cggtggtttt    4860
tttgtttgca agcagcagat tacgcgcaga aaaaaaggat ctcaagaaga tcctttgatc    4920
ttttctacgg ggtctgacgc tcagtggaac gaaaactcac gttaagggat tttggtcatg    4980
acattaacct ataaaatag gcgtatcacg aggccctttc gtctcgcgcg tttcggtgat    5040
gacggtgaaa acctctgaca catgcagctc ccggagacgg tcacagcttg tctgtaagcg    5100
gatgccggga gcagacaagc ccgtcagggc gcgtcagcgg gtgttggcgg gtgtcggggc    5160
tggcttaact atgcggcatc agagcagatt gtactgagag tgcaccatat ggacatattg    5220
tcgttagaac gcggctacaa ttaatacata accttatgta tcatacacat acgatttagg    5280
tgacactata gaacggcgcg cca                                            5303
```

<210> SEQ ID NO 80
<211> LENGTH: 258
<212> TYPE: PRT
<213> ORGANISM: Euglena anabaena

<400> SEQUENCE: 80

```
Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
```

```
                    20                  25                  30
Leu Tyr Leu Ser Val Ala Phe Val Ala Ile Lys Phe Met Leu Arg Pro
            35                  40                  45

Leu Asp Leu Lys Arg Gln Ala Thr Leu Lys Lys Leu Phe Thr Ala Tyr
        50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu

<210> SEQ ID NO 81
<211> LENGTH: 263
<212> TYPE: PRT
<213> ORGANISM: Isochrysis galbana

<400> SEQUENCE: 81

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
                20                  25                  30

Leu Leu Arg Asn Ser Gly Leu Val Asp Glu Lys Lys Gly Ala Tyr Arg
            35                  40                  45

Thr Ser Met Ile Trp Tyr Asn Val Leu Leu Ala Leu Phe Ser Ala Leu
        50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140
```

```
Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 82
<211> LENGTH: 258
<212> TYPE: PRT
<213> ORGANISM: Euglena gracilis

<400> SEQUENCE: 82

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255
```

Ile Gln

<210> SEQ ID NO 83
<211> LENGTH: 259
<212> TYPE: PRT
<213> ORGANISM: Eutreptiella sp. CCMP389

<400> SEQUENCE: 83

```
Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
                35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
                100                 105                 110

Phe Tyr Tyr Ser Lys Phe Leu Glu Tyr Ile Asp Ser Phe Tyr Leu Pro
            115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp
```

DELTA-9 FATTY ACID ELONGASE GENES AND THEIR USE IN MAKING POLYUNSATURATED FATTY ACIDS

FIELD OF THE INVENTION

This invention is in the field of biotechnology, in particular, it pertains to polynucleotide sequences encoding delta-9 elongases and the use of these elongases in making long-chain polyunsaturated fatty acids (PUFAs).

BACKGROUND OF THE INVENTION

Certain PUFAs are important biological components of healthy cells and are recognized as: "essential" fatty acids that cannot be synthesized de novo in mammals and instead must be obtained either in the diet or derived by further elongation and desaturation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg et al., *Amer. J. Clin. Nutr.* 28:958-966 (1975); Dyerberg et al., *Lancet* 2(8081):117-119 (1978); Shimokawa, H., *World Rev. Nutr. Diet* 88:100-108 (2001); von Schacky et al., *World Rev. Nutr. Diet* 88:90-99 (2001)). Numerous other studies document wide-ranging health benefits conferred by administration of omega-3 and/or omega-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high-level production of various long-chain ω-3/ω-6 PUFAs. Accordingly, production of arachidonic acid (ARA; 20:4 ω-6), eicosapentaenoic acid (EPA; 20:5 ω-3) and docosahexaenoic acid (DHA; 22:6 ω-3) all may require expression of either the Δ9 elongase/Δ8 desaturase pathway (which operates in some organisms, such as euglenoid species, and which is characterized by the production of eicosadienoic acid (EDA; 20:2 ω-6) and/or eicosatrienoic acid (ETrA; 20:3 ω-3)) or the Δ6 desaturase/Δ6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3)) (FIG. 1).

The Δ8 desaturase enzymes identified thus far have the ability to convert both EDA to dihomo-γ-linolenic acid (DGLA; 20:3 ω-6) and ETrA to eicosatetraenoic acid (ETA; 20:4 ω-3) (wherein ARA are EPA are subsequently synthesized from DGLA and ETA, respectively, following reaction with a Δ5 desaturase, while DHA synthesis requires subsequent expression of an additional $C_{20/22}$ elongase and a Δ4 desaturase; FIG. 1).

Based on the role Δ8 desaturase enzymes play in the synthesis of, e.g., ARA, EPA and DHA, there has been effort to identify and characterize these enzymes. Initial efforts on the isolation and characterization of Δ8 desaturases from *Euglena gracilis* and several sequence variations within the *Euglena gracilis* Δ8 desaturase have been reported (see, e.g., Wallis et al., *Arch. Biochem. and Biophys.* 365(2):307-316 (1999); PCT Publication No. WO 2000/34439; U.S. Pat. No. 6,825,017; PCT Publication No. WO 2004/057001). Also, Applicants' Assignee's co-pending U.S. Patent Application No. 2006/0195939 and U.S. Pat. No. 7,256,033 disclose amino acid and nucleic acid sequences for a *Euglena gracilis* Δ8 desaturase. In other work, commonly owned, co-pending U.S. patent application Ser. Nos. 11/635,258 and 11/951,697 describe a synthetically engineered mutant Δ8 desaturase, derived from *Euglena gracilis*. PCT Publication No. WO 2005/103253 discloses amino acid and nucleic acid sequences for a Δ8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ Δ8 desaturase. Also, Applicants' Assignee's co-pending U.S. patent application Ser. No. 11/737,772 discloses amino acid and nucleic acid sequences for a Δ8 desaturase enzyme from *Pavlova lutheri* (CCMP459) whereas U.S. Patent Application No. 2008/0095915 discloses amino acid and nucleic acid sequences for a Δ8 desaturase enzyme from *Tetruetreptia pomquetensis* CCMP1491, *Eutreptiella* sp. CCMP389 and *Eutreptiella* cf_*gymnastica* CCMP1594. Applicants' Assignee's co-pending U.S. patent application Ser. No. 12/099,799 discloses amino acid and nucleic acid sequences for a Δ8 desaturase enzyme from *Euglena anabaena*.

Based on the utility of expressing Δ8 desaturases in conjunction with Δ9 elongases, there has also been effort to identify and characterize Δ9 elongases from various sources. Most Δ9 elongase enzymes identified so far have the ability to convert both LA to EDA and ALA to ETrA (wherein DGLA and ETA are subsequently synthesized from EDA and ETrA, respectively, following reaction with a Δ8 desaturase; ARA and EPA are subsequently synthesized from DGLA and ETA, respectively, following reaction with a Δ5 desaturase; and DHA synthesis requires subsequent expression of an additional $C_{20/22}$ elongase and a Δ4 desaturase; FIG. 1). A Δ9 elongase from *Isochrysis galbana* has been publicly available (described in GenBank Accession No. AAL37626, as well as PCT Publication No. WO 02/077213). Applicants' Assignee's co-pending U.S. Patent Application No. 2007/0118929 discloses a Δ9 elongase from *Eulgena gracilis*. Applicants' Assignee's co-pending U.S. Patent Application No. 2007/0117190 discloses a Δ9 elongase from *Eutreptiella* sp. CCMP389. Applicants' Assignee's co-pending U.S. patent application Ser. No. 12/102,979 (filed Apr. 15, 2008) discloses amino acid and nucleic acid sequences for a Δ9 elongase enzyme from *Euglena anabaena*.

Most delta-5 desaturase enzymes identified so far have the primary ability to convert DGLA to ARA, with secondary activity in converting ETA to EPA (where DHA is subsequently synthesized from EPA following reaction with an additional $C_{20/22}$ elongase and a delta-4 desaturase). The delta-5 desaturase has a role in both the delta-6 desaturase/delta-6 elongase pathway and the delta-9 elongase/delta-8 desaturase pathway (FIG. 1). Furthermore, based on the role delta-5 desaturase enzymes play in the synthesis of, e.g., ARA, EPA and DHA, there has also been an effort to identify and characterize these enzymes from various sources. As such, delta-5 desaturases have been disclosed in both the open literature (e.g., GenBank Accession Nos. AF199596, AF226273, AF320509, AB072976, AF489588, AJ510244, AF419297, AF07879, AF067654 and AB022097) and the patent literature (e.g., U.S. Pat. Nos. 5,972,664 and 6,075,183). Applicants' Assignee's co-pending U.S. Patent Application No. 2007/0271632 discloses a Δ5 desaturase from *Peridinium* sp. CCMP626 whereas Applicants' Assignee's co-pending U.S. Patent Application No. 2007/0292924 discloses a Δ5 desaturase from *Euglena gracilis*. Applicants' Assignee's co-pending U.S. patent application Ser. No. 12/111,228 (filed Apr. 23, 2008) discloses amino acid and nucleic acid sequences for a Δ5 desaturase enzyme from *Euglena anabaena*.

Applicants' Assignee has a number of patent applications concerning the production of PUFAs in oleaginous yeasts (e.g., *Yarrowia lipolytica*), including: PCT Publication Nos. WO 2004/101757 and WO 2004/101753; U.S. Patent Application Nos. 2006/0115881, 2006/0094092, and 2006/0110806; and U.S. patent application Ser. No. 12/061,738 (filed Apr. 3, 2008).

Relatedly, PCT Publication No. WO 2004/071467 (published Aug. 26, 2004) concerns the production of PUFAs in plants.

Despite the disclosures cited above, there is a need for additional genes encoding polypeptides having Δ9 elongase activity as it is mainly through genetic variation that a wide variety of host cells may be optimized for PUFA production.

SUMMARY OF THE INVENTION

Applicants address the stated need herein by reporting the isolation of novel genes encoding Δ9 fatty acid elongases.

The present invention concerns an isolated polynucleotide comprising: (a) a nucleotide sequence encoding a polypeptide comprising Δ9 elongase activity and Δ5 elongase activity, wherein said polypeptide has at least 70% sequence identity, based on the Clustal V method of alignment, when compared to the sequence set forth in SEQ ID NO:2; or (b) a full-length complement of the nucleotide sequence of (a).

In a second embodiment, the invention concerns a recombinant DNA construct comprising any of the isolated polynucleotides of the invention operably linked to a regulatory sequence.

In a third embodiment, the invention concerns a cell comprising in its genome the recombinant DNA construct of the invention.

In a fourth embodiment, the invention concerns a plant comprising in its genome the recombinant DNA construct of the invention.

In a fifth embodiment, the invention concerns a transgenic seed comprising in its genome the recombinant DNA construct of the invention or a transgenic seed obtained from a plant made by a method of the invention. Also of interest is oil or by-products obtained from such transgenic seeds.

In a sixth embodiment, the invention concerns food or feed incorporating an oil or seed of the invention or food or feed comprising an ingredient derived from the processing of the seeds.

In a seventh embodiment, the invention concerns a method for transforming a cell, comprising transforming a cell with the isolated polynucleotide of the invention.

In a eight embodiment, the invention concerns a method for producing a plant comprising transforming a plant cell with the isolated polynucleotide of the invention and regenerating a plant from the transformed plant cell.

In an ninth embodiment, the invention concerns an isolated polypeptide encoded by the isolated polynucleotide of the invention.

In a tenth embodiment, the invention concerns the isolated polynucleotide of the invention comprising:
(a) a nucleotide sequence encoding a polypeptide having Δ9 elongase activity when expressed in a plant of at least 27% conversion of oleic acid to eicosenoic acid and/or linoleic acid to eicosadienoic acid and/or α-linoleic acid to eicosatrienoic acid, or
(b) a full-length complement of the nucleotide sequence of (i).

In an eleventh embodiment, the invention concerns a method of screening for polypeptides having increased Δ9 elongase activity, increased Δ5 elongase activity, and/or decreased Δ6 elongase activity comprising: (a) providing a first polynucleotide which encodes a polypeptide having Δ9 elongase activity and/or Δ5 elongase activity and/or Δ6 elongase activity; (b) measuring baseline Δ9 elongase activity and/or Δ5 elongase activity and/or Δ6 elongase activity of the first polypeptide; (c) recombining the first polynucleotide of (a) with at least one variant form of said first polynucleotide to produce a second polynucleotide having at least one nucleotide difference from the first polynucleotide; (d) measuring Δ9 elongase activity and/or Δ5 elongase activity and/or Δ6 elongase activity of the polypeptide encoded by said second polynucleotide; and (e) comparing the activities of (b) with the activities of (d) whereby greater activity of (d) compared to (b) for Δ9 elongase activity and/or Δ5 elongase activity is indicative of increased activity for Δ9 elongase and/or Δ5 elongase and lower activity of (d) compared to (b) for Δ6 elongase activity is indicative of decreased activity of Δ6 elongase.

In a thirteenth embodiment, the invention concerns progeny plants obtained from a plant made by the method of the invention or an oilseed plant of the invention.

In a fourteenth embodiment, the invention concerns a method for producing at least one polyunsaturated fatty acid in an oilseed plant cell comprising: (a) transforming an oilseed plant cell with a first recombinant DNA construct comprising an isolated polynucleotide as disclosed herein, operably linked to at least one regulatory sequence and at least one additional recombinant DNA construct comprising an isolated polynucleotide, operably linked to at least one regulatory sequence, encoding a polypeptide selected from the group consisting of a Δ4 desaturase, a Δ5 desaturase, a Δ6 desaturase, a Δ8 desaturase, a Δ12 desaturase, a Δ15 desaturase, a Δ17 desaturase, a Δ9 desaturase, a Δ9 elongase, a $C_{14/16}$ elongase, a $C_{16/18}$ elongase, a $C_{18/20}$ elongase and a $C_{20/22}$ elongase; (b) regenerating an oilseed plant from the transformed cell of step (a); and (c) selecting those seeds obtained from the plants of step (b) having an altered level of polyunsaturated fatty acids when compared to the level in seeds obtained from a nontransformed oilseed plant.

Another embodiment is for an isolated polynucleotide comprising: (a) a nucleotide sequence encoding a polypeptide having Δ9 elongase activity and Δ5 elongase activity, wherein said polypeptide has at least 90% sequence identity, based on the Clustal V method of alignment, when compared to the sequence set forth in SEQ ID NO:77, provided that said polypeptide does not have the sequence set forth in SEQ ID NO:2; or (b) a full-length complement of the nucleotide sequence of (i).

A further embodiment relates to an isolated polynucleotide comprising:
(i) a nucleotide sequence encoding a polypeptide having Δ9 elongase activity and Δ5 elongase activity, said polypeptide having the amino acid sequence of SEQ ID NO:2 and provided that said polypeptide has a modification to SEQ ID NO:2 selected from the group consisting of:
(a) at amino acid residue number 5, substitution of alanine (A) with valine (V), (b) at amino acid residue number 9, substitution of proline (P) with leucine (L),
(c) at amino acid residue number 62 substitution of glutamic acid (E) with aspartic acid (D),
(d) at amino acid residue number 79, substitution of leucine (L) with methionine (M),
(e) at amino acid residue number 80, substitution isoleucine (I) with of leucine (L),
(f) at amino acid residue number 106, substitution of phenylalanine (F) with tyrosine (Y),
(g) at amino acid residue number 110, substitution of histidine (H) with tyrosine (Y),
(h) at amino acid residue number 117, substitution of isoleucine (I) with leucine (L),
(i) at amino acid residue number 130, substitution of tyrosine (Y) with phenylalanine (F),
(j) at amino acid residue number 138, substitution of glutamic acid (E) with glutamine (Q),
(k) at amino acid residue number 162, substitution of isoleucine (I) with leucine (L),
(l) at amino acid residue number 169, substitution of methionine (M) with leucine (L),
(m) at amino acid residue number 171, substitution of methionine (M) with leucine (L),
(n) at amino acid residue number 174, substitution of lysine (K) with arginine (R),
(o) at amino acid residue number 191, substitution of isoleucine (I) with leucine (L),
(p) at amino acid residue number 208, substitution tyrosine (Y) with tryptophan (W),
(q) at amino acid residue number 213, substitution of leucine (L) with methionine (M),
(r) at amino acid residue number 237, substitution of phenylalanine (F) with leucine (L),
(s) at amino acid residue number 242, substitution of isoleucine (I) with leucine (L),
(t) at amino acid residue number 253, substitution of methionine (M) with leucine (L),
(u) at amino acid residue number 276, substitution of isoleucine (I) with leucine (L),
(v) at amino acid residue number 277, substitution of threonine (T) with alanine (A),
(w) at amino acid residue number 287, substitution of methionine (M) with leucine (L),
(x) at amino acid residue number 297, substitution of lysine (K) with arginine (R); and
(y) a combination thereof;
(ii) a nucleotide sequence encoding a polypeptide having having Δ9 elongase activity and/or Δ5 elongase activity and/or Δ6 elongase activity, said polypeptide having at least 90% sequence identity to the polypeptide of (i), provided that the polypeptide of (ii) has at least one of the modifications of (i); or
(ii) a full-length complement of the nucleotide sequence of (i) or (ii).

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 1 is a representative omega-3 and omega-6 fatty acid pathway providing for the conversion of myristic acid through various intermediates to docosahexaenoic acid (DHA).

FIG. 2 is a comparative amino acid alignment between the *Mortierella alpina* delta-6 elongase (SEQ ID NO:4), the *Mortierella alpina* delta-6 elongase codon optimized for expression in *Yarrowia* (SEQ ID NO:2), and a selection of the gene products of the invention (SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30) using the Clustal V method (Higgins, D. G. and Sharp, P. M., *Comput. Appl. Biosci.* 5:151-153 (1989); Higgins et al., *Comput. Appl. Biosci.* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

FIG. 3 shows the % identity of the amino acid sequence of a selection of the novel delta-9 elongases of the invention (SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30) and the amino acid sequence of the *Mortierella alpina* delta-6 elongase (NCBI Accession No. AAF70417.1; SEQ ID NO:4) versus the *Mortierella alpina* delta-6 elongase codon optimized for expression in *Yarrowia* (SEQ ID NO:2). Sequence percent identity calculations performed by the BlastP and Clustal V method.

In FIG. 6, delta-9% conversion activity (delta-9% conversion) is calculated as ([ERA+EDA+20:1+DGLA+ETA+ARA+EPA+SCI+JUP+DPA]/[ERA+EDA+20:1+DGLA+ETA+ARA+EPA+SCI+JUP+DPA+OA+LA+ALA]*100).

Figure 8:
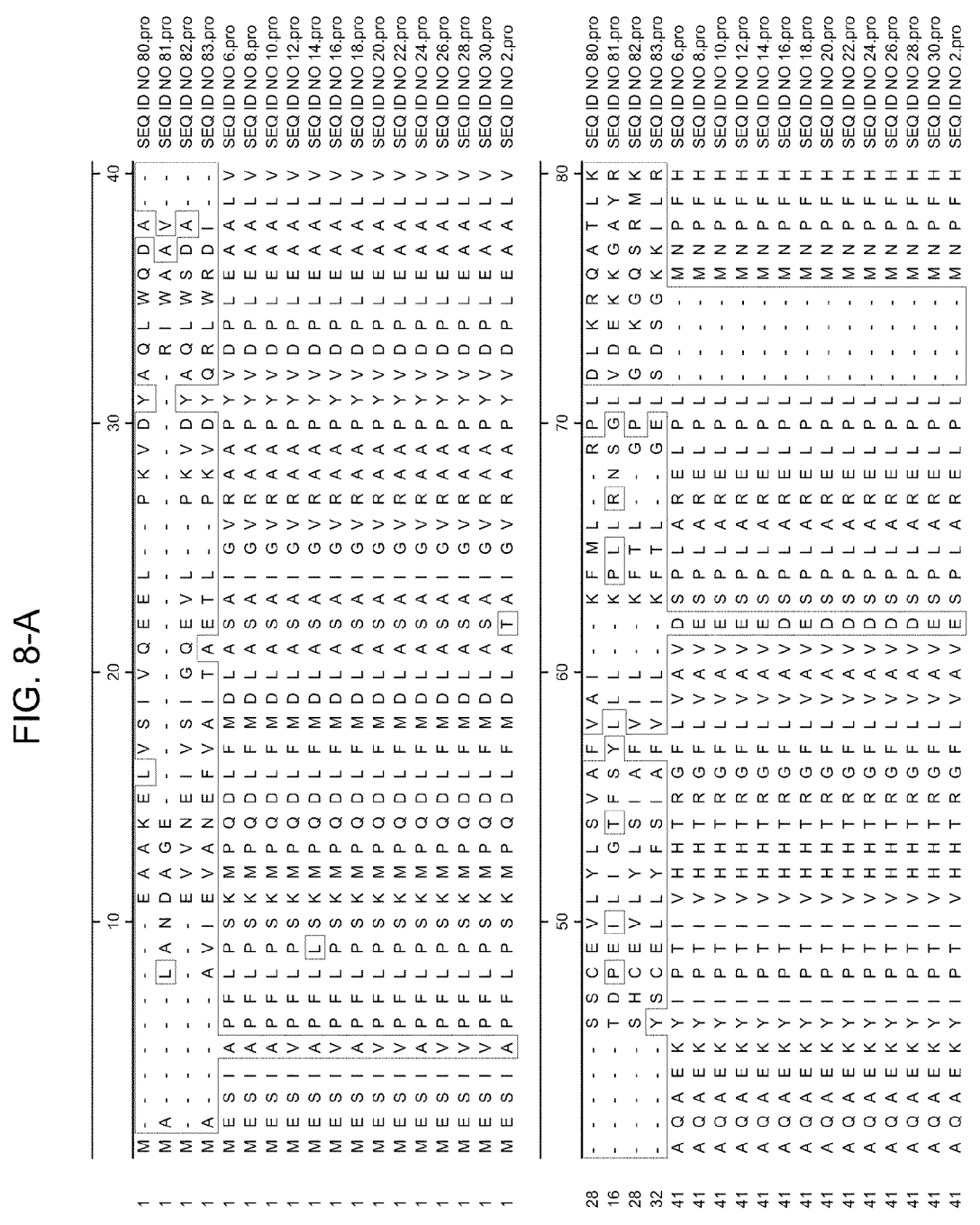
Figure 8:
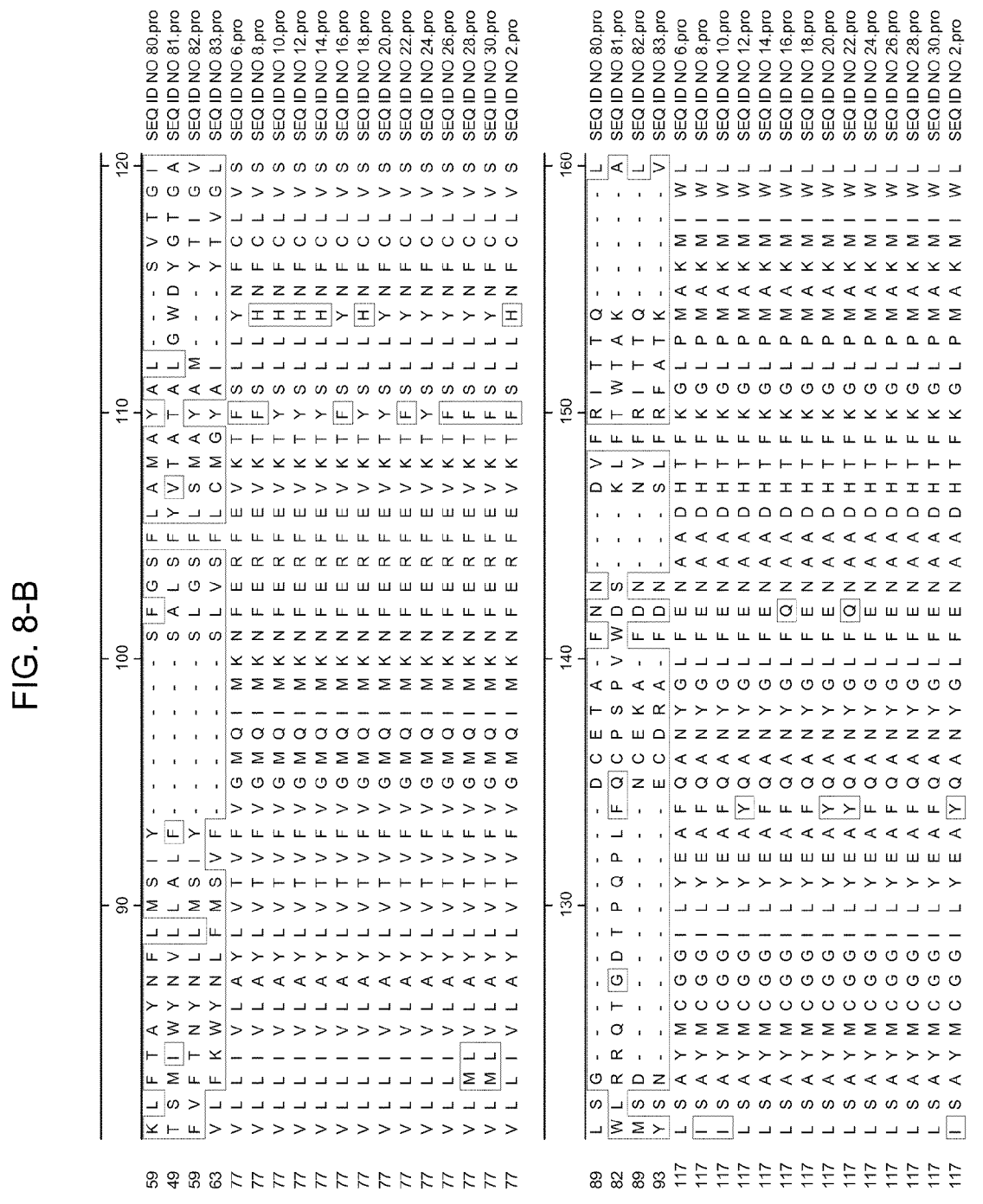
Figure 8:
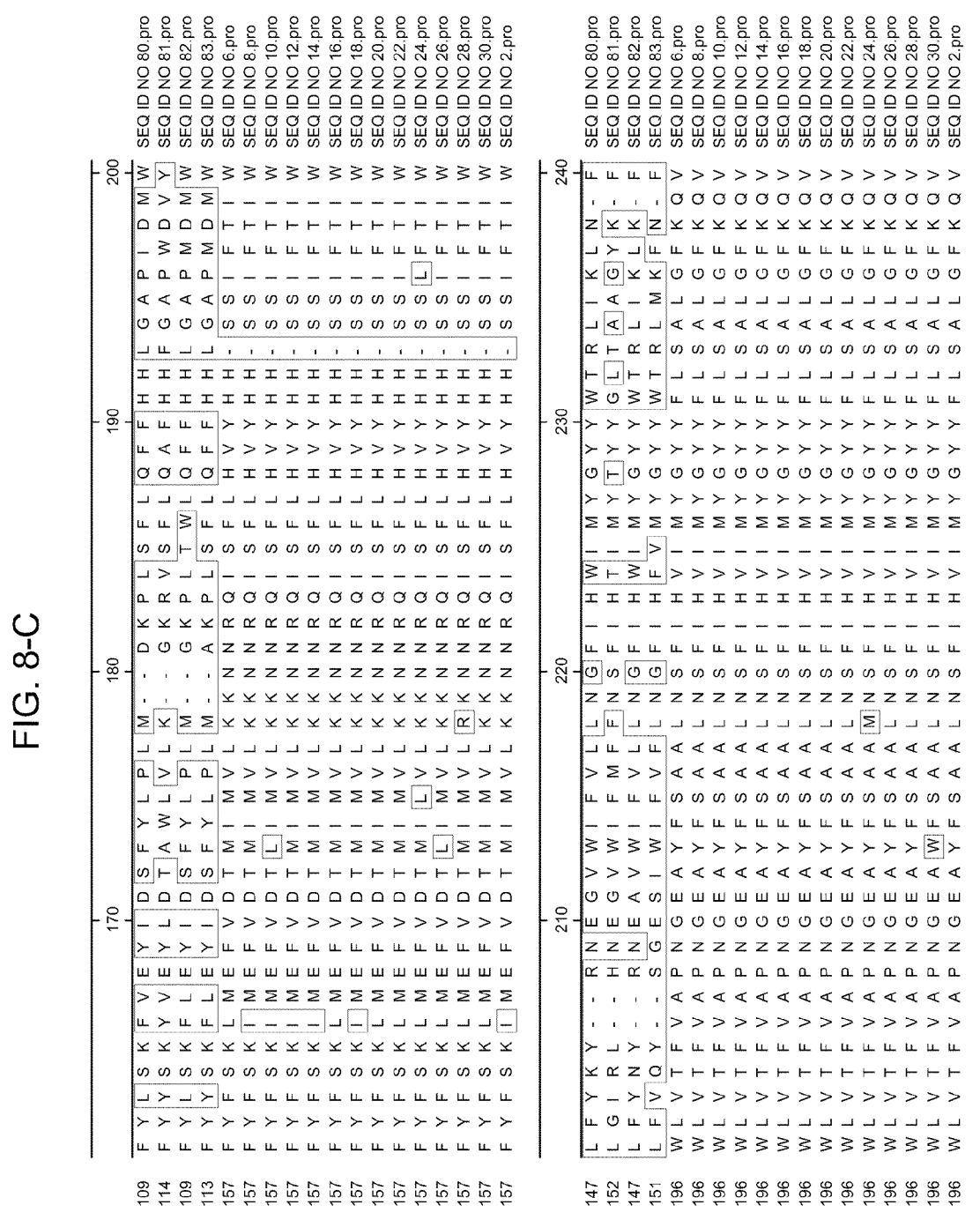
Figure 8:
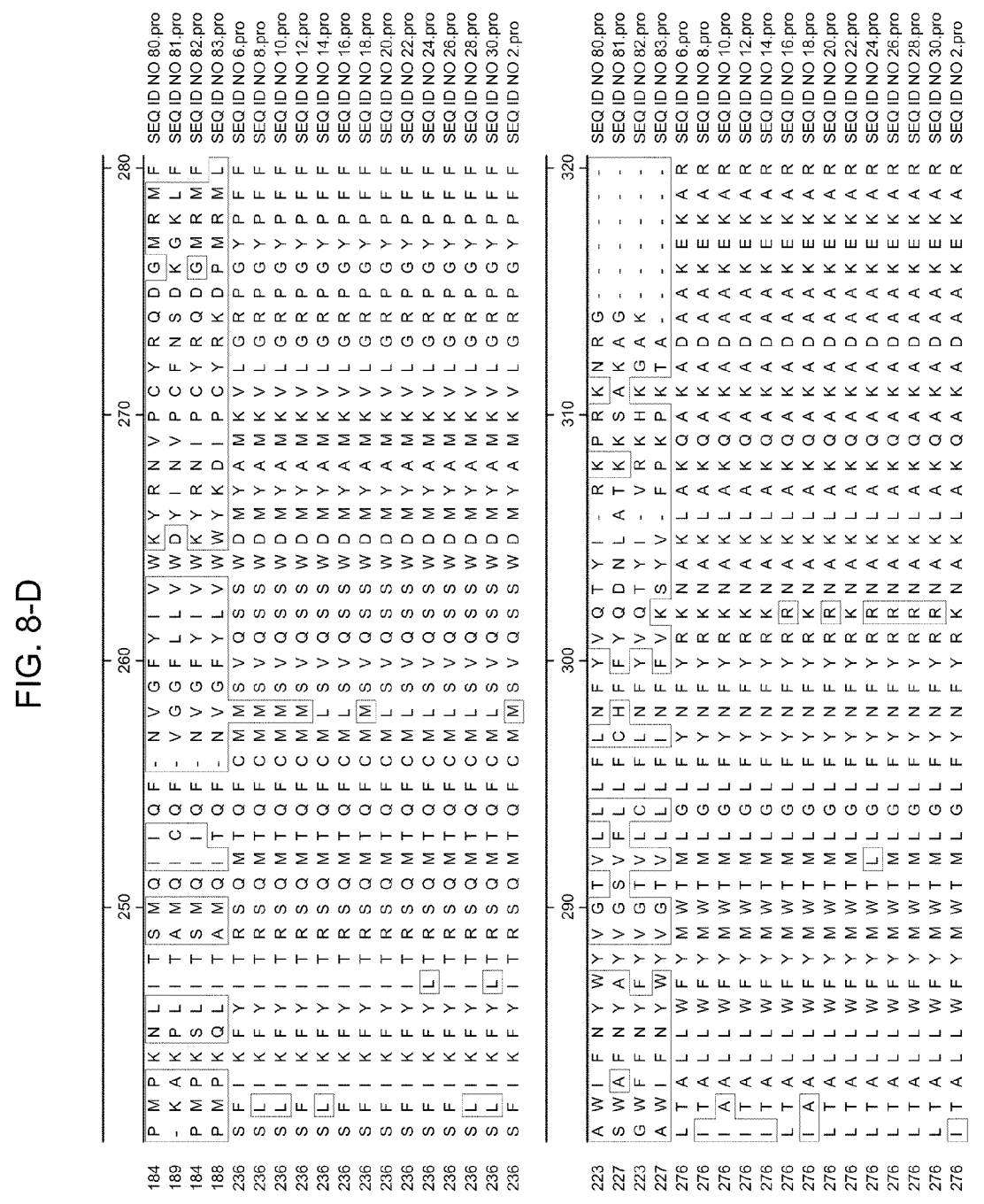
Figure 1:
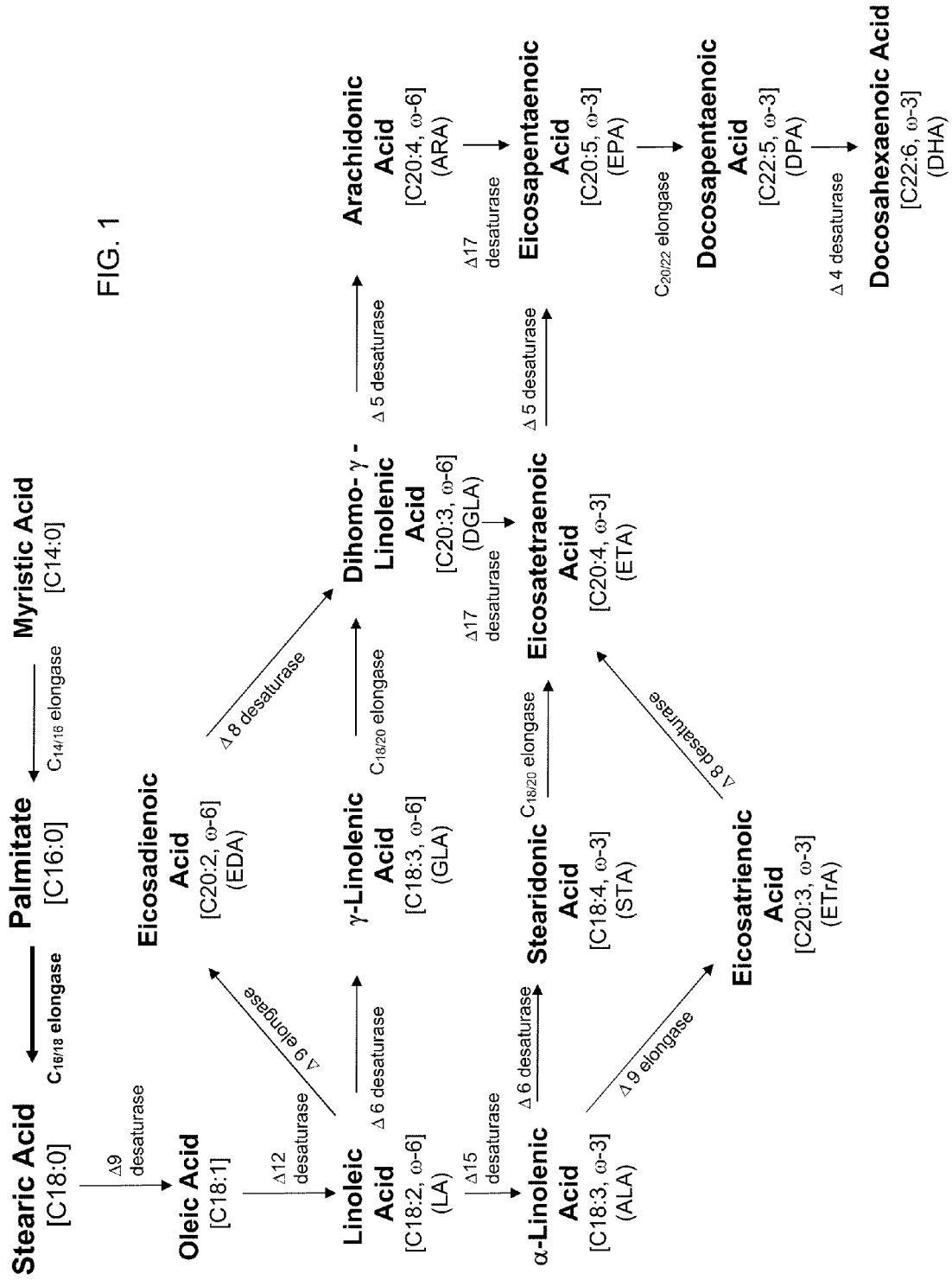

FIG. 8 is a comparative amino acid alignment between the delta-9 elongase from *Euglena anabaena* (SEQ ID NO:80), the delta-9 elongase from *Isochrysis galbana* (SEQ ID NO:81), the delta-9 elongase from *Eulgena gracilis* (SEQ ID NO:82), the delta-9 elongase from *Eutreptiella* sp. CCMP389 (SEQ ID NO: 83), a selection of the gene products of the invention (SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30) and the *Mortierella alpina* delta-6 elongase (SEQ ID NO:2) using the Clustal V method (Higgins, D. G. and Sharp, P. M., *Comput. Appl. Biosci.* 5:151-153 (1989); Higgins et al., *Comput. Appl. Biosci.* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10).

FIG. 9 shows the percent identity of the amino acid sequence of the delta-9 elongase from *Euglena anabaena* (SEQ ID NO:80), the delta-9 elongase from *Isochrysis galbana* (SEQ ID NO:81), the delta-9 elongase from *Eulgena gracilis* (SEQ ID NO:82), the delta-9 elongase from *Eutreptiella* sp. CCMP389 (SEQ ID NO: 83), a selection of the novel delta-9 elongases of the invention (SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30) and the *Mortierella alpina* delta-6 elongase (SEQ ID NO:2).

The sequence descriptions summarize the Sequences Listing attached hereto. The Sequence Listing contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

SEQ ID NO:1 is nucleotide sequence of the *Mortierella alpina* delta-6 elongase, codon optimized for expression in *Yarrowia* (MaD6ES).

SEQ ID NO:2 is the deduced amino acid sequence of SEQ ID NO:1.

SEQ ID NO:3 is the nucleotide sequence of the *Mortierella alpina* delta-6 elongase (NCBI Accession No. AF206662.1 (GI:7861835) locus AF206662, Proc. Natl. Acad. Sci. U.S.A. 97 (15), 8284-8289 (2000)).

SEQ ID NO:4 is the amino acid sequence of the *Mortierella alpina* delta-6 elongase (NCBI Accession No. AAF70417.1 (GI:7861836), locus AAF70417, Proc. Natl. Acad. Sci. U.S.A. 97 (15), 8284-8289 (2000)).

SEQ ID NO:5 is the nucleotide sequence of a gene product of the present invention, clone 004-3.1b-f2.

SEQ ID NO:6 is the deduced amino acid sequence of SEQ ID NO:5 (clone 004-3.1b-f2).

SEQ ID NO:7 is the nucleotide sequence of a gene product of the present invention, clone 006-2.1b-e11.

SEQ ID NO:8 is the deduced amino acid sequence of SEQ ID NO:7 (clone 006-2.1b-e11).

SEQ ID NO:9 is the nucleotide sequence of a gene product of the present invention, clone 009-2.1b-h9.

SEQ ID NO:10 is the deduced amino acid sequence of SEQ ID NO:9 (clone 009-2.1b-h9).

SEQ ID NO:11 is the nucleotide sequence of a gene product of the present invention, clone 010-2.1b-c3.

SEQ ID NO:12 is the deduced amino acid sequence of SEQ ID NO:11 (clone 010-2.1b-c3).

SEQ ID NO:13 is the nucleotide sequence of a gene product of the present invention, clone 012-2.1b-d5.

SEQ ID NO:14 is the deduced amino acid sequence of SEQ ID NO:13 (clone 012-2.1b-d5).

SEQ ID NO:15 is the nucleotide sequence of a gene product of the present invention, clone 014-3.1b-F1.

SEQ ID NO:16 is the deduced amino acid sequence of SEQ ID NO:15 (clone 014-3.1b-F1).

SEQ ID NO:17 is the nucleotide sequence of a gene product of the present invention, clone 027-2.1b-e9.

SEQ ID NO:18 is the deduced amino acid sequence of SEQ ID NO:17 (clone 027-2.1b-e9).

SEQ ID NO:19 is the nucleotide sequence of a gene product of the present invention, clone 046-3.1b-C2.

SEQ ID NO:20 is the deduced amino acid sequence of SEQ ID NO:19 (clone 046-3.1b-C2).

SEQ ID NO:21 is the nucleotide sequence of a gene product of the present invention, clone 051-3.1b-B5.

SEQ ID NO:22 is the deduced amino acid sequence of SEQ ID NO:21 (clone 051-3.1 b-B5).

SEQ ID NO:23 is the nucleotide sequence of a gene product of the present invention, clone 052-3.1b-C9.

SEQ ID NO:24 is the deduced amino acid sequence of SEQ ID NO:23 (clone 052-3.1b-C9).

SEQ ID NO:25 is the nucleotide sequence of a gene product of the present invention, clone 062-3.1b-C5.

SEQ ID NO:26 is the deduced amino acid sequence of SEQ ID NO:25 (clone 062-3.1b-05).

SEQ ID NO:27 is the nucleotide sequence of a gene product of the present invention, clone 077-3.1b-B1.

SEQ ID NO:28 is the deduced amino acid sequence of SEQ ID NO:27 (clone 077-3,1b-B1).

SEQ ID NO:29 is the nucleotide sequence of a gene product of the present invention, clone 078-3.1b-B4.

SEQ ID NO:30 is the deduced amino acid sequence of SEQ ID NO:29 (clone 078-3.1b-B4).

SEQ ID NO:31 is the nucleotide sequence of pY115.

SEQ ID NO:32 is the nucleotide sequence of the *Isochrysis galbana* delta-9 elongase codon optimized for expression in *Yarrowia* (IgD9ES).

SEQ ID NO:33 is the nucleotide sequence of pKUNF1-KEA_HD.

SEQ ID NO:34 is the nucleotide sequence of pY116.

SEQ ID NO:35 is the nucleotide sequence of plasmid pBY1.

SEQ ID NO:36 is the nucleotide sequence of plasmid 027-2.1b-e9/pY116.

SEQ ID NO:37 is the nucleotide sequence of plasmid 077-3.1b-b1/pY116.

SEQ ID NO:38 is the nucleotide sequence of plasmid 046-3.1b-c2/pY116.

SEQ ID NO:39 is the nucleotide sequence of plasmid 052-3.1b-c9/pY116.

SEQ ID NO:40 is the nucleotide sequence of plasmid 078-3.1b-b4/pY116.

SEQ ID NO:41 is the nucleotide sequence of plasmid 014-3.1b-f1/pY116.

SEQ ID NO:42 is the nucleotide sequence of plasmid 051-3.1b-b5/pY116.

SEQ ID NO:43 is the nucleotide sequence of plasmid 062-3.1b-c5/pY116.

SEQ ID NO:44 is the nucleotide sequence of plasmid KS366.

SEQ ID NO:45 is the nucleotide sequence of plasmid KS120.

SEQ ID NO:46 is the nucleotide sequence of plasmid KS367.

SEQ ID NO:47 is the nucleotide sequence of plasmid KS374.

SEQ ID NO:48 is the nucleotide sequence of plasmid KS375.

SEQ ID NO:49 is the nucleotide sequence of plasmid KS380.

SEQ ID NO:50 is the nucleotide sequence of plasmid KS382.

SEQ ID NO:51 is the nucleotide sequence of plasmid KS383.

SEQ ID NO:52 is the nucleotide sequence of plasmid KS384.

SEQ ID NO:53 is the nucleotide sequence of plasmid KS385.

SEQ ID NO:54 is the nucleotide sequence of plasmid KS386.

SEQ ID NO:55 is the nucleotide sequence of plasmid pLF128.

SEQ ID NO:56 is the nucleotide sequence of the MaD9elSHFL-4 elongase of the present invention described in example 11.

SEQ ID NO:57 is the deduced amino acid sequence of SEQ ID NO:56.

SEQ ID NO:58 is the nucleotide sequence of plasmid pY183.

SEQ ID NO:59 is the nucleotide sequence of the *Euglena gracilis* delta-8 desaturase (EgD8).

SEQ ID NO:60 is the nucleotide sequence of the *Mortierella alpina* delta-5 desaturase (MaD5).

SEQ ID NO:61 is the nucleotide sequence of the *Saprolegnia diclina* delta-17 desaturase (SdD17)

SEQ ID NO:62 is the nucleotide sequence of the *Fusarium monoliforme* delta-15 desaturase (FmD15).

SEQ ID NO:63 is the nucleotide sequence of plasmid pKR1230.

SEQ ID NO:64 is the nucleotide sequence of plasmid pKR1231.

SEQ ID NO:65 is the nucleotide sequence of plasmid pKR1232.

SEQ ID NO:66 is the nucleotide sequence of plasmid pKR954.

SEQ ID NO:67 is the nucleotide sequence of plasmid 004-3.1b-f2/pY116

SEQ ID NO:68 is the nucleotide sequence of plasmid 006-2.1b-e11/pY116.

SEQ ID NO:69 is the nucleotide sequence of plasmid 009-2.1b-h9/pY116.

SEQ ID NO:70 is the nucleotide sequence of plasmid 010-2.1b-c3/pY116.

SEQ ID NO:71 is the nucleotide sequence of 012-2.1b-d5/pY116.

SEQ ID NO:72 is the nucleotide sequence of plasmid KS369.

SEQ ID NO:73 is the nucleotide sequence of plasmid KS370.

SEQ ID NO:74 is the nucleotide sequence of plasmid KS371.

SEQ ID NO:75 is the nucleotide sequence of plasmid KS372.

SEQ ID NO:76 is the nucleotide sequence of plasmid KS376.

SEQ ID NO:77 is the nucleotide sequence of the *Mortierella alpina* delta-6 elongase, with possible modifications noted.

SEQ ID NO:78 is the nucleotide sequence of plasmid pKR952.

SEQ ID NO:79 is the nucleotide sequence of plasmid pKR325.

SEQ ID NO:80 is the amino acid sequence of the *Euglena anabaena* delta-9 elongase (EaD9EIo1, Applicants' Assignee's co-pending U.S. patent application Ser. No. 12/102,979).

SEQ ID NO:81 is the amino acid sequence of the *Isochrysis galbana* delta-9 elongase (GenBank Accession AAL37626; GI:17226123).

SEQ ID NO:82 is the amino acid sequence of the *Euglena gracilis* delta-9 elongase (Applicants' Assignee's co-pending U.S. Patent Application Publication No. 2007/0118929).

SEQ ID NO:83 is the amino acid sequence from *Eutreptiella* sp. CCMP389. (Applicants' Assignee's co-pending U.S. Patent Application Publication No. 2007/0117190).

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The present invention relates to novel delta-9 elongase enzymes and nucleic acids. These are useful for, inter alia, for the manipulation of biochemical pathways for the production of PUFAs. PUFAs, or derivatives thereof, made by the methodology disclosed herein can be used as dietary substitutes, or supplements, particularly infant formulas, for patients undergoing intravenous feeding or for preventing or treating malnutrition. Alternatively, purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

The present invention concerns an isolated polynucleotide including a nucleotide sequence encoding a polypeptide including Δ9 elongase activity and Δ5 elongase activity, but not limited to these activities. In order to create PUFAs with increased DPA a Δ5 elongase activity is desirable, in addition to the Δ9 elongase activity.

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 1. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the table summarizes the common names of omega-3 and omega-6 fatty acids and their precursors, the abbreviations that will be used throughout the remainder of the specification, and each compound's chemical name.

TABLE 1

Nomenclature of Polyunsaturated Fatty Acids

| Common Name | Abbreviation | Chemical Name | Shorthand Notation |
|---|---|---|---|
| Myristic | — | tetradecanoic | 14:0 |
| Palmitic | PA or Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| eicosenoic | — | cis-9-eicosenoic | 20:1 |
| Eicosadienoic | EDA | cis-11,14-eicosadienoic | 20:2 ω-6 |
| Dihomo-γ-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA or ERA | cis-11,14,17-eicosatrienoic | 20:3 ω-3 |
| Eicosa-tetraenoic | ETA | cis-8,11,14,17-eicosatetraenoic | 20:4 ω-3 |
| Juniperonic | JUP | cis-5,11,14,17-eicosatrienoic | 20:4b ω-3 |
| Docosatrienoic | DRA | cis-10,13,16-docosatrienoic | 22:3 ω-6 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and/or DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulum membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

The term "omega-3/omega-6 fatty acid biosynthetic pathway" refers to a set of genes which, when expressed under the appropriate conditions, encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion will generate omega-6 fatty acids.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the PUFA biosynthetic pathway enzyme genes are required, as a number of fatty acid products will only require the expression of a subset of the genes of this pathway.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidylethanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., an elongase) can convert substrate to product. The conversion efficiency is measured according to the following formula: ([product]/[substrate+product])*100, where 'product' includes the immediate product and all products in the pathway derived from it.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example: (1) delta-5 desaturases that catalyze the conversion of DGLA to ARA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitic acid to palmitoleic acid (16:1) and/or stearic acid to oleic acid (18:1). In the art, delta-15 and delta-17 desaturases are also occasionally referred to as "omega-3 desaturases", "w-3 desaturases", and/or "ω-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid elongase by transforming a suitable host with the gene for the fatty acid elongase and determining its effect on the fatty acid profile of the host.

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETRA and EPA to DPA.

Figure 5:
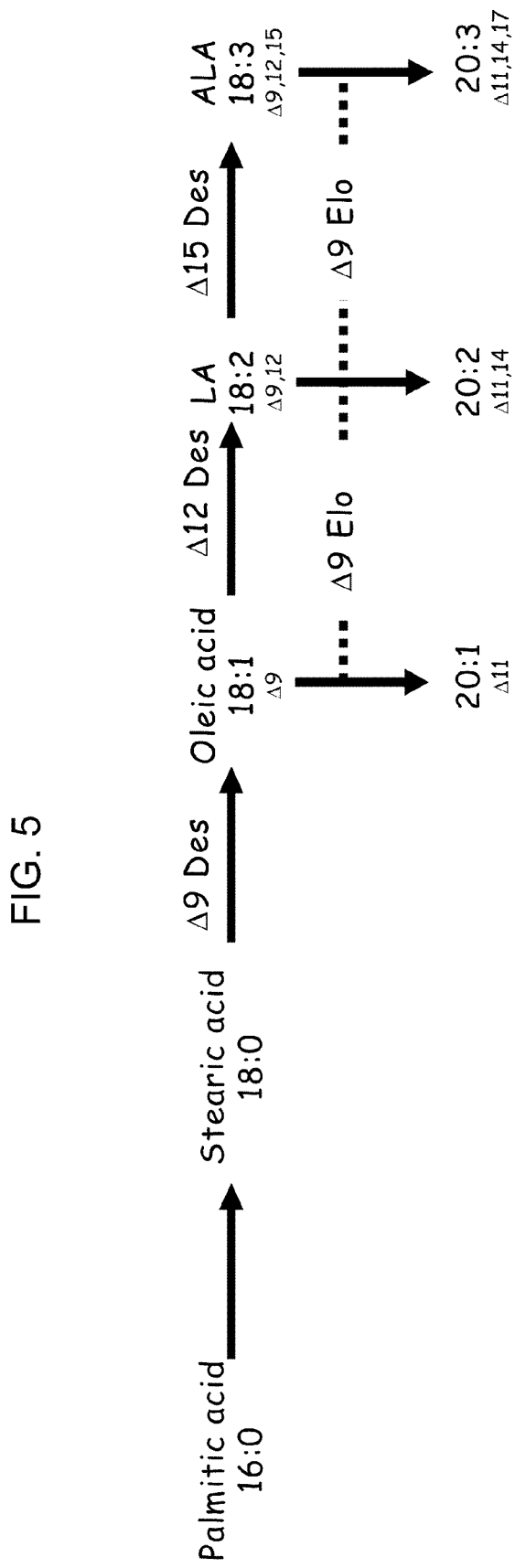
FIG. 5 is a representative fatty acid pathway showing the Δ9 elongation activity of the polypeptide of the present invention when expressed in soybean.

For the purposes herein, an enzyme catalyzing the first condensation reaction (i.e., conversion of malonyl-CoA and long-chain acyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). Similarly, a "delta-9 elongase" may be able to catalyze the conversion of LA to EDA and/or ALA to ETrA and/or 18:1 to 20:1 (see also FIG. 5). It is important to note that some elongases have broad specificity and thus a single enzyme may be capable of catalyzing several elongase reactions. Thus, for example, a delta-9 elongase may also act as a $C_{16/18}$ elongase, $C_{18/20}$ elongase and/or $C_{20/22}$ elongase and may have alternate, but not preferred, specificities for delta-5 and delta-6 fatty acids such as EPA and/or GLA, respectively.

Measurable delta-6 elongase activity can be defined as any activity greater than 0.9% elongase activity.

Measurable delta-5 activity elongase can be defined as any activity greater than 0.9% elongase activity.

Measurable delta-9 elongase activity can be defined as any activity greater than 0.9% elongase activity.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS. 5:151-153 (1989); Higgins, D. G. et al. (1992) Comput. Appl. Biosci. 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" refers to the following: (1) the entire complement of genetic material (genes and non-coding sequences) that is present in each cell of an organism, or virus or organelle; and/or (2) a complete set of chromosomes inherited as a (haploid) unit from one parent. Genome, as it applies to a plant cells, encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

Polynucleotide sequences produced by diversity generation methods or recursive sequence recombination ("RSR") methods (e.g., DNA shuffling), which can be accomplished in vitro, in vivo, in silico, or a combination thereof are a feature of the invention. A diversification method can include recursively recombining one or more nucleotide sequences of the invention as described below with one or more additional nucleotides. The recombining steps are optionally performed in vivo, ex vivo, in silico or in vitro. This diversity generation or recursive sequence recombination produces at least one library of recombinant modified fatty acid elongase polynucleotides. Polypeptides encoded by members of this library are included in the invention.

Fatty acid elongase polynucleotides of the invention can be readily modified using methods that are well known in the art to improve or alter elongase activity. A variety of diversity generating protocols are available and described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, nucleic acid libraries) which are useful for the engineering or rapid evolution of nucleic acids, proteins, pathways, cells and/or organisms with new and/or improved characteristics.

While distinctions and classifications are made in the course of the ensuing discussion for clarity; it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids that encode proteins with or which confer desirable properties. Following diversification by one or more of the methods herein, or otherwise available to one of skill, any nucleic acids that are produced can be selected for a desired activity or property, e.g. elongase activity. A variety of related (or even unrelated) properties can be evaluated, in serial or in parallel, at the discretion of the practitioner.

Descriptions of a variety of diversity generating procedures, including multigene shuffling and methods for generating modified nucleic acid sequences encoding multiple enzymatic domains, are found in, e.g., the following publications and the references cited therein: Soong, N. et al. (2000) "Molecular breeding of viruses" Nat Genet. 25(4):436-39; Stemmer, et al. (1999) "Molecular breeding of viruses for targeting and other clinical properties" Tumor Targeting 4:1-4; Ness et al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid from large numbers of oligodeoxy-ribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Additional details regarding various diversity generating methods can be found in, e.g., the following U.S. patents, PCT publications, and EPO publications: U.S. Pat. Nos. 5,605,793, 5,811,238, 5,830,721, 5,834,252, and 5,837,458; WO 95/22625; WO 96/33207; WO 97/20078; WO 97/35966; WO 99/41402; WO 99/41383; WO 99/41369; WO 99/41368; EP 752008; EP 0932670; WO 99/23107; WO 99/21979; WO 98/31837; WO 98/27230; WO 98/13487; WO 00/00632; WO 00/09679; WO 98/42832; WO 99/29902; WO 98/41653; WO 98/41622; WO 98/42727; WO 00/18906; WO 00/04190; WO 00/42561; WO 00/42559; WO 00/42560; WO 01/23401; and WO 01/64864.

Additional details regarding various diversity generating methods can be found in, e.g., U.S. patent application Ser. Nos. 09/407,800 and 60/186,482; U.S. Pat. Nos. 6,379,964, 6,376,246, 6,436,675, 6,642,426, and 7,024,312; WO 00/42561; WO 00/42560; and WO 00/42559.

In brief, several different general classes of sequence modification methods, such as mutation, recombination, etc. are set forth in the references above. Accordingly, the elongase nucleic acids of the invention can be generated from wild type sequences. Moreover, the elongase nucleic acid sequences of the invention can be modified to create modified sequences with the same or different activity.

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561, WO 01/23401, WO 00/42560, and WO 00/42559.

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on crossover site selection) as well as designed, pseudo-random or random recombination methods are described in WO 00/42560 and WO 00/42559. Extensive details regarding in silico recombination methods are found in these applications. This methodology is generally applicable to the present invention in providing for recombination of nucleic acid sequences and/or gene fusion constructs encoding proteins involved in various metabolic pathways (such as those responsible for PUFA biosynthesis) in silico and/or the generation of corresponding nucleic acids or proteins.

Many of the above-described methodologies for generating modified polynucleotides generate a large number of diverse variants of a parental sequence or sequences. In some preferred embodiments of the invention, the modification technique (e.g., some form of shuffling) is used to generate a library of variants that is then screened for a modified polynucleotide or pool of modified polynucleotides encoding some desired functional attribute, e.g., improved elongase activity. Exemplary enzymatic activities that can be screened for include catalytic rates (conventionally characterized in terms of kinetic constants such as $k_{cat}$ and $K_M$), substrate specificity, and susceptibility to activation or inhibition by substrate, product or other molecules (e.g., inhibitors or activators).

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that, since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved).

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). A class of plants identified as oleaginous are commonly referred to as "oilseed" plants. Examples of oilseed plants include, but are not limited to: soybean (*Glycine* and *Soja* sp.), flax (*Linum* sp.), rapeseed (*Brassica* sp.), maize, cotton, safflower (*Carthamus* sp.) and sunflower (*Helianthus* sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many grass-green chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. The term "plant organ" refers to plant tissue or a group of tissues that constitute a morphologically and functionally distinct part of a plant.

"Progeny" comprises any subsequent generation of a plant.

An Overview Microbial Biosynthesis of Fatty Acids and Triacyglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long chain omega-3/omega-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific long chain omega-3/omega-6 fatty acid.

Specifically, all pathways require the initial conversion of oleic acid to LA, the first of the omega-6 fatty acids, by a delta-12 desaturase. Then, using the "delta-9 elongase/delta-8 desaturase pathway", long chain omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of long chain omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (also known as delta-6 elongase, the terms can be used interchangeably) (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be introduced into a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; and/or (4) co-factors required by the polypeptide. The expressed polypeptide preferably has parameters compatible with the biochemical environment of its location in the host cell (see PCT Publication No. WO 2004/101757 for additional details).

Additionally, it will be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Delta-9 Elongases

In the present invention, nucleotide sequences encoding novel delta-9 elongases have been isolated. Thus, in one embodiment, the present invention concerns an isolated polynucleotide comprising a nucleotide sequence encoding a polypeptide having Δ9 elongase activity and Δ5 elongase activity, wherein said polypeptide has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, based on the Clustal V method of alignment, when compared to the sequence set forth in SEQ ID NO:2; or a full-length complement of the nucleotide sequence thereof.

In some embodiments, the nucleotide sequence encoding a polypeptide having Δ9 elongase activity and Δ5 elongase activity, said polypeptide has at least one of the following modifications to SEQ ID NO:2:
(a) at amino acid residue number 5, substitution of alanine (A) with valine (V),
(b) at amino acid residue number 9, substitution of proline (P) with leucine (L),
(c) at amino acid residue number 62 substitution of glutamic acid (E) with aspartic acid (D),
(d) at amino acid residue number 79, substitution of leucine (L) with methionine (M),
(e) at amino acid residue number 80, substitution isoleucine (I) with of leucine (L),
(f) at amino acid residue number 106, substitution of phenylalanine (F) with tyrosine (Y),
(g) at amino acid residue number 110, substitution of histidine (H) with tyrosine (Y),
(h) at amino acid residue number 117, substitution of isoleucine (I) with leucine (L),
(i) at amino acid residue number 130, substitution of tyrosine (Y) with phenylalanine (F),
(j) at amino acid residue number 138, substitution of glutamic acid (E) with glutamine (Q),
(k) at amino acid residue number 162, substitution of isoleucine (I) with leucine (L),
(l) at amino acid residue number 169, substitution of methionine (M) with leucine (L),
(m) at amino acid residue number 171, substitution of methionine (M) with leucine (L),
(n) at amino acid residue number 174, substitution of lysine (K) with arginine (R),
(o) at amino acid residue number 191, substitution of isoleucine (I) with leucine (L),
(p) at amino acid residue number 208, substitution tyrosine (Y) with tryptophan (W),
(q) at amino acid residue number 213, substitution of leucine (L) with methionine (M),
(r) at amino acid residue number 237, substitution of phenylalanine (F) with leucine (L),
(s) at amino acid residue number 242, substitution of isoleucine (I) with leucine (L),
(t) at amino acid residue number 253, substitution of methionine (M) with leucine (L),
(u) at amino acid residue number 276, substitution of isoleucine (I) with leucine (L),
(v) at amino acid residue number 277, substitution of threonine (T) with alanine (A),
(w) at amino acid residue number 287, substitution of methionine (M) with leucine (L),
(x) at amino acid residue number 297, substitution of lysine (K) with arginine (R).

Another aspect concerns a nucleotide sequence encoding a polypeptide having Δ9 elongase activity and Δ5 elongase activity, wherein said polypeptide has 2, 3, 4, 5, 6, 7, 8, 9, 10, 11, 12, 13, 14, 15, 16, 17, 18, 19, 20, 21, 22, 23, or all of the modifications (a)-(x).

Still another embodiment concerns a nucleotide sequence encoding a polypeptide having Δ9 elongase activity and Δ5 elongase activity, wherein said polypeptide comprises the amino acid sequence set forth SEQ ID NO:2, provided that said polypeptide has at least one of the modifications (a)-(x).

Still another embodiment concerns a nucleotide sequence encoding a polypeptide having Δ9 elongase activity and Δ5 elongase activity, wherein said polypeptide has the amino acid sequence set forth SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30.

Still another embodiment concerns a nucleotide sequence encoding a polypeptide having Δ9 elongase activity and Δ5 elongase activity, wherein said polypeptide comprises the nucleotide sequence set forth in SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29.

Identification and Isolation of Homologs

Any of the instant elongase sequences or portions thereof may be used to search for delta-9 elongase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant elongase sequences or portions thereof may also be employed as hybridization reagents for the identification of delta-9 elongase homologs. The basic components of a nucleic acid hybridization test include a probe, a sample suspected of containing the gene or gene fragment of interest and a specific hybridization method. Probes are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-9 elongase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. USA* 82:1074 (1985); or strand displacement amplification (SDA), Walker et al., *Proc. Natl. Acad. Sci. U.S.A.,* 89:392 (1992)]; and (3) methods of library construction and screening by complementation.

For example, genes encoding similar proteins or polypeptides to the delta-9 elongases described herein could be isolated directly by using all or a portion of the instant nucleic acid fragments as DNA hybridization probes to screen libraries from e.g., any desired yeast or fungus using methodology well known to those skilled in the art (wherein those organisms producing DGLA and/or ETA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, any of the delta-9 elongase nucleic acid fragments described herein (or any homologs identified thereof) may be used for creation of new and improved fatty acid elongases. As is well known in the art, in vitro mutagenesis and selection, chemical mutagenesis, "gene shuffling" methods or other means can be employed to obtain mutations of naturally occurring elongase genes. Alternatively, improved fatty acids may be synthesized by domain swapping, wherein a functional domain from any of the delta-9 elongase nucleic acid fragments described herein are exchanged with a functional domain in an alternate elongase gene to thereby result in a novel protein. As used herein, "domain" or "functional domain" refer to nucleic acid sequence(s) that are capable of eliciting a biological response in plants.

Methods for Production of Various Omega-3 and/or Omega-6 Fatty Acids

It is expected that introduction of chimeric genes encoding the delta-9 elongases described herein or mutant enzymes, codon-optimized enzymes or homologs thereof), under the control of the appropriate promoters will result in increased production of DGLA and/or ETA in the transformed host organism, respectively. As such, the present invention encompasses a method for the direct production of PUFAs comprising exposing a fatty acid to the elongase enzymes described herein, such that the substrate is converted to the desired fatty acid product.

Plant Expression Systems, Cassettes and Vectors, and Transformation

One embodiment concerns a recombinant construct comprising any one of the delta-9 elongase polynucleotides of the invention operably linked to at least one regulatory sequence suitable for expression in a plant. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-9 elongase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of the beta conglycinin promoter, the Kunitz trypsin inhibitor 3 promoter, the annexin promoter, the glycinin Gy1 promoter, the beta subunit of the beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J. Biol. Chem.* 265(21):12486-93 (1990)); (4) a tomato ubiquitin gene promoter (Rollfinke et al., *Gene.* 211 (2):267-76 (1998)); (5) a soybean heat shock protein promoter (Schoffl et al., *Mol Gen Genet.* 217 (2-3): 246-53 (1989)); and (6) a maize H3 histone gene promoter (Atanassova et al., *Plant Mol. Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-9 elongase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual*; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

Thus, this invention also concerns a method for transforming a cell, comprising transforming a cell with the recombinant construct of the invention and selecting those cells transformed with the recombinant construct of the invention.

Also of interest is a method for producing a transformed plant comprising transforming a plant cell with the delta-9 elongase polynucleotides of the instant invention and regenerating a plant from the transformed plant cell.

One embodiment concerns a plant comprising in its genome the recombinant construct of the invention. Suitable plants include, but are not limited to, soybean, *Brassica* species, sunflower, maize, cotton, flax and safflower.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage.

Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of PUFAs having at least twenty carbon atoms and four or more carbon-carbon double bonds include, but are not limited to, omega-3 fatty acids such as EPA, DPA and DHA and the omega-6 fatty acid ARA. Seeds obtained from such plants are also within the scope of this invention as well as oil obtained from such seeds.

Microbial Expression Systems, Cassettes and Vectors, and Transformation

The delta-9 elongase genes and gene products described herein may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-9 elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-9 elongase described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

The preferred method of expressing genes in *Yarrowia lipolytica* is by integration of linear DNA into the genome of the host, and integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra) to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl. Microbiol. Biotechnol.*, 48(2):232-235 (1997)).

For convenience, a host cell that has been manipulated by any method to take up a DNA sequence (e.g., an expression cassette) will be referred to as "transformed" or "recombinant" herein. Thus, the term "transformed" and "recombinant" are used interchangeably herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO 2004/101757 and WO 2006/052870. Preferred selection methods for use herein are resistance to kanamycin, hygromycin and the amino glycoside G418, as well as ability to grow on media lacking uracil, leucine, lysine, tryptophan or histidine, In alternate embodiments, 5-FOA is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura-mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura-phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3-strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-9 elongase (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes described in the instant invention can be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Oleaginous yeasts are particularly suitable because these organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase, lipases, polyhydroxyalkanoates, citric acid, erythritol, 2-oxoglutaric acid, γ-decalactone, γ-dodecalatone, and pyruvic acid. Specific teachings applicable for engineering ARA, EPA and DHA production in *Y. lipolytica* are provided in U.S. Patent Application Nos. 2006/0094092, 2006/0115881, and 2006/0110806, respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-9 elongase genes under the control of inducible or regulated promoters could yield a transformant organism capable of synthesizing increased quantities of DGLA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

Metabolic Engineering of Omega-3 and/or Omega-6 Fatty Acid Biosynthesis in Microbes Methods for manipulating biochemical pathways are well known to those skilled in the art, and it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media should contain a suitable carbon source. Suitable carbon sources are taught in, e.g., PCT Publication No. WO 2004/101757. Although it is contemplated that the source of carbon utilized may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12 (5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean by-products are produced using the generalized steps shown in Table 2.

TABLE 2

Generalized Steps for Soybean Oil and By-product Production

| Process Step | Process | Impurities Removed and/or By-Products Obtained |
|---|---|---|
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation, a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. The term "meat" includes "red meats" produced from cattle, hogs and sheep. In addition to the red meats there are poultry items which include chickens, turkeys, geese, guineas, ducks, fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat), and generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants, and, although breast-feeding is still the best nourishment for infants, infant formula is a close enough second that babies not only survive but thrive.

A dairy product is a product derived from milk. A milk analog or nondairy product is derived from a source other than milk, for example, soymilk as discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils For Use in Animal Feeds

Animal feeds are generically defined herein as products intended for use as feed or for mixing in feed for animals other than humans. The plant/seed oils and altered seeds of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of Yarrowia lipolytica:

Yarrowia lipolytica strains with ATCC Accession Nos. 20362, 76982 and 90812 were purchased from the American Type Culture Collection (Rockville, Md.). Yarrowia lipolytica strains were typically grown at 28° C. on YPD agar (1% yeast extract, 2% bactopeptone, 2% glucose, 2% agar).

Transformation of Yarrowia lipolytica was performed according to the method of Chen, D. C. et al. (Appl. Microbiol. Biotechnol. 48(2):232-235 (1997)), unless otherwise noted. Briefly, Yarrowia was streaked onto a YPD plate and grown at 30° C. for approximately 18 h. Several large loopfuls of cells were scraped from the plate and resuspended in 1 mL of transformation buffer containing: 2.25 mL of 50% polyethylene glycol (PEG), average MW 3350; 0.125 mL of 2 M Li acetate, pH 6.0; 0.125 mL of 2 M dithiothreitol (DTT); and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days. Alternatively, Yarrowia was transformed using the Fast Yeast Transformation Kit™ from Gene Technologies Inc.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Fatty Acid Analysis of Yarrowia lipolytica:

For fatty acid analysis, cells were collected by centrifugation and lipids were extracted as described in Bligh, E. G. & Dyer, W. J. (Can. J. Biochem. Physiol. 37:911-917 (1959)). Fatty acid methyl esters were prepared by transesterification of the lipid extract with sodium methoxide (Roughan, G. and Nishida, I., Arch Biochem Biophys. 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, Yarrowia culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

Synthesis of a Codon-Optimized Delta-6 elongase Gene Derived from M. alpina

Plasmid pY115 (SEQ ID NO:31), comprising the Isochrysis galbana delta-9 elongase codon optimized for expression in Yarrowia (IgD9ES; SEQ ID NO:32), is described in U.S. Patent Application No. 2007/0118929, the contents of which are hereby incorporated by reference.

The Mortierella alpina elongase, codon optimized for expression in Yarrowia (MaD6ES; SEQ ID NO:1), was released from pKUNF1-KEA_HD (SEQ ID NO:33, called pKUNF1-KEA and described in U.S. Patent Application No. 2007/0249026, the contents of which are hereby incorporated by reference) by digestion with NcoI/INotI and the fragment containing MaD6ES was cloned into the NcoI/NotI fragment of pY115 containing the vector backbone and promoter to give pY116 (SEQ ID NO:34). There is a one amino acid change (T→S at position 22) between the amino acid sequence coded for by the wild type (SEQ ID NO:4) and the amino acid sequence coded for the codon optimized M. alpina delta-6 elongase (SEQ ID NO:2) that does not affect the activity.

Example 2

Generation of DNA Libraries Containing Novel Delta-9 Elongase Genes

Several libraries of modified fatty acid elongase polynucleotides were generated using recursive sequence recombination. Some of these libraries incorporated diversity from related enzymes while others incorporated random changes.

In all cases, the polynucleotide sequence in which the diversity was incorporated was the codon-optimized delta-6 elongase gene derived from *M. alpina* (SEQ ID NO:1) contained within pY116 (SEQ ID NO:34) as described in Example 1. These libraries were cloned in *E. coli* and transferred to *Yarrowia lipolytica* as described in Example 3 and screened for the presence of delta-9 elongase activity as described in Example 4.

A second round of library generation included information obtained during the initial screening as well as further diversity from related enzymes. These libraries were cloned in *E. coli* and transferred to *Yarrowia lipolytica* as described in Example 3 and screened for the presence of delta-9 elongase activity as described in Example 4. A third round of library generation included information obtained during the second round of screening as well as further diversity from related enzymes. These libraries were cloned in *E. coli* and transferred to *Yarrowia lipolytica* as described in Example 3 and screened for the presence of delta-9 elongase activity as described in Example 4.

Example 3

Construction of Yarrowia lipolytica Expression Vectors for Expression of Novel Delta-9 Elongase Genes DNA sequences generated during the first round of recursive sequence recombination (RSR) were cloned in PENTR (INVITROGEN™) and then recombined into pBY1 (SEQ ID NO:35) using the Gateway recombination System (INVITROGEN™). *E. coli* colonies were harvested from LB-agar plates and used to make plasmid DNA which was transformed into *Yarrowia lipolytica*. Individual *Yarrowia lipolytica* colonies were screened as described in Example 4. pBY1 is pY116 with the codon-optimized delta-6 elongase gene derived from *M. alpina* replaced with the Gateway Reading Frame cassette (INVITROGEN™).

DNA sequences generated during the second and third round of recursive sequence recombination were created incorporating a NcoI restriction enzyme site on the 5' end of the protein encoding sequence and an NotI restriction enzyme site on the 3' end of the protein. These DNA sequences were digested with NotI and NcoI and ligated into vector pY116 digested with NcoI and NotI. *E. coli* colonies were harvested from LB-agar plates and used to make plasmid DNA which was transformed into *Yarrowia lipolytica* using the protocol describes above (see "Transformation and Cultivation of *Yarrowia lipolytica*").

Individual *Yarrowia lipolytica* colonies were screened as described below in Example 4.

Example 4

Screening of Yarrowia lipolytica Colonies for the Presence of Delta-9 Elongase Activity In order to identify proteins with delta 9-elongase activity, *Yarrowia lipolytica* colonies containing the DNA sequences generated during the first round of RSR (described in Example 3), were grown in 96 well plates for three days in media with glycerol to generate a stock culture. This stock culture was then used to inoculate an additional 96 well plate. The *Yarrowia lipolytica* from the additional 96 well plate were collected by centrifugation and fatty acid esters were analyzed as described above (see "Fatty Acid Analysis of *Yarrowia lipolytica*"). For analysis of proteins generated during the second round of RSR (described in Example 3), *Yarrowia lipolytica* colonies were grown and analyzed as described previously except the colonies were grown in 96-well plate for two days in media without glycerol. For analysis of proteins generated during the third round of RSR (described in Example 3), *Yarrowia lipolytica* colonies were harvested directly from agar plates. *Yarrowia lipolytica* colonies were resuspended in trimethylsulfonium hydroxide and fatty acid esters and analyzed as described above (see "Fatty Acid Analysis of *Yarrowia lipolytica*").

In all cases, *Yarrowia lipolytica* colonies that exhibited increased delta 9-elongase activity when compared to the *M. alpina* elongase, codon optimized for expression in *Yarrowia* (MaD6ES), were screened again for presence of delta-9 elongase activity. Those *Yarrowia lipolytica* colonies that confirmed an increased delta 9-elongase activity when compared to MaD6ES were used to isolate plasmid DNA. This plasmid DNA was transformed into *E. coli* and then plasmid DNA was isolated from the *E. coli* and the nucleotide fragment encoding the novel delta-9 elongases was completely sequenced using standard methods. The resulting DNA sequences (SEQ ID NOs: 5, 7, 9, 11, 13, 15, 17, 19, 21, 23, 25, 27, 29) and corresponding amino acid sequences (SEQ ID NOs: 6, 8, 10, 12, 14, 16, 18, 20, 22, 24, 26, 28, 30) are shown in Table 3.

TABLE 3

Summary of *Yarrowia lipolytica* vectors for expression of novel delta-9 elongase genes

| Vector | Gene Name | Gene Nucleotide SEQ ID NO: | Gene Amino Acid SEQ ID NO: |
|---|---|---|---|
| 004-3.1b-f2/pY116 (SEQ ID NO: 67) | 004-3.1b-f2 | 5 | 6 |
| 006-2.1b-e11/pY116 (SEQ ID NO: 68) | 006-2.1b-e11 | 7 | 8 |
| 009-2.1b-h9/pY116 (SEQ ID NO: 69) | 009-2.1b-h9 | 9 | 10 |
| 010-2.1b-c3/pY116 (SEQ ID NO: 70) | 010-2.1b-c3 | 11 | 12 |
| 012-2.1b-d5/pY116 (SEQ ID NO: 71) | 012-2.1b-d5 | 13 | 14 |
| 027-2.1b-e9/pY116 (SEQ ID NO: 36) | 027-2.1b-e9 | 17 | 18 |
| 077-3.1b-b1/pY116 (SEQ ID NO: 37) | 077-3.1b-B1 | 27 | 28 |
| 046-3.1b-c2/pY116 (SEQ ID NO: 38) | 046-3.1b-C2 | 19 | 20 |
| 052-3.1b-c9/pY116 (SEQ ID NO: 39) | 052-3.1b-C9 | 23 | 24 |
| 078-3.1b-b4/pY116 (SEQ ID NO: 40) | 078-3.1b-B4 | 29 | 30 |
| 014-3.1b-f1/pY116 (SEQ ID NO: 41) | 014-3.1b-F1 | 15 | 16 |
| 051-3.1b-b5pY116 (SEQ ID NO: 42) | 051-3.1b-B5 | 21 | 22 |
| 062-3.1b-c5pY116 (SEQ ID NO: 43) | 062-3.1b-C5 | 25 | 26 |

Example 5

Construction of Soybean Expression Vectors for Expression of Novel Delta-9 Elongase Genes In order to test the activity of novel delta-9 elongases, DNA sequences encoding the modified fatty acid elongase polynucleotides described in Example 2 were cloned into soybean expression vectors and transformed into soybean somatic embryos. Fatty acid identities in soybean somatic embryos have previously been shown to be predictive of fatty acid identities in soybean seeds. Soybean expression vectors were made as follows using standard cloning methods well known to those skilled in the art (Sambrook et al. (1989) Molecular Cloning, CSHL Press, New York).

The soybean expression vector KS366 (SEQ ID NO:44) includes a Beta conglycinin alpha' promoter and a Phaseolin terminator separated by a 486 bp spacer region that is flanked by unique NcoI and NotI restriction sites. KS366 also includes the ampicillin resistance gene for selection on antibiotic. The soybean expression vector KS366 was digested with NcoI and NotI restriction enzymes removing a 0.486 kb (NcoI/NotI) fragment containing a spacer from the middle of the Beta conglycinin promoter and Phaseolin terminator leaving a 4.727 kb (NcoI/NotI) fragment. The 0.954 kb (NcoI/NotI) fragment containing the novel delta-9 elongase was removed from its pY116 based vector by digesting with NcoI and NotI restriction enzymes. The fragments were isolated by size on a 1% agarose gel and purified on a Zymoclean™ Gel DNA spin column (Zymo Research, catalogue number D4002). The NcoI/NotI elongase fragment was then ligated directionally into KS366. The resulting vectors are shown in Table 4.

Each of the final vectors containing the novel delta-9 elongase (Table 4) were co-bombarded in a 10:1 molar ratio with KS120 (SEQ ID NO:45), a vector containing a hygromycin B phosphotransferase (HPT) obtained from *E. coli* strain W677 under the control of a T7 promoter and the 35S cauliflower mosaic virus promoter. Plasmid KS120 contains the T7 promoter/HPT/T7 terminator cassette for expression of the HPT enzyme in certain strains of *E. coli*, such as NovaBlue (DE3) [Novagen®], that are lysogenic for lambda DE3 (which carries the T7 RNA Polymerase gene under lacV5 control). Plasmid KS120 also contains the 35S/HPT/NOS cassette for constitutive expression of the HPT enzyme in plants, such as soybean. The combination of KS366 and KS120 allows selection for growth in the presence of hygromycin to be used as a means of identifying cells that contain the plasmid in both bacterial and plant systems.

A summary of soybean vectors for expression of novel delta-9 elongase genes is shown in Table 4.

TABLE 4

Summary of soybean vectors for expression of novel delta-9 elongase genes

| Vector | Gene Name | Gene Nucleotide SEQ ID NO: | Gene Amino Acid SEQ ID NO: |
|---|---|---|---|
| KS367 (SEQ ID NO: 46) | MaD6ES | 1 | 2 |
| KS374 (SEQ ID NO: 47) | 027-2.1b-e9 | 17 | 18 |
| KS375 (SEQ ID NO: 48) | 014-3.1b-F1 | 15 | 16 |
| KS380 (SEQ ID NO: 49) | 062-3.1b-C5 | 25 | 26 |
| KS382 (SEQ ID NO: 50) | 051-3.1b-B5 | 21 | 22 |
| KS383 (SEQ ID NO: 51) | 078-3.1b-B4 | 29 | 30 |
| KS384 (SEQ ID NO: 52) | 046-3.1b-C2 | 19 | 20 |
| KS385 (SEQ ID NO: 53) | 052-3.1b-C9 | 23 | 24 |
| KS386 (SEQ ID NO: 54) | 077-3.1b-B1 | 27 | 28 |
| KS376 (SEQ ID NO: 76) | 004-3.1b-f2 | 5 | 6 |
| KS372 (SEQ ID NO: 75) | 006-2.1b-e11 | 7 | 8 |
| KS369 (SEQ ID NO: 72) | 009-2.1b-h9 | 9 | 10 |

TABLE 4-continued

Summary of soybean vectors for expression of novel delta-9 elongase genes

| Vector | Gene Name | Gene Nucleotide SEQ ID NO: | Gene Amino Acid SEQ ID NO: |
|---|---|---|---|
| KS370 (SEQ ID NO: 73) | 010-2.1b-c3 | 11 | 12 |
| KS371 (SEQ ID NO: 74) | 012-2.1b-c3 | 13 | 14 |

Example 6

Primary Sequence Analysis of novel Delta-9 Elongase Sequences

The amino acid sequences of novel delta-9 elongases (SEQ ID NOs 6, 8, 10, 12, 14, 16, 18, 20, 22, 24, 26, 28, 30) were compared to *M. alpina* elongase, codon optimized for expression in *Yarrowia* (MaD6ES; SEQ ID NO:2) using the Clustal V method (Higgins, D. G. and Sharp, P. M., *Comput. Appl. Biosci.* 5:151-153 (1989); Higgins et al., *Comput. Appl. Biosci.* 8:189-191 (1992)) using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10) as shown in FIG. 2.

Figure 2:
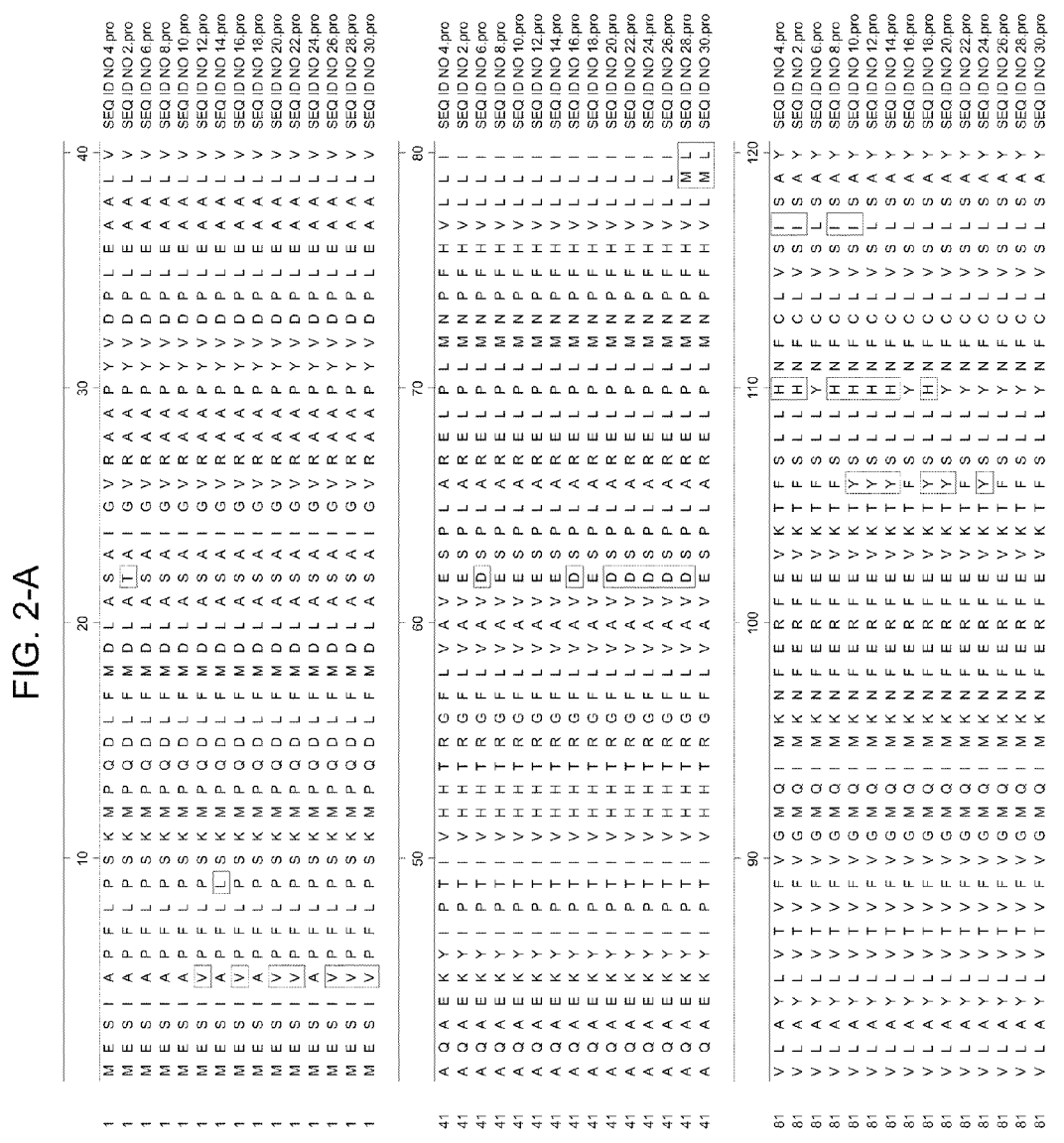
Figure 2:
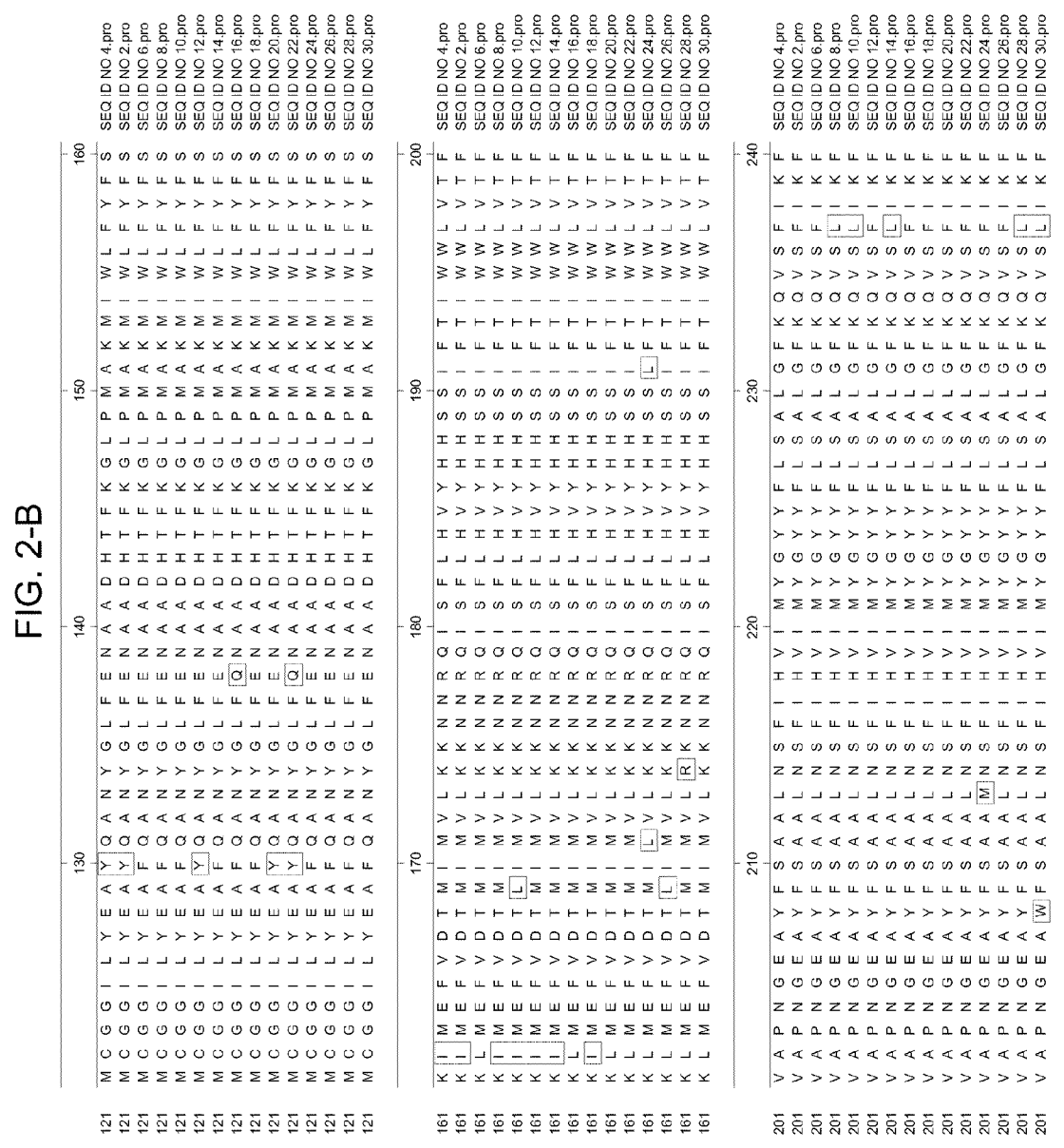
Figure 2:
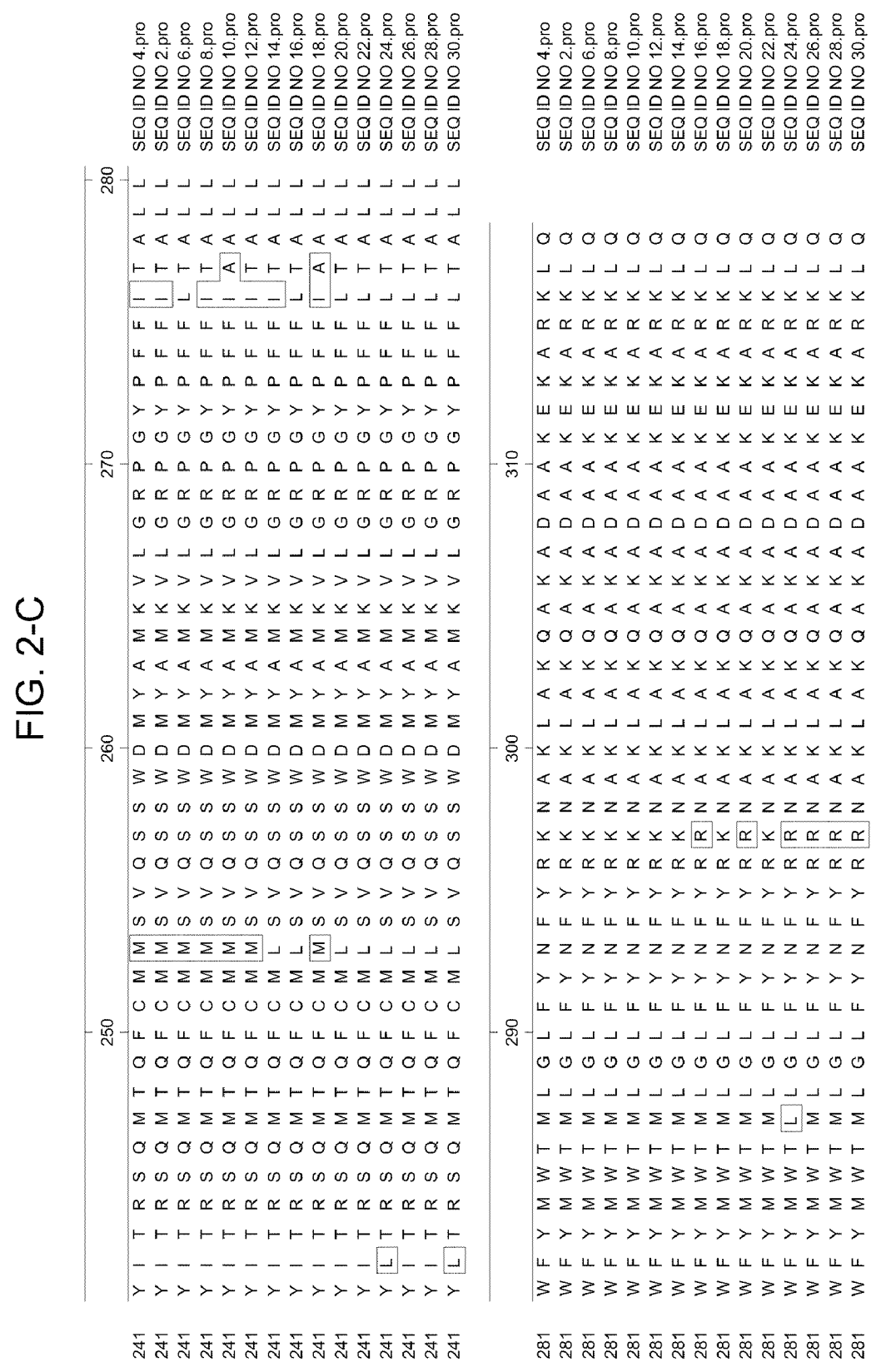
Figure 3:
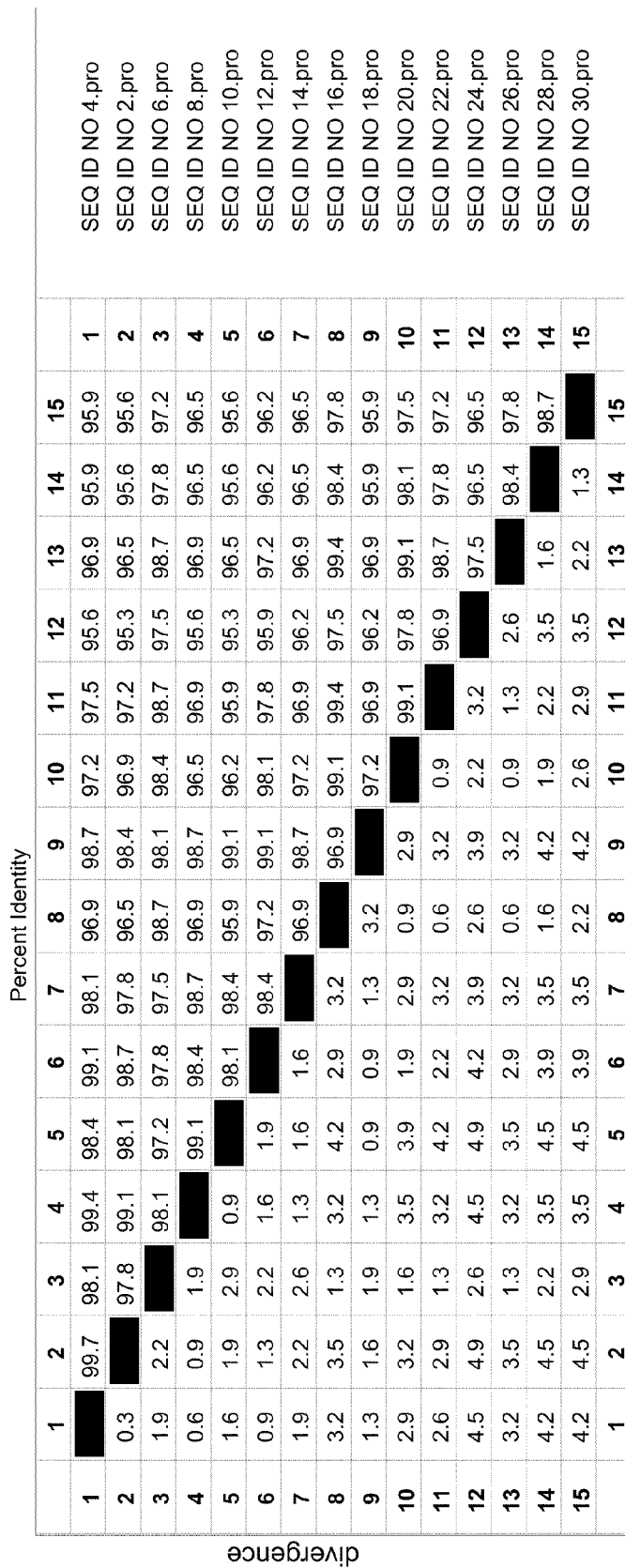

The amino acid sequences of novel delta-9 elongases shown in FIG. 2 (SEQ ID NOs 6, 8, 10, 12, 14, 16, 18, 20, 22, 24, 26, 28, 30) contained at least one of the following modifications when compared to the amino acid sequence of the *Mortierella alpina* delta-6 elongase, codon optimized for expression in *Yarrowia* (MaD6ES; SEQ ID NO:2).
(a) at amino acid residue number 5, substitution of alanine (A) with valine (V),
(b) at amino acid residue number 9, substitution of proline (P) with leucine (L),
(c) at amino acid residue number 62 substitution of glutamic acid (E) with aspartic acid (D),
(d) at amino acid residue number 79, substitution of leucine (L) with methionine (M),
(e) at amino acid residue number 80, substitution isoleucine (I) with of leucine (L),
(f) at amino acid residue number 106, substitution of phenylalanine (F) with tyrosine (Y),
(g) at amino acid residue number 110, substitution of histidine (H) with tyrosine (Y),
(h) at amino acid residue number 117, substitution of isoleucine (I) with leucine (L),
(i) at amino acid residue number 130, substitution of tyrosine (Y) with phenylalanine (F),
(j) at amino acid residue number 138, substitution of glutamic acid (E) with glutamine (Q),
(k) at amino acid residue number 162, substitution of isoleucine (I) with leucine (L),
(l) at amino acid residue number 169, substitution of methionine (M) with leucine (L),
(m) at amino acid residue number 171, substitution of methionine (M) with leucine (L),
(n) at amino acid residue number 174, substitution of lysine (K) with arginine (R),
(o) at amino acid residue number 191, substitution of isoleucine (I) with leucine (L), (p) at amino acid residue number 208, substitution tyrosine (Y) with tryptophan (W),
(q) at amino acid residue number 213, substitution of leucine (L) with methionine (M),
(r) at amino acid residue number 237, substitution of phenylalanine (F) with leucine (L),
(s) at amino acid residue number 242, substitution of isoleucine (I) with leucine (L),
(t) at amino acid residue number 253, substitution of methionine (M) with leucine (L),
(u) at amino acid residue number 276, substitution of isoleucine (I) with leucine (L),
(v) at amino acid residue number 277, substitution of threonine (T) with alanine (A),
(w) at amino acid residue number 287, substitution of methionine (M) with leucine (L),
(x) at amino acid residue number 297, substitution of lysine (K) with arginine (R);

Sequence percent identity calculations performed by the BlastP and Clustal V method as described above. Sequence percent identity calculations performed by the Jotun Hein method (Hein, J. J., *Meth. Enz.* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). FIG. 3 shows the sequence identity table of the amino acid sequence of novel delta-9 elongases (SEQ ID NOs 6, 8, 10, 12, 14, 16, 18, 20, 22, 24, 26, 28, 30) compared to *M. alpina* elongase, codon optimized for expression in *Yarrowia* (MaD6ES; SEQ ID NO:2).

Example 7

Production and Model System Transformation of Somatic Soybean Embryo Cultures with Soybean Expression Vectors and Plant Regeneration Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures are transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of Ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. When cultures are being prepared for production transformation, cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 µE/m2/s for eight weeks, with a media change after 4 weeks. When cultures are being prepared for model system experiments, cotyledons are transferred to plates containing SB199 medium (25-30 cotyledons per plate) for 2 weeks, and then transferred to SB1 for 2-4 weeks. Light and temperature conditions are the same as described above. After incubation on SB1 medium, secondary embryos are cut and placed into SB196 liquid media for 7 days.

Preparation of DNA for Bombardment:

Either an intact plasmid or a DNA plasmid fragment containing the genes of interest and the selectable marker gene are used for bombardment. Fragments from soybean expression plasmids are obtained by gel isolation of digested plasmids. In each case, 100 µg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 hr. The resulting DNA fragments are separated by gel electrophoresis on 1% SeaPlaque GTG agarose (BioWhitaker Molecular Applications), and the DNA fragments containing gene cassettes are cut from the agarose gel. DNA is purified from the agarose using the GELase digesting enzyme following the manufacturer's protocol.

A 50 µL aliquot of sterile distilled water containing 3 mg of gold particles (3 mg gold) is added to 30 µL of a 10 ng/µL DNA solution (either intact plasmid or DNA fragment prepared as described herein), 25 µL 5M $CaCl_2$ and 20 µL of 0.1 M spermidine. The mixture is shaken 3 min on level 3 of a vortex shaker and spun for 10 sec in a bench microfuge. The supernatant is removed, followed by a wash with 400 µL 100% ethanol and another brief centrifugation. The 400 µl ethanol is removed and the pellet is resuspended in 40 µL of 100% ethanol. Five µL of DNA suspension is dispensed to each flying disk of the Biolistic PDS1000/HE instrument disk. Each 5 µL aliquot contains approximately 0.375 mg gold per bombardment (e.g., per disk).

For model system transformations, the protocol is identical except for a few minor changes (i.e., 1 mg of gold particles is added to 5 µL of a 1 µg/µL DNA solution, 50 µL of a 2.5M $CaCl_2$ is used and the pellet is ultimately resuspended in 85 µL of 100% ethanol thus providing 0.058 mg of gold particles per bombardment).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury (685.8-711.2 mmHg), and tissue is bombarded one or two shots per plate with membrane rupture pressure set at 1100 PSI (77.356 kg/cm). Tissue is placed approximately 3.5 inches (8.89 cm) from the retaining/stopping screen. Model system transformation conditions are identical except 100-150 mg of embryogenic tissue is used, rupture pressure is set at 650 PSI and tissue is place approximately 2.5 inches (6.35 cm) from the retaining screen.

Selection of Transformed Embryos:

Transformed embryos are selected either using hygromycin (when the hygromycin B phosphotransferase (HPT) gene is used as the selectable marker) or chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing either 30 mg/L hygromycin or 100 ng/mL chlorsulfuron, depending on the selectable marker used. The selection media is refreshed weekly. Four to six weeks post-selection, green, transformed tissue is observed growing from untransformed, necrotic embryogenic clusters.

Embryo Maturation:

For production transformations, isolated, green tissue is removed and inoculated into multiwell plates to generate new, clonally propagated, transformed embryogenic suspension cultures. Transformed embryogenic clusters are cultured for four-six weeks in multiwell plates at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2 s$. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for alterations in their fatty acid compositions as described previously.

For model system transformations, embryos are matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters are removed to 35 mL of SB228 (SHaM liquid media) in a 250 mL Erlenmeyer flask. Tissue is maintained in SHaM liquid media on a rotary shaker at 130 rpm and 26° C. with cool white fluorescent lights on a 16:8 hr day/night photoperiod at a light intensity of 60-85 $\mu E/m2/s$ for 2 weeks as embryos mature. Embryos grown for 2 weeks in SHaM liquid media are equivalent in size and fatty acid content to embryos cultured on SB166/SB103 for 5-8 weeks.

After maturation in SHaM liquid media, individual embryos are removed from the clusters, dried and screened for alterations in their fatty acid compositions as described previously.

Media Recipes:

SB 196—FN Lite Liquid Proliferation Medium (Per Liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| KNO$_3$ | 2.83 gm |
| (NH$_4$)$_2$SO$_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 Solid Medium (Per Liter)

1 package MS salts (Gibco/BRL - Cat. No. 11117-066)
1 mL B5 vitamins 1000X stock
31.5 g glucose
2 mL 2,4-D (20 mg/L final concentration)
pH 5.7
8 g TC agar

SB199 Solid Medium (Per Liter)

1 package MS salts (Gibco/BRL - Cat. No. 11117-066)
1 mL B5 vitamins 1000X stock
30 g Sucrose
4 ml 2,4-D (40 mg/L final concentration)
pH 7.0
2 gm Gelrite

SB 166 Solid Medium (Per Liter)

1 package MS salts (Gibco/BRL - Cat. No. 11117-066)
1 mL B5 vitamins 1000X stock
60 g maltose
750 mg MgCl$_2$ hexahydrate
5 g activated charcoal
pH 5.7
2 g gelrite

SB 103 Solid Medium (Per Liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite

SB 71-4 Solid Medium (Per Liter)

| | |
|---|---|
| 1 bottle Gamborg's B5 salts w/sucrose (Gibco/BRL - Cat. No. 21153-036) pH 5.7 5 g TC agar 2,4-D Stock | |

Obtain premade from Phytotech Cat. No. D 295 - concentration 1 mg/mL

B5 Vitamins Stock (per 100 mL)

| | |
|---|---|
| Store aliquots at −20° C. | |
| 10 g myo-inositol 100 mg nicotinic acid 100 mg pyridoxine HCl 1 g thiamine | |

If the solution does not dissolve quickly enough, apply a low level of heat via the hot stir plate.

SB 228—Soybean Histodifferentiation & Maturation (SHaM) (Per Liter)

| | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL pH 5.8 Autoclave Add to cooled media (≦30° C.): | |
| *Glutamine (final concentration 30 mM) 4% | 110 mL |

*Note: Final volume will be 1010 mL after glutamine addition. Since glutamine degrades relatively rapidly, it may be preferable to add immediately prior to using media. Expiration 2 weeks after glutamine is added; base media can be kept longer w/o glutamine.

FN-Lite Macro for SHAM 10X—Stock #1 (Per Liter)

| | |
|---|---|
| $(NH_4)_2SO_4$ (ammonium sulfate) | 4.63 g |
| $KNO_3$ (potassium nitrate) | 28.3 g |
| $MgSO_4*7H_2O$ (magnesium sulfate heptahydrate) | 3.7 g |
| $KH_2PO_4$ (potassium phosphate, monobasic) Bring to volume Autoclave | 1.85 g |

MS Micro 1000X—Stock #2 (Per 1 Liter)

| | |
|---|---|
| $H_3BO_3$ (boric acid) | 6.2 g |
| $MnSO_4*H_2O$ (manganese sulfate monohydrate) | 16.9 g |
| $ZnSO_4*7H_2O$ (zinc sulfate heptahydrate) | 8.6 g |
| $Na_2MoO_4*2H_2O$ (sodium molybdate dihydrate) | 0.25 g |
| $CuSO_4*5H_2O$ (copper sulfate pentahydrate) | 0.025 g |
| $CoCl_2*6H_2O$ (cobalt chloride hexahydrate) | 0.025 g |
| KI (potassium iodide) Bring to volume Autoclave | 0.8300 g |

FeEDTA 100X—Stock #3 (Per Liter)

| | |
|---|---|
| $Na_2EDTA*$ (sodium EDTA) | 3.73 g |
| $FeSO_4*7H_2O$ (iron sulfate heptahydrate) Bring to Volume Solution is photosensitive. Bottle(s) should be wrapped in foil to omit light. Autoclave | 2.78 g |

*EDTA must be completely dissolved before adding iron.

Ca 100X—Stock #4 (Per Liter)

| | |
|---|---|
| $CaCl_2*2H_2O$ (calcium chloride dihydrate) Bring to Volume Autoclave | 44 g |

B5 Vitamin 1000X—Stock #5 (Per Liter)

| | |
|---|---|
| Thiamine*HCl | 10 g |
| Nicotinic Acid | 1 g |
| Pyridoxine*HCl | 1 g |
| Myo-Inositol Bring to Volume Store frozen | 100 g |

4% Glutamine—Stock #6 (Per Liter)

| | |
|---|---|
| DDI water heated to 30° C. | 900 mL |
| L-Glutamine Gradually add while stirring and applying low heat. Do not exceed 35° C. Bring to Volume Filter Sterilize Store frozen* | 40 g |

*Note: Warm thawed stock in 31° C. bath to fully dissolve crystals.

Regeneration of Soybean Somatic Embryos into Plants:

In order to obtain whole plants from embryogenic suspension cultures, the tissue must be regenerated. Embryos are matured as described in above. After subculturing on medium SB103 for 3 weeks, individual embryos can be removed from the clusters and screened for alterations in their fatty acid compositions as described in Example 8. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to a 10" (25.4 cm) pot of Redi-Earth with up to 3 plantlets per pot. After 10 to 16 weeks, mature seeds are harvested, chipped and analyzed for fatty acids.

Example 8

Fatty Acid Analysis of Transgenic Somatic Soybean Embryos

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

A subset of soybean embryos for each event generated from either production transformation or model system transformation (as described in Example 7) are harvested in the following way. Embryos (5-10 embryos) from each event are picked into glass GC vials, and fatty acid methyl esters are prepared by transesterification. For transesterification, 50 µL of trimethylsulfonium hydroxide (TMSH) and 0.5 mL of hexane is added to the embryos in glass vials and incubated for 30 min at room temperature while shaking. Fatty acid methyl esters (5 µL injected from hexane layer) are separated and quantified using a Hewlett-Packard 6890 Gas Chromatograph fitted with an Omegawax 320 fused silica capillary column (Cat. No. 24152, Supelco Inc.). The oven temperature is programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Events having good phenotype can be re-analyzed by GC using identical conditions except the oven temperature is held at 150° C. for 1 min and then increased to 240° C. at 5° C.

Example 9

Functional Analysis of a Novel Delta-9 Elongase in Yarrowia lipolytica

A uracil ura3 auxotrophic strain of Yarrowia lipolytica (strain Y2224; described in WO200706174; WO2007061845; U.S. Patent Application No. 2007/0118929, the contents of which are hereby incorporated by reference, was used for functional assays of the novel delta-9 elongases.

Yarrowia lipolytica strain Y2224 was grown and transformed with the vectors summarized in Table 3 as described herein.

For delta-9 elongase activity measurements, single colonies of each Yarrowia lipolytica transformant were grown in 3 mL minimal media lacking uracil at 30° C. to an $OD_{600}$~1.0. Cells were subsequently washed with water, collected by centrifugation and lipids transesterified with sodium methoxide as described supra. Fatty Acid Methyl Esters (FAMEs) from cells containing each vector were analyzed by GC where FAMES (5 µL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 220° C. for 2.7 min, increase to 240° C. at 20° C./min and then hold for an additional 2.3 min. Results are shown in Table 5.

For delta-6 and delta-5 elongase activity measurements, single colonies of each Yarrowia lipolytica transformant were grown in 3 mL minimal media lacking uracil at 30° C. to an $OD_{600}$~1.0, after which 0.1 mL was transferred to 3 mL of the same medium supplemented with GLA (for delta-6 elongase activity measurements) or EPA (for delta-5 elongase activity measurements) to a final concentration of 0.175 mM. These were incubated for 16 h at 30° C., 250 rpm, pellets were obtained by centrifugation and fatty acids were analyzed as described above (see "Fatty Acid Analysis of Yarrowia lipolytica). Results are shown in Table 5.

In Table 5, elongation activity is calculated according to the following formula: ([product]/[substrate+product])*100. More specifically, the percent elongation for GLA (Δ6% Conv.) is determined by the formula: ([DGLA]/[DGLA+GLA])*100, the percent elongation for EPA (Δ5% Conv.) is determined by the formula: ([DPA]/[DPA+EPA])*100, the percent elongation for LA (18:2 to 20:2% Conv.) is determined by the formula: ([EDA]/[EDA+LA])*100 and, the percent elongation for OA (18:1 to 20:1% Conv.) is determined by the formula: ([20:1]/[20:1+OA])*100. The total delta-9% conversion activity (delta-9% Conv.) represents the total elongation of OA, LA and ALA and is calculated as ([ERA+EDA+20:1]/[ERA+EDA+20:1+OA+LA+ALA]*100).

TABLE 5

Elongation activity expressed as % conversion (% Conv.) of the novel Delta-9 Elongase in Yarrowia lipolytica.

| Sample Name | Δ6 % Conv. | Δ5 % Conv. | 18:2 to 20:2 % Conv. | 18:1 to 20:1 % Conv. | Δ9 % Conv. |
|---|---|---|---|---|---|
| pY116 | 74.11 | 2.21 | 1.64 | 0.52 | 0.98 |
| 027-2.1b | 60.93 | 5.88 | 4.85 | 2.37 | 3.42 |
| 077-3.1b-B1 | 42.64 | 1.19 | 7.91 | 2.98 | 5.30 |

TABLE 5-continued

Elongation activity expressed as % conversion (% Conv.) of the novel Delta-9 Elongase in *Yarrowia lipolytica*.

| Sample Name | Δ6 % Conv. | Δ5 % Conv. | 18:2 to 20:2 % Conv. | 18:1 to 20:1 % Conv. | Δ9 % Conv. |
|---|---|---|---|---|---|
| 046-3.1b-C2 | 58.67 | 2.34 | 8.02 | 3.04 | 5.04 |
| 052-3.1b-C9 | 51.54 | 4.91 | 8.00 | 3.22 | 4.92 |
| 078-3.1b-B4 | 59.34 | 3.55 | 8.07 | 3.44 | 5.33 |
| pY115 | 0.90 | 0.00 | 11.13 | 0.60 | 5.73 |
| 014-3.1b-F1 | 61.42 | 3.73 | 8.36 | 3.70 | 5.98 |
| 051-3.1b-B5 | 62.00 | 5.23 | 9.79 | 3.68 | 5.93 |
| 062-3.1b-C5 | 60.47 | 3.97 | 9.93 | 3.99 | 6.11 |

Example 10

Functional Analysis of a Novel Delta-9 Elongase in Somatic Soybean Embryos

Soybean embryogenic suspension culture (cv. Jack) was transformed with each of the vectors described in Table 4 (Example 5), and embryos were matured in soybean histodifferentiation and maturation liquid medium (SHaM liquid media; Schmidt et al., *Cell Biology and Morphogenesis*, 24:393 (2005)), as described in Example 7 and previously described in U.S. Patent Application No. 2007/0292924 (the contents of which are hereby incorporated by reference).

After maturation in SHaM liquid media, a subset of transformed soybean embryos (i.e., 5-6 embryos per event) were harvested and fatty acids analyzed as described in Example 8.

Figure 4:
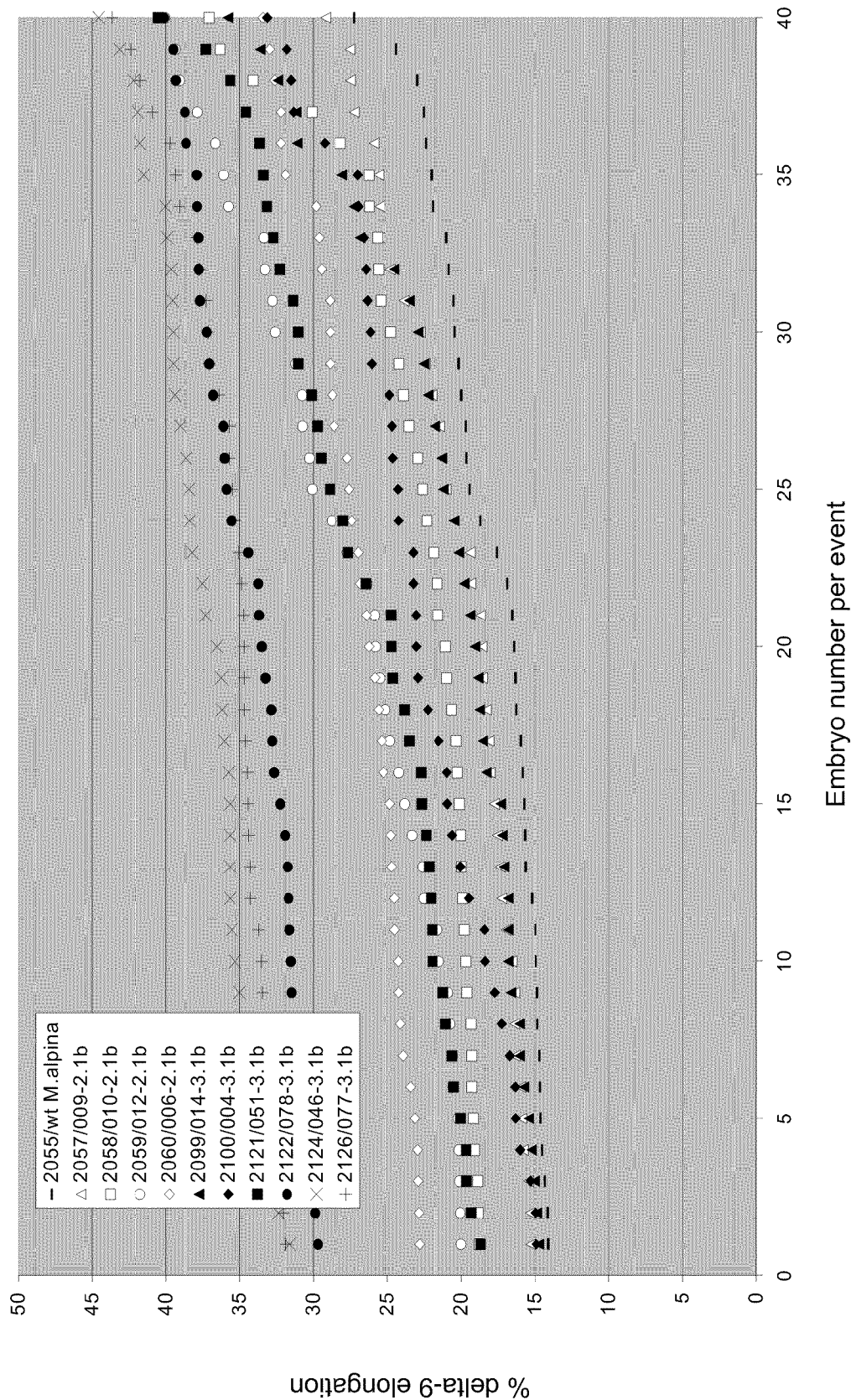
FIG. 4 shows the % delta-9 elongation, defined as ((20:1+20:2+20:3)/(18:1+18:2+18:3+20:1+20:2+20:3))*100 of ten soybean events (top 40 somatic soybean embryos per event) transformed with vectors described in Table 4, versus a control soybean event ((2055/wt *M. alpina*) expressing *M. alpina* delta-6 elongase SEQ ID NO:2).

In this way, approximately 30 events transformed with each of the vectors described in Table 4 and KS120 were analyzed. A summary of the total delta-9 elongation activity for each event (average of 5 embryos) from all experiments is shown in FIG. 4. In FIG. 4, delta-9% conversion activity (delta-9% Conv.) represents the total elongation of OA, LA and ALA and is calculated as ([ERA+EDA+20:1]/[ERA+EDA+20:1+OA+LA+ALA]*100).

The results for events with the highest delta-9 elongation activity (delta-9% Conv.) for each experiment is summarized in Table 6.

TABLE 6

Highest delta-9% conversion in somatic soybean embryo events transformed with expression cassettes described in Example 5.

| Model System Number | Event | Gene Name | Highest delta-9% Conv. |
|---|---|---|---|
| 2124 | 046-3.1b | 046-3.1b-C2 | 44.55 |
| 2126 | 077-3.1b | 077-3.1b-B1 | 43.64 |
| 2122 | 078-3.1b | 078-3.1b-B4 | 40.14 |
| 2100 | 004-3.1b | 004-3.1b-f2 | 33.15 |
| 2121 | 051-3.1b | 051-3.1b-B5 | 40.53 |
| 2099 | 014-3.1b | 014-3.1b-F1 | 35.84 |
| 2059 | 012-2.1b | 012-2.1b-c3 | 40.05 |
| 2058 | 010-2.1b | 010-2.1b-c3 | 37.08 |
| 2060 | 006-2.1b | 006-2.1b-e11 | 33.44 |
| 2057 | 009-2.1b | 009-2.1b-c3 | 29.18 |
| 2055 | *M. alpina* | MaD6ES | 27.24 |

Example 11

Cloning a Novel Delta-9 Elongase Gene into a Yarrowia Expression Vector and Functional Characterization of Delta-9 Elongase and Delta-5 Elongase Activities The present example describes the creation of a novel delta-9 elongase by combining together DNA fragments from individual novel elongases. Specifically, the 5' end of novel elongase 077-3.1b-B1 (SEQ ID NO:27) was combined with the 3' end of novel elongase 051-3.1b-B5 (SEQ ID NO:21), as described below, in an attempt to further enhance either delta-9 or delta-5 elongating activities as described below.

The NcoI/BsrGI fragment of KS386 (SEQ ID NO:54), containing the 5' end of the 077-3.1b-B1 was cloned into the BsrGI/NcoI fragment of KS382 (SEQ ID NO:50), containing the 3' end of 051-3.1b-B5, to produce pLF128 (SEQ ID NO:55). In this way, a new novel elongase, called MaD9elSHFL-4 was formed, and the nucleotide and amino acid sequences of MaD9elSHFL-4 are set forth in SEQ ID NO:56 and SEQ ID NO:57, respectively.

The NcoI/NotI fragment of pLF128 (SEQ ID NO:55), containing MaD9elSHFL-4 (SEQ ID NO:56), was cloned into the NotI/NcoI fragment of pY115 (SEQ ID NO:31), containing the vector backbone and promoter, to produce pY183 (SEQ ID NO:58). In this way, MaD9elSHFL-4 (SEQ ID NO:57) could be expressed in *Yarrowia* under control of a strong, constitutive promoter.

Vectors pY116 (SEQ ID NO:34), 077-3.1b-b1/pY116 (SEQ ID NO:37), 051-3.1b-b5/pY116 (SEQ ID NO:42) and pY183 (SEQ ID NO:58) were transformed into *Yarrowia lipolytica* (strain Y2224) as described herein. Three transformants for each vector were grown as described in Example 9 and used for delta-9 elongase activity measurements. EPA feeding experiments for delta-5 elongase activity measurements were also carried out as described in Example 9. Delta-6 elongase activities were not measured. Results for an average of three transformants are shown in Table 7 and elongation activities are calculated as described in Example 8.

TABLE 7

Elongation activity expressed as % conversion of the novel Delta-9 Elongase in *Yarrowia lipolytica*.

| Sample Name | Δ5 % Conv. | 18:2 to 20:2 % Conv. | 18:1 to 20:1 % Conv. | Δ9 % Conv. |
|---|---|---|---|---|
| pY116 | 1.57 | 1.52 | 2.27 | 1.69 |
| pY 077-3.1b-B1 | 1.72 | 6.18 | 4.01 | 5.74 |
| pY 051-3.1b-B5 | 4.35 | 8.55 | 5.35 | 7.91 |
| pY183 | 4.28 | 9.56 | 5.75 | 8.79 |

Table 7 shows that the delta-5 elongation activity MaD9elSHFL-4 (pY183) is similar to that of 051-3.1b-B5 while the delta-9 elongase activity of pY183 is improved over 051-3.1b-B5.

Example 12

Cloning a Novel Delta-9 Elongase Gene into a Soy Expression Vector and Functional Characterization of Delta-9 Elongase and Delta-5 Elongase Activities The present example describes the creation of vectors for co-expressing either MaD6ES (SEQ ID NO:1) or MaD9elSHFL-4 (SEQ ID NO:56) with other LCPUFA biosynthetic genes in order to produce EPA and DPA in soy somatic embryos. The creation of a soy expression vector pKR1230 (SEQ ID NO: 63) comprising MaD6ES (which is the *Euglena gracilis* delta-8 desaturase (EgD8; SEQ ID NO:59) described in U.S. Patent Application No. 2006/0195939, the contents of which are incorporated by reference) and the *Mortierella alpina* delta-5 desaturase (MaD5; SEQ ID NO:60, which is described in U.S. Pat. No. 6,075,183 and U.S. Patent Publication Nos. 20070237876 and 2005/0132441, the contents all of which are hereby incorporated by reference) is described. The present example further describes the creation of soy expression vector pKR1231 (SEQ ID NO:64) comprising MaD9elSHFL-4 (SEQ ID NO:56), EgD8 (SEQ ID NO:59), and MaD5 (SEQ ID NO:60). The present example also describes the creation of soy expression vector pKR1232 (SEQ ID NO:65) comprising the *Saprolegnia diclina* delta-17 desaturase (SdD17; SEQ ID NO:61), which is described in PCT Publication No. WO 2004/071467 and the *Fusarium monoliforme* delta-15 desaturase (FmD15; SEQ ID NO:63), which is described in PCT Publication No. WO 2005/047479.

Construction of pKR1230 Comprising MaD6ES, EgD8 and MaD5

Vector pKR952 (SEQ ID NO: 78), which is described in PCT Publication No. WO2007/127381, the contents of which are hereby incorporated by reference, contains the MaD5 flanked by the soybean glycinin Gy1 promoter and the pea leguminA2 3' termination region.

Vector pKR680, which is described in U.S. Patent Publication No. 2007/0118929, the contents of which are hereby incorporated by reference, contains the EgD8 flanked by the Kunitz soybean Trypsin Inhibitor (KTi) promoter (Jofuku et al., *Plant Cell* 1:1079-1093 (1989)) and the KTi 3' and soy albumin termination region.

The BsiWI fragment of pKR680, containing the EgD8, was cloned in to the BsiWI site of pKR952 to produce pKR954 (SEQ ID NO:66).

Vector pKR197, which was previously described in U.S. Patent Publication No. 2007/0237876 (the contents of which are hereby incorporated by reference), contains a NotI restriction site, flanked by the promoter for the α' subunit of β-conglycinin (Beachy et al., *EMBO J.* 4:3047-3053 (1985)) and the 3' transcription termination region of the Phaseolin gene (Doyle et al., *J. Biol. Chem.* 261:9228-9238 (1986)).

Through a number of subcloning steps, a NotI site was added to the 5' end of MaD6ES (SEQ ID NO:1), thus providing a DNA fragment (MaD6ES-NotI) where MaD6ES is flanked on both ends by NotI sites. The MaD6ES-NotI fragment was cloned into the NotI site of pKR197 to produce pKR1216. Vector pKR1216 was then digested with SbfI/BsiWI and the fragment containing the β-conglycinin/MaD6ES/Phaseolin cassette was cloned into the SbfI/BsiWI fragment of pKR954 (SEQ ID NO:67) containing the EgD8 and MaD5 to produce pKR1230 (SEQ ID NO:63).

Construction of pKR1230 comprising MaD9elSHFL-4. EqD8 and MaD5

Through a number of subcloning steps, a NotI site was added to the 5' end of MaD9elSHFL-4 from pY183 (SEQ ID NO:58), thus providing a DNA fragment where MaD9elSHFL-4 is flanked on both ends by NotI sites (called MaD9elSHFL-4-NotI)

The MaD9elSHFL-4-NotI fragment was cloned into the NotI site of pKR197 to produce vector pKR1217 Vector pKR1217 was then digested with SbfI/BsiWI and the fragment containing the β-conglycinin/MaD9elSHFL-4/Phaseolin cassette was cloned into the SbfI/BsiWI fragment of pKR954 containing the EgD8 and MaD5 to produce pKR1231 (SEQ ID NO: 64).

Construction of pKR1232 Comprising SdD17 and FmD15

Vector pKR873, which is described in U.S. Patent Publication No. 2007/0118929, the contents of which are hereby incorporated by reference, contains the SdD17 flanked by the soy annexin promoter and the soy BD30 3' terminator as well as the FmD15 flanked by the soy albumin promoter and the soy albumin 3' terminator.

Vector pKR873 was digested with BamHI, and the fragment containing SdD17 and FmD15 was ligated into the BamHI fragment of pKR325 (SEQ ID NO: 79), which is described in PCT Publication No. WO2007/127381, containing the hygromycin gene under control of the 35S promoter to produce pKR1232 (SEQ ID NO:65).

Functional Analysis of MaD6ES or MaD9elSHFL-4 in Soy Somatic Embryos

Soybean embryogenic suspension culture (cv. Jack) was transformed with pKR1232 (SEQ ID NO:65; comprising SdD17 and FmD15) and either pKR1230 (SEQ ID NO:63; comprising MaD6Es, EgD8, MaD5) or pKR1231 (SEQ ID NO:64; comprising MaD9elSHFL-4, EgD8, MaD5) and embryos were matured in soybean histodifferentiation and maturation liquid medium (SHaM liquid media; Schmidt et al., *Cell Biology and Morphogenesis*, 24:393 (2005)), as described in Example 7 and previously described in U.S. Patent Publication No. 2007/0292924 (the contents of which are hereby incorporated by reference).

After maturation in SHaM liquid media, a subset of transformed soybean embryos (i.e., 5-6 embryos per event) were harvested and analyzed as described herein.

In this way, approximately 30 events transformed with pKR1232 and pKR1230 (Experiment MSE2175) or pKR1232 and pKR1231 (Experiment MSE2176) were analyzed. The elongation activity for the five events having the highest average EPA content (average of the 5-6 embryos analyzed) are shown in Table 8.

Figure 6:
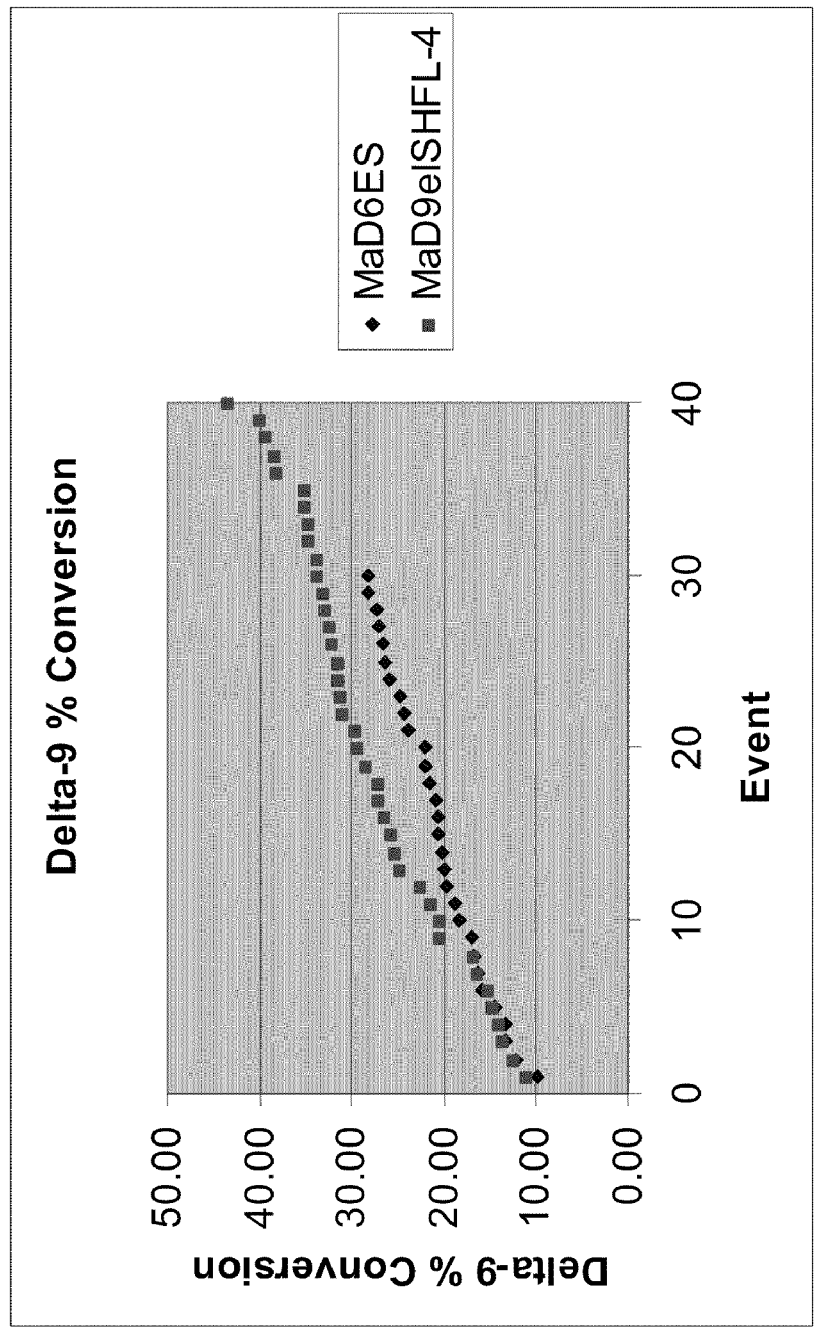
FIG. 6 shows a summary of the total delta-9 elongation activity for each event (average of 5 embryos) from MSE2175 (MaD6ES) and MSE2176 (MaD9elSHFL-4).

A summary of the total delta-9 elongation activity for each event (average of 5 embryos) from MSE2175 (MaD6ES) and MSE2176 (MaD9elSHFL-4) is shown in FIG. 6. In FIG. 6, delta-9% conversion activity (delta-9% conversion) represents the total elongation of OA, LA and ALA to all elongated products. These products include 20:1, EDA, ERA as well as the products that are derived of 20:1, EDA, ERA due to further desaturation or elongation (for example delta-8 desaturation (DGLA, ETA), delta-5 desaturation (ARA, EPA, SCI, JUP) and delta-5 elongation (DPA). Hence the delta-9% conversion activity in FIG. 6 and Table 8 is calculated as ([ERA+EDA+20:1+DGLA+ETA+ARA+EPA+SCI+JUP+DPA]/[ERA+EDA+20:1+DGLA+ETA+ARA+EPA+SCI+JUP+DPA+OA+LA+ALA]*100).

Figure 7:
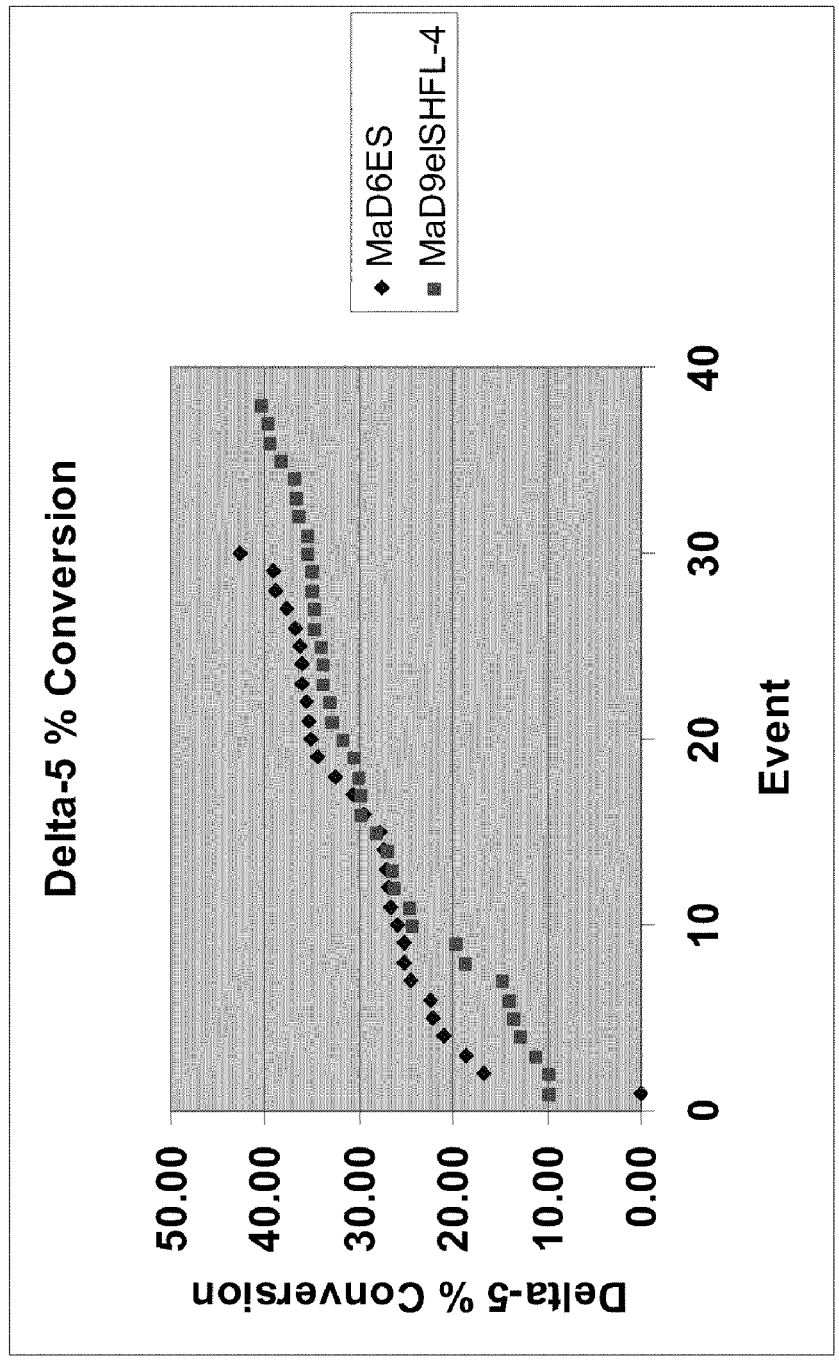
FIG. 7 shows a summary of the total delta-5 elongation activity for each event (average of 5 embryos) from MSE2175 (MaD6ES) and MSE2176 (MaD9elSHFL-4). The delta-5% conversion activity (delta-5% conversion) represents the elongation of EPA to DPA and is calculated as ([DPA]/[EPA+DPA]*100).

A summary of the total delta-5 elongation activity for each event (average of 5 embryos) from MSE2175 (MaD6ES) and MSE2176 (MaD9elSHFL-4) is shown in FIG. 7. In FIG. 7 the delta-5% conversion activity (delta-5% conversion) represents the elongation of EPA to DPA and is calculated as ([DPA]/[EPA+DPA]*100).

The results for events with the highest delta-9% conversion (event 2176-5-4-1) and delta-5% conversion activity (event 2176-3-8-1) or each experiment is summarized in Table 8.

TABLE 8

Highest delta-9% conversion or delta-5% conversion activity expressed as % conversion (% Conv.) of novel Delta-9 Elongase in soybean somatic embryos.

| Event | Gene | Δ5 % Conv. |
|---|---|---|
| 2175-2-16-1 | MaD6ES | 42.77 |
| 2176-3-8-1 | MaD9elSHFL-4 | 40.27 |
| 2175-5-6-1 | MaD6ES | 28.19 |
| 2176-5-4-1 | MaD9elSHFL-4 | 43.27 |

What is claimed is:

1. An isolated polynucleotide comprising:
   (i) a nucleotide sequence encoding a polypeptide comprising Δ9 elongase activity and Δ5 elongase activity, wherein said polypeptide has at least 70% sequence identity, based on the Clustal V method of alignment, when compared to the sequence set forth in SEQ ID NO:2, wherein said polypeptide has at least one of the following modifications to SEQ ID NO:2:
   (a) at amino acid residue number 5, substitution of alanine (A) with valine (V),
   (b) at amino acid residue number 9, substitution of proline (P) with leucine (L),
   (c) at amino acid residue number 62 substitution of glutamic acid (E) with aspartic acid (D),
   (d) at amino acid residue number 79, substitution of leucine (L) with methionine (M),
   (e) at amino acid residue number 80, substitution isoleucine (I) with of leucine (L),
   (f) at amino acid residue number 106, substitution of phenylalanine (F) with tyrosine (Y),
   (g) at amino acid residue number 110, substitution of histidine (H) with tyrosine (Y),
   (h) at amino acid residue number 117, substitution of isoleucine (I) with leucine (L),
   (i) at amino acid residue number 130, substitution of tyrosine (Y) with phenylalanine (F),
   (j) at amino acid residue number 138, substitution of glutamic acid (E) with glutamine (Q), (k) at amino acid residue number 162, substitution of isoleucine (I) with leucine (L),
(l) at amino acid residue number 169, substitution of methionine (M) with leucine (L),
(m) at amino acid residue number 171, substitution of methionine (M) with leucine (L),
(n) at amino acid residue number 174, substitution of lysine (K) with arginine (R),
(o) at amino acid residue number 191, substitution of isoleucine (I) with leucine (L),
(p) at amino acid residue number 208, substitution tyrosine (Y) with tryptophan (W),
(q) at amino acid residue number 213, substitution of leucine (L) with methionine (M),
(r) at amino acid residue number 237, substitution of phenylalanine (F) with leucine (L),
(s) at amino acid residue number 242, substitution of isoleucine (I) with leucine (L),
(t) at amino acid residue number 253, substitution of methionine (M) with leucine (L),
(u) at amino acid residue number 276, substitution of isoleucine (I) with leucine (L),
(v) at amino acid residue number 277, substitution of threonine (T) with alanine (A),
(w) at amino acid residue number 287, substitution of methionine (M) with leucine (L), or
(x) at amino acid residue number 297, substitution of lysine (K) with arginine (R); or
(ii) a full-length complement of the nucleotide sequence of (i).

2. The polynucleotide of claim 1, wherein the amino acid sequence of the polypeptide has at least 80% sequence identity, based on the Clustal V method of alignment, when compared to SEQ ID NO:2.

3. The polynucleotide of claim 1, wherein the amino acid sequence of the polypeptide has at least 90% sequence identity, based on the Clustal V method of alignment, when compared to SEQ ID NO:2.

4. The polynucleotide of claim 1, wherein the amino acid sequence of the polypeptide has at least 95% sequence identity, based on the Clustal V method of alignment, when compared to SEQ ID NO:2.

5. The isolated polynucleotide of claim 1, wherein the polypeptide comprises $\Delta 9$ elongase activity when expressed in a plant of at least 27% conversion of oleic acid to eicosenoic and/or linoleic acid to eicosadienoic acid and/or $\alpha$-linoleic acid to eicosatrienoic acid and $\Delta 5$ elongase activity of at least 5% conversion of eicosapentaenoic acid to docosapentaenoic.

6. The isolated polynucleotide of claim 5, wherein said $\Delta 9$ elongase activity is at least one of 30%, 35%, 40%, 45% or 50% conversion of oleic acid to eicosenoic and/or linoleic acid to eicosadienoic acid and/or $\alpha$-linoleic acid to eicosatrienoic acid.

7. The isolated polynucleotide of claim 5, wherein said $\Delta 5$ elongase activity is at least one of 5%, 10%, 20%, 30% or 40% conversion of eicosapentaenoic acid to docosapentaenoic acid.

8. The isolated polynucleotide of claim 5, wherein said plant is selected from the group consisting of soybean, Brassica species, sunflower, maize, cotton, flax, and safflower.

9. The isolated polynucleotide of claim 1, wherein said polypeptide comprises $\Delta 9$ elongase activity when expressed in yeast of at least 1.7% conversion of oleic acid to eicosenoic and/or linoleic acid to eicosadienoic acid, and $\Delta 5$ elongase activity of at least 1.2% conversion of eicosapentaenoic acid to docosapentaenoic acid, and optionally $\Delta 6$ elongase activity of less than 70% conversion of $\gamma$-linolenic acid to dihomo-$\gamma$-linolenic acid and/or stearidonic acid to eicosatetraenoic acid.

10. The isolated polynucleotide of claim 9, wherein said $\Delta 9$ elongase activity is at least one of 2%, 3%, 4%, 5%, 6%, 7%, 8% or 9% conversion of oleic acid to eicosenoic and/or linoleic acid to eicosadienoic acid.

11. The isolated polynucleotide of claim 9, wherein said $\Delta 5$ elongase activity is at least one of 2%, 3%, 4% or 5% conversion of eicosapentaenoic acid to docosapentaenoic acid.

12. The isolated polynucleotide of claim 9, wherein said $\Delta 6$ elongase activity is less than one of 65%, 60%, 55%, 50%, 45% or 40% conversion of $\gamma$-linolenic acid to dihomo-$\gamma$-linolenic acid and/or stearidonic acid to eicosatetraenoic acid.

13. The isolated polynucleotide of claim 9, wherein said yeast is *Yarrowia lipolytica*.

14. A vector comprising the isolated polynucleotide of claim 1.

15. A recombinant DNA construct comprising the isolated polynucleotide of claim 1 operably linked to a regulatory sequence.

16. A cell comprising the recombinant DNA construct of claim 15.

17. A plant comprising the recombinant DNA construct of claim 15.

18. A transgenic seed comprising the recombinant DNA construct of claim 15.

19. The isolated polynucleotide of claim 1, wherein said polypeptide has 2, 3, 4, 5, 6, 7, 8, 9, 10, 11, 12, 13, 14, 15, 16, 17, 18, 19, 20, 21, 22, 23, or all of the modifications (a)-(x).

20. The isolated polynucleotide of claim 1, wherein said polypeptide has the amino acid sequence set forth SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30.

21. The isolated polynucleotide of claim 1, wherein said isolated polynucleotide comprises the nucleotide sequence set forth in SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29.

22. A method for transforming a cell, comprising transforming a cell with the isolated polynucleotide of claim 1.

23. A method for producing a plant comprising transforming a plant cell with the isolated polynucleotide of claim 1 and regenerating a plant from the transformed plant cell.

24. The method of claim 23, wherein the plant is selected from the group consisting of soybean, *Brassica* species, sunflower, maize, cotton, flax, and safflower.

25. Progeny plants obtained from the plant made by the method of claim 24, wherein said progeny plants comprise the polynucleotide of claim 1.

26. A method for producing at least one polyunsaturated fatty acid in a plant cell comprising:
(a) transforming a plant cell with a first recombinant DNA construct comprising an isolated polynucleotide encoding at least one $\Delta 9$ elongase polypeptide of claim 1, operably linked to at least one regulatory sequence and at least one additional recombinant DNA construct comprising an isolated polynucleotide, operably linked to at least one regulatory sequence, encoding a polypeptide selected from the group consisting of a $\Delta 4$ desaturase, a $\Delta 5$ desaturase, a $\Delta 6$ desaturase, a $\Delta 8$ desaturase, a $\Delta 12$ desaturase, a Δ15 desaturase, a Δ17 desaturase, a Δ9 desaturase, a Δ9 elongase, a $C_{14/16}$ elongase, a $C_{16/18}$ elongase, a $C_{18/20}$ elongase and a $C_{20/22}$ elongase;
(b) regenerating an oilseed plant from the transformed cell of step (a); and,
(c) selecting those seeds obtained from the plants of step (b) having an altered level of polyunsaturated fatty acids when compared to the level in seeds obtained from a nontransformed oilseed plant.

27. The method of claim 26, wherein the plant is selected from the group consisting of soybean, *Brassica* species, sunflower, maize, cotton, flax, and safflower.

28. Progeny plants obtained from the plant made by the method of claim 26.

* * * * *